(12) United States Patent
Butera et al.

(10) Patent No.: US 6,451,827 B2
(45) Date of Patent: Sep. 17, 2002

(54) 2,3,5-SUBSTITUTED BIPHENYLS USEFUL IN THE TREATMENT OF INSULIN RESISTANCE AND HYPERGLYCEMIA

(75) Inventors: John A. Butera, Clarskburg, NJ (US); Craig E. Caufield, New York, NY (US); Russell F. Graceffa, Hampton, NH (US); Alexander Greenfield, Princeton Junction, NJ (US); Eric G. Gundersen, Plainsboro, NJ (US); Lisa Marie Havran, Bordentown, NJ (US); Alan H. Katz, Lawrenceville, NJ (US); Joseph R. Lennox, Morrixville, NC (US); Scott C. Mayer, Robbinsville; Robert E. McDevitt, Somerset, both of NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/771,469

(22) Filed: Jan. 26, 2001

Related U.S. Application Data

(62) Division of application No. 09/307,850, filed on May 10, 1999, now Pat. No. 6,214,877.
(60) Provisional application No. 60/108,154, filed on May 12, 1998, now abandoned.

(51) Int. Cl.[7] ................... A61K 31/44; C07D 213/04
(52) U.S. Cl. .................. 514/357; 546/300; 544/162; 548/217; 548/335.5; 548/469; 549/491; 514/237.8; 514/375; 514/399; 514/415; 514/471
(58) Field of Search ............... 514/357, 237.8, 514/375, 399, 415, 471; 546/300; 544/162; 548/217, 335.5, 469; 549/491

(56) References Cited

U.S. PATENT DOCUMENTS

| | | |
|---|---|---|
| 3,394,193 A | 7/1968 | Reppe et al. |
| 3,666,473 A | 5/1972 | Colom |
| 3,800,051 A | 3/1974 | Barnhart et al. |
| 4,117,151 A | 9/1978 | Deschamps et al. |
| 4,613,611 A | 9/1986 | Floyd et al. |
| 4,808,599 A | 2/1989 | Dubroeucq et al. |
| 5,235,064 A | 8/1993 | Gapinski |
| 5,334,598 A | 8/1994 | Bagley et al. |
| 5,523,302 A | 6/1996 | Cain et al. |
| 5,596,106 A | 1/1997 | Cullinan et al. |
| 5,688,821 A | 11/1997 | Kees |
| 5,698,574 A | 12/1997 | Riedl et al. |
| 5,753,687 A | 5/1998 | Mjalli et al. |

FOREIGN PATENT DOCUMENTS

| | | |
|---|---|---|
| DE | 1249869 | 9/1967 |
| DE | 1291197 | 3/1969 |
| DE | 2616414 | 10/1977 |
| DE | 3110460 | 12/1982 |
| DE | 3342624 | 3/1984 |
| EP | 0276064 | 7/1988 |
| EP | 0568289 | 11/1993 |
| EP | 0693491 | 1/1996 |
| GB | 1293396 | 11/1969 |
| GB | 1248107 | 9/1971 |
| GB | 1450005 | 9/1976 |
| JP | 58150948 | 9/1983 |
| JP | 60172946 | 9/1985 |
| JP | 6236661 | 2/1987 |
| JP | 6236662 | 2/1987 |
| JP | 63161449 | 7/1988 |
| JP | 3247655 | 11/1991 |
| JP | 4016854 | 1/1992 |
| JP | 6348018 | 12/1994 |
| WO | 9111909 | 8/1991 |
| WO | 9422834 | 10/1994 |
| WO | 9422835 | 10/1994 |
| WO | 9608483 | 3/1996 |
| WO | 9609818 | 4/1996 |
| WO | 9634851 | 11/1996 |
| WO | 9708934 | 3/1997 |
| WO | 9721693 | 6/1997 |
| WO | 9739748 | 10/1997 |

OTHER PUBLICATIONS

Ahmad et al., Biochemica et Biophysica Acta, 1248, 1995, 57–69.
Chang et al., Diabetes, 32, 1983, 830–838.
Coleman et al., Diabetologia, 14, 1978, 141–148.
DeFronzo et al., Diabetes Care, 14(3), 1991, 173–194.
Goldstein, Receptor, 3, 1993, 1–15.
Goldstein et al., Mol. and Cell. Biochem., 109, 1992, 107–113.
Goldstein, Cell. Biochem., 48, 1992, 33–42.
Haring, Diabetologia, 34, 1991, 848–861.
Harris et al., Diabetes in America, 1985, Chapter 29, 1–48.
Jarrett, Diabetes/Metabolism Reviews, 5(7), 1989, 547–558.
Lanzetta et al., Analytical Biochem., 100, 1979, 95–97.
McGuire et al., Diabetes, 40, Jul. 1991, 939–942.
Meyerovitch et al., J. Clin. Invest., 87, Apr. 1991, 1286–1294.

(List continued on next page.)

Primary Examiner—C. S. Aulakh
(74) Attorney, Agent, or Firm—Michael R. Nagy

(57) ABSTRACT

This invention provides compounds of Formula I having the structure

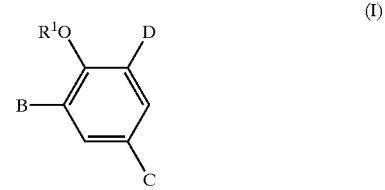

(I)

wherein: B, C, D, and $R^1$ are as defined hereinbefore in the specification, or a pharmaceutically acceptable salt thereof, which are useful in treating metabolic disorders related to insulin resistance or hyperglycemia.

24 Claims, No Drawings

OTHER PUBLICATIONS

Meyerovitch et al., J. Clin. Invest., 84, Sep. 1989, 976–983.
Mitsunobu, Synthesis, Jan. 1981, 1–28.
Nutaitis, Organic Preparations and Procedures Int., 23(4), 1991, 403–411.
Perlich et al., Synthesis, Feb. 1988, 142–144.
Phillion et al., Tetrahedron, 27(13), 1986, 1477–1480.
Pyorala et al., Diabetes/Metabolism Reviews, 3(2), 1987, 463–524.
Reaven et al., Amer. J. Med., 60, 1976, 80–88.
Stredy et al., Metabolism, 44(8), 1995, 1074–1081.
Stout, Metabolism, 34(2) (*Suppl 1*), Dec. 1985, 7–12.
Zask et al., J. Med. Chem., 33, 1990, 1418–1423.
Chen et al., Indian J. Chem., 35B, Dec. 1996, 1304–1307.
d'Ischia et al., Tetrahedron, 43(2), 1987, 431–434.
Dryhurst et al., J. Am. Chem. Soc,. 111, 1989, 719–726.
Guirguis et al., J. Prakt. Chemie, 332(3), 1990, 414–418.
Guirguis et al., Liebigs Ann. Chem., 1986, 1003–1011.
Han et al., Tetrahedron Letter, 31(8), 1990, 1181–1182.
Hashem, J. Prakt. Chemie, 319(4), 1977, 689–692.
Konopelski et al., Synlett Letters, Jul. 1996, 609–611.
Kuroda et al., J. Org. Chem., 59, 1994, 7353–7357.
Kuroda et al., J. Chem. Soc., Chem. Commun., 1991, 1635–1636.
Lefker et al., Tetrahedron Letters, 35(29), 1994, 5205–5208.
Molina et al., Tetrahedron, 50(17), 1994, 5027–5036.
Molina et al., Tetrahedron Letters, 34(17), 1993, 2809–2812.
Napolitano et al., Tetrahedron, 45(21), 1989, 6749–6760.
Schuster et al, J. Org. Chem., 53, 1988, 5819–5825.
Buu–Hoi et al., J. Chem. Soc., 1957, 625–628.
Brown et al., J. Med. Chem., 14(1), 1971, 84–85.
Kimura et al., Tetrahedron Letters, 36(7), 1995, 1079–1080.
Schuster et al., J. Org. Chem., 53, 1988, 5819–5825.
Kano et al., Heterocycles, 19(6), 1982, 1033–1037.
Martin et al., J. Org. Chem., 49, 1984, 2512–2513.
Eckert et al., Arch. Pharm., 315, 1982, 569–570.
Goldenberg et al., Eur. J. Med. Chem., Chim. Ther., 12(1), Jan.–Feb. 1977, 81–86.
Artini et al., Arzneim.–Forsch. (Drug Res.), 21(1), 1971, 30–36.
Ayyangar et al., Synthesis, Apr. 1991, 322–324.
Darchen et al., J. C. S. Chem. Comm., 1976, 820.
De Cointet et al., Chimie Therapeutique, 5, Sep.–Oct. 1973, 574–587.
Hamacher, Arch. Pharmaz., 308, 1975, 290–301.
Massolini et al., Il Farmaco, 45(2), 1990, 263–268.
Miyaura et al., Synthetic Communications, 11(7), 1981, 513–519.
Barraclough et al., Arch. Pharm., 323, 1990, 507–512.
Liebeskind et al., J. Org. Chem., 55, 1990, 5359–5364.
Toth, Liebigs Ann. Chem., 1994, 685–688.
Watanabe et al., Chem. Abstracts, 124:116928s, 1996.
Abdurasuleva et al., Chem. Abstracts, 63:10356a, 1965.
Richter et al., Chem. Abstracts, 67:21652n, 1967.
Kryuchkova et al., Chem. Abstracts, 55:3488i, 1961.
Zavgorodini et al., Chem. Abstracts, 57:14982ia, 1962.
Boit, Beilstein Handbook of Org. Chem. $4^{th}$ ed., $3^{rd}$ Supp., vol. VI, 1966, p. 1374–1381, 1384, 1749, 3330–3339, 3361–3364.
Richter, Beilstein Handbook of Org. Chem. $4^{th}$ ed., $1^{st}$ Supp., vols. XIII/XIV, 1933, p. 183–185, 217, 218.
Luckenbach, Beilstein Handbook of Org. Chem. $4^{th}$ ed., $4^{th}$ Supp., vol. VI, 1979, p. 2141–2146, 3268, 3271.
Aldrich Catalog, 1996, p. 596.

2,3,5-SUBSTITUTED BIPHENYLS USEFUL IN THE TREATMENT OF INSULIN RESISTANCE AND HYPERGLYCEMIA

This application is a divisional application of U.S. patent application Ser. No. 09/307,850, filed May 10, 1999 now U.S. Pat. No. 6,214,877, which claimed the benefit of U.S. Provisional Application No. 60/108,154, which was converted from U.S. patent application Ser. No. 09/076,709, filed May 12, 1998, now abandoned, pursuant to a petition filed under 37 C.F.R. 1.53(c)(2)(i).

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in, IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. J. Goldstein, *Receptor* 1993, 3, 1–15, ; F. Ahmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest.* 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

P. N. Devine et al (WO 97/21693; Jun. 19, 1997) disclosed examples D under a method of preparation (B, D (independently=halogen, phenyl, alkyl; X=alkyl, aryl; Y=$(CH_2)_{0-3}CH_3$, Ph, $NH(CH_2)_{0-3}CH_3$, $N((CH_2)_{0-3}CH_3)_2$, $NH_2$, $NO_2$, $NHCO(CH_2)_{0-3}CH_3$, $NHCO_2(CH_2)_{0-3}CH_3$, $CH_2O(CH_2)_{0-3}CH_3$, OPh; $O(CH_2)_{1-4}O(CH_2)_{0-5}CH_3$, $O(CH_2)_{1-4}OPh$, $OCO_2(CH_2)_{0-5}CH_3$, $CON((CH_2)_{0-5}CH_3)_2$, $O(CH_2)_{1-4}O(CH_2)_{1-6}Ph)$. The synthetic process to prepare the compounds represented by compounds D was different to the processes used to prepare the 2,3,5-substituted biphenyls of this invention.

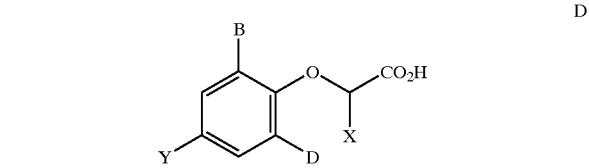

D

G. Cain and C. J. Eyermann (U.S. Pat. No. 5,523,302; Jun. 4, 1996) disclosed examples A (B, D (independently= cycloalkyl, alkyl, aralkyl) as agents which inhibit platelet aggregation, as thrombolytics, and/or for the treatment of thromboembolic disorders. The synthetic process to prepare the compounds represented by compounds A was different to the processes used to prepare the 2,3,5-substituted biphenyls of this invention.

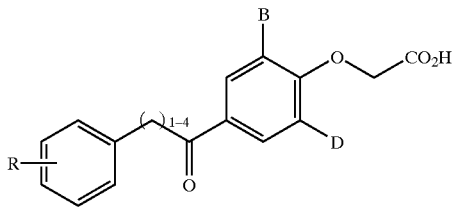

A

M. Wayne et al (WO 94/22835, WO 94/22834; Oct. 13, 1994) disclosed examples B (B, D (independently=alkyl, halogen) as agents which inhibit platelet aggregation, as thrombolytics and/or for the treatment of thromboembolic disorders. The synthetic process to prepare the compounds represented by compounds B was different to the processes used to prepare the 2,3,5-substituted biphenyls of this invention

B

S. W. Bagley et al (U.S. Pat. No. 5,334,598; Aug. 2, 1994) disclosed examples C (B, D (independently=phenyl, naphthyl, alkyl, halogen) as agents which have endothelin antagonist activity and are therefore useful in treating cardiovascular disorders. Our present invention does not claim a compound of this genus, namely 2-phenyl-2-phenoxy acetic acids. The synthetic process to prepare the compounds represented by compounds C was different to the processes used to prepare the 2,3,5-substituted biphenyls of this invention. A similar set of compounds is disclosed in C. M. Harvey et al (WO 96/09818; Apr. 4, 1996), W. J. Greenlee et al (WO 91/11909; Aug. 22, 1991), and W. J. Greenlee et al (WO 91/12002; Aug. 22, 1991). A similar set of arguments apply.

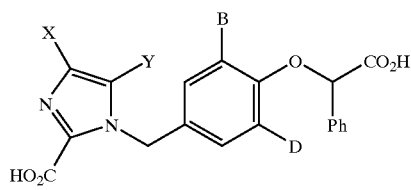

C

DESCRIPTION OF THE INVENTION

This invention provides a compound of formula I having the structure

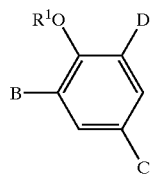

(I)

wherein:
B and D are each, independently, hydrogen, halogen, alkyl of 1–6 carbon atoms, cycloalkyl of 3–8 carbon atoms, aryl, heteroaryl, aralkyl of 6–12 carbon atoms, or heteroaralkyl of 6–12 carbon atoms except where B and D both are hydrogen;

$R^1$ is hydrogen, alkyl of 1–6 carbon atoms, —$SO_2Ph(OH)$ ($CO_2H$), —$CH(R^2)W$; —$CH_2CH_2Y$, or —$CH_2CH_2CH_2Y$;

$R^2$ is hydrogen, alkyl of 1–6 carbon atoms, aralkyl of 6–12 carbon atoms, —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), or —$CH_2$(3-pyridyl);

W is —$CO_2R^3$, —CONHOH, —CN, —$CONHR^3$, aryl, heteroaryl, —CHO, —CH=$NOR^3$, or —CH=$NHNHR^3$;

Y is —W, —$OCH_2CO_2R^3$, aryl, heteroaryl, —C(=NOH)$NH_2$, —$OR^3$, —O(C=O)$NR^4R^5$, —$NR^3$(C=O)$OR^3$, —$NR^3$(C=O)$NR^4R^5$, or —$NR^4R^5$;

$R^3$ is hydrogen or alkyl of 1–6 carbon atoms;

$R^4$ and $R^5$ are each, independently, hydrogen, or alkyl of 1–6 carbon atoms or $R^4$ and $R^5$ are, together, —$(CH_2)_n$—, or —$CH_2CH_2XCH_2CH_2$—;

X is O, S, SO, $SO_2$, $NR^3$, or $CH_2$;

n is 2 to 5;

C is alkyl of 1–18 carbon atoms, aryl, heteroaryl, aralkyl of 6–20 carbon atoms, heteroaralkyl of 6–20 carbon atoms, —$CONR^6R^7$, —$NR^3CONR^6R^7$, —$NR^3COR^6$, —$OR^6$, —$O_2CNR^6R^7$, —$NR^3CO_2R^6$, —$O_2CR^6$, —$CH_2OR^6$, —$NR^6R^7$, —$CR^3$=$CR^3R^8$, —$CPh_3$, —$CH_2NR^6R^7$, or

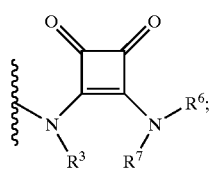

$R^6$ and $R^7$ are each, independently, hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —$(CH_2CH_2O)_nCH_3$, —$(CH_2)_mA$ or $R^6$ and $R^7$ are, together, —$(CH_2)_p$—, —$(CH_2)_2N(CH_3)(CH_2)_4$—, —$(CH_2)_2N(R^8)(CH_2)_2$—, or —$(CH_2)_2CH(R^8)$—$(CH_2)_2$—;

$R^8$ is hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —$(CH_2CH_2O)_nCH_3$, —$(CH_2CH_2CH_2O)_nCH_3$, or —$(CH_2)_mA$;

A is aryl, heteroaryl, aryloxy, heteroaryloxy, arylthio, heteroarylthio, arylsulfoxy, heteroarylsulfoxy, arylsulfonyl, heteroarylsulfonyl, —$CHF_2$, —CH$_2$F, —CF$_3$, —(CH$_2$CH$_2$O)$_n$CH$_3$, —(CH$_2$CH$_2$CH$_2$O)$_n$CH$_3$, —CO$_2$R$^3$, —O(C=O)NR$^6$R$^7$, aralkyloxy, or heteroaralkyloxy;

m is 2 to 16 p is 2 to 12 or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Alkyl includes both straight chain as well as branched moieties. Halogen means bromine, chlorine, fluorine, and iodine. It is preferred that the aryl portion of the aryl, aralkyl, aryloxy, or aralkyloxy substituent is a phenyl or naphthyl; with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms. The heteroaryl portion of the heteroaryl, heteroaralkyl, heteroaryloxy, or heteroaralkyloxy substituent may be pyridyl, furyl, thienyl, quinolinyl, isoquinolinyl, tetrazolyl, triazolyl, thiazolyl, oxazolyl, imidazolyl, oxadiazolyl, benzofuranyl, benzothiophenyl, benzimidazolyl, benzoxazolyl, and benzothiazolyl. The heteroaryl moiety may be optionally mono-, di-, or tri-substituted in the case of pyridyl, furyl, thienyl, quinolinyl, isoquinolinyl, benzofuranyl, benzothiophenyl, benzimidazolyl, benzoxazolyl, or benzothiazolyl, may be optionally mono- or di-substituted in the case of thiazolyl, oxazolyl, or imidazolyl, and may be optionally monosubstituted in the case of oxadiazolyl, tetrazolyl, or triazolyl, with a substituent selected from the group consisting of alkyl of 1–6 carbon atoms, alkoxy of 1–6 carbon atoms, trifluoromethyl, halogen, alkoxycarbonyl of 2–7 carbon atoms, alkylamino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers, as well as the racemic and resolved, enantiomerically pure R and S stereoisomers, as well as other mixtures of the R and S stereoisomers and pharmaceutically acceptable salts thereof.

Preferred compounds are those in which B is aryl and D is either aryl or halogen. More preferred compounds of this invention are:

(3,3"-Dichloro-5'-dodecylcarbamoyl-[1,1';3',1"]terphenyl-2'-yloxy)acetic acid;

(3-Bromo-3'-chloro-5-dodecylcarbamoyl-biphenyl-2-yloxy)acetic acid

[3,3"-Dichloro-5'-(8-phenyl-octylcarbamoyl)-[1,1';3',1"]terphenyl-2"-yloxy]acetic acid;

(5'-Octadecyloxy-[1,1';3',1"]terphenyl-2"-yloxy)acetic acid;

(5'-dodecylcarbamoyl-3,3"-bis-trifluoromethyl-{1,1';3',1"]terphenyl-2'-yloxy)acetic acid;

(3-bromo-5-dodecylcarbamoyl-3'-trifluoromethyl-biphenyl-2-yloxy)acetic acid;

(5"-(8-phenyloctylcarbamoyl-3,3"-bis-trifluoromethyl-{1,1';3',1"]terphenyl-2"-yloxy)-acetic acid;

(5'-Dodecylcarbamoyl-[1,1';3',1"]terphenyl-2'-yloxy)-acetic acid (5'-Dodecylcarbamoyl-4,4"-dimethoxy-[1,1';3',1"]terphenyl-2'-yloxy)-acetic acid (3-Chloro-5"-dodecylcarbamoyl-4"-methoxy-[1,1';3']terphenyl-2"-yloxy)-acetic acid (5'-Dodecylcarbamoyl-3,3"-dimethoxy-[1,1';3'1"]terphenyl-2'-yloxy)-acetic acid

[2-(3,3"-Dichloro-5"-dodecylcarbamoyl-[1,1';3',1"]terphenyl-2'-yloxy-ethoxy]acetic acid {5"-[6-(4-tert-Butyl-benzyloxy)-hexylcarbamoyl]-3,3"-bis-tifluoromethyl-[1,1';3',1"]terphenyl-2'-yloxy}-acetic acid {5"-[6-(4-Benzyloxy-benzyloxy)-hexylcarbamoyl]-3,3"-bis-trifluoromethyl-[1,1';3'1"]terphenyl-2"-yloxy}-acetic acid

[3'-Chloro-4-methoxy-5'-(8-phenyl-octylcarbamoyl)-[1,1';3',1"]terphenyl-2'-yloxy]-acetic acid {3"-Chloro-4-methoxy-5"-[methyl-(8-phenyl-octyl)-carbamoyl]-[1,1';3',1"]terphenyl-2'-yloxy}-acetic acid

[3,3"-Dimethoxy-5"-(8-phenyl-octylcarbamoyl)-[1,1";3',1"]terphenyl-2-yloxy]-acetic acid {2-[5'-(6-Phenyl-hexylcarbamoyl)-3,3"-bis-trifluoromethyl-[1,1';3',1"]terphenyl-2'-yloxy]ethoxy}acetic acid {5"-[6-(2,4-Difluoro-benzyloxy)-hexylcarbamoyl]-3,3"-bis-trifluoromethyl-[1,1';3'1"]terphenyl-2'-yloxy}-acetic acid {5'-[6-(Biphenyl-4-ylmethoxy)-hexylcarbamoyl]-3,3"-bis-trifluoromethyl-[1,1';3',1"]terphenyl-2"-yloxy}-acetic acid {3,3"-Dimethoxy-5"-[methyl-(8-phenyl-octyl)-carbamoyl]-[1,1';3',1"]terphenyl-2'-yloxy}-acetic acid {2-[3,5,3",5"-Tetrachloro-5'-[(6-phenyl-hexylcarbamoyl)-[1,1';3',1"]terphenyl-2'-ethoxy}-acetic acid

[4,4"-Dimethoxy-5'-(8-phenyl-octylcarbamoyl)-[1,1';3',1"]terphenyl-2'-yloxy]acetic acid sodium salt (3,3"-Dichloro-5'-dodecylcarbamoyl-4,4"-difluoro[1,1';3',1"]terphenyl(-2'-yloxy)-acetic acid sodium salt

[3,3"-Dichloro-4-4"difluoro-5'-(8-phenyl-octylcarbamoyl)[-1,1';3',1"]terphenyl-2"-yloxy]-acetic acid {3,3"-Dichloro-5'-(6-(2,5-dimethyl-furan-3-ylmethoxy)-hexylcarbamoyl]4-4"-difluoro-[1,1';3',1"]terphenyl-2'-yloxy}-acetic acid

[3,5-Dichloro-5"-(8-phenyl-octylcarbamoyl)-[1,1';3',1"]terphenyl-2"-yloxy]-acetic acid

[5"-(8-Phenyl-octylcarbamoyl)-3-trifluoromethyl-[1,1";3',1"]terphenyl-2"-yloxy]-acetic acid 4,4"-Difluoro-5'-(8-phenyl-octylcarbamoyl)-3,3"-bis-trifluoromethyl-[1,1';3',1"]terphenyl-2'-yloxy]-acetic acid {5'-[6-(2,5-Dimethyl-furan-3-ylmethoxy)-hexylcarbamoyl]-3,3"-bis-trifluoromethyl-[1,1';3',1"]terphenyl-2"-yloxy}-acetic acid (3-Bromo-5-dodecylcarbamoyl-4'-methoxy-biphenyl-2-yloxy)-acetic acid

[5"-(2-Hexadecylamino-3,4-dioxo-cyclobut-1-enylamino)-[1,1';3',1"]terphenyl-2'-yloxy]-acetic acid (3,3"-Dichloro-5'-dodecylcarbamoyl-[1,1';3',1"]terphenyl-2'-yloxy)-acetic acid (3-Bromo-3'-chloro-5-dodecylcarbamoyl-biphenyl-2-yloxy)-acetic acid

[3,3"-Dichloro-5'-(8-phenyl-octylcarbamoyl)-[1,1';3',1"]terphenyl-2"-yloxy]acetic acid (5'-Octadecyloxy-[1,1';3',1"]terphenyl-2'-yloxy)-acetic acid (5"-Benzo[b]naphtho[2,3-d]thiophen-11-yl-[1,1';3',1"]terphenyl-2"-yloxy)-acetic acid (5'-Nitro-[1,1';3',1"]terphenyl-2'-yloxy)-acetic acid (5'-Methoxy-[1,1';3',1"]terphenyl-2'-yloxy)acetic acid (5"-Bromo-[1,1';3',1"]terphenyl-2'-yloxy)-acetic acid

[(5'-Phenyl[1,1';3',1"-terphenyl]-2'-yl)oxy]acetic acid (1,3-Diphenyl-dibenzofuran-2-yloxy)-acetic acid (2-Benzoyl-4,6-dibromo-benzofuran-5-yloxy)acetic acid (5"-Butoxy-[1,1';3',1"]terphenyl-2'-yloxy)acetic acid (5'-Octyloxy-[1,1';3',1"]terphenyl-2'-yloxy)acetic acid (3,3"-Dichloro-5'-octyloxy-[1,1';3',1"]terphenyl-2'-yloxy)acetic acid (3,3"-Bis-acetylamino-5'-octyloxy-[1,1';3',1"]terphenyl-2'-yloxy)acetic acid (5'-Octyloxy-3,3"-bis-trifluoromethyl-[1,1';3',1"]terphenyl-2'-yloxy)acetic acid (3,3"-Dinitro-5'-octyloxy-[1,1';3',1"]terphenyl-2'-yloxy)acetic acid (3,3"-Dimethoxy-5"-octyloxy-[1,1';3',1"]terphenyl-2'-yloxy)acetic acid

[3,3"-Dichloro-5'-(3-phenyl-propylcarbamoyl)-[1,1';3'1"]terphenyl-2'-yloxy]acetic acid

[3,3"-Dichloro-5'-(2-pyridin-2-yl-ethylcarbamoyl)-[1,1';3'1"]terphenyl-2'-yloxy]acetic acid

[5'-(Benzyl-phenethyl-carbamoyl)-3,3"-Dichloro-[1,1';3'1"]terphenyl-2'-yloxy]acetic acid

[3,3"-Dichloro-5'-(4phenyl-butylcarbamoyl)-[1,1';3'1"]terphenyl-2'-yloxy]acetic acid

[5-(Benzyl-phenethyl-carbamoyl)-3-bromo-3'-chloro-biphenyl-2-yloxy]acetic acid

[3-Bromo-3'-chloro-5-(2-pyridin-2-yl-ethylcarbamoyl)-biphenyl-2-yloxy]acetic acid

[5'-(Benzyl-phenethyl-carbamoyl)-3"-chloro-3-trifluoromethyl-[1,1';3'1"]-terphenyl-2'-yloxy]acetic acid

[3"-Chloro-5"-(2-pyridin-2-yl-ethylcarbamoyl)-3-trifluoromethyl-([1,1';3'1"]-terphenyl-2'-yloxy]acetic acid

[3"-Chloro-5"-(3-phenyl-propylcarbamoyl)-3-trifluoromethyl-[1,1";3'1"]terphenyl-2'-yloxy]acetic acid

[3"-Chloro-5'-(4phenyl-butylcarbamoyl)-3-trifluoromethyl-[1,1';3'1"]terphenyl-2'-yloxy]acetic acid

[3"-Chloro-5'-(3-cyclopentyl-propylcarbamoyl)-3-trifluoromethyl-[1,1';3'1"]-terphenyl-2'-yloxy]acetic acid

[3-Bromo-3'-chloro-5-(3-cyclopentyl-propylcarbamoyl)-biphenyl-2-yloxy]acetic acid {5'-[2-(4-Bromo-phenyl)-ethylcarbamoyl]-3"-chloro-3-trifluoromethyl-[1,1';3'1"]-terphenyl-2'-yloxy]acetic acid

[3,3"-Dichloro-5'-(3-cyclopentyl-propylcarbamoyl)-[1,1';3'1"]terphenyl-2'-yloxy]acetic acid

[4"-Methoxy-5'-(2-pyridin-2-yl-ethylcarbamoyl)-3-trifluoromethyl-[1,1';3'1"]-terphenyl-2'-yloxy]acetic acid

[5'-(3-Cyclopentyl-propylcarbamoyl)-4"-methoxy-3-trifluoromethyl-[1,1';3'1"]-terphenyl-2'-yloxy]acetic acid

[5"-(Benzyl-phenethyl-carbamoyl)-4"-methoxy-3-trifluoromethyl-[1,1';3'1"]-terphenyl-2'-yloxy]acetic acid

[5'-(Benzyl-phenethyl-carbamoyl)-2-fluoro-4"-methoxy-[1,1';3'1"]-terphenyl-2'-yloxy]acetic acid

[5-(Benzylphenethyl-carbamoyl)-3-bromo-2'-fluoro-biphenyl-2-yloxy]acetic acid

[2-Fluoro-4"-methoxy-5'-(2-pyridin-2-yl-ethylcarbamoyl)-[1,1';3'1"]-terphenyl-2'-yloxy]acetic acid

[2-Fluoro-4"-methoxy-5'-(3-phenyl-propylcarbamoyl)-[1,1';3'1"]-terphenyl-2'-yloxy]acetic acid

[3-Bromo-2'-fluoro-5-(2-pyridin-2-yl-ethylcarbamoyl)biphenyl-2-yloxy]acetic acid

[3-Bromo-2'-fluoro-5-(3-phenyl-propylcarbamoyl)-biphenyl-2-yloxy]acetic acid

[5'-(3-Cyclopentyl-propylcarbamoyl)-2-fluoro-4"-Methoxy-[1,1';3'1"]-terphenyl-2"-yloxy]acetic acid

[3-Bromo-5-(3-cyclopentyl-propylcarbamoyl)-2"-fluoro-biphenyl-2-yloxy]acetic acid

[2-Fluoro-4"-methoxy-5'-(8-phenyl-octylcarbamoyl)-[1,1';3'1"]-terphenyl-2'-yloxy]acetic acid

[3-Bromo-2'-fluoro-5-(8-phenyl-octylcarbamoyl)-biphenyl-2-yloxy]acetic acid

[2-Fluoro-4"-methoxy-5'-(6-phenyl-hexylcarbamoyl)-[1,1';3'1"]-terphenyl-2'-yloxy]acetic acid

[3-Bromo-2'-fluoro-5-(6-phenyl-hexylcarbamoyl)-biphenyl-2-yloxy]acetic acid

[3,3"-Dichloro-5'-(6-phenyl-hexylcarbamoyl)-[1,1';3'1"]terphenyl-2"-yloxy]acetic acid {4"-Methoxy-5'-[methyl-(8-phenyl-octyl)-carbamoyl]-3-trifluoromethyl-[1,1';3'1"]-terphenyl-2'-yloxy}acetic acid {3,3"-Dichloro-5'-[methyl-(8-phenyl-octyl)-carbamoyl]-[1,1';3'1"]terphenyl-2'-yloxy}acetic acid

[3,3"-Difluoro-5'-(8-phenyl-octylcarbamoyl)-[1,1';3'1"]terphenyl-2'-yloxy]acetic acid {3,3"-Difluoro-5'-[methyl-(8-phenyl-octyl)-carbamoyl]-[1,1';3'1"]terphenyl-2'-yloxy}acetic acid

[3,3"-Dichloro-5'-(8-morpholin-4-yl-octylcarbamoyl)-[1,1';3'1"]terphenyl-2"-yloxy]acetic acid {3,3"-Dichloro-5'-[8-(2,6-dimethoxy-phenoxy)-octylcarbamoyl]-[1,1';3'1"]-terphenyl-2'-yloxy}acetic acid {5'-[8-(Benzoxazol-2-ylsulfanyl)-octylcarbamoyl]-3,3"-dichloro-[1,1';3'1"]-terphenyl-2'-yloxy}acetic acid

[3,3"-Dichloro-5"-(8-indol-1-yl-octylcarbamoyl)-[1,1';3'1"]terphenyl-2'-yloxy]acetic acid {3,3"-Dichloro-5'-[8-(3-cyano-phenoxy)-octylcarbamoyl]-[1,1";3'1"]terphenyl-2'-yloxy}acetic acid {3,3"-Dichloro-5'-[8-(4-chloro-benzyloxy)-octylcarbamoyl]-[1,1';3'1"]terphenyl-2'-yloxy}acetic acid {3,3"-Dichloro-5"-[8-(4-fluoro-3-methyl-phenoxy)-octylcarbamoyl]-[1,1';3'1"]-terphenyl-2'-yloxy}acetic acid

[3,3"-Dichloro-5"-(8-imidazol-1-yl-octylcarbamoyl)-[1,1';3'1"]terphenyl-2'-yloxy]acetic acid {3,3"-Dichloro-5"-[6-(naphthalen-1-ylcarbamoyloxy)-hexylcarbamoyl]-[1,1';3'1"]-terphenyl-2"-yloxy}acetic acid {3,3"-Dichloro-5'-[6-(2,4-difluoro-phenylcarbamoyloxy)-hexylcarbamoyl]-[1,1';3'1"]terphenyl-2'-yloxy}acetic acid {3,3"-Dichloro-5'-[6-(4-phenoxy-phenylcarbamoyloxy)-hexylcarbamoyl]-[1,1';3'1"]terphenyl-2'-yloxy}acetic acid {3,3"-Dichloro-5'-[8-(5-fluoro-indol-1-yl)-octylcarbamoyl]-[1,1';3'1"]terphenyl-2'yloxy}acetic acid {3,3"-Dichloro-5'-[8-(5-methoxy-indol-1-yl)-octylcarbamoyl]-[1,1';3'1"]terphenyl-2'-yloxy}acetic acid {3,3"-Dichloro-5"-[8-(2,5-dimethyl-indol-1-yl)-octylcarbamoyl]-[1,1';3'1"]-terphenyl-2'-yloxy}acetic acid {3,3"-Dichloro-5"-[8-(5-methoxy-2-methyl-indol-1-yl)-octylcarbamoyl]-[1,1';3'1"]-terphenyl-2"-yloxy}acetic acid (3,3"-Dichloro-5"-{[-(4-phenyl-butoxymethyl)-cyclopropylmethyl]-carbamoyl}-[1,1';3'1"]terphenyl-2'-yloxy)acetic acid

[5"-(Benzofuran-2-carbonyl)-[1,1";3'1"]terphenyl-2"-yloxy]acetic acid

3-[3"-(2—Carboxy-vinyl)-2'-methoxy-5'-(8-phenyl-octylcarbamoyl)-[1,1';3'1"]-terphenyl-3-yl]-acrylic acid 3-[3"-(2—Carboxy-ethyl)-2'-methoxy-5'-(8-phenyl-octylcarbamoyl)-[1,1';3'1"]-terphenyl-3-yl]-propionic acid {5'-[(2-Butyl-benzofuran-3-ylmethyl)-amino]-[1,1';3',1"]terphenyl-2'-ylolxy}acetic acid methyl ester {5'-[(2-Butyl-benzofuran-3-ylmethyl)-amino-[1,1';3',1"]terphenyl-2'-yloxy}acetic acid {2,6-Dibromo-4-[(2-butyl-benzofuran-3-ylmethyl)-amino-phenoxy}acetic acid methyl ester {2,6-Dibromo-4-[(2-butyl-benzofuran-3-ylmethyl)-amino]-phenoxy}acetic acid

[2"-Fluoro-5'-(8-phenyl-octylcarbamoyl)-3-trifluoromethyl-[1,1';3',1"]terphenyl-2'-yloxy)-acetic acid (5'-Dodecylcarbamoyl-2"-fluoro-3-trifluoromethyl-[1,1";3',1"]terphenyl-2'-yloxy)-acetic acid (5'-Dodecylcarbamoyl-2,2"-difluoro-[1,1";3',1"]terphenyl-2'-yloxy)-acetic acid

[2,2"-Difluoro-5'-(8-phenyl-octylcarbamoyl)-[1,1';3',1"]terphenyl-2'-yloxy)-acetic acid

[2,2"-Difluoro-5'-(6-phenyl-hexylcarbamoyl)-[1,1';3',1"]terphenyl-2'-yloxy)-acetic acid {5'-[6-(2,4-Difluoro-phenoxy)-hexylcarbamoyl]-2,2"-difluoro-[1,1';3',1"]terphenyl-2'-yloxy]-acetic acid (3"-Chloro-5'-dodecylcarbamoyl-2-fluoro-[1,1';3',1"]terphenyl-2'-yloxy)-acetic acid

[3"-Chloro-2-fluoro-5'-(8-phenyl-octylcarbamoyl)-[1,1';3',1"]terphenyl-2'-yloxy]acetic acid {3-Chloro-5'-[6-(2,4-difluoro-phenoxy)-hexylcarbamoyl]-2"-fluoro-[1,1';3',1"]terphenyl-2'-yloxy}-acetic acid {3"-Chloro-2-fluoro-5'-[methyl-(8-phenyl-octyl)-carbamoyl]-[1,1';3',1"]terphenyl-2'-yloxy)}-acetic acid {2,2"-Difluoro-5'-[methyl-(8-phenyl-octyl)-carbamoyl]-[1,1';3',1"]terphenyl-2'-yloxy}-acetic acid {3,3"-Dichloro-5'-[8-(4-chloro-benzenesulfinyl)-octylcarbamoyl]-[1,1';3',1"]terphenyl-2'-yloxy}-acetic acid {3,3"-Dichloro-5'-[8-(2,4-difluoro-phenoxy)-octylcarbamoyl]-[1,1";3',1"]terphenyl-2'-yloxy}-acetic acid {3,3"-Dichloro-5'-[12-(2,4-difluoro-phenoxy)-dodecylcarbamoyl]-[1,1';3',1"]terphenyl-2'-yloxy 3-acetic acid {3,3"-Dichloro-5'-[8-(4-trifluoromethyl-benzyloxy)-octylcarbamoyl]-[1,1';3',1"]terphenyl-2'-yloxy}-acetic acid

[3,3"-Dichloro-5'-(8-{3-[3-(3-methoxy-propoxy)-propoxy]-propoxy}-octylcarbamoyl)-[1,1';3',1"]terphenyl-2'-yloxy]-acetic acid (3,3"-Dichloro-5'-dicyclohexylcarbamoyl-[1,1';3',1"]terphenyl-2'-yloxy)-acetic acid 4-[4,4"-Dimethoxy-5'-(7-phenyl-heptylcarbamoyl)-[1,1";3',1"]terphenyl-2'-yloxy]-butyric acid 4-[3,3"-Dichloro-5'-(7-phenyl-heptylcarbamoyl)-[1,1";3',1"]terphenyl-2'-yloxy]-butyric acid

[5'-(7-Phenyl-heptylcarbamoyl)-3,3"-bis-trifluoromethyl-[1,1";3',1"]terphenyl-2'-yloxymethyl]-phosphonic acid diethyl ester

[5'-(7-Phenyl-heptylcarbamoyl)-3,3"-bis-trifluoromethyl-[1,1";3',1"]terphenyl-2'-yloxymethyl]-phosphonic acid 2,2-Dimethyl-3-[5'-(7-phenyl-heptylcarbamoyl)-3,3"-bis-trifluoromethyl-[1,1';3',1"]terphenyl-2'-yloxy]-propionic acid 4-[5'-(7-Phenyl-heptylcarbamoyl)-3,3"-bis-trifluoromethyl-[1,1'3',1"]terphenyl-2'-yloxymethyl]-benzenesulfonic acid

[[4,4'-Dimethoxy-5'-[4-[[(7-phenylheptyl)amino]carbonyl]phenyl][1,1';3',1'-terphenyl]-2'-yl]oxy]acetic acid

[[5'-[4-[[(7-Phenylheptyl)amino]carbonyl]phenyl]-3,3'-bis(trifluoromethyl) [1,1';3',1'-terphenyl]-2'-yl]oxy]acetic acid 4-[[[4,4'-Dimethoxy-5'-[4-[[(7-phenylheptyl)amino]carbonyl]phenyl][1,1';3',1'-terphenyl]-2'-yloxymethyl]-benzoic acid 4-[5'-(7-Phenyl-heptylcarbamoyl)-3,3"-bis-trifluoromethyl-[1,1";3',1"]terphenyl-2'-yloxymethyl]-benzoic acid (3-Bromo-3'-chloro-5-dodecylcarbamoyl-4'-fluoro-biphenyl-2-yloxy)acetic acid

[3'-Chloro-4'-fluoro-5-(8-phenyl-octylcarbamoyl)-biphenyl-2-yloxy]acetic acid (3-Bromo-5-dodecylcarbamoyl-3'-methoxy-biphenyl-2-yloxy)acetic acid 5-Bromo-6-(2-tetrazol-1-yl-ethoxy)-3'-methoxy-biphenyl-3-carboxylic acid dodecylamide 5-Bromo-3'-chloro-6-(2-tetrazol-2-yl-ethoxy)-biphenyl-3-carboxylic acid dodecylamide 5-Bromo-3'-chloro-6-(2-tetrazol-1-yl-ethoxy)-biphenyl-3-carboxylic acid dodecylamide

[3,5,3",5"-Tetramethyl-5'-(8-phenyl-octylcarbamoyl)-[1,1';3',1"]terphenyl-2'-yloxy]acetic acid

[4,4"-Difluoro-3,3"-dimethyl-5'-(8-phenyloctylcarbamoyl)-[1,1":3',1"]terphenyl-2'-yloxy]acetic acid 2'-Hydroxy-3,5,3",5"-tetramethyl-[1,1';3',1"]terphenyl-5'-carboxylic acid (7-phenyl-heptyl)-amide 2'-Hydroxy-3,3"-dimethyl-[1,1';3',1"]terphenyl-5'-carboxylic acid (7-phenyl-heptyl)-amide

[3,3"-Dimethyl-5'-(7-phenyl-heptylcarbamoyl)-[1,1';3',1"]terphenyl-2'-yloxy]acetic acid 4-[3,3"-Dimethyl-5'-(7-phenyl-heptylcarbamoyl)-[1,1';3',1"]terphenyl-2'-yloxy]-butyric acid

[3,5,3",5"-Tetramethyl-5'-(7-phenyl-heptylcarbamoyl)-[1,1';3',1"]terphenyl-2'-yloxymethyl]-phosphonic acid diethyl ester 4-[3,5,3",5"-Tetramethyl-5'-(7-phenyl-heptylcarbamoyl)-[1,1';3',1"]terphenyl-yloxy]-butyric acid 3,3"-Diformyl-2'-methoxymethoxy-[1,1":3',1"]terphenyl-5'-carboxylic acid (7-phenyl-heptyl)-amide 3,3"-Diformyl-2'-hydroxy-[1,1';3',1"]terphenyl-5'-carboxylic acid (7-phenyl-heptyl)-amide 3,3",4,4"-Bis-methylenedioxy-5'-(7-phenyl-heptylcarbamoyl)-[1,1';3',1"]terphenyl-2'-yloxy]acetic acid 3'-Bromo-2'-hydroxy-5'-(8-phenyl-octylcarbamoyl)-biphenyl-3-carboxylic acid 4-chloro-butyl ester (3"-Chloro-5'-dodecylcarbamoyl-3-trifluoromethyl-[1,1";3',1"]terphenyl-2'-yloxy)acetic acid (5'-Dodecylcarbamoyl-4"-methoxy-3-trifluoromethyl-[1,1";3',1"]terphenyl-2'-yloxy)acetic acid (5'-Dodecylcarbamoyl-2"-fluoro-4-methoxy-[,1';3',1"]terphenyl-2'-yloxy)acetic acid 3-Bromo-5-dodecylcarbamoyl-2'-fluoro-biphenyl-2-yloxy)acetic acid

[4"-Methoxy-5'-(6-phenyl-hexylcarbamoyl)-3-trifluoromethyl-[1,1';3',1"]terphenyl-2'-yloxy]acetic acid

[4"-Methoxy-5'-(8-phenyl-octylcarbamoyl)-3-trifluoromethyl-[1,1";3',1"]terphenyl-2'-yloxy]acetic acid (3,5,3",5"-Tetrachloro-5'-dodecylcarbamoyl-[1,1";3',1"]terphenyl-2'-yloxy)acetic acid

[3,5,3",5"-Tetrachloro-5'-(8-phenyl-octylcarbamoyl)-[1,1";3',1"]terphenyl-2"-yloxy]acetic acid

[3,5,3",5"-Tetrachloro-5'-(6-phenyl-hexylcarbamoyl)-[1,1";3',1"]terphenyl-2'-yloxy]acetic acid

[3,3"-Dichloro-5'-(4-heptyloxy-benzylcarbamoyl)-[1,1";3',1"]terphenyl-2'-yloxy]acetic acid 8-[(2'-Carboxymethoxy-3,3"-dichloro-[1,1';3',1"]terphenyl-5'-carbonyl)-amino]-octanoic acid methyl ester 5-[3,3"-Dichloro-5'-(8-indol-1-yl-octylcarbamoyl)-[1,1";3',1"]terphenyl-2'-yl]-pentanoic acid 4-{2-[3,3"-Dichloro-5'-(8-indol-1-yl-octylcarbamoyl)-[1,1';3',1"]terphenyl-5'-ethoxy}benzoic acid 4-Methoxybenzoic acid 6-[(2'-carboxymethoxy-3,3"-dichloro-[1,1';3',1"]terphenyl-5'-carbonyl)-amino]-hexyl ester

[3,3"-Dichloro-5'-(6-hydroxy-hexylcarbamoyl)-[1,1';3',1"]terphenyl-2'-yloxy]acetic acid 2-[3,3"-Dichloro-5'-(8-indol-1-yl-octylcarbamoyl)-[1,1';3',1"]terphenyl-2'-ethoxy}acetic acid (5'-Hexyl-[1,1';3',1"]terphenyl-2'-yloxy)acetic acid (5'-Nonyl-[1,1';3',1"]terphenyl-2'-yloxy)acetic acid (5'-Tridecyl-[1,1';3',1"]terphenyl-2'-yloxy)acetic acid (5'-Decyloxy-[1,1';3',1"]terphenyl-2'-yloxy)acetic acid 5'-Tetradecyloxy-[1,1";3',1"]terphenyl-2'-yloxy)acetic acid (5'-Trityl-[1,1';3',1"]terphenyl-2'-yloxy)acetic acid (5"-Dodecylcarbamoyl-3,3"-bis-trifluoromethyl-{1,1';3',1"] terphenyl-2"-yloxy)-acetic acid (3-Bromo-5-dodecylcarbamoyl-3'-trifluoromethyl-biphenyl-2-yloxy)-acetic acid (5"-(8-Phenyl-octylcarbamoyl-3,3"-bis-trifluoromethyl-{1,1';3',1"]terphenyl-2"-yloxy)-acetic acid (3-Bromo-5-(8-phenyl-octylcarbamoyl)-3'-trifluoromethyl-biphenyl-2-yloxy)-acetic acid 4-(3-Bromo-5-dodecylcarbamoyl-3"-trifluoromethyl-biphenyl-2-yloxysulfonyl)-2-hydroxy-benzoic acid 5-Bromo-6-(2-[1,2,3]triazol-2-yl-ethoxy)-3'-trifluoromethyl-biphenyl-3-carboxylic acid dodecylamide 5-Bromo-6-(2-[1,2,3]triazol-1-yl-ethoxy)-3'-trifluoromethyl-biphenyl-3-carboxylic acid dodecylamide 5-Bromo-6-(2-tetrazol-2-yl-ethoxy)-3'-trifluoromethyl-biphenyl-3-carboxylic acid dodecylamide 5-Bromo-6-(2-tetrazol-1-yl-ethoxy)-3'-trifluoromethyl-biphenyl-3-carboxylic acid dodecylamide Carbamic acid 2-[3-bromo-5-(8-phenyl-octylcarbamoyl)-3'-trifluoromethyl-biphenyl-2-yloxy]-ethyl ester 5-Bromo-6-(2-morpholin-4-yl-ethoxy)-3'-trifluoromethyl-biphenyl-3-carboxylic acid dodecylamide 6-(Amino-ethoxy)-5-bromo-3'-trifluoromethyl-biphenyl-3-carboxylic acid dodecylamide 5-Bromo-3'-trifluoromethyl-6-(2-ureido-ethoxy)-biphenyl-3-carboxylic acid dodecylamide

[2-(3-Bromo-5-dodecylcarbamoyl-3'-trifluoromethyl-biphenyl-2-yloxy)-ethyl]-carbamic acid methyl ester

[5"-(6-Phenyl-hexylcarbamoyl)-3,3"-bis-trifluoromethyl-[1,1';3',1"]}terphenyl-2"-yloxy]-acetic acid

[3-Bromo-5-(6-phenyl-hexylcarbamoyl)-3"-trifluoromethyl-biphenyl-2-yloxy]-acetic acid 2'-Hydroxy-3,3"-bis-trifluoromethyl-[1,1';3'1"]terphenyl-5'-carboxylic acid (8-phenyl-octyl)-amide 5-[5'-(8-Phenyl-octylcarbamoyl)-3,3"-bis-trifluoromethyl-1,1';3'1"]terphenyl-2'-yloxy]-pentanoic acid 5-Bromo-6-(2-piperazin-1-yl-ethoxy)-3'-trifluoromethyl-biphenyl-3-carboxylic acid (8-phenyl-octyl)-amide 5-Bromo-6-hydroxy-3'-trifluoromethyl-biphenyl-3-carboxylic acid (8-phenyl-octyl)-amide 4-[3-Bromo-5-(8-phenyl-octylcarbamoyl)-3"-trifluoromethyl-biphenyl-2-yloxysulfonyl]-2-hydroxy-benzoic acid 7-[5'-(8-Phenyl-octylcarbamoyl)-3,3"-bis trifluoromethyl-[1,1';3',1"]terphenyl-2'-yloxy]-heptanoic acid 2'-(2-Hydroxy-3,4-dioxo-cyclobut-1-enylamino)-
  ethoxy]-3,3"-bis-trifluoromethyl-[1,1';3',1"]terphenyl-
  5'-carboxylic acid (8-phenyl-octyl amide)
2"-4-(1H-Tetrazol-5-yl)-butoxy-3,3"-bis-trifluoromethyl-
  [1,1';3'1"]terphenyl-5"-carboxylic acid (8-phenyl-
  octyl)-amide
2-Methoxy-4-[5"-(8-phenyl-octylcarbamoyl)-3,3"-bis-
  trifluoromethyl-[1,1';3'1"]terphenyl-2'-yloxymethyl]-
  benzoic acid
2-Hydroxy-4-[5'-(8-phenyl-octylcarbamoyl)-3,3"-bis-
  trifluoromethyl-[1,1';3'1"]terphenyl-2'-yloxymethyl]-
  benzoic acid
2-Hydroxy-4-[5'-(8-phenyl-octylcarbamoyl)-3,3"-bis-
  trifluoromethyl-[1,1';3'1"]terphenyl-2'-yloxymethyl]-
  benzoic acid methyl ester
4-{2-[3-Bromo-5-(8-phenyl-octylcarbamoyl)-3'-
  trifluoromethyl-biphenyl-2-yloxy]-ethoxy}-2-
  hydroxy-benzoic acid
2-Hydroxy-4-[5'-(8-phenyl-octylcarbamoyl)-3,3"-bis-
  trifluoromethyl-[1,1';3'1"]terphenyl-2'-yloxysulfonyl]-
  benzoic acid
4-[3-Bromo-5-(8-phenyl-octylcarbamoyl)-3'-
  trifluoromethyl-biphenyl-2-yloxymethyl]-2-methoxy-
  benzoic acid
5-Bromo-6-(1H-tetra-5-ylmethoxy)-3'-trifluoromethyl-
  biphenyl-3-carboxylic acid (8-phenyl-octyl)-amide
2"-(1H-Tetrazol-5-ylmethoxy)-3,3"-bis-trifluoromethyl-
  [1,1';3'1"]terphenyl-5"-carboxylic acid (8-phenyl-
  octyl)-amide
4-(3-Bromo-5-(8-phenyl-octylcarbamoyl)-3'-
  trifluoromethyl-biphenyl-2-yloxymethyl]-2-hydoxy-
  benzoic acid methyl ester
4-[3-Bromo-5-(8-phenyl-octylcarbamoyl)-3'-
  trifluoromethyl-biphenyl-2-yloxymethyl]-2-hydroxy-
  benzoic acid
2'-Amino-3,3"-bis-trifluoromethyl-[1,1';3'1"]terphenyl-
  5'-carboxylic acid (8-phenyl-octyl)-amide
4-[2-Bromo-4-(8-phenyl-octylcarbamoyl)-
  phenoxysulfonyl]-2-hydroxy-benzoic acid
2-Hydroxy-4-{2-[5'-(8-phenyl-octylcarbamoyl)-3,3"-bis-
  trifluoromethyl-[1,1';3',1"]terphenyl-2'-yloxy]-
  ethoxy}-benzoic acid
{3-Bromo-5-[methyl-(8-phenyl-octyl)-carbamoyl]-3'-
  trifluoromethyl-biphenyl-2-yloxy}-acetic acid
{3,3"-Dichloro-4,4"difluoro-5'-[methyl-(8-phenyl-octyl)-
  carbamoyl]-[1,1';3',1"terphenyl-2'-yloxy )-acetic acid
[5-Methyl-(8-phenyl-octyl)-carbamoyl]-3,3"-bis-
  trifluoromethyl-[1,1';3',1"]terphenyl-2'-yloxy}-acetic
  acid
[5'-(3-Benzyloxy-benzylcarbamoyl)-3,3"-bis-
  trifluoromethyl-[1,1';3',1"]terphenyl-2'-yloxy]-acetic
  acid
(2-(R)-3-Phenyl-2-[5-(8-phenyl-octylcarbamoyl)-4'-
  trifluoromethyl-biphenyl-2-yloxy-propionic acid
2-(R)-3-Phenyl-2-[4'-chloro-5-(8-phenyl-
  octylcarbamoyl)-biphenyl-2-yloxy]-propionic acid
2-(R)-3-Phenyl-2-[4'-fluoro-5-(8-phenyl-
  octylcarbamoyl)-biphenyl-2-yloxy]-propionic acid
2-(R)-3-Phenyl-2-[4'-methoxy-5-(8-phenyl-
  octylcarbamoyl)-biphenyl-2-yloxy]-propionic acid
2-(R)-3-Phenyl-2-[5-(8-phenyl-octylcarbamoyl)-4'-
  trifluoromethoxy-biphenyl-2-yloxy]-propionic acid
or a pharmaceutically acceptable salt thereof.

The compounds of this invention were be prepared according to the following schemes from commercially available starting materials or starting materials which can be prepared using to literature procedures. These schemes show the preparation of representative compounds of this invention.

Scheme 1

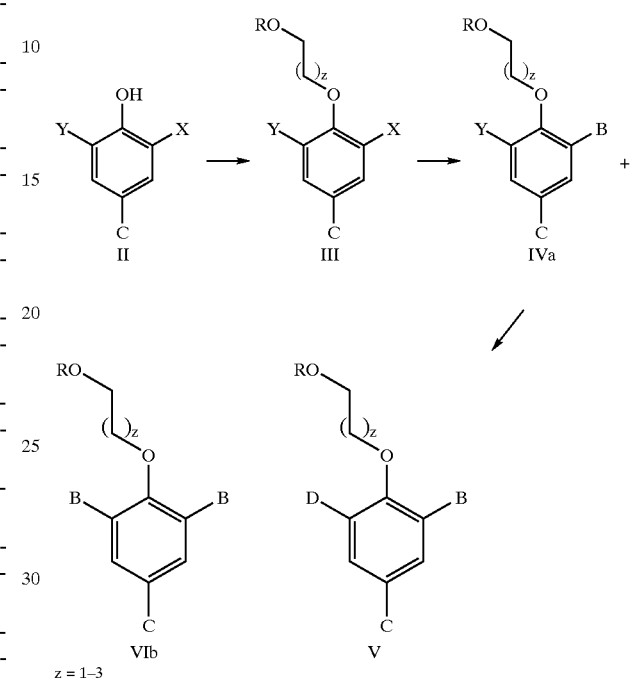

z = 1–3

In Scheme 1, the 2-bromophenol (IIa; X=H; Y=Br; C=—CO$_2$Et, —NO$_2$, —CN), available by the procedure of Oberhauser (*J. Org. Chem*, 1997, 62, 4504) is treated with two or more equivalents of iodine in an aqueous potassium carbonate/THF solution at temperatures between 0° C. and room temperature to give the 2-bromo-6-iodophenol (IIb; R=H; X=I; Y=Br; C=—CO$_2$Et, —NO$_2$, —CN). The 2-bromo-6-iodophenol (IIb; R=H; X=I; Y=Br; C=—CO$_2$Et, —NO$_2$, —CN), the 2-chloro-6-bromophenol (IIc; X=Br; Y=Cl; C=—CO$_2$Et, —NO$_2$, —CN), the 2-chloro-6-iodophenol (IId; X=I; Y=Cl; C=—CO$_2$Et, —NO$_2$, —CN, —Br), the 2-fluoro-6-bromophenol (IIc; X=Br; Y=F; C=—CO$_2$Et, —NO$_2$, —CN), or the 2-fluoro-6-iodophenol (IId; X=I; Y=F; C=—CO$_2$Et, —NO$_2$, —CN, —Br) is then subjected to Mitsunobu conditions (for a review see Oyo Mitsunobu *Synthesis* 1981, 1–27) using ethylene glycol, propane-1,3-diol, or butane-1,4-diol as the nucleophile to give IIIa (R=H; X=I; Y=Br; C=—CO$_2$Et, —NO$_2$, —CN), IIIb (R=H; X=Br; Y=Cl; F; C=—CO$_2$Et, —NO$_2$, —CN), or IIIc (R=H; X=I; Y=Cl; F; C=—CO$_2$Et, —NO$_2$, —CN, —Br). The other co-reagents necessary to effect the Mitsunobu reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene, or toluene at temperatures ranging from −20° C. to 120° C. at temperatures ranging from −20° C. to 120° C. This compound is then subjected to Suzuki or Stille coupling conditions using of 1.0 to 1.8 equivalents of a coupling partner to give IVa (Y=Br; R=H; B H, halogen; C=—CO$_2$Et, —NO$_2$, —CN) and VIa (R=H; B H, halogen;

C=—CO$_2$Et, —NO$_2$, —CN); or IVa (Y=Cl, F; R=H; B H, halogen; C=—CO$_2$Et, —NO2, —CN). Typical conditions used to carry out the Suzuki reaction include the use of a boronic acid or ester as the coupling partner, a palladium catalyst (2 to 20 mole %) such as Pd(PPh$_3$)$_4$ or [1,1'bis(diphenylphosphino)-ferrocene]dichloro-palladium(II), and a base such as potassium carbonate, barium hydroxide, potassium phosphate, or triethylamine in a suitable solvent such as aqueous dimethoxyethane, THF, acetone, or DMF at temperatures ranging from 25° C. to 125° C. Typical conditions used to carry out the Stille reaction include the use of an organostannane as the coupling partner, a palladium catalyst (2 to 20 mole %) such as Pd(PPh$_3$)$_4$ or [1,1'bis(diphenylphosphino)ferrocene]-dichloro-palladium(II), and a salt such as potassium fluoride or lithium chloride in a suitable anhydrous solvent such as dimethoxyethane, THF, acetone, or DMF at temperatures ranging from 25° C. to 125° C.

To obtain the unsymmetrical compound Va (R=H, B H, halogen; D H, halogen; C=—CO$_2$Et, —NO$_2$, —CN), compound IVa (Y=Br; R=H; B H, halogen; C=—CO$_2$Et, —NO$_2$, —CN) is subjected again to the above Suzuki or Stille conditions using 1.0 to 1.8 equivalents of a different boronic acid, ester, or organostannane as the coupling partner.

Alternatively, the 2,6-dibromophenol (IIc; X=Y=Br; C=—CO$_2$Et, —NO$_2$, —CN) or the 2,6-diiodophenol (IId; X=Y=I; C=—CO$_2$Et, —NO$_2$, —CN, —Br) can be used as the starting material. Subjection of IIc or IId to Mitsunobu conditions (for a review see Oyo Mitsunobu *Synthesis* 1981, 1–27) using ethylene glycol, 1,3-propanediol, or 1,4-butanediol as the nucleophile gives 3,5-dihalo derivatives IIIb (R=H; X=Y=Br; C=—CO$_2$Et, —NO$_2$, —CN) or IIIc (R=H; X=Y=I; C=—CO$_2$Et, —NO$_2$, —CN, —Br). The other co-reagents necessary to. effect the Mitsunobu reaction include one or more molar equivalents of a lower alkyl azodicarboxylate diester such as diethyl azodicarboxylate or diisopropyl azodicarboxylate and one or more molar equivalents of triarylphosphine such as triphenylphosphine in a suitable solvent such as diethyl ether, THF, benzene, or toluene at temperatures ranging from −20° C. to 120° C. at temperatures ranging from −20° C. to 120° C. This compound is then subjected to Suzuki or Stille coupling conditions using 2.0 equivalents of coupling partner to give VIb (R=H; B H, halogen; C=—CO$_2$Et, —NO$_2$, —CN, Br). Typical conditions used to carry out the Suzuki reaction include the use of a boronic acid or ester as the coupling partner, a palladium catalyst (2 to 20 mole %) such as Pd(PPh$_3$)$_4$ or [1,1'bis(diphenylphosphino)ferrocene] dichloropalladium(II), and a base such as potassium carbonate, barium hydroxide, potassium phosphate, or triethylamine in a suitable solvent such as dimethoxyethane, THF, acetone, or DMF in the presence of a small amount of water at temperatures ranging from 25° C. to 125° C. Typical conditions used to carry out the Stille reaction include the use of an organostannane as the coupling partner, a palladium catalyst (2 to 20 mole % such as Pd(PPh$_3$)$_4$ or [1,1'bis(diphenylphosphino)ferrocene]-dichloropalladium (II), and a salt such as potassium fluoride or lithium chloride in a suitable anhydrous solvent such as dimethoxyethane, THF, acetone, or DMF at temperatures ranging from 25° C. to 125° C. Further Suzuki or Stille reaction of VIb (R=H; B H, halogen; C=Br) would give the derivative VIb (R=H; B H, halogen; C=alkyl of 1–18 carbon atoms, aryl, heteroaryl, aralkyl of 6–20 carbon atoms, heteroaralkyl of 6–20 carbon atoms).

Protection of the primary alcohol in IIIa, IIIb, IIIc, IVa, VIb, or Va can be achieved by reaction with an electrophile such as tBuMe$_2$SiCl, methoxymethyl chloride (MOM—Cl), or methoxyethoxymethyl chloride (MEM—Cl) to give IIIa, IIIb, or IIIc (R=—SiMe$_2$tBu, —MOM, —MEM), IVa (R=—SiMe$_2$tBu, —MOM, —MEM), VIb (R=—SiMe$_2$tBu, —MOM, —MEM), or Va (R=—SiMe$_2$tBu, —MOM, —MEM). The other co-reagents necessary to effect the protection include an amine base such as pyridine, triethylamine, diisopropylethylamine, or 4-dimethylaminopyridine in an appropriate anhydrous solvent such as dichloromethane, DMF, or toluene at temperatures ranging from −78° C. to 125° C. Alternatively, protection of the primary alcohol in IIIa, IIIb, IIIc, IVa, VIb, or Va can be achieved by reaction with a reagent such as 3,4-dihydro-2H-pyran in the presence of a mild acid such as, but not limited to, pyridinium p-toluenesulfonate (PPTS), in a solvent such as dichloromethane to afford the tetrahydropyranyl ethers IIIa, IIIb, or IIIc (R=—THP), IVa (R=—THP), VIb (R=—THP), or Va (R=—THP).

Conversion of IIa, IIIb, IIIc, IVa, VIb, or Va (R=H, —SiMe$_2$tBu, —MOM, —MEM, —THP; C=—CN, —CO$_2$Et) to the corresponding aldehydes IIa, IIIb, IIIc, IVa, VIb, or Va (R=—SiMe$_2$tBu, —MOM, —MEM, —THP; C=—CHO) can be accomplished by reaction with diisobutylaluminum hydride in THF or toluene at −78° C. to −100° C. These aldehydes can be converted to the corresponding IIa, IIIb, IIIc, IVa, VIb, or Va (R=H, —SiMe$_2$tBu, —MOM, —MEM, —THP; C=alkyl of 1–18 carbon atoms, aralkyl of 6–20 carbon atoms, heteroaralkyl of 6–20 carbon atoms) through the hydrogenolysis (H$_2$, Pd on C, alcohol solvent, 1 atm, room temperature) of the corresponding IIIa, IIIb, IIc, IVa, VIb, or Va (R=—SiMe$_2$tBu, —MOM, —MEM, —THP; C=CR$^3$=CR$^3$R$^8$) formed by Wittig, or Homer-Emmons reaction with 1.0 to 5.0 equivalents of a suitable phosphonium salt or phosphonate ester. The other co-reagents necessary to effect the transformation include 1.0 to 5.0 equivalents of a strong base such as potassium t-butoxide, sodium ethoxide, sodium hydride or n-BuLi in a solvent such as THF, DME, or Et$_2$O at temperatures ranging from −78° C. to 25° C.

The aldehydes IIIa, IIb, IIIc, IVa, VIb, or Va (R=—SiMe$_2$tBu, —MOM, —MEM, —THP; C=—CHO) can further be elaborated by Bayer-Villager oxidation to the formate esters IIa, IIIb, IIIc, IVa, VIb, or Va (R=H, —SiMe$_2$tBu, —MOM, —MEM, —THP; C=—OCHO) followed by saponification to the phenols IIIa, IIIb, IIIc, IVa, VIb, or Va (R=—SiMe$_2$tBu, —MOM, —MEM, —THP; C=—OR$^6$; R$^6$=H). The Bayer-Villager oxidation is generally performed with 1.0 to 5.0 equivalents of m-chloroperbenzoic acid or other peracid in a solvent such as dichloromethane, chloroform, or benzene at temperatures ranging from 0° C. to 125° C. Saponification of the formate esters is usually performed in an alcoholic solution of a metal hydroxide, typically sodium hydroxide, at temperatures ranging from 0° C. to 125° C. The phenols IIIa, IIIb, IIIc, IVa, VIb, or Va (R=H, —SiMe$_2$tBu, —MOM, —MEM, —THP; C=—OR$^6$; R$^6$=H) can be further elaborated by alkylation with a suitable electrophilic iodide, bromide, tosylate, mesylate, or triflate to give ethers IIIa, IIIb, IIIc, IVa, VIb, or Va (R=—SiMe$_2$tBu, —MOM, —MEM, —THP; C=—OR$^6$, R$^6$ H). The other co-reagents necessary to effect the transformation include 1.0 to 5.0 equivalents of a base such as cesium carbonate, potassium carbonate, sodium ethoxide, or sodium hydride in a solvent such as THF, DME, DMF, DMSO, or Et$_2$O at temperatures ranging from 0° C. to 125° C.

The phenols IIIa, IIIb, IIIc, IVa, VIb, or Va (R=—SiMe$_2$tBu, —MOM, —MEM, —THP; C=—OR$^6$; R$^6$=H)

can be further elaborated to the corresponding carboxylic acid esters IIIa, IIIb, IIIc, IVa, VIb, or Va (R=—SiMe$_2$tBu, —MOM, —MEM, —THP; C=—O$_2$CR$^6$) by reaction with a suitable carboxylic acid halide, carboxylic acid anhydride, or reaction with a carboxylic acid in the presence of an activating agent such as dicyclohexylcarbodiimide or isobutyl chloroformate. The other co-reagents necessary to effect the transformation include 1.0 to 5.0 equivalents of a nonnucleophilic base such as pyridine, triethylamine, dimethylaminopyridine, or diisopropylethylamine in a solvent such as dichloromethane, toluene, or THF at temperatures ranging from 0° C. to 125° C.

The phenols IIIa, IIIb, IIIc, IVa, VIb, or Va (R=—SiMe$_2$tBu, —MOM, —MEM, —THP; C=—OR$^6$; R$^6$=H) can be further elaborated to the corresponding carbamates IIIa, IIIb, IIIc, IVa, VIb, or Va (R=—SiMe,tBu, —MOM, —MEM, —THP; C=—O$_2$CNR$^6$R$^7$) by reaction with a suitable carbamoyl halide or isocyanate. The other co-reagents necessary to effect the transformation include 1.0 to 5.0 equivalents of a nonnucleophilic base such as pyridine, triethylamine, dimethylaminopyridine, or diisopropylethylamine in a solvent such as dichloromethane, toluene, or THF at temperatures ranging from 0° C. to 125° C.

Conversion of carboxylic acid esters IIa, IIIb, IIIc, IVa, Va, or VIa (R=H, —SiMe$_2$tBu, —MOM, —MEM, —THP; C=—CO$_2$Et) to primary, secondary, or tertiary amides IIIa, IIIb, IIIc, IVa, Va, or VIa (R=H, —SiMe$_2$tBu, —MOM, —MEM, —THP; C=—CONR$^6$R$^7$) can be accomplished by reaction with 2.0 to 5.0 equivalents of lithium amides (derived from reaction of the corresponding amines with BuLi in hexanes in THF or DME at temperatures ranging from −20° C. to 25° C.) in THF or DME at temperatures ranging from −20° C. to 25° C. Alternatively, the same conversion could be accomplished by treatment of these esters with 2.0 to 5.0 equivalents of aluminum amides (derived from reaction of AlMe$_3$ with the corresponding amines or their hydrochloride salts in benzene or toluene at temperatures ranging from 25° C. to 110° C.) in benzene or toluene at temperatures ranging from 25° C. to 110° C.

Conversion of carboxylic acid esters IIIa, IIIb, IIIc, IVa, Va, or VIa (R=—SiMe$_2$Bu, —MOM, —MEM, —THP; C=—CO$_2$Et) to the corresponding benzyl alcohols IIIa, IIIb, IIIc, IVa, Va, or VIa (R=—SiMe$_2$Bu, —MOM, —MEM, —THP; C=—CH$_2$OH) can be accomplished by treatment with a suitable reducing agent such as diisobutylaluminum hydride or lithium aluminum hydride in THF or DME at temperatures ranging from −20° C. to 60° C. The benzyl alcohols can be converted to the corresponding ethers IIIa, IIb, IIIc, IVa, Va, or VIa (R=—SiMe$_2$tBu, —MOM, —MEM, —THP; C=—CH$_2$OR$^6$) by treatment with a suitable base such as sodium hydride followed by reaction with an electrophilic iodide, bromide, mesylate, tosylate, or triflate in a solvent such as THF, DME, or DMF at temperatures ranging from −20° C. to 60° C.

Conversion of primary, secondary, or tertiary amides IIIa, IIIb, IIIc, IVa, Va, or VIa (R=—SiMe$_2$Bu, —MOM, —MEM, —THP; C=—CONR$^6$R$^7$) to amines IIIa, IIIb, IIIc, IVa, Va, or VIa (R=—SiMe$_2$Bu, —MOM, —MEM, —THP; C=—CH$_2$NR$^6$R$^7$) can be accomplished by reaction with 2.0 to 5.0 equivalents appropriate reducing agent such as diborane or lithium aluminum hydride in THF or DME at temperatures ranging from −20° C. to 125° C.

Conversion of IIIa, IIIb, IIIc, IVa, VIb, or Va (R=—SiMe$_2$tBu, —MOM, —MEM, —THP; C=—NO$_2$) to the corresponding primary anilines IIIa, 11b, IIIc, IVa, VIb, or Va (R=H, —SiMe$_2$tBu, —MOM, —MEM, —THP; C=—NH$_2$) can be accomplished by reaction with an appropriate reducing agent such as iron, sodium dithionite, or H$_2$ using a palladium on carbon catalyst in THF or toluene at −78° C. to 100° C. These primary anilines can be alkylated in a stepwise fashion to give secondary and tertiary anilines IIIa, IIIb, IIIc, IVa, VIb, or Va (R=—SiMe$_2$tBu, —MOM, —MEM, —THP; C=—NR$^6$R$^7$; where R$^6$, R$^7$ (together) H). This can be accomplished by sequential reaction of the anilines with appropriate aldehydes in the presence of a reducing agent such as sodium cyanoborohydride in a solvent such as EtOH. The primary and secondary anilines IIIa, IIIb, IIIc, IVa, VIb, or Va (R=—SiMe$_2$tBu, —MOM, —MEM, —THP; C=—NR$^6$R$^7$; R$^6$=H) can be converted to the corresponding carbamates IIIa, IIIb, IIIc, IVa, VIb, or Va (R=—SiMe$_2$Bu, —MOM, —MEM, —THP; C=—NR$^3$CO$_2$R$^6$) by reaction with a suitable haloformate. The other co-reagents necessary to effect the transformation include 1.0 to 5.0 equivalents of a nonnucleophilic base such as pyridine, triethylamine, dimethylamino-pyridine, or diisopropylethylamine in a solvent such as dichloromethane, toluene, or THF at temperatures ranging from 0° C. to 125° C. The primary and secondary anilines IIIa, IIIb, IIIc, IVa, VIb, or Va (R=—SiMe$_2$Bu, —MOM, —MEM, —THP; C=—NR$^6$R$^7$; R$^6$=H) can be converted to the corresponding ureas IIIa, IIIb, IIIc, IVa, VIb, or Va (R=—SiMe$_2$Bu, —MOM, —MEM, —THP; C=—NR$^3$CONR$^6$R$^7$) by reaction with a suitable carbamoyl halide or isocyanate. The other co-reagents necessary to effect the transformation include 1.0 to 5.0 equivalents of a nonnucleophilic base such as pyridine, triethylamine, dimethylaminopyridine, or diisopropylethylamine in a solvent such as dichloromethane, toluene, or THF at temperatures ranging from 0° C. to 125° C. The primary and secondary anilines IIIa, IIIb, IIIc, IVa, VIb, or Va (R=—SiMe$_2$Bu, —MOM, —MEM, —THP; C=—NR$^6$R$^7$; R$^6$=H) can be converted to the corresponding anilides IIIa, IIIb, IIIc, IVa, VIb, or Va (R=—SiMe$_2$Bu, —MOM, —MEM, —THP; C=—NR$^3$COR$^6$) by reaction with a suitable carboxylic acid halide, carboxylic acid anhydride, or reaction with a carboxylic acid in the presence of an activating agent such as dicyclohexylcarbodiimide. The other co-reagents necessary to effect the transformation include 1.0 to 5.0 equivalents of a nonnucleophilic base such as pyridine, triethylamine, dimethylaminopyridine, or diisopropylethylamine in a solvent such as dichloromethane, toluene, or THF at temperatures ranging from 0° C. to 125° C.

The primary and secondary anilines IIIa, IIIb, IIIc, IVa, VIb, or Va (R=—SiMe$_2$Bu, —MOM, —MEM, —THP; C=—NR$^6$R$^7$; R$^6$=H) can be converted to the corresponding N-aryl-1,2-diaminocyclobutene-3,4-diones IIIa, IIIb, IIIc, IVa, VIb, or Va (R=—SiMe$_2$Bu, —MOM, —MEM, —THP; C=

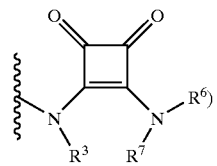

by reaction with a suitably substituted 1-ethoxy-2-aminocyclobutene-3,4-dione in an appropriate solvent such as acetonitrile or ethanol at temperatures ranging from room temperature to 80° C. Alternatively, the order of reaction can be reversed, where the primary or secondary anilines IIIa, IIIb, IIIc, IVa, VIb, or Va (R=—SiMe$_2$Bu, —MOM, —MEM, —THP; C=—NR$^6$R$^7$; R$^6$=H) could be reacted with diethoxysquaric acid in a solvent such as ethanol at temperatures ranging from room temperature to 80° C. to afford the 1-amino-2-ethoxycyclobutene-3,4-dione which, in turn, could be treated with an appropriate amine in an appropriate solvent such as acetonitrile or ethanol at temperatures ranging from room temperature to 80° C. to give the same N-aryl-1,2-diaminocyclobutene-3,4-diones IIIa, IIIb, IIIc, IVa, VIb, or Va (R=—SiMe$_2$tBu, —MEM, —THP; C=

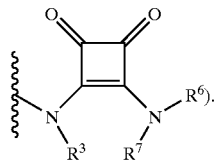

The alcohol protecting groups used in the above transformations IIIa, IIIb, IIIc, IVa, VIb, or Va (R=—SiMe$_2$tBu, —MOM, —MEM, —THP) could be removed to give the free alcohol IIIa, IIIb, IIIc, IVa, VIb, or Va (R=H) in a number of ways. The tBuMe$_2$Si group could be removed by treatment with tetrabutylammonium fluoride in a solvent such as THF at temperatures ranging from 0° C. to 25° C. The MEM group could be removed by treatment with ZnBr$_2$ or TiCl$_4$ in dichloromethane at temperatures ranging from 0° C. to 25° C. The THP and MOM groups could be removed by treatment with aqueous acetic acid in THF at temperatures ranging from room temperature to 60° C.

Further modifications could be performed on the free alcohols of Scheme 1 (IIIa, IIIb, IIIc, IVa, VIb, or Va (R=H)) depicted as the free alcohols VII (R=H) as shown in Scheme 2. Treatment with an oxidizing agent such as tetrapropylammonium perruthenate (TPAP) with 2 or more equivalents of N-methylmorpholine N-oxide (NMMO) or, alternatively, CrO$_3$, in a solvent such as acetontrile at room temperature gave the corresponding carboxylic acids VIII (R=OH). Treatment with TPAP and 1 equivalent of NMMO gave the corresponding aldehydes IX. Conversion of the free alcohol VII (R=H) to the corresponding mesylate, tosylate, or triflate VII (R=—SO$_2$Me, —SO$_2$PhMe, —SO$_2$CF$_3$) could be accomplished by treatment with mesyl chloride, tosyl chloride, or triflyl chloride in the presence of a nonnucleophilic base such as pyridine, triethylamine, diisopropylethylamine, collidine, or 2,6-di-tert-butyl-4-methylpyridine in a solvent such as dichloromethane at temperatures ranging from −78° C. to 25° C. Conversion of the free alcohol VII (R=H) to the corresponding bromide or iodide XI (X=Br, I) could be accomplished by treatment with carbon tetrabromide and triphenylphosphine (X=Br) or with iodine and triphenylphosphine in a solvent such as dichloromethane or THF at temperatures ranging from −20° C. to 60° C. Conversion of either VII (R=—SO$_2$Me, —SO$_2$PhMe, —SO$_2$CF$_3$) or XII to the nitriles X could be accomplished by reaction with an appropriate alkali metal cyanide such as sodium cyanide in a solvent such as DMF, DMSO, or THF at temperatures ranging from −20° C. to 60° C. Transformation of the nitrile X to the amide oxime XIII could be accomplished by reaction with hydroxylamine hydrochloride and sodium methoxide in methanol at temperatures ranging from −20° C. to 80° C. The amide oximes XII could then be converted to the substituted oxadiazoles XIII (R=CH$_3$, H) by reaction with a carboxylic acid chloride, a trialkylorthoester, carboxylic acid anhydride, or a carboxylic acid (in the presence of an activating agent such as dicyclohexylcarbodiimide) in a solvent such as dichloromethane, THF, or acetone at temperatures ranging from −20° C. to 60° C. followed by dehydration (Dean-Stark trap, refluxing toluene). Conversion of nitriles X to tetrazoles XIV can be accomplished by reaction with an appropriate metal azide such as sodium azide in the presence of a tertiary amine hydrochloride salt such as triethylammonium chloride in a solvent such as DMF, DMA, or N-methylpyrrolidinone at temperatures ranging from 100° C. to 160° C. The N-alkylated tetrazoles XV (S=T=U=N, X=CR$^3$ and S=T=X=N, U=CR$^3$), N-alkylated 1,2,3-triazoles XV (S=X=CR$^3$, U=T=N; and S=T=N, X=U=CR$^3$), N-alkylated 1,2,4-triazoles XV (S=X=N, U=T=CR$^3$; and X=T=N, S=U=CR$^3$) and N-alkylated imidazole XV (S=N, X=T=U=CR$^3$) could be made from VII (R=—SO$_2$Me, —SO$_2$PhMe, —SO$_2$CF$_3$) or XI (X=Br, I) by reaction of the anion formed from treatment of tetrazole, 1,2,3-triazole, 1,2,4-triazole, or imidazole with a strong base such as sodium hydride in a solvent such as THF, DME, DMF, or DMSO at temperatures ranging from −20° C. to 80° C. The amines XVI (R$^4$H) could be made from VII (R=—SO$_2$Me, —SO$_2$PhMe, —SO$_2$CF$_3$) or XI (X=Br, I) by reaction with 2 or more equivalents of pyrrolidine, piperidine, morpholine, N-methylpiperazine or simple disubstituted amines in a solvent such as dichloromethane, THF, DME, or DMF at temperatures ranging from −20° C. to 80° C. Alternatively, reaction of VII (R=—SO$_2$Me, —SO$_2$PhMe, —SO$_2$CF$_3$) or XI (X=Br, I) with an alkali metal azide such as sodium azide in a solvent such as DMF, DMSO, or THF at temperatures ranging from −20° C. to 80° C. would give the azides XI (X=N$_3$). Subsequent treatment of the azides XI (X=N$_3$) with triphenylphosphine in wet THF would give the primary amines XVI (R$^4$=R$^5$=H). Secondary amines XVI (R$^4$=H; R$^5$H) could be made by reaction of the aldehydes IX with primary amines in the presence of a suitable reducing agent such as sodium cyanoborohydride in a solvent such as ethanol or isopropanol at temperatures ranging from −20° C. to 80° C. The aldehydes IX can be further elaborated by reaction with hydroxylamines or hydrazines in a solvent such as methanol or ethanol at temperatures ranging from 0° C. to 60° C. to form oximes XVII (X=OR$^3$) and hydrazones XVII (X=NHR$^3$). The alcohols VII (R=H) can be further elaborated by reaction with an appropriate electrophilic alkylating agent such as an alkyl or carboalkoxyalkyl bromide, iodide, mesylate, tosylate, or triflate in the presence of a base such as sodium hydride in a solvent such as THF, DMF, or DME at temperatures ranging from −20° C. to 80° C. to give ethers VII (R=R$^3$, —CH$_2$CO$_2$R$^3$). The alcohols VII (R=H) can be further elaborated by reaction with an appropriate isocyanate in a solvent such as dichloromethane at temperatures ranging from 0° C. to 100° C. to give the corresponding carbamates VII (R=CONR$^4$R$^5$). The primary or secondary amines XVI (R$^4$=H) could be converted into the corresponding carbamates XI (X=NR$^5$CO$_2$R$^3$, R$^3$H) by treatment with a suitable haloformate in a solvent such as dichloromethane in the presence of a base such as triethylamine, pyridine, or collidine at temperatures ranging from −20° C. to 50° C. The carbamates XI (X=NR$^5$CO$_2$R$^3$, R$^3$=p-nitrophenyl) could be converted into the ureas XI (X=NR$^3$CNR$^4$R$^5$) by treatment with a suitable amine in a solvent such as dichloromethane at temperatures ranging from 0° C. to 100° C. Alternatively, the ureas XI (X=NR$^3$CNR$^4$R$^5$) could be synthesized from the amines XVI (R$^4$=H) by treatment with a suitable isocyanate in a solvent such as dichloromethane at temperatures ranging from 0° C. to 100° C.

Scheme 2

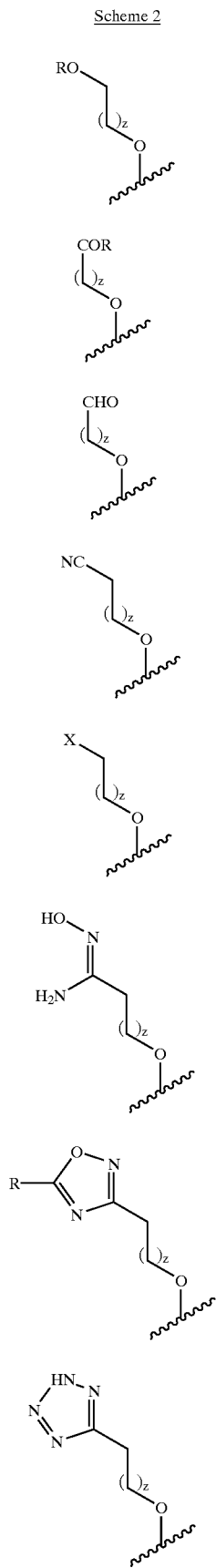

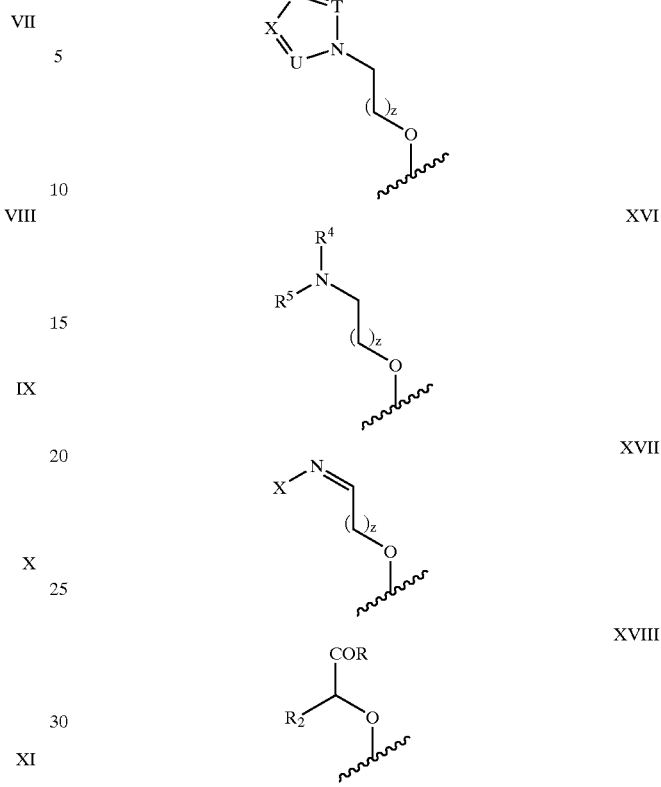

z = 1–3, y = 1–2

The carboxylic acids VIII (R=OH) can be converted into the carboxylic acid esters VIII (R=OR³, R³H) by reaction with a suitable alcohol in the presence of a strong acid catalyst such as sulfuric acid, toluenesulfonic acid, or camphorsulphonic acid in a solvent such as toluene at reflux utilizing a Dean-Stark trap for removal of water. Alternatively, activation of the acid with a reagent such as dicyclohexylcarbodiimide or isobutyl choroformate in the presence of a nonnucleophilic base such as triethyl amine, pyridine, or diisopropylethylamine in a solvent such as dichloromethane at temperatures ranging from −20° C. to 40° C. followed by reaction with a suitable alcohol would achieve the same goal. The esters VIII (R=OR³, R³H, z=1) can be transformed into the alkylated esters XVIII (R=OR³; R³H; R²H) by reaction with a suitable base such as LDA or sodium hexamethyldisilazide followed by reaction with a suitable alkylating agent in a solvent such as THF or DME at temperatures ranging from −78° C. to 25° C. Saponification of the ester would then lead to the alkylated acids. The conditions to effect this transformation include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Alternatively, acid conditions may also be employed in which the above mentioned carboxylic acid ester XVIII (R=OR³; R³H) is reacted with one or more molar equivalents of a mineral acid such as HCl or sulfuric acid in water with or without a co-solvent such as THF at temperatures ranging from room temperature to 80° C.

The esters VIII (R=OR³, R³ H) or XVIII (R=OR³; R³H; R²H) can be transformed into the primary amides VIII (R=NH$_2$) or XVIII (R=NH$_2$; R$^3$H; R$^2$H) by reacting the ester starting material with ammonia gas dissolved in a lower alcohol solvent such as methanol or ethanol at temperatures ranging from 0° C. to 100° C.

Alternatively, the carboxylic acids VIII (R=OH) or XVIII (R=OH; R$^2$H) can be transformed into their carboxylic acid amide analogs VIII (R=NH$_2$, NHOH, NHR$^3$) or XVIII (R=NH$_2$, NHOH, NHR$^3$; R$^2$H) This transformation can be accomplished using standard methods to effect carboxylic acid to carboxylic acid amide transformations. These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C.

Alternatively, the carboxylic acid amide analogs VIII (R=NH$_2$) or XVIII (R=NH$_2$) can be converted to their nitrile analogs XI (X=CN) by using reagents that dehydrate the primary carboxamide function to the nitrile function. One set of conditions to effect this transformation include reacting the said primary carboxylic acid amide with one or more molar equivalents of trifluoroacetic anhydride and two or more molar equivalents of pyridine in a suitable solvent such as dioxane at temperatures ranging from 60° C. to 120° C.

The amines of this invention used as reagents in the conversion to the products of this invention can be either commercially obtained or synthesized by a variety of methods. A carboxylic acid amide can be converted to an amine by reduction with diborane or lithium aluminum hydride in a solvent such as THF, DME, or ether at temperatures ranging from −20° C. to room temperature. A halide can be converted to an amine by reaction with the sodium salt of phthalimide in a solvent such as THF or DMF at temperatures ranging from −20° C. to room temperature followed by reaction with hydrazine hydrate in a solvent such as methanol at reflux. Alternatively, conversion to the azide by reaction with an alkali metal azide such as sodium azide in a solvent such as DMF or THF at temperatures ranging from −20° C. to room temperature followed by reaction with triphenylphosphine in aqueous THF at room temperature gives the amine.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedure which measures the inhibition of PTPase.

Inhibition of Tri-Phosphorylated Insulin Receptor Dodecaphosphopeptide Dephosphorylation by hPTP1B This standard pharmacological test procedure assesses the inhibition of recombinant, human protein tyrosine phosphatase (PTP) 1B activity. The substrate for the PTPase assay is a dodecaphosphopeptide corresponding to amino acids 1142–1153 of the insulin receptor (IR) kinase domain that was synthesized to contain phosphotyrosine at residues 1146, 1150 and 1151. The procedure used and results obtained are briefly described below.

Human, recombinant PTP1B (hPTP1B) was prepared as described by Goldstein (see Goldstein et al. Mol. Cell. Biochem. 109, 107, 1992). The enzyme preparation used was stored in microtubes containing 4000–10000 μg/ml protein in 10 mM Tris-HCl, 0.2 mM EDTA, 25 mM NaCl, 50% glycerol and 3 mM DTT. Measurement of PTPase activity. The malachite green-ammonium molybdate method is used for the nanomolar detection of liberated phosphate by recombinant PTP1B as described (Lanzetta et al. Anal. Biochem. 100, 95, 1979). The assay was adapted for use with a 96-well microtiter platereader. The test procedure uses a dodecaphosphopeptide (TRDIpYETDpYpYRK) custom synthesized by AnaSpec, Inc. (San Jose, Calif.) corresponding to amino acids 1142–1153 of the insulin receptor β-subunit. Phosphotyrosine is incorporated at residues 1146, 1150, and 1151 as indicated. The recombinant hPTP1B is diluted to 1 μg/ml with buffer containing 10 mM Tris-HCl pH 7.4, 10 mM β-mercaptoethanol, and 30% Glycerol yielding an approximate activity of 10000–20000 nmoles inorganic phosphate released/min/mg protein. The diluted enzyme (166.5 μl) is added to 621 μl of reaction buffer containing 81.83 mM HEPES pH 7.4, 1.1 mM β-mercaptoethanol and then preincubated for 5 min at 37° C. with 2.5 μl of either test compound or DMSO as control. The dephosphorylation reaction is initiated by adding an aliquot (39.5 μl) of the recombinant hPTP1B:inhibitor preincubation mixture to the appropriate wells of a 96-well microtiter plate containing 10.5 μl of IR triphosphopeptide substrate pre-equilibrated to 37° C. A final concentration of 50 mM HEPES, 8.46 mM β-mercaptoethanol and 50 μM IR triphosphopeptide is achieved in the well. After 5 min at 37° C., the reaction is terminated by the addition of 200 μl of malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 μl MG/AM/Tw to wells containing 10.5 μl of IR triphosphopeptide substrate followed by the addition of 39.5 μl of the recombinant enzyme preincubated with either DMSO or drug. The colored product is allowed to develop at room temperature for 25 min. Sample absorbance is determined at 650 nm using a 96-well microtiter platereader (Bio-Tek). Samples and blanks are prepared in Calculation: PTPase activity, expressed as nmoles of inorganic phosphate released/min/mg protein, is quantified by extrapolation from a standard curve using known quantities of potassium phosphate. Inhibition of recombinant hPTP1B by test compounds is calculated as a percentage of control (i.e. activity achieved in the presence of DMSO alone. A four parameter, non-linear logistic regression of PTPase activities using SAS release 6.08, PROC NLIN, is used for determining IC$_{50}$ values of test compounds. The following results were obtained. Other examples not listed in the table below had PTPase inhibitory activity at concentrations less than 50 μM.

| Example | IC50 (μM) |
| --- | --- |
| 1 | 0.063 |
| 2 | 0.183 |
| 3 | 0.111 |
| 4 | 0.024 |
| 5 | 0.050 |
| 6 | 0.121 |
| 7 | 0.104 |
| 8 | 0.195 |
| 9 | 0.165 |
| 10 | 0.102 |
| 11 | 0.115 |
| 12 | 0.015 |
| 13 | 0.320 |
| 14 | 0.366 |
| 15 | 0.186 |
| 16 | 0.343 |
| 17 | 0.284 |
| 18 | 0.710 |
| 19 | 0.728 |
| 20 | 0.379 |
| 21 | 0.880 |
| 22 | 0.250 |
| 23 | 0.365 |
| 24 | 0.044 |
| 25 | 0.123 |
| 26 | 0.207 |
| 30 | 0.220 |
| 31 | 0.203 |
| 32 | 0.017 |
| 36 | 0.024 |
| 37 | 0.118 |
| 46 | 0.121 |
| 47 | 0.300 |
| 48 | 0.145 |
| 49 | 0.400 |
| 50 | 0.254 |
| 80 | 0.600 |
| 81 | 0.330 |
| 82 | 0.179 |
| 83 | 0.536 |
| 84 | 1.03 |
| 87 | 0.332 |
| 88 | 0.137 |
| 89 | 0.173 |
| 90 | 0.100 |
| 91 | 0.313 |
| 92 | 0.471 |
| 95 | 0.641 |
| 96 | 0.137 |
| 97 | 0.186 |
| 98 | 0.132 |
| 99 | 0.267 |
| 100 | 0.389 |
| 108 | 0.450 |
| 109 | 0.187 |
| 110 | 0.300 |
| 111 | 0.700 |
| 114 | 0.055 |
| 115 | 0.287 |
| 118 | 0.423 |
| 119 | 0.627 |
| 120 | 0.053 |
| 121 | 0.015 |
| 122 | 0.092 |
| 124 | 0.595 |
| 128 | 0.264 |
| 129 | 0.162 |
| 130 | 0.056 |
| 131 | 0.124 |
| 132 | 0.084 |
| 133 | 0.102 |
| 134 | 0.057 |
| 135 | 0.130 |
| 136 | 0.455 |
| 141 | 0.071 |
| 145 | 1.15 |
| 146 | 0.258 |
| 148 | 0.249 |
| 149 | 0.405 |
| 152 | 0.396 |
| 153 | 0.098 |
| 154 | 0.129 |
| 155 | 0.139 |
| 156 | 0.278 |
| 158 | 0.246 |
| 159 | 0.044 |
| 160 | 0.054 |
| 161 | 0.033 |
| 162 | 0.136 |
| 164 | 0.191 |
| 165 | 0.077 |
| 167 | 0.231 |
| 168 | 0.077 |
| 169 | 0.905 |
| 170 | 0.178 |
| 171 | 0.018 |
| 172 | 0.154 |
| 173 | 0.028 |
| 174 | 0.633 |
| 175 | 0.050 |
| 176 | 0.121 |
| 177 | 0.104 |
| 179 | 0.025 |
| 189 | 0.336 |
| 192 | 0.107 |
| 194 | 0.640 |
| 195 | 0.073 |
| 196 | 0.150 |
| 197 | 0.099 |
| 198 | 0.217 |
| 199 | 0.102 |
| 200 | 0.125 |
| 203 | 0.050 |
| 204 | 0.073 |
| 206 | 0.286 |
| 208 | 0.083 |
| 210 | 0.530 |
| 211 | 0.060 |
| 212 | 0.272 |
| 213 | 0.198 |
| Phenylarsine oxide (reference standard) | 39.7 |
| Sodium orthovanadate (reference standard) | 244.8 |
| Ammonium molybdate tetrahydrate (reference standard) | 8.7 |

Based on the results obtained in the standard pharmacological test procedure, representative compounds of this invention have been shown to inhibit PTPase activity and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

3-Bromo-4-hydroxybenzoic Acid Ethyl Ester

This procedure is modified from the work of Oberhauser (*J. Org. Chem*, 1997, 62,4504). To a solution of 4-hydroxybenzoic acid ethyl ester (57.8 g, 348 mmol) in 480 mL of dry acetonitrile was added $HBF_4 \cdot Et_2O$ (54% in $Et_2O$, 32.9 mL). The solution was cooled to −15° C. with an ice/methanol bath. N-bromosuccinimide (67.2 g, 378 mmol) was added portionwise at a rate where the temperature would not rise above −10° C. After addition was complete, the cooling bath was removed and the reaction mixture was allowed to stir overnight at room temperature. Worked up by pouring the reaction mixture into aqueous sodium bisulfite (38%, 200 mL) and extracting four times with ethyl acetate. The organic layers were combined, washed with water, saturated brine, dried over anhydrous sodium sulfate, decanted, and concentrated in vacuo to give a white solid. Recrystallization from ethyl acetate/hexane gave 3-bromo-4-hydroxybenzoic acid ethyl ester (70.7 g, 83%) as a white solid. $^1$H NMR (300 MHz, $CDCl_3$) δ 1.39 (t, J=6.7 Hz, 3H, —$CO_2CH_2CH_3$), 4.34 (t, J=6.7 Hz, 2H, —$CO_2CH_2CH_3$), 7.02 (d, 1H, arom), 7.91 (dd, 1H, arom), 8.19 (d, 1H, arom).

3-Bromo-4-hydroxy-5-iodobenzoic Acid Ethyl Ester

To a mixture of 3-bromo-4-hydroxybenzoic acid ethyl ester (69.2 g, 282 mmol) in 2N aqueous potassium carbonate (423 mL) was added sufficient THF to completely dissolve the phenol and make the solution clear (~300 to 500 mL). The solution was cooled to 0° C. and $I_2$ (158 g, 621 mmol) was added portionwise at such a rate as not to accumulate a large amount of solid $I_2$ on the bottom of the flask. After addition was complete, the ice bath was removed, and the solution was allowed to warm to room temperature. The reaction was complete in 2 h. Worked up by adding (slowly with caution) solid sodium bisulfite at a rate so excess foaming doesn't occur. Sodium bisulfite was added until nearly decolorized. The mixture was acidified with concentrated hydrochloric acid, extracted several times with ethyl acetate, the organic layers combined, washed with brine, dried over anhydrous sodium sulfate, decanted, and concentrated in vacuo to give 3-bromo-4-hydroxy-5-iodobenzoic acid ethyl ester (94.6 g, 90%) as a pale yellow solid. NMR indicated it was suitable for use in the next step without further purification. $^1$H NMR (300 MHz, $CDCl_3$) δ 1.39 (t, J=6.8 Hz, 3H, —$CO_2CH_2CH_3$), 4.32 (t, J=6.8 Hz, 2H, —$CO_2CH_2CH_3$), 8.14 (d, 1H, arom), 8.32 (d, 1H, arom).

3-Bromo-4-(2-hydroxyethoxy)-5-iodobenzoic Acid Ethyl Ester

To a mixture of 3-bromo-4-hydroxy-5-iodobenzoic acid ethyl ester (94.6 g, 255 mmol) in 1 L of dry THF was added ethylene glycol (63.2 mL, 1.02 mol) and triphenylphosphine (87 g, 322 mmol). The solution was cooled to 0° C. and diisopropyl azodicarboxylate (60.2 mL, 306 mmol) was added dropwise with stirring. After addition was complete, the ice bath was removed, and the solution was allowed to warm to room temperature. The reaction was complete after 3 h. Worked up by removing ~½ of the THF via concentration in vacuo, adding water, and extracting with ethyl acetate several times. The organic layers were combined, washed with saturated brine, dried over anhydrous $Na_2SO_4$, decanted, and concentrated in vacuo to give a viscous oil which solidified on standing. The major portion of the solid byproducts were removed by stirring with 50% ethyl acetate/hexane. The solid byproduct was filtered off and the liquid was concentrated in vacuo to give a solid which was further purified. Flash chromatography eluting with 5–15% ethyl acetate hexane gave pure 3-bromo-4-(2-hydroxyethoxy)-5-iodobenzoic acid ethyl ester (65 g, 62%). $^1$H NMR (300 MHz, $CDCl_3$) δ 1.37 (t, J=6.5 Hz, 3H, —$CO_2CH_2CH_3$), 3.95 (t, J=5 Hz, 2H, —$OCH_2CH_2OH$), 4.19 (t, J=5 Hz, 2H, —$OCH_2CH_2OH$), 4.32 (t, J=6.5 Hz, 2H, —$CO_2CH_2CH_3$), 8.18 (d, 1H, arom), 8.37 (d, 1H, arom).

EXAMPLE 1

(3,3"-Dichloro-5'-dodecylcarbamoyl-[1,1';3',1"] terphenyl-2'-yloxy)-acetic Acid

Step 1 3,5-bis-(3-Chlorophenyl)-4-(2-hydroxyethoxy) benzoic Acid Ethyl Ester

To a stirred solution of $K_2CO_3$ (17.2 g, 124 mmol) in $H_2O$ (62 mL) at room temperature was added dioxane (490 mL), 3-bromo-4-(2-hydroxyethoxy)-5-iodobenzoic acid ethyl ester (17.2 g, 41.4 mmol), 3-chlorophenylboronic acid (7.77 g, 49.7 mmol), and [1,1'bis(diphenylphosphino)ferrocene] dichloropalladium(II), complex with $CH_2Cl_2$ (0.676 g, 0.828 mmol). This mixture was stirred at room temperature for 4 h, and it appeared to be in progress but not done by TLC and HPLC. Another 0.1 eq. of 3-chloro-phenyl boronic acid (0.647 g) was added, and the reaction stirred an additional 24 h. Over the next 4 days, 0.1 eq. of the boronic acid was added at one a day intervals until the reaction was almost completely done by HPLC (60% bis-arylated, 25.4% mono-arylated, and 12.6% SM). The reaction was diluted with HCl (1187 mL, 0.17 M) and the resulting solution was extracted with EtOAc (1×300 mL and 3×200 mL). The combined organic layers were washed with 0.1 N HCl (2×90 mL), H$_2$O (2×90 mL), and brine (2×90 mL) and then dried (Na$_2$SO$_4$). After concentration, the residue was first purified by flash chromatography (0 to 50% EtOAc/hexane gradient) and then HPLC [60% CH$_2$Cl$_2$ (6% methyl t-butyl ether):40% hexane] to afford the bis-arylated product (6.16 g, 35%) as a viscous faint yellow oil (for mono-arylated product, see step 1 of Example 2); $^1$H NMR (400 MHz, DMSO-d$_6$) δ 1.31 (t, J=7.0 Hz, 3H), 3.12 (q, J=5.5 Hz, 2H), 3.28 (t, J=5.7 Hz, 2H), 4.32 (dd, J=7.0, 14.1 Hz, 2H), 4.45 (t, J=5.5 Hz, 1H), 7.45–7.53 (m, 4H), 7.53–7.58 (m, 2H), 7.67–7.69 (m, 2H), 7.91 (s, 2H); IR (film) 3440, 3090, 2990, 2930, 2860, 1720, 1610, 1570, 1475, 1425, 1390, 1360, 1340, 1310, 1245, 1160, 1120, 1100, 1090, 1065, 1025, 770, 710, and 500 cm$^{-1}$; mass spectrum [(+) APCI], m/z 431/433 (M+H)$^+$, 448/450 (M+NH$_4$)$^+$.

Step 2 N-Dodecyl-3,5-bis(3-chlorophenyl)-4-(2-hydroxyethoxy)benzamide

To a flamed dried round bottom flask with dodecyl amine (0.519 g, 2.80 mmol) and THF (8 mL) cooled to 0° C. was added n-BuLi (1.12 mL, 2.5 M in hexane, 2.80 mmol) dropwise over a 5 min. period. The resulting solution was stirred at this temperature for 40 min. and then cooled to −45° C. To this solution was added dropwise a solution (at 0° C.) of 3,5-bis-(3-chlorophenyl)-4-(2-hydroxyethoxy) benzoic acid ethyl ester (0.302 g, 0.700 mmol) in THF (8 mL) over 5 min. This final mixture was stirred and warmed to room temperature over 30 min. At this point, the reaction mixture was quenched with H$_2$O (3 mL) and diluted with EtOAc (40 mL). The organic layer was washed with 1 N HCl (3×7 mL), brine (7 mL), and H$_2$O:brine (1:1, 14 mL) and then dried (Na$_2$SO$_4$). After concentration, the residue was purified by flash chromatography (0 to 15% EtOAc/hexane gradient) to afford the product (0.286 g, 72%) as an oily white solid; $^1$H NMR (400 MHz, DMSO-d$_6$) δ 0.86 (t, J=7.7 Hz, 3H), 1.20–1.37 (m, 18H), 1.46–1.57 (m, 2H), 3.13 (dd, J=6.9, 11.5 Hz, 2H), 3.20–3.33 (m, 4H), 4.46 (t, J=6.2 Hz, 1H), 7.43–7.57 (m, 4H), 7.59–7.63 (m, 2H), 7.68–7.73 (m, 2H), 7.89 (s, 2H), 8.67 (t, J=6.2 Hz, 1H); mass spectrum [(+) APCI], m/z 570 (M+H)$^+$.

Step 3 (3,3''-Dichloro-5'-dodecylcarbamoyl-[1,1';3',1''] terphenyl-2'-yloxy)-acetic Acid To a stirred solution of N-dodecyl-3,5-bis(3-chlorophenyl)-4-(2-hydroxyethoxy)-benzamide (0.277 g, 0.485 mmol) in CH$_3$CN:CH$_2$Cl$_2$ (5:3, 8 mL) at room temperature was added N-methylmorpholine-N-oxide (NMMO) (0.114 g, 0.970 mmol) followed by tetrapropylammonium perruthenate (TPAP) (0.017 g, 0.0485 mmol). After 2 h, the reaction mixture still showed presence of intermediate aldehyde. Another 0.3 eq. of NMMO (0.017 g) and 0.02 eq. TPAP (0.003 g) was added, and the reaction was stirred for an additional 3 h. The mixture was quenched with H$_2$O (2 mL) followed by aq 10% NaHSO$_3$ (15 mL). After stirring for 20 min., the mixture was diluted with EtOAc (40 mL). The resulting organic layer was washed with 1 N HCl (3×7 mL) and brine (2×7 mL) and then dried (Na$_2$SO$_4$). After concentration, the residue was purified by preparatory plate chromatography (100% EtOAc) to afford the product (0.081 g, 29%) as a gray solid, mp 151–156° C.; $^1$H NMR (400 MHz, DMSO-d$_6$) δ 0.83 (t, J=6.8 Hz, 3H), 1.15–1.32 (m, 18H), 1.46–1.55 (m, 2H), 3.25 (dd, J=7.2, 13.2 Hz, 2H), 3.84 (s, 2H), 7.44–7.52 (m, 4H), 7.57 (t, J=2.0 Hz, 1H), 7.58 (t, J=1.8 Hz, 1H), 7.67–7.70 (m, 2H), 7.86 (s, 2H), 8.55 (t, J=5.7 Hz, 1H), 12.54–12.86 (bs, 1H); IR (KBr) 3360, 2930, 2850, 1725, 1620, 1565, 1465, 1385, 1345, 1245, 1200, 1150, 1075, 1065, 880, 800, 755, and 705 cm$^{-1}$; mass spectrum [(−) ESI], m/z 582/584/586 (M−H)$^-$; Anal. Calcd. for C$_{33}$H$_{39}$Cl$_2$NO$_4$: C, 67.80; H, 6.72; N, 2.40, Found: C, 67.63; H, 6.77; N, 2.34.

EXAMPLE 2

(3-Bromo-3'-chloro-5-dodecylcarbamoyl-biphenyl-2-yloxy)acetic Acid

Step 1 3-Bromo-5-(m-chlorophenyl)-4-(2-hydroxyethoxy) benzoic Acid Ethyl Ester

3-Bromo-5-(m-chlorophenyl)-4-(2-hydroxyethoxy) benzoic acid ethyl ester was prepared as a white solid (5.01 g, 30%) from 3-bromo-4-(2-hydroxyethoxy)-5-iodobenzoic acid ethyl ester using the procedure to step 1 of Example 1 (product 2: mono-arylation), mp 107.5–110.5° C.; $^1$H NMR (400 MHz, DMSO-d$_6$) δ 1.33 (t, J=7.0 Hz, 3H), 3.45 (q, J=5.5 Hz, 2H), 3.61 (t, J=5.5 Hz, 2H), 4.33 (dd, J=7.2, 14.3 Hz, 2H), 4.69 (t, J=5.7 Hz, 1H), 7.50–7.56 (m, 3H), 7.64–7.66 (m, 1H), 7.88 (d, J=2.2 Hz, 1H), 8.15 (d, J=2.2 Hz, 1H); IR (KBr) 3240, 3090, 2980, 2930, 1720, 1600, 1570, 1465, 1445, 1380, 1365, 1355, 1305, 1265, 1240, 1180, 1120, 1080, 1055, 1030, 890, 875, 810, 760, and 705 cm$^{-1}$; mass spectrum [(+) APCI], m/z 399/401 (M+H)$^+$, 416/418 (M+NH$_4$)$^+$.

Step 2 N-Dodecyl-3-bromo-5-(m-chlorophenyl)-4-(2-hydroxyethoxy)benzamide

N-Dodecyl-3-bromo-5-(m-chlorophenyl)-4-(2-hydroxyethoxy)benzamide was prepared as a colorless oil (0.110 g, 33%) from 3-bromo-5-(m-chlorophenyl)-4-(2-hydroxyethoxy)benzoic acid ethyl ester using a procedure similar to step 2 of Example 1; $^1$H NMR (400 MHz, DMSO-d$_6$) δ 0.86 (t, J=7.7 Hz, 3H), 1.17–1.36 (m, 18H), 1.46–1.57 (m, 2H), 3.20–3.30 (m, 2H), 3.46 (dd, J=5.4, 11.5 Hz, 2H), 3.58 (t, J=5.4 Hz, 2H), 4.69 (t, J=6.2 Hz, 1H), 7.48–7.60 (m, 3H), 7.65–7.71 (m, 1H), 7.87 (d, J=2.3 Hz, 1H), 8.10 (d, J=2.3 Hz, 1H), 8.58 (t, J=6.2 Hz, 1H); mass spectrum [(−) ESI], m/z 536 (M−H)$^-$, 596/598/600 (M+OAc—H)$^-$.

Step 3 (3-Bromo-3'-chloro-5-dodecylcarbamoyl-biphenyl-2-yloxy)acetic Acid

The title compound was prepared as an gray solid (0.051 g, 43%) from N-dodecyl-3-bromo-5-(m-chlorophenyl)-4-(2-hydroxyethoxy)benzamide using a procedure similar to step 3 of Example 1, mp>100° C. (decomp.); $^1$H NMR (400 MHz, DMSO-d$_6$) δ 0.83 (t, J=6.8 Hz, 3H), 1.18–1.31 (m, 18H), 1.49 (t, J=6.8 Hz, 2H), 3.23 (dd, J=6.8, 13.0 Hz, 2H), 3.77 (s, 2H), 7.41–7.47 (m, 2H), 7.57–7.60 (m, 1H), 7.66–7.68 (m, 1H), 7.79 (d, J=2.2 Hz, 1H), 8.04 (d, J=2.2 Hz, 1H), 8.53 (t, J=5.3 Hz, 1H); IR (KBr) 3290, 3090, 2930, 2850, 1630, 1555, 1465, 1430, 1325, 1225, 1190, 1110, 1075, 1020, 920, 885, 840, 800, 770, 710, 690, and 600 cm$^{-1}$; mass spectrum [(+) ESI], m/z 552/554/556 (M+H)$^+$; Anal. Calcd. for C$_{27}$H$_{35}$BrClNO$_4$·1.33H$_2$O: C, 56.21; H, 6.58; N, 2.43, Found: C, 56.01; H, 5.96; N, 2.39.

EXAMPLE 3

[3,3''-Dichloro-5'-(8-phenyl-octylcarbamoyl)-[1,1';3',1'']terphenyl-2'-yloxy]-acetic Acid Step 1 N-(8-Phenyl-octyl)-3,5-bis-(m-chlorophenyl)-4-(2-hydroxyethoxy)-benzamide To a flamed dried round bottom flask with 8-phenyloctyl amine (0.484 mL, 2.43 mmol) and THF (5 mL) cooled to 0° C. was added n-BuLi (0.972 mL, 2.5 M in hexane, 2.43 mmol) dropwise over a 5 min. period. The resulting solution was allowed to stir 5 min. and then warmed to room temperature for 30 min. This solution was then added dropwise to a solution of 3,5-bis-(m-chlorophenyl)-4-(2-hydroxyethoxy)benzoic acid ethyl ester (0.300 g, 0.696 mmol) in THF (15 mL) at −20° C. This final mixture was stirred at −20° C. for 15 min and then warmed to room temperature for 15 min. At this point, the reaction mixture was quenched with H$_2$O (10 mL) and diluted with EtOAc (200 mL). The organic layer was washed with 1 N HCl (20 mL), sat. aq. NaHCO$_3$ (20 mL), and brine (20 mL) and then dried (MgSO$_4$). After concentration, the residue was purified by the Biotage Flash 40 (20 to 40% EtOAc/petroleum ether gradient) to afford the product (0.267 g, 65%) as a clear oil; $^1$H NMR (400 MHz, CDCl$_3$) δ 1.09–1.48 (m, 9H), 1.48–1.72 (m, 4H), 2.58 (t, J=6.8 Hz, 2H), 3.30–3.35 (m, 2H), 3.35–3.41 (m, 2H), 3.46 (dd, J=6.8, 13.0 Hz, 2H), 6.07–6.18 (m, 1H), 7.11–7.19 (m, 3H), 7.19–7.31 (m, 2H), 7.35–7.44 (m, 4H), 7.44–7.57 (m, 2H), 7.63 (s, 2H), 7.77 (s, 2H; mass spectrum [(+) ESI], m/z 590 (M)$^+$.

Step 2 [3,3"-Dichloro-5'-(8-phenyl-octylcarbamoyl)-[[1,1';3',1"]terphenyl-2'-yloxy-acetic Acid The title compound was prepared as an off white solid (0.151 g, 57%) from N-(8-phenyl-octyl)-3,5-bis-(m-chlorophenyl)-4-(2-hydroxyethoxy)benzamide using a procedure similar to step 3 of Example 1, mp 165–167° C.; $^1$H NMR (400 MHz, DMSO-d$_6$) δ 1.20–1.32 (m, 8H), 1.46–1.57 (m, 4H), 2.51 (dd, J=7.7, 15.6 Hz, 2H), 3.25 (dd, J=6.8, 13.2 Hz, 2H), 3.83 (s, 2H), 7.10–7.17 (m, 3H), 7.21–7.26 (m, 2H), 7.44–7.51 (m, 4H), 7.56–7.59 (m, 2H), 7.67–7.69 (m, 2H), 7.86 (s, 2H), 8.56 (t, J=5.5 Hz, 1H), 12.45–12.94 (bs, 1H); IR (KBr) 3320, 3090, 3030, 2920, 2830, 2520, 1730, 1610, 1565, 1475, 1455, 1390, 1340, 1310, 1245, 1200, 1075, 1055, 875, 800, 780, 755, and 700 cm$^{-1}$; mass spectrum [(+) ESI], m/z 604 (M+H)$^+$; Anal. Calcd. for C$_{35}$H$_{35}$Cl$_2$NO$_4$·0.5H$_2$O: C, 68.51; H, 5.91; N, 2.28, Found: C, 68.36; H, 5.83; N, 2.32.

EXAMPLE 4

(5'-Octadecyloxy-[1,1';3',1"]terphenyl-2'-yloxy)-acetic Acid

Step 1 (5'-Octadecyloxy-[1,1';3',1"]terphenyl-2'-yloxy) acetic Acid Methyl Ester To a stirred solution of 5'-octadecyloxy[1,1';3',1"]terphenyl-2'-ol (0.250 g, 0.486 mmol, Akzo Chemie, Netherlands, Stabilizer A-2751) and K$_2$CO$_3$ (0.0739 g, 0.535 mmol) in DMF (9 mL) and THF (4 mL) at room temperature was added dropwise methyl bromoacetate (0.0922 mL, 0.972 mmol). After 7 days at this temperature, it was diluted with H$_2$O (50 mL) followed by excess EtOAc (400 mL). The organic layer was washed with 1 N HCl (50 mL), sat. aq. NaHCO$_3$ (50 mL), and brine (50 mL) and then dried (MgSO$_4$). After concentration, the residue was purified by flash chromatography (0 to 15% EtOAc/petroleum ether gradient) to afford the product (0.225 g, 79%) as a white solid, mp 66–69° C.; $^1$H NMR (DMSO-d$_6$) δ 0.84 (t, J=7.0 Hz, 3H), 1.17–1.34 (m, 28H), 1.34–1.43 (m, 2H), 1.65–1.74 (m, 2H), 3.36 (s, 3H), 3.75 (s, 2H), 4.01 (t, J=6.2 Hz, 2H), 6.86 (s, 2H), 7.33–7.45 (m, 6H), 7.56 (d, J=7.2 Hz, 4H); IR (KBr) 3420, 3050, 2920, 2860, 1770, 1600, 1575, 1465, 1420, 1365, 1235, 1210, 1200, 35 1095, 1060, 755, and 710 cm$^{-1}$; mass spectrum [(+) FAB], m/z 587 (M+H)$^+$, 609 (M+Na)$^+$; Anal. Calcd. for C$_{39}$H$_{54}$NO$_4$: C, 79.82; H, 9.27; N, 0.00, Found: C, 79.47; H, 9.21; N, −0.01.

Step 2 (5'-Octadecyloxy-[1,1';3',1"]terphenyl-2'-yloxy)-acetic Acid

To a stirred solution of (5'-octadecyloxy-[1,1';3',1"] terphenyl-2'-yloxy)acetic acid methyl ester (0.182 g, 0.310 mmol) in THF:MeOH (3:2, 10 mL) at room temperature was added dropwise 1 N KOH (1.55 mL, 1.55 mmol). After 2 h at this temperature, it was concentrated and diluted with H$_2$O. The solution was then acidified to pH 1 with 2 N HCl. The resulting solid was filtered off, washed with H$_2$O, and dried on the high vacuum for 18 h to afford the product (0.166 g, 93%) as a white solid, mp 90.5–92° C.; $^1$H NMR (DMSO-d$_6$) δ 0.83 (t, J=6.8 Hz, 3H), 1.16–1.35 (m, 28H), 1.35–1.44 (m, 2H), 1.65–1.74 (m, 2H), 3.63 (s, 2H), 4.01 (t, J=6.4 Hz, 2H), 6.86 (s, 2H), 7.32–7.44 (m, 6H), 7.58 (dd, J=1.5, 8.3 Hz, 4H), 12.20–12.75 (bs, 1H), IR (KBr) 3430, 3070, 2920, 2840, 1725, 1600, 1575, 1465, 1410, 1360, 1265, 1220, 1200, 1090, 750, and 695 cm$^{-1}$; mass spectrum [EI], m/z 572 (M)$^+$; Anal. Calcd. for C$_{38}$H$_{52}$NO$_4$: C, 79.68; H, 9.15; N, 0.00, Found: C, 79.25; H, 8.99; N, 0.09.

EXAMPLE 5

(5'-Dodecylcarbamoyl-3,3"-bis-trifluoromethyl-[1,1';3',1"]terphenyl-2'-yloxy)-acetic Acid Step 1 3,5-bis-(m-Trifluoromethylphenyl)-4-(2-hydroxyethoxy)benzoic Acid Ethyl Ester To stirred solution of K$_2$CO$_3$ (2 M in H$_2$O) (1.9 mL, 3.6 mmol) at room temperature was added dioxane (14.3 mL), 3-bromo-4-(2-hydroxyethoxy)-5-iodobenzoic acid ethyl ester (0.503 g, 1.21 mmol) and 3-trifluoromethyl-phenyl boronic acid (0.299 g, 1.57 mmol). The reaction mixture was purged with N$_2$ for a few minutes and then [1,1'bis (diphenylphosphino)ferrocene]dichloropalladium(II), complex with CH$_2$Cl$_2$ (0.030 g, 0.036 mmol) was added. The reaction was stirred at room temperature for 1.5 h and then heated at reflux for 2 h. After cooling to room temperature, it was poured into a 0.1 N HCl solution and extracted with EtOAc. The combined organic layers were washed with brine and dried over MgSO$_4$. After concentration in vacuo, the residue was first purified by flash chromatography (25% EtOAc:hexane) and then HPLC [60% CH$_2$Cl$_2$ (6% MTBE) :40% hexane to afford 3,5-bis-(m-trifluoromethylphenyl)-4-(2-hydroxyethoxy)benzoic acid ethyl ester (0.215 g, 36%) as a white solid $^1$H NMR (CDCl$_3$) δ 8.09 (s, 2H); 7.94 (m, 2H); 7.86–7.80 (m, 2H); 7.71–7.58 (m, 4H); 4.42 (q, 2H) 3.63 (m, 4H); 1.42 (t, 3H) and 3-Bromo-5-(m-trifluoromethylphenyl)-4-( 2-hydroxyethoxy)benzoic acid ethyl ester (0.173 g, 33%) as a white solid $^1$H NMR (CDCl$_3$) δ 8.29 (d, 1H); 8.00 (d, 1H); 7.86 (m, 1H); 7.80–7.55 (m, 3H); 4.40 (q, 2H); 3.74–3.60 (m, 4H); 1.92 (t, 1H); 1.40 (t, 3H).

Step 2 N-Dodecyl-3,5-bis(m-trifluoromethylphenyl)-4-(2-hydroxyethoxy)-benzamide

To a flame-dried flask containing dodecyl amine (0.278 g, 1.5 mmol) in THF (5 mL) cooled to −78° C. was added n-BuLi (titrated to 2.37 M in hexanes) (0.670 mL, 1.59 mmol) dropwise. The solution was stirred at −78° C. for 20 min. and then warmed to room temperature over 20 min. The reaction was then recooled to −40° C. and 3,5-bis-(m-trifluoromethylphenyl)-4-(2-hydroxyethoxy)benzoic acid ethyl ester (0.215 g, 0.43 mmol) in THF (5 mL) was added. This mixture was allowed to warm to room temperature over 20 min. The reaction mixture was then poured into 0.1 N HCl solution and extracted with EtOAc. The combined organic layers were washed with 2 N HCl solution (3×), dried over MgSO$_4$ and concentrated in vacuo. The residue was purified by flash chromatography (30% EtOAc:hexane) to afford N-dodecyl-3,5-bis(m-trifluoromethylphenyl)-4-(2-hydroxyethoxy)benzamide (0.254 g, 93%) as a white solid. $^1$H NMR (CDCl$_3$) δ 7.90 (m, 2H); 7.82–7.76 (m, 4H); 7.65–7.56 (m, 4H); 6.22 (bt, 1H); 3.45 (dd, 2H); 3.30 (m, 4H); 1.60 (m, 2H); 1.25 (m, 18H); 0.84 (m, 3H).

Step 3 (5'-Dodecylcarbamoyl-3,3"-bis-trifluoromethyl-[1,1';3',1"]terphenyl-2'-yloxy)-acetic Acid To a solution of N-dodecyl-3,5-bis(m-trifluoromethylphenyl)-4-(2-hydroxyethoxy)benzamide (0.254 g, 0.40 mmol) in $CH_3CN$ was added NMO (0.145 g, 0.89 mmol) and TPAP (0.014 g, 0.04 mmol). The reaction was stirred at room temperature overnight. Additional NMO (0.045 g, 0.38 mmol) and TPAP (0.013 g, 0.04 mmol) were required as indicated by TLC. After stirring 48 h, 10% $NaHSO_3$ solution was added and the resulting biphasic mixture was stirred vigorously for 30 min. Conc. HCl (2 mL) was added and stirring was continued for 10 min. The layers were separated and the aqueous layer was extracted with EtOAc. The combined organics were washed with brine, dried over $Na_2SO_4$, and concentrated in vacuo. The residue was purified by flash chromatography (30% EtOAc:Hexane+1% Formic acid) followed by preparatory plate chromatography (30% EtOAc:Hexane+1% Formic acid) to afford the title compound (0.089 g, 34%) as a white solid. mp 154.3–158.2° C.; $^1H$ NMR (DMSO-$d_6$) δ 8.55 (t, 1H); 7.98–7.88 (m, 6H); 7.78–7.67 (m, 4H); 3.57 (s, 2H); 3.25 (m, 2H); 1.50 (m, 2H); 1.23 (m, 18H); 0.82 (t, 3H); IR (KBr) 3275, 2900, 1725, 1600, 1575, 1460, 1325, 1190, 1125, 1075, 775, 725, 700, 625 $cm^{-1}$; mass spectrum [(–) ESI], m/z 650 (M–H)$^-$; Anal. Calcd. for $C_{35}H_{39}F_6NO_4$: C, 64.51; H, 6.03; N, 2.15, Found: C, 62.50; H, 5.99; N, 2.01.

EXAMPLE 6

(3-Bromo-5-dodecylcarbamoyl-3'-trifluoromethyl-biphenyl-2-yloxy)-acetic Acid Step 1 N-Dodecyl-3-bromo-5-(m-trifluoromethylphenyl)-4-(2-hydroxyethoxy)-benzamide N-Dodecyl-3-bromo-5-(m-trifluoromethylphenyl)-4-(2-hydroxyethoxy)-benzamide was prepared as a white solid (0.116 g, 51%) from 3-bromo-5-(m-trifluoromethylphenyl)-4-(2-hydroxyethoxy)benzoic acid ethyl ester using a procedure similar to step 2 of Example 1. $^1H$ NMR (CDCl$_3$) δ 7.98 (d, 1H); 7.85–7.54 (m, 5H); 6.25 (m, 1H); 3.70–3.58 (m, 4H); 3.48–3.36 (dd, 2H); 1.60 (m, 2H); 1.24 (m, 18H), 0.86 (m, 3H).

Step 2 (3-Bromo-5-dodecylcarbamoyl-3'-trifluoromethyl-biphenyl-2-yloxy)-acetic Acid The title compound was prepared as a white foam (0.058 g, 50%) from N-dodecyl-3-bromo-5-(m-trifluoromethylphenyl)-4-(2-hydroxyethoxy)benzamide using a procedure similar to step 3 of Example 1. $^1H$ NMR (DMSO-$d_6$) δ 13.75 (bs, 1H); 8.57 (t, 1H); 8.12 (d, 1H), 7.92 –7.68 (m, 5H); 4.15 (s, 2H); 3.24 (dd, 2H); 1.49 (m, 2H); 1.26 (m, 18H); 0.83 (m, 3H); IR (KBr) 3350, 2910, 2830, 1740, 1650, 1550, 1460, 1440, 1340, 1175, 1140, 1050, 900, 800, 760, 700, 675 $cm^{-1}$; mass spectrum [(–)ESI], m/z 584/586 (M–H)$^-$; Anal. Calcd. for $C_{28}H_{35}BrF_3NO4$: C, 57.34; H, 6.02; N, 2.39, Found: C, 59.34; H, 6.64; N, 2.16.

EXAMPLE 7

(5'-(8-Phenyl-octylcarbamoyl-3,3"-bis-trifluoromethyl-[1,1';3',1"]terphenyl-2'-yloxy)-acetic Acid Step 1 N-(8-Phenyloctyl)-3,5-bis(m-trifluoromethylphenyl)-4-(2-hydroxyethoxy)-benzamide N-(8-phenyl-octyl)-3,5-bis(m-trifluoromethylphenyl)-4-(2-hydroxyethoxy)-benzamide was prepared as a white solid (0.331 g, 74%) from 3,5-bis-(m-trifluoromethylphenyl)-4-(2-hydroxyethoxy)benzoic acid ethyl ester and phenyloctyl amine using a procedure similar to step 2 of Example 1. $^1H$ NMR (CDCl$_3$) δ 7.96–7.50 (m, 10H); 7.35–7.10 (m, 5H); 6.28 (m, 1H); 3.45 (m, 2H); 3.31 (m, 4H); 2.60 (m, 2H); 1.60 (m, 4H); 1.33 (m, 8H).

Step 2 (5'-(8-Phenyl-octylcarbamoyl-3,3"-bis-trifluoromethyl-[1,1';3',1"]terphenyl-2'-yloxy)acetic Acid The title compound was prepared as a white solid (0.058 g, 50%) from N-(8-phenyloctyl)-3,5-bis(m-trifluoromethylphenyl)-4-(2-hydroxyethoxy)benzamide using a procedure similar to step 3 of Example 1. mp 143–145.4° C. $^1H$ NMR (DMSO-$d_6$) δ 12.70 (bs, 1H); 8.56 (t, 1H); 7.97–7.91 (m, 2H); 7.78–7.69 (m, 4H); 7.25–7.21 (m, 2H); 7.15–7.10 (m, 3H); 3.78 (s, 2H); 3.26 (m, 2H); 2.49 (m, 2H); 1.50 (m, 4H); 1.27 (m, 8H) IR (KBr) 3370, 2920, 2880, 1725, 1625, 1560, 1475, 1340, 1225, 1175, 1125, 1075, 900, 810, 700, 660, 620 $cm^{-1}$; mass spectrum [(–) ESI], m/z 670 (M–H)$^-$; Anal. Calcd. for $C_{37}H_{35}F_6NO_4$: C, 66.16; H, 5.25; N, 2.08, Found: C, 65.58; H, 5.37; N, 2.05.

EXAMPLE 8

(5'-Dodecylcarbamoyl-[1,1';3',1"]terphenyl-2'-yloxy)-acetic Acid

Step 1 3,5-Diiodo-4-hydroxybenzoic Acid Methyl Ester

To a stirring solution of 3,5-diiodo-4-hydroxybenzoic acid (10.00 g, 25.65 mmol) in dry methanol (250 mL) was added TiCl$_4$ (1.41 mL, 12.82 mmol) in one lot. The reaction was stirred at reflux for 6 h and was then stirred at room temperature for 24 h. The mixture was concentrated down and the residue was taken up in diethyl ether and filtered through a plug of silica gel. The filtrate was concentrated down and the residue was recrystallized from hot methanol to give 7.84 g (76%) of the ester as white crystalline needles. $^1H$ NMR (DMSO-$d_6$) δ 10.41 (br s, 1H), 8.22 (s, 2H), 3.79 (s, 3H).

Step 2 3,5-bis-Phenyl-4-hydroxybenzoic Acid Methyl Ester

To a stirred solution of phenylboronic acid (4.95 g, 40.57 mmol), Ba(OH)$_2$.H$_2$O (10.48 g, 55.33 mmol), and Pd(OAc)$_2$ (0.414 g, 1.84 mmol) in DME/H$_2$O (110 mL/20 mL) was added 3,5-diiodo-4-hydroxybenzoic acid methyl ester (7.45 g, 18.44 mmol). The mixture was stirred at 85° C. for 3 h and was then cooled and concentrated. The residue was partitioned between ethyl acetate/2N HCl. The organic phase was dried (MgSO$_4$) and concentrated to give a solid which was triturated with diethyl ether/petroleum ether to give 3.51 g (62.5%) of product as a white solid. $^1H$ NMR (DMSO-$d_6$) δ 9.27 (s, 1H), 7.27 (s, 2H), 7.25–7.40 (m, 10H), 3.81 (s, 3H).

Step 3 (5'-Carbomethoxy-[1,1';3',1"]terphenyl-2'-yloxy)-acetic Acid tert-Butyl Ester To the phenol from Step 2 (3.50 g, 11.5 mmol) in acetonitrile (40 mL) was added tert-butyl bromoacetate (3.39 mL, 23 mmol) and K$_2$CO$_3$ (1.93 g, 12.65 mmol). The mixture was heated for 2 h at 70° C. then cooled to room temperature and concentrated. The residue was partitioned between ethyl acetate/H$_2$O. The organic phase was dried (MgSO$_4$) and concentrated to give crude product. The compound was purified by passing it through a short filter column (SiO$_2$) using hexane as the elutant. Concentration afforded 4.63 g (96%) of product as a clear oil. $^1H$ NMR (DMSO-$d_6$) δ 7.86 (s, 2H), 7.60–7.40 (m, 10H), 3.85 (2s, 5H), 1.19 (s, 9H).

Step 4 (5'-Carboxy-[1,1';3',1"]terphenyl-2'-yloxy)acetic Acid tert-Butyl Ester

To a stirring solution of the above ester (5.95 g, 14.22 mmol) in THF (100 mL) was added aqueous 1.0 N LiOH (15.6 mL, 15.6 mmol). The mixture was stirred overnight at room temperature and was then concentrated in vacuo. The resulting residue was partitioned between 0.1 N HCl/diethyl ether. The organic phase was dried (MgSO$_4$) and concentrated to give crude product. Purification by HPLC (1:5 hexanes/ethyl acetate) gave 2.31 g (40%; 59% based on recovered starting material) of product. $^1H$ NMR (DMSO-d$_6$) δ 13.02 (br s, 1H), 7.85 (s, 2H), 7.60–7.40 (m, 10H), 3.84 (s, 2H), 1.20 (s, 9H).

Step 5 (5'-Dodecylcarbamoyl-[1,1';3',1"]terphenyl-2'-yloxy)-acetic Acid-tert-Butyl Ester To a stirred solution of the above acid (0.50 g, 1.236 mmol) and 1-hydroxybenzotriazole hydrate (0.2 g, 1.483 mmol) in DMF (8 mL) was added 1-(3-dimethylaminopropyl)-3-ethylcarbodiimide hydrochloride (0.28 g, 1.483 mmol). After stirring for 2 h at room temperature, dodecylamine (0.412 g, 2.225 mmol) and triethylamine (0.206 mL, 1.483 mmol) were added and the mixture was stirred overnight at room temperature. The mixture was diluted with brine and extracted with diethyl ether. The organic phase was dried (MgSO$_4$) and concentrated to give 0.65 g (92%) of product as an oil. $^1$H NMR (DMSO-d$_6$) δ 7.75 (s, 2H), 7.8–7.25 (m, 10H), 6.40 (t, 1H), 3.75 (s, 2H), 2.42 (m, 2H), 1.61 (m, 2H), 1.25 (m, 27H), 0.82 (br t, 3H).

Step 6 (5'-Dodecylcarbamoyl-[1,1';3',1"]terphenyl-2'-yloxy)-acetic Acid

The above tert-butyl ester (0.65 g, 1.137 mmol) was dissolved in H$_2$O/acetonitrile (1.7 mL/3.3 mL) and treated with trifluoroacetic acid (0.44 mL, 5.63 mmol). The mixture was heated overnight. The reaction was cooled and concentrated. The residue was partitioned between brine and ethyl acetate. The organic phase was dried (MgSO$_4$) and concentrated to give crude acid. Trituration with diethyl ether/hexanes afforded 0.47 g (80%) of product as a white solid: mp 150–153° C.; $^1$H NMR (DMSO-d$_6$) δ 12.57 (bs, 1H); 8.55 (t, 1H); 7.84 (s, 2H), 7.62 (m, 4H), 7.50–7.35 (m, 6H), 3.84 (s, 2H), 3.26 (q, 2H), 1.51 (m, 2H), 1.22 (m, 18H), 0.84 (t, 3H); IR (KBr) 3350, 2920, 2880, 1730, 1650, 1570, 1200, 700 cm$^{-1}$; mass spectrum [EI], m/z 515 (M$^+$); Anal. Calcd. for C$_{33}$H$_{41}$NO$_4$.1.0 H$_2$O: C, 74.27; H, 8.12; N, 2.62, Found: C, 74.43; H, 8.04; N, 2.82.

EXAMPLE 9

(5'-Dodecylcarbamoyl-4,4"-dimethoxy-[1,1';3',1"]terphenyl-2'-yloxy)-acetic Acid

Step 1 3,5-bis-(4-Methoxyphenyl)-4-(2-hydroxyethoxy)benzoic Acid Ethyl Ester

To a stirred solution of 2N K$_2$CO$_3$ (108 mL) was added dioxane (875 mL), 3-bromo-4-(2-hydroxyethoxy)-5-iodobenzoic acid ethyl ester (25.34 g, 61.05 mmol), 4-methoxyphenyl boronic acid (12.43 g, 79.37 mmol), and [1,1'-bis(diphenyl-phosphino)ferrocene]dichloropalladium (II), complex with CH$_2$Cl$_2$ (1.49 g, 1.83 mmol). After stirring at room temperature for 1 h, the mixture was heated at 60° C. for 2.5 h. Progress was monitored by TLC. Additional quantities of catalyst and boronic acid (0.5 g) were added to push the reaction to completion. The reaction was cooled and partitioned between ethyl acetate/0.5 N HCl. The organic phase was washed with 0.5 N HCl, then brine. It was dried (MgSO$_4$), decolorized (charcoal), and concentrated to give a residue which was filtered through a pad of SiO$_2$. Purification by HPLC (ethyl acetate/hexane) afforded 11.47 g (47.5%) of mono-arylated product as a white solid [$^1$H NMR (DMSO-d$_6$) δ 8.08 (d, 1H), 7.82 (d, 1H), 7.50 (d, 2H), 7.02 (d, 2H), 4.65 (t, 1H), 4.30 (q, 2H), 3.81 (s, 3H), 3.59–3.42 (m, 4H), 1.29 (t, 3H)] and 6.61 g (25.6%), of bis-arylated product as a brown oil: $^1$H NMR (DMSO-d$_6$) δ 7.82 (s, 2H), 7.52 (d, 4H), 7.00 (d, 4H), 4.30 (q, 2H), 3.80 (s, 6H), 3.25 (m, 2H), 3.12 (m, 2H), 11.31 (t, 3H).

Step 2 5'-Dodecylcarbamoyl-4-4"-dimethoxy-[1,1';3',1"]terphenyl-2'-yloxy)-acetic Acid To a stirring solution of the above alcohol (0.553 g, 1.31 mmol) in acetone (10 mL) at 0° C. was added dropwise Jones reagent (1.04 mL; 6.7 g CrO$_3$/6 mL H$_2$SO$_4$/13 mL H$_2$O; ≡3.27 mmol). The mixture was warmed to room temperature and stirred for 1 h. The reaction was warmed to room temperature and stirred for 1 h. The reaction was quenched by addition of i-propanol and was then partitioned between ethyl acetate/brine. The organic phase was concentrated and the crude acid was purified by prep. TLC. Yield: 0.314 g, (55%) as a white solid. The compound (0.314 g, 0.718 mmol) and dissolved in THF (8 mL). In a separate flask, n-BuLi (1.01 mL, 2.5 N in hexane; 2.51 mmol) was added dropwise to a stirring solution of dodecylamine (0.466 g, 2.51 mmol) in THF (8 mL) at –40° C. under N$_2$. After 15 min. the THF solution of the above ester was added dropwise to the stirring Li salt of dodecylamine. After completion of addition, the reaction was allowed to stir at room temperature for 15 min and was then quenched by addition of 1.0 N HCl (20 mL). The mixture was extracted with ethyl acetate and the organic phase was dried (MgSO$_4$) and concentrated. The product was purified by prep. TLC (10% CH$_3$OH/CH$_2$Cl$_2$) to afford 0.262 g (63%) of amide as a white foam: mp 65–68° C., $^1$H NMR (DMSO-d$_6$) δ 8.51 (t, 1H), 7.76 (s, 2H), 7.55 (d, 4H), 7.00 (d, 4 h), 3.81 (s, 6H), 3.75 (s, 2H), 3.23 (m, 2H), 1.51 (m, 2H), 1.22 (m, 18H), 0.85 (t, 3H); IR (KBr) 3350, 2920, 2850, 1510, 1250 cm$^{-1}$; mass spectrum [+APCI] M/Z 576 (M+H)$^+$; Anal. Calcd. For C$_{35}$H$_{45}$NO$_6$.0.3H$_2$O; C, 72.34; H, 7.91; N, 2.41, Found: C, 72.32; H, 7.94; N, 2.63.

EXAMPLE 10

(3-Chloro-5'-dodecylcarbamoyl-4"-methoxy-[1,1';3']terphenyl-2'-yloxy)-acetic Acid Step 1 N-Dodecyl-3-(3-chlorophenyl)-5-(4-methoxyphenyl)-4-(2-hydroxyethoxy)-benzamide In a manner similar to Example 1, Step 2, the title compound, 0.45 g (80%), was formed from 2-(3-chlorophenyl)-5-(4-methoxyphenyl)-4-(2-hydroxy ethoxy)benzoic acid ethyl ester (0.422 g, 0.989 mmol) and dodecylamine (0.642 g, 3.46 mmol). $^1$H NMR (CDCl$_3$) δ 7.75 (d, 1H), 7.70 (d, 1H), 7/63 (s, 1H), 7.55 (m, 3H), 7.40 (m, 2H), 7.00 (d, 2H), 6.15 (t, 1H), 3.85 (s, 3H), 3.5–3.30 (m, 6H), 1.60 (m, 2H), 1.30 (m, 18H), 0.85 (t, 3H).

Step 2 (3-Chloro-5'-dodecylcarbamoyl-4"-methoxy-[1,1';3',1"]-terphenyl-2'-yloxy)-acetic Acid In a manner similar to Example 1, Step 3, the title compound, 0.100 g (22%) was formed by oxidation of the above compound: mp 114–117° C.; $^1$H NMR (DMSO-d$_6$) δ 12.65 (br s, 1H), 8.53 (t, 1H), 7.80 (dd, 2H), 7.67 (s, 1H), 7.53 (m, 3H), 7.45 (m, 2H), 7.03 (d, 2H), 3.82 (s, 2H), 3.79 (s, 3H), 3.25 (m, 2H), 1.50 (m, 2H), 1.21 (m, 18H), 0.83 (t, 3H); IR (KBr) 3330, 2920, 2860, 1730, 1620, 1550, 1250, 1200 cm$^{-1}$; Mass Spectrum [–ESI] M/Z 578 (M–H)$^-$; Anal. Calcd. For C$_{34}$H$_{42}$ClNO$_5$: C, 70.39; H, 7.30; N, 2.41, Found: C, 70.29; H, 2.63; N, 2.47.

EXAMPLE 11

(5'-Dodecylcarbamoyl-3,3"-dimethoxy-[1,1';3',1"]terphenyl-2'-yloxy)-acetic Acid

Step 1 (N-Dodecyl-3,5-bis-(3-methoxyphenyl)-4-(2-hydroxyethoxy)benzamide

In a manner similar to Example 1, Step 2, the title compound (0.386 g, 65%) was prepared from 3,5-bis-(3-methoxyphenyl)-4-(2-hydroxyethoxy) benzoic acid ethyl ester (0.44 g, 1.04 mmol) and dodecylamine (0.676 g, 3.65 mmol), $^1$H NMR (CDCl$_3$) δ 7.75 (s, 2H), 7.38 (m, 2H), 7.19 (m, 4H), 6.94 (m, 2H), 6.21 (t, 1H), 3.85 (s, 6H), 3.41 (m, 4H), 3.28 (m, 2H), 1.60 (m, 2H), 1.23 (m, 18H), 0.85 (t, 3H).

Step 2 (5'-Dodecylcarbamoyl-3,3"-dimethoxy[1,1';3',1"]terphenyl-2'-yloxy)-acetic Acid In a manner similar to Example 1, Step 3, the title compound, 0.108 g, (27%) was prepared by oxidation of the above compound: mp 57–58° C.; $^1$H NMR (DMSO-d$_6$) δ 12.60 (br s, 1H), 8.53 (t, 1H), 7.82 (s, 2H), 7.39 (m 2H), 7.16 (in, 4H), 6.95 (m, 2H), 3.80 (s and m, 5 h), 3.24 (m, 2H), 1.50 (m, 2H), 1.21 (m, 18H), 0.31 (t, 3H); IR (KBr) 3310, 2920, 2830, 1750, 1220 cm$^{-1}$; Mass Spectrum [–ESI] M/Z 574 (M–H)$^-$; Anal. Calcd. For C$_{35}$H$_{45}$NO$_6$: C, 73.02; H, 7.88; N, 2.43. Found: C, 73.24; H, 8.14; N, 2.36.

EXAMPLE 12

[2-(3,3"-Dichloro-5'-dodecylcarbamoyl-[1,1';3',1"]terphenyl-2'-yloxy-ethoxy]-acetic Acid Step 1 [2-(3,3"-Dichloro-5'-dodecylcarbamoyl-[1,1';3',1"]terphenyl-2'-yloxy-ethoxy]-acetic Acid Methyl Ester To a stirred solution of N-dodecyl-3,5-bis(3-chlorophenyl)-4-(2-hydroxyethoxy)benzamide (Example 1, Step 2), (0.866 g, 1.52 mmol) in THF (8 mL) was added NaH (0.10 g, 80%, 3.34 mmol). The mixture was stirred at 60° C. for 50 min and was then cooled to room temperature. Methyl bromoacetate (0.158 mL, 2.67 mmol) was added and the mixture was stirred at 60° C. overnight. The reaction was cooled, quenched with 1.0 N HCl, and extracted with ethyl acetate. The organic phase was dried (MgSO$_4$) and concentrated. Crude product was purified by HPLC. Yield: 0.177 g (18%) of product as an oil. $^1$H NMR (CDCl$_2$) δ 7.72 (s, 2H), 7.63 (s, 2H), 7.50 (m, 2H), 7.39 (m, 4H), 6.20 (t, 1H), 3.78 (m, 5H), 3.49 (m, 4H), 3.31 (m, 2H), 1.68 (m, 2H), 1.30 (m, 18H), 0.88 (t, 3H).

Step 2 [2-(3,3"-Dichloro-5'-dodecylcarbamoyl-[1,1';3',1"]terphenyl-2'-yloxy-ethoxy]-acetic Acid The above ester (0.177 g, 0.275 mmol) was dissolved in THF/MeOH (1 mL/1 mL). To it was added aqueous NaOH (0.55 mL, 1.0 N, 0.55 mmol). After stirring for 2 h, the reaction was quenched by addition of 1N HCl and was then extracted with ethyl acetate. The organic phase was dried (MgSO$_4$) and concentrated. Trituration with hexane/ethyl ether afforded 0.133 g (71%) of product as a light yellow oil: $^1$H NMR (DMSO-D$_6$) δ 12.44 (br s, 1H), 8.53 (t, 1H), 7.87 (s, 2H) 7.69 (s, 2H), 7.60 (m, 2H), 7.49 (m, 4H), 3.63 (s, 2H), 3.40–3.20 (m, 6H), 1.51 (m, 2H), 1.21 (m, 18H), 0.83 (t, 3H); IR (KBr) 3322, 3067, 2925, 2853, 1732, 1633, 1564 cm$^{-1}$; Mass Spectrum [+APCI] M/Z 628 (M+H)$^+$; Anal. Calcd. For C$_{35}$H$_{43}$Cl$_2$NO$_5$.0.3H$_2$O: C, 66.03; H, 6.93; N, 2.21, Found: C, 66.03; H, 6.82; N, 2.44.

EXAMPLE 13

{5'-[6-(4-tert-Butyl-benzyloxy)-hexylcarbamoyl]-3,3"-bis-trifluoromethyl-[1,1';3',1"]terphenyl-2'-yloxy}-acetic Acid Step 1 N-[6-(4-tert-Butyl-benzyloxy)]hexyl-3,5-bis(m-trifluoro-methylphenyl)-4-(2-hydroxyethyl)-benzamide In a manner similar to Example 5, Step 2, the title compound, 1.06 g, (98%) was prepared from 3,5-bis-(m-trifluoromethylphenyl)-4-(2-hydroxyethoxy)benzoic acid ethyl ester (0.686 g, 1.38 mol) and 6-(4-tert-butyl-benzyloxy)hexylamine (1.27 g, 4.81 mmol).

Step 2 {5'-[6-(4-tert-Butyl-benzyloxy)-hexylcarbamoyl]-3,3"-bis-trifluoromethyl-[1,1';3',1"]terphenyl-2'-yloxy}-acetic Acid In a manner similar to Example 5, Step 3, the title compound (0.045 g, 10%) was prepared by oxidation of the above alcohol: mp 156–158° C.; $^1$H NMR (DMSO-d$_6$) δ 12.60 (br s, 1H), 8.59 (t, 1H), 7.97 (s, 2H), 7.92 (m, 4H), 7.77 (m, 2H), 7.72 (m, 2H), 7.33 (d, 2H), 7.20 (d, 2H), 4.35 (s, 2H), 3.81 (s, 2H), 3.38 (t, 2H), 3.27 (m, 2H), 1.51 (m, 4H), 1.32 (m, 4H), 1.24 (s, 9H); IR (KBr) 3300, 2800, 1730, 1620, 1570, 1330 cm$^{-1}$; Mass Spectrum [–ESI] M/Z 728 (M–H)$^-$; Anal. Calcd. for C$_{40}$H$_{41}$F$_6$NO$_5$: C, 65.84; H, 5.66; N, 1.92, Found: C, 65.44; H, 5.81; N, 1.79.

EXAMPLE 14

{5'-[6-(4-Benzyloxy-benzyloxy)-hexylcarbamoyl]-3,3"-bis-trifluoromethyl-[1,1';3',1"]terphenyl-2'-yloxy}-acetic Acid Step 1 N-[6-(4-Benzyloxy-benzyloxy)]hexyl-3,5-bis(m-trifluoromethylphenyl)-4-hydroxy-benzamide A stirring solution of 3,5-bis-(m-trifluoromethylphenyl)-4-hydroxybenzoic acid (0.800 g, 1.87 mmol) in SOCl$_2$ (10 mL) was heated at reflux for 1.5 h, then cooled and concentrated in vacuo. The acid chloride was dried in vacuo overnight. The acid chloride was dissolved in CH$_2$Cl$_2$ (10 mL) and added to a solution of 6-(4-benzyloxy-benzyloxy)hexylamine (0.765 g, 2.44 mmol) and triethylamine (0.92 mL, 6.54 mmol) in CH$_2$Cl$_2$ (10 mL) at 0° C. After stirring for 4 h at 0° C., 1.0 N HCl was added, and the mixture was extracted with ethyl acetate. The organic phase was washed with brine, dried (MgSO$_4$), and concentrated to give 1.15 g (85%) of the amide as an oil: $^1$H NMR (DMSO-d$_6$) δ 9.30 (s, 1H), 8.44 (t, 1H), 7.94–7.70 (m, 10H), 7.41 (m, 4H), 7.20 (d, 2H), 6.95 (d, 2H), 5.08 (s, 2H), 4.35 (s, 2H), 3.42–3.20 (m, 4H), 1.50 (m, 4H), 1.32 (m, 4H).

Step 2 {5'-[6-(4-Benzyloxy-benzyloxy)-hexylcarbamoyl]-3,3"-bis-trifluoromethyl-[1,1';3',1"]terphenyl-2'-yloxy}-acetic Acid Methyl Ester To a stirring solution of the above phenol (1.14 g, 1.58 mmol) in DMF (10 mL) was added methyl bromoacetate (0.29 mL, 3.16 mmol) and K$_2$CO$_3$ (0.24 g, 1.74 mmol). The mixture was stirred at 60° C. for 5 h and then overnight at room temperature. The mixture was partitioned between water and ethyl acetate. The organic phase was dried (MgSO$_4$) and concentrated to give crude product which was purified by flash column chromatography (2:1 hexanes/ethyl acetate). Yield: 0.72 g (61%) of product as a clear oil.

Step 3 {5'-[6-(4-Benzyloxy-benzyloxy)-hexylcarbamoyl]-3,3"-bis-trifluoromethyl-[1,1';3',1"]terphenyl-2'-yloxy}-acetic Acid Hydrolysis of the above ester in a manner similar to that described in Example JB-5, Step 2, afforded 0.3007 g (41%) of title compound as a white solid: mp 127–130° C.; $^1$H NMR (DMSO-d$_6$) δ 12.64 (br s, 1H), 8.57 (t, 1H), 7.92 (s, 2H), 7.92 (m, 4H), 7.75 (m, 4H), 7.42–7.29 (m, 5H), 7.20 (d, 2H), 6.95 (d, 2H), 5.07 (s, 2H), 4.32 (s, 2H), 3.81 (s, 2H), 3.40–3.30 (m, 4H), 1.51 (m, 4H), 1.32 (m, 4H); IR (KBr) 3300, 2950, 1730, 1620 cm$^{-1}$; Mass Spectrum [–APCI] M/Z 778 (M–H)$^-$; Anal. Calcd. For C$_{43}$H$_{39}$F$_6$NO$_6$.H$_2$O: C, 64.74; H, 5.18; N, 1.76. Found: C, 64.85; H, 5.02; N, 1.71.

Utilizing identical synthetic routes and experimental procedures as those described above, the following terphenyl analogs were prepared:

EXAMPLE 15

[3"-Chloro-4-methoxy-5'-(8-phenyl-octylcarbamoyl)-[1,1';3',1"]terphenyl-2'-yloxy]-acetic Acid Using as starting materials 3-(m-chlorophenyl)-5-(p-methoxyphenyl)-4-(2-hydroxyethoxy)benzoic acid ethyl ester and 8-phenyloctylamine to give the title compound.

mp: 79.2–80.5; $^1$H NMR (DMSO-d$_6$) δ 12.7 (br s, 1H), 8.55 (t, 1H), 7.80 (d, 2H), 7.68 (s, 1H), 7.55 (m, 4H), 7.48

(m, 2H), 7.10 (m, 3H), 7.00 (d. 2H), 3.80 (2s, 5H), 3.22 (m, 2H), 2.52 (m, 2H), 1.51 (m, 4H), 1.23 (m, 10H); IR (KBr) 3400, 2925, 2840, 1745, 1605, 1250 cm$^{-1}$; Mass Spectrum [+APCI] M/Z 600 (M+H)$^+$; Anal. Calcd. For $C_{36}H_{38}ClNO_5.H_2O$: C, 69.95; H, 6.52; N, 2.27, Found: C, 69.94; H, 6.27; N, 2.28.

EXAMPLE 16

{3"-Chloro-4-methoxy-5'-[methyl-(8-phenyl-octyl)-carbamoyl]-[1,1';3',1"]terphenyl-2'-yloxy}-acetic Acid Using as starting materials 3-(m-chlorophenyl)-5-(p-methoxyphenyl)-4-(2-hydroxyethoxy)benzoic acid ethyl ester and N-(8-phenyloctyl)-N-methylamine to give the title compound.

mp: 66.8–67.5; $^1$H NMR (DMSO-d$_6$) δ 7.63 (s, 1H), 7.55 (m, 4H), 7.41 (m, 2H), 7.30 (s, 1H), 7.25 (m, 2H), 7.20 (m, 3H), 7.00 (d, 2H), 3.78 (2s, 5H), 3.3 (m, 2H), 2.93 (br s, 3H), 1.60–1.00 (m, 14H); IR (KBr) 3410, 2900, 1620, 1250 cm$^{-1}$; Mass Spectrum [+APCI] M/Z 614 (M+H)$^+$; Anal. Calcd. For $C_{37}H_{40}ClNO_5.1.3H_2O$: C, 69.70; H, 6.73; N, 2.20, Found: C, 69.44; H, 6.63; N, 2.30.

EXAMPLE 17

[3,3"-Dimethoxy-5'-(8-phenyl-octylcarbamoyl)-[1,1';3',1"]terphenyl-2-yloxy]-acetic Acid Using as starting materials 3,5-bis(m-methoxyphenyl)-4-(2-hydroxyethoxy)-benzoic acid ethyl ester and 8-phenyloctylamine to give the title compound.

mp: 67.3–68.7° C.; $^1$H NMR (DMSO-d$_6$) δ 12.75 (br s, 1H), 8.48 (t, 1H), 7.80 (s, 2H), 7.35 (m, 2H), 7.30–7.10 (m, 9H), 6.92 (dd, 2H), 3.80 (s, 6H), 3.25 (m, 2H), 2.50 (m, 2H), 1.51 (m, 4H), 1.25 (m, 8H); IR (KBr) 3350, 2910, 2820, 1700, 1600, 1210 cm$^{-1}$; Mass Spectrum [+APCI] M/Z 596 (M+H)$^+$; Anal. Calcd. For $C_{37}H_{41}NO_6.1.5H_2O$: C, 71.36; H, 7.12; N, 2.25, Found: C, 71.36; H, 6.72; N, 2.16.

EXAMPLE 18

{2-[5'-(6-Phenyl-hexylcarbamoyl)-3,3"-bis-trifluoromethyl-[1,1';3',1"]terphenyl-2'-yloxy]-ethoxy}acetic Acid Using as starting materials 3,5-bis(m-trifluoromethylphenyl)-4-(2-hydroxyethoxy)benzoic acid ethyl ester and 6-phenylhexylamine to give the title compound.

mp: 74.7–75.9° C.; $^1$H NMR (DMSO-d$_6$) δ 12.50 (br s, 1H), 8.59 (t, 1H), 7.98 (m, 6H), 7.75 (m, 4H), 7.25 (m, 2H), 7.15 (m, 3H), 3.52 (s, 2H), 3.40–3.15 (m, 6H), 3.52 (m, 2H), 1.53 (m, 4H), 1.30 (m, 4H); IR (KBr) 3400, 2850, 1730, 1630, 1325 cm$^{-1}$; Mass Spectrum [−ESI] M/Z 686 (M−H)$^-$; Anal. Calcd. For $C_{37}H_{35}F_6NO_5$: C, 64.62; H, 5.13; N, 2.04, Found: C, 64.08; H, 5.18; N. 1.88.

EXAMPLE 19

{5'-[6-(2,4-Difluoro-benzyloxy)-hexylcarbamoyl]-3,3"-bis-trifluoromethyl-[1,1';3',1"]terphenyl-2'yloxy}-acetic Acid Using as starting materials 3,5-bis(m-trifluoromethylphenyl)-4-(2-hydroxyethoxy)benzoic acid ethyl ester and 6-(2,4-difluorobeenzyloxy)hexylamine to give the title compound.

mp: 149.9–150.6; $^1$H NMR (DMSO-d$_6$) δ 12.60 (br s, 1H), 8.56 (t, 1H), 7.97 (s, 2H), 7.92 (m, 4H), 7.80–7.65 (m, 4H), 7.45 (m, 1H), 7.20 (m, 1H), 7.04 (m, 1H), 4.44 (s, 2H), 3.80 (s, 2H), 3.42 (t, 2H), 3.29 (m, 2H), 1.51 (m, 4H), 1.31 (m, 4H); IR (KBr) 3435, 2930, 1725, 1610, 1325 cm$^{-1}$; Mass Spectrum [−ESI] M/Z 708 (M−H)$^-$; Anal. Calcd. For $C_{36}H_{31}F_8NO_5.H_2O$: C, 59.42; H, 4.57; N, 1.92, Found: C, 59.36; H, 4.22; N, 1.98.

EXAMPLE 20

{5'-[6-(Biphenyl-4-ylmethoxy)-hexylcarbamoyl]-3,3"-bis-trifluoromethyl-[1,1';3',1"]terphenyl-2'-yloxy}-acetic Acid Using as starting materials 3,5-bis(m-trifluoromethylphenyl)-4-(2-hydroxyethoxy)benzoic acid ethyl ester and 6-(p-phenylbenzyloxy)hexylamine to give the title compound.

mp: 133.2–133.9; $^1$H NMR (DMSO-d$_6$) δ 12.65 (br s, 1H), 8.60 (t, 1H), 7.97 (s, 2H), 7.92 (m, 4H), 7.78 (m, 2H), 7.72 (m, 2H), 7.62 (m, 4H), 7.43 (m, 2H), 7.37 (m, 3H), 4.43 (s, 2H), 3.80 (s, 2H), 3.42 (t, 2H), 3.24 (m, 2H), 1.56 (m, 4H), 1.35 (m, 4H); IR (KBr) 3300, 2960, 1730, 1615, 1565, 1325, 1130 cm$^{-1}$; Mass Spectrum [−ESI] M/Z 748 (M−H)$^-$; Anal. Calcd. For $C_{42}H_{37}F_6NO_5$: C, 67.28; H, 4.97; N, 1.87. Found: C, 66.98; H, 5.11; N, 1.79.

EXAMPLE 21

{3,3"-Dimethoxy-5"-[methyl-(8-phenyl-octyl)-carbamoyl]-[1,1';3',1"]terphenyl-2'-yloxy}-acetic Acid Using as starting materials 3,5-bis(m-methoxyphenyl)-4-(2-hydroxyethoxy)benzoic acid ethyl ester and N-(8-phenyloctyl)-N-methylamine to give the title compound.

mp: 148.9–149.7; $^1$H NMR (DMSO-d$_6$) δ 12.52 (br s, 1H), 7.52 (m, 4H), 7.23 (m, 2H), 7.17 (m, 7H), 6.90 (dd, 2H), 3.75 (2s, 8H), 2.92 (s. 3H), 2.50 (m, 2H), 1.60–3.00 (m, 12H); IR (KBr) 3400, 2925, 1850, 1700, 1400 cm$^{-1}$; Mass Spectrum [+ESI] M/Z 610 (M+H)$^+$; Anal. Calcd. For $C_{38}H_{43}NO_6.0.5H_2O$: C, 73.76; H, 7.17; N, 2.26. Found: C, 73.50; H, 6.94; N, 2.28.

EXAMPLE 22

{2-[3,5,3",5"-Tetrachloro-5'-[(6-phenyl-hexylcarbamoyl))-[1,1';3',1"]terphenyl-2'-ethoxy}-acetic Acid Using as starting materials 3,5-bis(3',5'-dichlorophenyl)-4-(2-hydroxyethoxy)benzoic acid ethyl ester and 6-phenylhexylamine to give the title compound.

mp: 78.5–79.9; $^1$H, NMR (DMSO-d$_6$) δ 12.5 (br s, 1H), 8.52 (t, 1H), 7.92 (s 2H), 7.73 (s, 4H), 7.65 (s, 4H), 7.22 (m, 2H), 7.14 (m, 3H), 3.63 (s, 2H), 3.20 (m, 2H), 3.24. (m, 4H), 2.53 (m, 2H), 1.55 (m, 4H), 1.32 (m, 4H); IR (KBr) 2375, 2925, 1725, 1630, 1560 cm$^{-1}$; Mass Spectrum [+APCI] M/Z 688 (M+H)$^+$; Anal. Calcd. For $C_{35}H_{33}Cl_4NO_5$: C, 60.97; H, 4.82; N, 2.03. Found: C, 63.17; H, 5.23; N, 2.15.

EXAMPLE 23

[4,4"-Dimethoxy-5'-(8-phenyl-octylcarbamoyl)-[1,1';3',1"]terphenyl-2'yloxy]acetic Acid Sodium Salt Using as starting materials 3,5-bis(p-methoxyphenyl)-4-(2-hydroxyethoxy)benzoic acid ethyl ester and 8-phenyloctylamine to give the title compound.

mp: >95° C.; ¹H NMR (DMSO-d₆) δ 8.46 (t, 1 h), 7.73 (s, 2H), 7.57 (d, 4H), 7.24 (m, 2H), 7.15 (m, 3H), 6.97(d, 4H), 3.78 (s, 6H), 3.58 (s 2H), 3.22 (q, 2H), 2.58 (m, 2H), 1.50 (m, 4H), 1.27 (m, 8H); IR (KBr) 3410, 2900, 1630, 1600, 1510, 1250 cm⁻¹; Mass Spectrum [−ESI] M/Z 594 (M−H)⁻; Anal. Calcd. For C₃₇H₄₁NO₆Na: C, 71.83; H, 6.68; N, 2.26. Found: C, 71.30; H, 6.66; N, 2.22.

EXAMPLE 24

(3,3″-Dichloro-5′-dodecylcarbamoyl-4,4″-difluoro[1,1′;3′,1″]terphenyl(-2′-yloxy)-acetic Acid Sodium Salt Using as starting materials 3,5-bis(3′-chloro-4′-fluorophenyl)-4-(2-hydroxyethoxy)benzoic acid ethyl ester and dodecylamine to give the title compound.

mp: 140.2–141.0; ¹H NMR (DMS)-d₆) δ 8.53 (t, 1H), 7.82 (m, 4H), 7.60 (m, 2H), 7.46 (m, 3H), 3.77 (s, 2H), 3.27. (q, 2H), 1.47 (m, 2H), 1.17 (m, 18H), 0.79 (t, 3H); IR (KBr) 3375, 2930, 2870, 1720, 1615, 1500, 1200 cm⁻¹; (M+H)⁺; Mass Spectrum [+APCI] M/Z 620 (M+H)⁺; Anal. Calcd. For C₃₃H₃₇Cl₂F₂NO₄Na: C, 61.59; H, 5.80; N, 2.18. Found: C, 61.29; H, 5.57; N, 2.16.

EXAMPLE 25

[3,3″-Dichloro-4-4″difluoro-5′-(8-phenyl-octylcarbamoyl)[1,1′;3′,1″]terphenyl-2′-yloxy]-acetic Acid Using as starting materials 3,5-bis(3′-chloro-5′-fluorophenyl)-4-(2-hydroxyethoxy)benzoic acid ethyl ester and 8-phenyloctylamine to give the title compound.

mp: 157.0–158.8; ¹H NMR (DMSO-d₆) δ 12.5 (br s, 1H), 8.55 (t, 1H), 7.85 (m, 4H), 7.62 (m, 2H), 7.49 (m, 2H), 7.23 (m, 2H), 7.13 (m, 3H), 3.82 (s, 2H), 3.25 (q, 2H), 2.52 (t, 2H), 1.52 (m, 4H), 1.27 (m, 8H); IR (KBr) 3310, 2915, 1715, 1600, 1550, 1500 cm⁻¹; Mass Spectrum [−ESI] M/Z 638 (M−H)⁻; Anal. Calcd. For C₃₅H₃₃Cl₂F₂NO₄.0.7H₂O: C, 64.36; H, 5.31; N, 2.14. Found: C, 64.22; H, 4.95; N, 2.01.

EXAMPLE 26

{3,3″-Dichloro-5′-(6-(2,5-dimethyl-furan-3-ylmethoxy)-hexylcarbamoyl]-4-4″-difluoro-[1,1′;3′,1″]terphenyl-2′-yloxy}-acetic Acid Using as starting materials 3,5-bis(3′-chloro-4′-fluorophenyl)-4-(2-hydroxyethoxy)benzoic acid ethyl ester and 6-(2,5-dimethyl-3-furanyloxy)hexylamine to give the title compound.

mp: 90.0–91.2; ¹H NMR (DMSO-d₆) δ 8.53 (t, 1H), 7.83 (m, 4H), 7.62 (m, 2H), 7.47 (m, 2H), 5.89 (s, 1H), 4.12 (s, 2H), 3.70 (s, 2H), 3.30 (t, 2H), 3.22 (q, 2H), 2.14 (2s, 6H), 1.50 (m, 4H), 1.29 (m, 4H); IR (KBr) 3400, 1735, 1630, 1500 cm⁻¹; Mass Spectrum [−ESI] M/Z 658 (M−H)⁻; Anal. Calcd. For C₃₄H₃₃Cl₂F₂NO₆.H₂O: C, 60.18; H, 5.20; N, 2.06. Found: C, 59.77; H, 4.77; N, 1.74.

EXAMPLE 27

[3,5-Dichloro-5′-(8-phenyl-octylcarbamoyl)-[1,1′;3′,1″]terphenyl-2′-yloxy]-acetic Acid Using as starting materials 3-(m-chlorophenyl)-5-phenyl-4-(2-hydroxyethoxy)benzoic acid ethyl ester and 8-phenyloctylamine to give the title compound.

mp: 82.0–83.1; ¹H NMR (DMSO-d₆) δ 12.7 (br s, 1H), 8.53 (t, 1H), 7.85 (s, 2H), 7.69 (dd, 2H), 7.60 (m, 3H), 7.49 (m, 3H), 7.25 (m, 2H), 7.15 (m, 3H), 3.80 (s, 2H), 3.25 (m, 2H), 2.58 (m, 2H), 1.52 (m, 4H), 1.27 (m, 8H); IR (KBr) 3392, 2927, 2853, 1737, 1633, 1560 cm⁻¹; Mass Spectrum [−ESI] M/Z 602 (M−H)⁻; Anal. Calcd. For C₃₅H₃₅NCl₂O₄.2H₂O: C, 65.62; H, 6.14; N, 2.19. Found: C, 65.10; H, 5.61; N, 2.10.

EXAMPLE 28

[5′-(8-Phenyl-octylcarbamoyl)-3-trifluoromethyl-[1,1′;3′,1″]terphenyl-2′-yloxy]-acetic Acid Using as starting materials 3-(m-trifluoromethylphenyl)-5-phenyl-4-(2-hydroxyethoxy)benzoic acid ethyl ester and 8-phenyloctylamine to give the title compound.

mp: 143.3–145.5; ¹H NMR (DMSO-d₆) δ 8.55 (t, 1H), 7.46 (s, 1H), 7.86 (m, 3H), 7.75–7.70 (m, 2H), 7.60 (d, 2H), 7.50–7.38 (m, 3H), 7.23 (m, 2H), 7.12 (m, 3H), 3.77 (s, 2H), 3.24 (m, 2H), 2.59 (m, 2H), 1.52 (m, 4H), 1.27 (m, 8H); IR (KBr) 3345, 2929, 2855, 1729, 1617; Mass Spectrum [+ESI] M/Z 604 (M+H)⁺; Anal. Calcd. For C₃₅H₃₆F₃NO₄.H₂O: C, 69.55; H, 6.16; N, 2.25. Found: C, 69.81; H, 5.95; M, 2.42.

EXAMPLE 29

4,4″-Difluoro-5′-(8-phenyl-octylcarbamoyl)-3,3″-bis-trifluoromethyl-[1,1′;3′,1″]terphenyl-2′-yloxy]-acetic Acid Using as starting materials 3,5-bis(3′-trifluoromethyl-4-fluorophenyl)-4-(2-hydroxyethoxy)benzoic acid ethyl ester and 8-phenyloctylamine to give the title compound.

mp: 146–148; ¹H NMR (DMSO-d₆) δ 12.75 (br s, 1H), 12.54 (t, 1H), 8.00 (m, 4H), 7.91 (m, 3H), 7.60 (m, 3H), 7.22 (m, 4H), 7.12 (m, 3H), 3.81 (s, 2H), 3.31 (m, 2H), 2.59 (m, 2H), 1.50 (m, 4H), 1.27 (m, 8H); IR (KBr) 3355, 2930, 2857, 1725, 1622, 1506 cm⁻¹; Mass Spectrum [+ESI] M/Z 708 (M+H)⁺; Anal. Calcd. For C₃₇H₃₃F₈NO₄: C, 62.80; H, 4.70; N, 1.98. Found: C, 62.29; H, 4.84; N, 2.06.

EXAMPLE 30

{(5′-[6-(2,5-Dimethyl-furan-3-ylmethoxy)-hexylcarbamoyl]-3,3″-bis-trifluoromethyl-[1,1′;3′,1″]terphenyl-2′-yloxy}-acetic Acid Using as starting materials 3,5-bis(m-trifluoromethylphenyl)-4-(2-hydroxyethoxy)benzoic acid ethyl ester and 6-(2,5-dimethyl-3-furanyloxy)hexylamine to give the title compound.

mp: 107.9–108.5; ¹H NMR (DMSO-d₆) δ 12.5 (br s, 1H), 8.60 (t, 1H), 7.91 (m, 6H), 7.70 (m, 4H), 5.89 (s, 1H), 4.12 (s, 2H), 3.80 (s, 2H), 3.31 (m, 4H), 2.14 (2s, 6H), 1.50 (m, 4H), 1.29 (m, 4H); IR (KBr) 3351, 2936, 2861, 1729, 1636 cm⁻¹; Mass Spectrum [−APCI] M/Z 690 (M−H)⁻; Anal. Calcd. For C₃₆H₃₅F₆NO₆.0.5H₂O: C, 61.71; H, 5.18; N, 2.00. Found: C, 61.41; H, 5.05; N, 1.87.

EXAMPLE 31

(3-Bromo-5-dodecylcarbamoyl-4′-methoxy-biphenyl-2-yloxy)-acetic Acid

Using as starting materials 3-bromo-5-(p-methoxyphenyl)-4-(2-hydroxyethoxy)benzoic acid ethyl ester and dodecylamine to give the title compound.

¹H NMR (DMSO-d₆) δ 12.82 (br s, 1H), 8.54 (t, 1H), 8.03 (dd, 1H), 7.80 (dd, 1H), 7.51 (dd, 2H), 7.02 (dd, 2H), 4.07 (s, 2H), 3.80 (s, 3H), 3.22 (m, 2H), 1.45 (m, 2H), 1.22 (m,

18H), 0.83 (t, 3H); IR (KBr) 3350, 2915, 2850, 1745, 1610, 1550, 1510, 1250 cm$^{-1}$; Mass Spectrum [−ESI] M/Z 546/548 (M−H)$^-$; Anal. Calcd. For $C_{28}H_{38}BrNO_5$: C, 61.31; H, 6.98; N, 2.55. Found: C, 61.08; H, 6.79; N, 2.49.

EXAMPLE 32

[5'-(2-Hexadecylamino-3,4-dioxo-cyclobut-1-enylamino)-[1,1';3',1"]terphenyl-2'-yloxy]-acetic Acid To a stirring solution of 2,6-diiodo-4-nitrophenol (24.00, 61.40 mmol) in DME/H$_2$O (140 mL; 10:1) was added phenylboronic acid (16.47 g, 135.08 mmol), Ba(OH)$_2$.H$_2$O (34.88 g, 184.2 mmol), and Pd(OAc)$_2$ (1.37 g, 6.14 mmol). The mixture was stirred for 3 h at 80° C., cooled, diluted with water, and filtered through a pad of Celite. The filtrate was extracted with ethyl acetate. The organic phase was dried (MgSO$_4$) and decolorized (charcoal). Concentration afforded 15.31 g (86%) of bis-arylated product. The compound was treated with methyl bromoacetate (9.96 mL, 105.22 mmol) and K$_2$CO$_3$ (8.85 g, 57.87 mmol) in acetonitrile (200 mL). The mixture was stirred for 4 h at 70° C. then overnight at room temperature. Filtration, followed by concentration in vacuo and trituration of the residue with petroleum ether afforded 15.01 g (79%) of phenoxy acetic acid derivative. A portion of this compound (5.00 g, 13.81 mmol) was treated with iron powder (3.7 g, 66.30 mmol) and NH$_4$Cl (0.37 g, 6.91 mmol) in ethanol (50 mL)/water (25 mL). The mixture was heated at 80° C. for 18 h, cooled, and passed through a short column of celite. The filtrate was dried (MgSO$_4$), decolorized (charcoal) and concentrated to give 3.87 g (84%) of aniline compound. A portion of this compound (1.50 g, 4.52 mmol) was stirred in neat 3,4-diethoxy-3-cyclobutene-1,2-dione (2.71 g, 13.55 mmol) overnight at room temperature. The mixture was partitioned between water/ethyl acetate and the crude condensation product was purified by flash column using 40% ethyl acetate/hexanes to give 1.25 g (60%) of product. A portion of this compound (0.100 g, 0.22 mmol) was treated with hexadecylamine (0.08 g, 0.33 mmol) in ethanol (20 mL) at 70° C. The mixture was stirred overnight, cooled and filtered to give 0.14 g (100%) of [5'-(2-hexadecylamino-3,4-dioxo-cyclobut-1-enylamino)-[1,1';3',1"]terphenyl-2'-yloxy]acetic acid methyl ester. The ester was dissolved in methanol/THF (8 mL/12 mL) and treated with aqueous 1 N KOH (1.23 mL, 1.23 mmol). The reaction was stirred for 18 h, then concentrated in vacuo and diluted with water. Acidification with 1N HCl afforded a white precipitate which was collected by filtration and dried in vacuo. Yields of the compound: 0.092 g (58%): mp: 132.5–133.7; $^1$H NMR (DMSO-d$_6$) δ 12.45 (br s, 1H), 9.78 (br s, 1H), 7.60 (m, 5H), 7.48–7.30 (m, 8H), 3.70 (s, 2H), 3.60 (m, 2H), 1.55 (m, 2H), 1.24 (m, 26H), 0.80 (t, 3H); IR (KBr) 3275, 2920, 2810, 1800, 1675, 1575, 1450 cm$^{-1}$; Mass Spectrum [−ESI] M/Z 637 (M−H)$^-$; Anal. Calcd. For $C_{40}H_{50}N_2O_5$.H$_2$O: C, 73.14; H, 7.98; N, 4.26; N, 4.26. Found: C, 73.74; H, 7.67; N, 4.26.

EXAMPLE 33

(3,3"-Dichloro-5'-dodecylcarbamoyl-[1,1';3',1"]terphenyl-2'-yloxy)-acetic Acid

Step 1 3,5-bis-(m-Chlorophenyl)-4-(2-hydroxyethoxy)benzoic Acid Ethyl Ester

To a stirred solution of K$_2$CO$_3$ (17.2 g, 124 mmol) in H$_2$O (62 mL) at room temperature was added dioxane (490 mL), 3-bromo-4-(2-hydroxyethoxy)-5-iodobenzoic acid ethyl ester (17.2 g, 41.4 mmol), 3-chlorophenylboronic acid (7.77 g, 49.7 mmol), and [1,1'bis(diphenylphosphino)ferrocene]dichloropalladium(II), complex with CH$_2$Cl$_2$ (0.676 g, 0.828 mmol). This mixture was stirred at room temperature for 4 h, and it appeared to be in progress but not done by TLC and HPLC. Another 0.1 eq. of 3-chlorophenylboronic acid (0.647 g) was added, and the reaction stirred an additional 24 h. Over the next 4 days, 0.1 eq. of the boronic acid was added at one a day intervals until the reaction was almost completely done by HPLC (60% bis-arylated, 25.4% mono-arylated, and 12.6% SM). The reaction was diluted with HCl (1187 mL, 0.17 M) and the resulting solution was extracted with EtOAc (1×300 mL and 3×200 mL). The combined organic layers were washed wtih 0.1 N HCl (2×90 mL), H$_2$O (2×90 mL), and brine (2×90 mL) and then dried (Na$_2$SO$_4$). After concentration, the residue was first purified by flash chromatography (0 to 50% EtOAc/hexane gradient) and then HPLC [60% CH$_2$Cl$_2$ (6% MTBE):40% hexane] to afford the bis-arylated product (6.16 g, 35%) as a viscous faint yellow oil (for mono-arylated product, see step 1 of Example 33); $^1$H NMR (DMSO-d$_6$) δ 1.31 (t, J=7.0 Hz, 3H), 3.12 (q, J=5.5 Hz, 2H), 3.28 (t, J=5.7 Hz, 2H), 4.32 (dd, J=7.0, 14.1 Hz, 2H), 4.45 (t, J=5.5 Hz, 1H), 7.45–7.53 (m, 4H), 7.53–7.58 (m, 2H), 7.67–7.69 (m, 2H), 7.91 (s, 2H); IR (film) 3440, 3090, 2990, 2930, 2860, 1720, 1610, 1570, 1475, 1425, 1390, 1360, 1340, 1310, 1245, 1160, 1120, 1100, 1090, 1065, 1025, 770, 710, and 500 cm$^{-1}$; mass spectrum [(+) APCI], m/z 431/433 (M+H)$^+$, 448/450 (M+NH$_4$)$^+$.

Step 2 N-Dodecyl-3,5-bis(m-chlorophenyl)-4-(2-hydroxyethoxy)-benzamide

To a flamed dried round bottom flask with dodecyl amine (0.519 g, 2.80 mmol) and THF (8 mL) cooled to 0° C. was added n-BuLi (1.12 mL, 2.5 M in hexane, 2.80 mmol) dropwise over a 5 min. period. The resulting solution was stirred at this temperature for 40 min. and then cooled to −45° C. To this solution was added dropwise a solution (at 0° C.) of 3,5-bis-(m-chlorophenyl)-4-(2-hydroxyethoxy)benzoic acid ethyl ester (0.302 g, 0.700 mmol) in THF (8 mL) over 5 min. This final mixture was stirred and warmed to room temperature over 30 min. At this point, the reaction mixture was quenched with H$_2$O (3 mL) and diluted with EtOAc (40 mL). The organic layer was washed with 1 N HCl (3×7 mL), brine,(7 mL), and H$_2$O:brine (1:1, 14 mL) and then dried (Na$_2$SO$_4$). After concentration, the residue was purified by flash chromatography (0 to 15% EtOAc/hexane gradient) to afford the product (0.286 g, 72%) as an oily white solid; $^1$H NMR (DMSO-d$_6$) δ 0.86 (t, J=7.7 Hz, 3H), 1.20–1.37 (m, 18H), 1.46–1.57 (m, 2H), 3.13 (dd, J=6.9, 11.5 Hz, 2H), 3.20–3.33 (m, 4H), 4.46 (t, J=6.2 Hz, 1H), 7.43–7.57 (m, 4H), 7.59–7.63 (m, 2H), 7.68–7.73 (m, 2H), 7.89 (s, 2H), 8.67 (t, J=6.2 Hz, 1H); mass spectrum [(+) APCI], m/z 570 (M+H)$^+$.

Step 3 (3,3-Dichloro-5'-dodecylcarbamoyl-[1,1';3',1"]terphenyl-2'-yloxy)-acetic Acid To a stirred solution of N-dodecyl-3,5-bis(m-chlorophenyl)-4-(2-hydroxyethoxy)benzamide (0.277 g, 0.485 mmol) in CH$_3$CN:CH$_2$Cl$_2$ (5:3, 8 mL) at room temperature was added NMMO (0.114 g, 0.970 mmol) followed by TPAP (0.017 g, 0.0485 mmol). After 2 h, the reaction mixture still showed presence of intermediate aldehyde. Another 0.3 eq. of NMMO (0.017 g) and 0.02 eq. TPAP (0.003 g) was added, and the reaction was stirred for an additional 3 h. The mixture was quenched with H$_2$O (2 mL) followed by aq. 10% NaHSO$_3$ (15 mL). After stirring for 20 min., the mixture was diluted with EtOAc (40 mL). The resulting organic layer was washed with 1 N HCl (3×7 mL) and brine (2×7 mL) and then dried (Na$_2$SO$_4$). After concentration, the residue was purified by preparatory plate chromatography (100% EtOAc) to afford the product (0.081 g, 29%) as a gray solid, mp 151–156° C.; $^1$H NMR (DMSO-$d_6$) δ 0.83 (t, J=6.8 Hz, 3H), 1.15–1.32 (m, 18H), 1.46–1.55 (m, 2H), 3.25 (dd, J=7.2, 13.2 Hz, 2H), 3.84 (s, 2H), 7.44–7.52 (m, 4H), 7.57 (t, J=2.0 Hz, 1H), 7.58 (t, J=1.8 Hz, 1H), 7.67–7.70 (m, 2H), 7.86 (s, 2H), 8.55 (t, J=5.7 Hz, 1H), 12.54–12.86 (bs, 1H); IR (KBr) 3360, 2930, 2850, 1725, 1620, 1565, 1465, 1385, 1345, 1245, 1200, 1150, 1075, 1065, 880, 800, 755, and 705 cm$^{-1}$; mass spectrum [(−) ESI], m/z 582/584/586 (M−H)$^-$; Anal. Calcd. for $C_{33}H_{39}Cl_2NO_4$: C, 67.80; H, 6.72; N, 2.40, Found: C, 67.63; H, 6.77; N, 2.34.

EXAMPLE 34

(3-Bromo-3'-chloro-5-dodecylcarbamoyl-biphenyl-2-yloxy)-acetic Acid

Step 1 3-Bromo-5-(m-chlorophenyl)-4-(2-hydroxyethoxy) benzoic Acid Ethyl Ester

3-Bromo-5-(m-chlorophenyl)-4-(2-hydroxyethoxy) benzoic acid ethyl ester was prepared as a white solid (5.01 g, 30%) from 3-bromo-4-(2-hydroxyethoxy)-5-iodobenzoic acid ethyl ester using the procedure to step 1 of Example 33 (product 2: mono-arylation), mp 107.5–110.5 ° C.; $^1$H NMR (DMSO-$d_6$) δ 1.33 (t, J=7.0 Hz, 3H), 3.45 (q, J=5.5 Hz, 2H), 3.61 (t, J=5.5 Hz, 2H), 4.33 (dd, J=7.2, 14.3 Hz, 2H), 4.69 (t, J=5.7 Hz, 1H), 7.50–7.56 (m, 3H), 7.64–7.66 (m, 1H), 7.88 (d, J=2.2 Hz, 1H), 8.15 (d, J=2.2 Hz, 1H); IR (KBr) 3240, 3090, 2980, 2930, 1720, 1600, 1570, 1465, 1445, 1380, 1365, 1355, 1305, 1265, 1240, 1180, 1120, 1080, 1055, 1030, 890, 875, 810, 760, and 705 cm$^{-1}$; mass spectrum [(+) APCI], m/z 399/401 (M+H)$^+$, 416/418 (M+NH$_4$)$^+$.

Step 2 N-Dodecyl-3-bromo-5-(m-chlorophenyl)-4-(2-hydroxyethoxy)-benzamide

N-Dodecyl-3-bromo-5-(m-chlorophenyl)-4-(2-hydroxyethoxy)benzamide was prepared as a colorless oil (0.110 g, 33%) from 3-bromo-5-(m-chlorophenyl)-4-(2-hydroxyethoxy)benzoic acid ethyl ester using a procedure similar to step 2 of Example 33; $^1$H NMR (DMSO-$d_6$) δ 0.86 (t, J=7.7 Hz, 3H), 1.17–1.36 (m, 18H), 1.46–1.57 (m, 2H), 3.20–3.30 (m, 2H), 3.46 (dd, J=5.4, 11.5 Hz, 2H), 3.58 (t, J=5.4 Hz, 2H), 4.69 (t, J=6.2 Hz, 1H), 7.48–7.60 (m, 3H), 7.65–7.71 (m, 1H), 7.87 (d, J=2.3 Hz, 1H), 8.10 (d, J=2.3 Hz, 1H), 8.58 (t, J=6.2 Hz, 1H); mass spectrum [(−) ESI], m/z 536 (M−H)$^-$, 596/598/600 (M+OAc−H)$^-$.

Step 3 (3-Bromo-3'-chloro-5-dodecylcarbamoyl-biphenyl-2-yloxy)-acetic Acid

The title compound was prepared as an gray solid (0.051 g, 43%) from N-dodecyl-3-bromo-5-(m-chlorophenyl)-4-(2-hydroxyethoxy)benzamide using a procedure similar to step 3 of Example 33, mp>100° C. (decomp.); $^1$H NMR (DMSO-$d_6$) δ 0.83 (t, J=6.8 Hz, 3H), 1.18–1.31 (m, 18H), 1.49 (t, J=6.8 Hz, 2H), 3.23 (dd, J=6.8, 13.0 Hz, 2H), 3.77 (s, 2H), 7.41–7.47 (m, 2H), 7.57–7.60 (m, 1H), 7.66–7.68 (m, 1H), 7.79 (d, J=2.2 Hz, 1H), 8.04 (d, J=2.2 Hz, 1H), 8.53 (t, J=5.3 Hz, 1H; IR (KBr) 3290, 3090, 2930, 2850, 1630, 1555, 1465, 1430, 1325, 1225, 1190, 1110, 1075, 1020, 920, 885, 840, 800, 770, 710, 690, and 600 cm$^{-1}$; mass spectrum [(+) ESI], m/z 552/554/556 (M+H)$^+$; Anal. Calcd. for $C_{27}H_{35}BrClNO_4$·1.33H$_2$O: C, 56.21; H, 6.58; N, 2.43, Found: C, 56.01; H, 5.96; N, 2.39.

EXAMPLE 35

[3,3''-Dichloro-5'-(8-phenyl-octylcarbamoyl)-[1,1';3',1'']terphenyl-2'-yloxy]-acetic Acid Step 1 N-(8-Phenyl-octyl)-3,5-bis-(m-chlorophenyl)-4-(2-hydroxyethoxy)-benzamide To a flamed dried round bottom flask with 8-phenyloctyl amine (0.484 mL, 2.43 mmol) and THF (5 mL) cooled to 0° C. was added n-BuLi (0.972 mL, 2.5 M in hexane, 2.43 mmol) dropwise over a 5 min. period. The resulting solution was allowed to stir 5 min. and then warmed to room temperature for 30 min. This solution was then added dropwise to a solution of 3,5-bis-(m-chlorophenyl)-4-(2-hydroxyethoxy)benzoic acid ethyl ester (0.300 g, 0.696 mmol) in THF (15 mL) at −20° C. This final mixture was stirred at −20° C. for 15 min and then warmed to room temperature for 15 min. At this point, the reaction mixture was quenched with H$_2$O (10 mL) and diluted with EtOAc (200 mL). The organic layer was washed with 1 N HCl (20 mL), sat. aq. NaHCO$_3$ (20 mL), and brine (20 mL) and then dried (MgSO$_4$). After concentration, the residue was purified by the Biotage Flash 40 apparatus (20 to 40% EtOAc/petroleum ether gradient) to afford the product (0.267 g, 65%) as a clear oil; $^1$H NMR (CDCl$_3$) δ 1.09–1.48 (m, 9H), 1.48–1.72 (m, 4H), 2.58 (t, J=6.8 Hz, 2H), 3.30–3.35 (m, 2H), 3.35–3.41 (m, 2H), 3.46 (dd, J=6.8, 13.0 Hz, 2H), 6.07–6.18 (m, 1H), 7.11–7.19 (m, 3H), 7.21–7.31 (m, 2H), 7.35–7.44 (m, 4H), 7.44–7.57 (m, 2H), 7.63 (s, 2H), 7.77 (s, 2H); mass spectrum [(+) ESI], m/z 590 (M)$^+$.

Step 2 [3,3''-Dichloro-5'-(8-phenyl-octylcarbamoyl)-[1,1';3',1'']terphenyl-2'-yloxy]-acetic Acid The title compound was prepared as an off white solid (0.151 g, 57%) from N-(8-phenyl-octyl)-3,5-bis-(m-chlorophenyl)-4-(2-hydroxyethoxy)benzamide using a procedure similar to step 3 of Example 33, mp 165–167° C.; $^1$H NMR (DMSO-$d_6$) δ 1.20–1.32 (m, 8H), 1.46–1.57 (m, 4H), 2.51 (dd, J=7.7, 15.6 Hz, 2H), 3.25 (dd, J=6.8, 13.2 Hz, 2H), 3.83 (s, 2H), 7.10–7.17 (m, 3H), 7.21–7.26 (m, 2H), 7.44–7.51 (m, 4H), 7.56–7.59 (m, 2H), 7.67–7.69 (m, 2H), 7.86 (s, 2H), 8.56 (t, J=5.5 Hz, 1H), 12.45–12.94 (bs, 1H); IR (KBr) 3320, 3090, 3030, 2920, 2830, 2520, 1730, 1610, 1565, 1475, 1455, 1390, 1340, 1310, 1245, 1200, 1075, 1055, 875, 800, 780, 755, and 700 cm$^{-1}$; mass spectrum [(+) ESI], m/z 604 (M+H)$^+$; Anal. Calcd. for $C_{35}H_{35}Cl_2NO_4$·0.5H$_2$O: C, 68.51; H, 5.91; N, 2.28, Found: C, 68.36; H, 5.83; N, 2.32.

EXAMPLE 36

(5'-Octadecyloxy-[1,1';3',1'']terphenyl-2'-yloxy)-acetic Acid

Step 1 (5'-Octadecyloxy-[1,1';3',1'']terphenyl-2'-yloxy) acetic Acid Methyl Ester To a stirred solution of 5'-octadecyloxy-[1,1';3',1''] terphenyl-2'-ol (0.250 g, 0.486 mmol, Akzo Chemie, Netherlands, Stabilizer A-2751) and K$_2$CO$_3$ (0.0739 g, 0.535 mmol) in DMF (9 mL) and THF (4 mL) at room temperature was added dropwise methyl bromoacetate (0.0922 mL, 0.972 mmol). After 7 days at this temperature, it was diluted with H$_2$O (50 mL) followed by excess EtOAc (400 mL). The organic layer was washed with 1 N HCl (50 mL), sat. aq. NaHCO$_3$ (50 mL), and brine (50 mL) and then dried (MgSO$_4$). After concentration, the residue was purified by flash chromatography (0 to 15% EtOAc/petroleum ether gradient) to afford the product (0.225 g, 79%) as a white solid, mp 66–69° C.; $^1$H NMR (DMSO-$d_6$) δ 0.84 (t, J=7.0 Hz, 3H), 1.17–1.34 (m, 28H), 1.34–1.43 (m, 2H), 1.65–1.74 (m, 2H), 3.36 (s, 3H), 3.75 (s, 2H), 4.01 (t, J=6.2 Hz, 2H), 6.86 (s, 2H), 7.33–7.45 (m, 6H), 7.56 (d, J=7.2 Hz, 4H); IR (KBr) 3420, 3050, 2920, 2860, 1770, 1600, 1575, 1465, 1420, 1365, 1235, 1210, 1200, 1095, 1060, 755, and 710 cm$^{-1}$; mass spectrum [(+) FAB], m/z 587 (M+H)$^+$, 609 (M+Na)$^+$; Anal. Calcd. for $C_{39}H_{54}NO_4$: C, 79.82; H, 9.27; N, 0.00, Found: C, 79.47; H, 9.21; N, −0.01.

Step 2 (5'-Octadecyloxy-[1,1';3',1"]terphenyl-2'-yloxy) acetic Acid

To a stirred solution of (5'-octadecyloxy-[1,1';3',1"]terphenyl-2'-yloxy)acetic acid methyl ester (0.182 g, 0.310 mmol) in THF:MeOH (3:2, 10 mL) at room temperature was added dropwise 1 N KOH (1.55 mL, 1.55 mmol). After 2 h at this temperature, it was concentrated and diluted with $H_2O$. The solution was then acidified to pH 1 with 2 N HCl. The resulting solid was filtered off, washed with $H_2O$, and dried on the high vacuum for 18 h to afford the product (0.166 g, 93%) as a white solid, mp 90.5–92° C.; $^1$H NMR (DMSO-$d_6$) δ 0.83 (t, J=6.8 Hz, 3H), 1.16–1.35 (m, 28H), 1.35–1.44 (m, 2H), 1.65–1.74 (m, 2H), 3.63 (s, 2H), 4.01 (t, J=6.4 Hz, 2H), 6.86 (s, 2H), 7.32–7.44 (m, 6H), 7.58 (dd, J=1.5, 8.3 Hz, 4H), 12.20–12.75 (bs, 1H); IR (KBr) 3430, 3070, 2920, 2840, 1725, 1600, 1575, 1465, 1410, 1360, 1265, 1220, 1200, 1090, 750, and 695 cm$^{-1}$; mass spectrum [EI], m/z 572 (M)$^+$; Anal. Calcd. for $C_{38}H_{52}NO_4$: C, 79.68; H, 9.15; N, 0.00, Found: C, 79.25; H, 8.99; N, 0.09.

EXAMPLE 37

(5'-Benzo[b]naphtho[2,3-d]thiophen-11-yl-[1,1';3',1"]terphenyl-2'-yloxy)-acetic Acid Step 1 5'-Benzo[b]naphtho[2,3-d]thiophen-11-yl-[1,1';3',1"]terphenyl-2'-ol To a stirred solution of phenylboronic acid (0.232 g, 1.90 mmol), Ba(OH)$_2$.8H$_2$O (1.09 g, 3.46 mmol), and Pd(OAc)$_2$ (0.004 g, 0.0173 mmol) in DME:H$_2$O (6:1, 21 mL) at room temperature was added 4'-benzo[b]naphtho[2,3-d]thiophen-11-yl-2',6'-diiodophenol (0.500 g, 0.865 mmol)). The mixture was then heated at 80° C. for 72 h. At this point, the reaction was acidified to pH 1 with 1 N HCl and diluted with EtOAc (300 mL). The organic layer was washed with H$_2$O (30 mL) and brine (30 mL) and then dried (MgSO$_4$). After concentration, the residue was purified by flash chromatography (1 to 16% EtAOc/petroleum ether gradient) to afford the product (0.381 g, 92%) as a white glassy solid, mp>78° C. (decomp.); $^1$H NMR (DMSO-$d_6$) δ 7.07 (d, J=8.1 Hz, 1H), 7.22 (td, J=1.1, 8.1 Hz, 1H), 7.25 (s, 2H), 7.32 (tt, J=1.1, 6.6 Hz, 2H), 7.39–7.52 (m, 6H), 7.56–7.64 (m, 5H), 7.77 (d, J=8.8 Hz, 1H), 7.99 (d, J=7.9 Hz, 1H), 8.05 (d, J=8.1 Hz, 1H), 8.61 (s, 1H), 8.76 (s, 1H); IR (KBr) 3520, 3430, 3050, 2920, 1590, 1495, 1465, 1420, 1380, 1370, 1320, 1220, 1120, 1075, 1030, 755, 735, and 705 cm$^{-1}$; mass spectrum [EI], m/z 478 (M)$^+$; Anal. Calcd. for $C_{34}H_{22}OS.1.6H_2O$: C, 80.48; H, 5.01; N, 0.00, Found: C, 80.26; H, 4.63; N, 0.05.

Step 2 (5'-Benzo[b]naphtho[2,3-d]thiophen-11-yl-[1,1';3',1"]terphenyl-2'-yloxy)-acetic Acid Methyl Ester The title compound was prepared as a white foam (0.788 g, 85%) from 5'-benzo[b]naphtho[2,3-d]thiophen-11-yl-[1,1';3',1"]terphenyl-2'-ol using a procedure similar to step 1 of Example 36, mp>75° C. (decomp.); $^1$H NMR (DMSO-$d_6$) δ 3.45 (s, 3H), 4.13 (s, 2H), 6.91 (d, J=8.1 Hz, 1H), 7.22–7.27 (m, 1H), 7.33–7.38 (m, 2H), 7.40–7.49 (m, 7H), 7.49–7.56 (m, 1H), 7.58–7.66 (m, 5H), 7.76 (d, J=8.6 Hz, 1H), 7.99 (d, J=7.9 Hz, 1H), 8.07 (d, J=8.1 Hz, 1H), 8.64 (s, 1H); IR (KBr) 3430, 3060, 2940, 1760, 1740, 1615, 1590, 1500, 1465, 1420, 1410, 1390, 1380, 1305, 1200, 1070, 1035, 755, 700, and 615 cm$^{-1}$; mass spectrum [EI], m/z 550 (M)$^+$; Anal. Calcd. for $C_{37}H_{26}O_3S.0.75H_2O$ C, 78.77; H, 4.91; N, 0.00, Found: C, 78.90; H, 4.65; N, 0.06.

Step 3 (5'-Benzo[b]naphtho[2,3-d]thiophen-11-yl-[1,1';3',1"]terphenyl-2'-yloxy)acetic Acid To a stirred solution of (5'-benzo[b]naphtho[2,3-d]thiophen-11-yl-[1,1';3',1"]terphenyl-2'-yloxy)acetic acid methyl ester (0.094 g, 0.171 mmol) in THF:MeOH (3:2, 5 mL) at room temperature was added dropwise 1 N KOH (0.861 mL, 0.861 mmol). After 2 h at this temperature, it was concentrated and diluted with H$_2$O. The solution was then acidified to pH 1 with 2 N HCl. The resulting solid was filtered off, washed with H$_2$O, and dried on the high vacuum for 18 h. This compound was recrystallized from MeOH to afford the product (0.063 g, 69%) as an off white solid, mp>136° C. (decomp.); $^1$H NMR (DMSO-$d_6$) δ 4.02 (s, 2H), 6.91 (d, J=7.9 Hz, 1H), 7.22–7.27 (m, 1H), 7.33–7.38 (m, 2H), 7.39–7.48 (m, 7H), 7.50–7.55 (m, 1H), 7.58–7.63 (m, 1H), 7.64–7.68 (m, 4H), 7.77 (d, J=8.6 Hz, 1H), 7.99 (d, J=7.9 Hz, 1H), 8.07 (d, J=8.1 Hz, 1H), 8.64 (s, 1H), 12.51–12.70 (bs, 1H); IR (KBr) 3410, 3070, 2910, 1735, 1680, 1610, 1500, 1465, 1420, 1395, 1385, 1325, 1210, 1165, 1070, 1040, 755, 735, and 700 cm$^{-1}$; mass spectrum [(+) FAB], m/z 537 (M+H)$^+$; Anal. Calcd. for $C_{36}H_{24}O_3S.0.5H_2O$: C, 79.24; H, 4.62; N, 0.00, Found: C, 78.98; H, 4.32; N, 0.02.

EXAMPLE 38

(5'-Nitro-[1,1';3',1"]terphenyl-2'-yloxy)-acetic Acid

Step 1 (5'-Nitro-[1,1';3',1"]terphenyl-2'-yloxy)acetic Acid Methyl Ester

To a stirred solution of 5'-nitro-[1,1';3',1"]terphenyl-2'-ol (0.250 g, 0.858 mmol) and K$_2$CO$_3$ (0.130 g, 0.944 mmol) in DMF (9 mL) at room temperature was added dropwise methyl bromoacetate (0.162 mL, 1.72 mmol). After 72 h at this temperature, it was diluted with H$_2$O (20 mL) followed by excess EtOAc (200 mL). The organic layer was washed with 1 N HCl (50 mL), sat. aq. NaHCO$_3$ (50 mL), and brine (50 mL) and then dried (MgSO$_4$). After concentration, the residue was purified by flash chromatography (5 to 30% acetone/hexane gradient) to afford the product (0.309 g, 99%) as a clear oil; $^1$H NMR (DMSO-$d_6$) δ 3.37 (s, 3H), 4.03 (s, 2H), 7.43–7.53 (m, 6H), 7.60–7.64 (m, 4H), 8.14 (s, 2H); IR (film) 3420, 3080, 2950, 1770, 1745, 1590, 1530, 1500, 1455, 1440, 1410, 1350, 1305, 1210, 1110, 1070, 910, 745, and 700 cm$^{-1}$; mass spectrum [EI], m/z 363 (M)$^+$; Anal. Calcd. for $C_{21}H_{17}NO_5.0.75H_2O$: C, 66.93; H, 4.95; N, 3.72, Found: C, 66.89; H, 4.67; N, 3.51.

Step 2 (5'-Nitro-[1,1';3',1"]terphenyl-2'-yloxy)-acetic Acid

The title compound was prepared as a white solid (0.229 g, 86%) from (5'-nitro-[1,1';3',1"]terphenyl-2'-yloxy)acetic acid methyl ester using a procedure similar to step 2 of Example 36, mp 153.5–156° C.; $^1$H NMR (DMSO-$d_6$) δ 3.92 (s, 2H), 7.42–7.52 (m, 6H), 7.61–7.65 (m, 4H), 8.13 (s, 2H), 12.15–13.20 (bs, 1H); IR (KBr) 3410, 3070, 2910, 2570, 1750, 1705, 1590, 1525, 1500, 1450, 1410, 1395, 1350, 1305, 1290, 1250, 1220, 1110, 1070, 910, 745, 725, and 710 cm$^{-1}$; mass spectrum [EI], m/z 349 (M)$^+$; Anal. Calcd. for $C_{20}H_{15}NO_5$: C, 68.76; H, 4.33; N, 4.01, Found: C, 68.66; H, 4.33; N, 3.89.

EXAMPLE 39

(5'-Methoxy-[1,1';3',1"]terphenyl-2'-yloxy)acetic Acid

Step 1 2,6-Dibromo-4-methoxyphenol

To a stirred solution of 4-methoxyphenol (0.500 g, 4.03 mmol) in CH$_2$Cl$_2$:MeOH (5:2, 70 mL) at room temperature was added BTMABr$_3$ (3.30 g, 8.46 mmol). After 18 h at this temperature, it was concentrated and diluted with EtOAc (150 mL) and H$_2$O (50 mL). The organic layer was washed with brine (50 mL) and then dried (MgSO$_4$). After concentration, the residue was purified by flash chromatography (2 to 12% EtOAc/petroleum ether gradient) and recrystallization from MeOH:H$_2$O (1:3) to afford the product (1.00 g, 88%) as a tan solid, mp 83–86° C.; $^1$H NMR (DMSO-d$_6$) δ 3.70 (s, 3H), 7.15 (s, 2H), 9.33 (s, 1H); IR (KBr) 3390, 2960, 2830, 1610, 1575, 1480, 1430, 1410, 1360, 1250, 1210, 1165, 1040, 845, 775, and 745 cm$^{-1}$; mass spectrum [EI], m/z 280 (M)$^+$; Anal. Calcd. for C$_7$H$_6$Br$_2$O$_2$: C, 29.82; H, 2.15; N, 0.00, Found: C, 30.04; H, 2.15; N, 0.00.

Step 2 5'-Methoxy-[1,1';3',1"]terphenyl-2'-ol

To a stirred solution of phenylboronic acid (0.0842 g, 0.691 mmol), Ba(OH)$_2$.8H$_2$O (0.396 g, 1.26 mmol), and Pd(OAc)$_2$ (0.0014 g, 0.00628 mmol) in DME:H$_2$O (6:1, 7 mL) at room temperature was added 2,6-dibromo-4-methoxyphenol (0.0885 g, 0.314 mmol)). The mixture was then heated at 80° C. for 18 h. The reaction was 50% complete, and an additional 2.2 eq. of phenylboronic acid and 0.02 eq. Pd(OAc)$_2$ were added and continued heating for another 24 h. At this point, the reaction was acidified to pH 1 with 1 N HCl and diluted with EtOAc (100 mL). The organic layer was washed with H$_2$O (10 mL) and brine (10 mL) and then dried (MgSO$_4$). After concentration, the residue was purified by flash chromatography (1 to 5% EtAOc/petroleum ether gradient) to afford the product (0.029 g, 33%) as a clear oil; $^1$H NMR (CDCl$_3$) δ 3.83 (s, 3H), 5.04 (s, 1H), 6.86 (s, 2H), 7.37–7.42 (m, 2H), 7.45–7.50 (m, 4H), 7.54–7.68 (m, 4H); IR (film) 3540, 3060, 2930, 2820, 1605, 1580, 1500, 1470, 1425, 1360, 1330, 1210, 1175, 1120, 1060, 1040, 1025, 755, 700, and 500 cm$^{-1}$; mass spectrum [EI], m/z 276 (M)$^+$; Anal. Calcd. for C$_{19}$H$_{16}$O$_2$.0.80H$_2$O: C, 78.49; H, 6.10; N, 0.00, Found: C, 78.19; H, 5.54; N, 0.19.

Step 3 (5'-Methoxy-[1,1';3',1"]terphenyl-2'-yloxy)acetic Acid Methyl Ester

The title compound was prepared as a solid (0.106 g, 99%) from 5'-methoxy-[1,1';3',1"]terphenyl-2'-ol using a procedure similar to step 1 of Example 36; $^1$H NMR (CDCl$_3$) δ 3.46 (s, 3H), 3.77 (s, 2H), 3.86 (s, 3H), 6.89 (s, 2H), 7.32–7.46 (m, 6H), 7.63 (d, J=8.3 Hz, 4H).

Step 4 (5'-Methoxy-[1,1';3',1"]terphenyl-2'-yloxy)acetic Acid

The title compound was prepared as a white solid (0.099 g, 91%) from (5'-methoxy-[1,1';3',1"]terphenyl-2'-yloxy) acetic acid methyl ester using a procedure similar to step 2 of Example 36, mp 143–145° C.; $^1$H NMR (DMSO-d$_6$) δ 3.65 (s, 2H), 3.80 (s, 3H), 6.89 (s, 2H), 7.33–7.39 (m, 2H), 7.39–7.45 (m, 4H), 7.57–7.61 (m, 4H), 12.40–12.46 (bs, 1H); IR (KBr) 3380, 3080, 2920, 2890, 2810, 1770, 1740, 1600, 1575, 1495, 1470, 1425, 1360, 1240, 1210, 1180, 1160, 1070, 1045, 755, and 700 cm$^{-1}$; mass spectrum [EI], m/z 334 (M)$^+$; Anal. Calcd. for C$_{21}$H$_{18}$O$_4$.0.25H$_2$O: C, 74.43; H, 5.50; N, 0.00, Found: C, 74.21; H, 5.49; N, 0.09.

EXAMPLE 40

(5'-Bromo-[1,1';3',1"]terphenyl-2'-yloxy)-acetic Acid

Step 1 4-Bromo-2,6-diiodophenol

To a stirred solution of 4-bromophenol (0.500 g, 2.89 mmol) and ground NaOH pellets (0.231 g, 5.78 mmol) in MeOH (18 mL) at 0° C. was added 12 (1.83 g, 7.23 mmol) portionwise over 1 h. After 2 h at this temperature, it was acidified to pH 1 with 2 N HCl and then further diluted with H$_2$O (50 mL). This aqueous solution was extracted with EtOAc (200 mL). The organic layer was washed with 10% aq. Na$_2$S$_2$O$_3$ (50 mL), H$_2$O (30 mL), and brine (30 mL) and then dried (MgSO$_4$). After concentration, the residue was purified by flash chromatography (2 to 10% EtOAc/petroleum ether gradient) to afford the product (0.525 g, 43%) as a solid, mp 122–124° C.; $^1$H NMR (CDCl$_3$) δ 5.74 (s, 1H), 7.79 (s, 2H).

Step 2 5'-Bromo-[1,1';3',1"]terphenyl-2'-ol

The title compound was prepared as a solid (0.081 g, 42%, product 1: bis-arylated) from 4-bromo-2,6-diiodophenol using a procedure similar to step 1 of Example 37; $^1$H NMR (CDCl$_3$) δ 5.37 (s, 1H), 7.34–7.58 (m, 12H); (for tris-arylated product—see step 1 of Example 41).

Step 3 (5'-Bromo-[1,1';3',1"]terphenyl-2'-yloxy)acetic Acid Methyl Ester

The tide compound was prepared as a solid (0.085 g, 96%) from 5'-bromo-[1,1';3',1"]terphenyl-2'-ol using a procedure similar to step 1 of Example 36; $^1$H NMR (CDCl$_3$) δ 3.47 (s, 3H), 3.80 (s, 2H), 7.34–7.50 (m, 8H), 7.59 (d, J=8.2 Hz, 4H).

Step 4 (5'-Bromo-[1,1';3',1"]terphenyl-2'-yloxy)acetic Acid

The title compound was prepared as a white solid (0.062 g, 83%) from (5'-bromo-[1,1';3',1"]terphenyl-2'-yloxy) acetic acid methyl ester using a procedure similar to step 2 of Example 36, mp>50° C. (decomp.); $^1$H NMR (CDCl$_3$) δ 3.81 (s, 2H), 7.38–7.50 (m, 7H), 7.52–7.56 (m, 5H); IR (KBr) 3400, 3050, 2900, 1730, 1565, 1495, 1460, 1420, 1210, 1060, 875, 735, 700, and 610 cm$^{-1}$; mass spectrum [(+) FAB], m/z 382 (M)$^+$, 405 (M+Na)$^+$; Anal. Calcd. for C$_{20}$H$_{15}$BrO$_3$: C, 62.68; H, 3.95; N, 0.00, Found: C, 62.25; H, 4.01; N, 0.01.

EXAMPLE 41

[(5'-Phenyl[1,1';3',1"-terphenyl]-2'-yl)oxy]acetic Acid

Step 1 5'-Phenyl[1,1';3',1"-terphenyl]-2'-ol

The title compound was prepared as a solid (0.055 g, 28%, product 2: tris-arylation) from 4-bromo-2,6-diiodophenol using the procedure to step 2 of Example 40; $^1$H NMR (CDCl$_3$) δ 5.45 (s, 1H), 7.27–7.57 (m, 11H), 7.62 (d, J=8.3 Hz, 6H).

Step 2 [(5'-Phenyl[1,1';3',1"-terphenyl]-2'-yl)oxy]acetic Acid

The title compound was prepared as a white solid (0.040 g, 72%) using 5'-phenyl[1,1';3',1"-terphenyl]-2'-ol and a procedure similar to steps 3 and 4 of Example 40, mp>68° C. (decomp.); $^1$H NMR (CDCl$_3$) δ 3.89 (s, 2H), 7.35–7.52 (m, 9H), 7.59 (s, 2H), 7.60–7.65 (m, 6H); IR (KBr) 3420, 3040, 2910, 1730, 1610, 1495, 1460, 1420, 1215, 1090, 880, 750, and 700 cm$^{-1}$; mass spectrum [(+) FAB], m/z 380 (M)$^+$, 403 (M+Na)$^+$; Anal. Calcd. for C$_{26}$H$_{20}$O$_3$.0.25H$_2$O: C, 81.12; H, 5.37; N, 0.00, Found: C, 80.94; H, 5.46; N, 0.03.

EXAMPLE 42

(1,3-Diphenyl-dibenzofuran-2-yloxy)-acetic Acid

Step 1 1,3-Dibromodibenzofuran-2-ol

The title compound was prepared as a tan solid (0.840 g, 91%) from 2-hydroxydibenzofuran using a procedure similar to step 1 of Example 39, mp 176–178° C.; $^1$H NMR (DMSO-d$_6$) δ 7.46 (td, J=0.88, 8.1 Hz, 1H), 7.58–7.63 (m, 1H), 7.72 (d, J=8.3 Hz, 1H), 8.05 (s, 1H), 8.44 (dt, J=0.44, 7.9 Hz, 1H), 9.85 (s, 1H); IR (KBr) 3420, 3110, 1630, 1460, 1425, 1375, 1340, 1230, 1170, 1150, 1120, 880, 860, 845, 745, and 715 cm$^{-1}$; mass spectrum [EI], m/z 340 (M)$^+$; Anal. Calcd. for C$_{12}$H$_6$Br$_2$O$_2$: C, 42.14; H, 1.77; N, 0.00, Found: C, 42.11; H, 1.74; N, 0.09.

Step 2 1,3-Diphenyldibenzofuran-2-ol

The title compound was prepared as a light yellow-orange solid (0.058 g, 59%) from 1,3-dibromodibenzofuran-2-ol using a procedure similar to step 2 of Example 39, mp>46° C. (decomp.); $^1$H NMR (CDCl$_3$) δ 5.14 (s, 1H), 6.99–7.08 (m, 2H), 7.35–7.44 (m, 2H), 7.48–7.68 (m, 11H); IR (KBr) 3530, 3060, 1600, 1500, 1460, 1450, 1420, 1320, 1260, 1220, 1160, 1130, 1070, 890, 800, 750, and 700 cm$^{-1}$; mass spectrum [EI], m/z 336 (M)$^+$; Anal. Calcd. for $C_{24}H_{16}O_2 \cdot 1.0H_2O$: C, 81.34; H, 5.12; N, 0.00, Found: C, 81.12; H, 4.79; N, −0.03.

Step 3 (1,3-Diphenyl-dibenzofuran-2-yloxy)acetic Acid Methyl Ester

The title compound was prepared as a solid (0.115 g, 79%) from 1,3-diphenyldibenzofuran-2-ol using a procedure similar to step 1 of Example 36; $^1$H NMR (CDCl$_3$) δ 3.46 (s, 3H), 3.86 (s, 2H), 7.00–7.15 (m, 2H), 7.30–7.77 (m, 13H).

Step 4 (1,3-Diphenyl-dibenzofuran-2-yloxy)acetic Acid

The title compound was prepared as a white solid (0.091 g, 88%) from (1,3-diphenyl-dibenzofuran-2-yloxy)acetic acid methyl ester using a procedure similar to step 2 of Example 36, mp>120° C. (decomp.); $^1$H NMR (DMSO-d$_6$) δ 3.66 (s, 2H), 6.80 (d, J=7.5 Hz, 1H), 7.09–7.15 (m, 1H), 7.33–7.39 (m, 1H), 7.39–7.47 (m, 3H), 7.48–7.56 (m, 5H), 7.68 (d, J=8.1 Hz, 1H), 7.70–7.74 (m, 3H); IR (KBr) 3420, 3070, 2950, 2910, 1730, 1610, 1500, 1465, 1455, 1405, 1330, 1310, 1240, 1220, 1175, 1155, 1070, 750, and 700 cm$^{-1}$; mass spectrum [EI], m/z 394 (M)$^+$; Anal. Calcd. for $C_{26}H_{18}O_4 \cdot 1.25H_2O$: C, 74.90; H, 4.96; N, 0.00, Found: C, 75.07; H, 4.89; N, 0.06.

EXAMPLE 43

(2-Benzoyl-4,6-dibromo-benzofuran-5-yloxy)acetic Acid

Step 1 Benzofuran-5-ol

To a stirred solution of 5-methoxybenzofuran (0.100 g, 0.675 mmol) in CH$_2$Cl$_2$ (10 mL) at −78° C. was added dropwise a 1.0 M solution of boron tribromide in CH$_2$Cl$_2$ (2.16 mL, 2.16 mmol). After 1 h at this temperature, it was warmed to room temperature and stirred an additional 18 h. At this point, the reaction was quenched with H$_2$O and diluted with EtOAc (50 mL). The organic layer was washed brine (10 mL) and then dried (MgSO$_4$). After concentration, the residue was purified by the Biotage Flash 40 apparatus (15 to 30% acetone/hexane gradient) to afford the product (0.064 g, 71%) as a waxy off white solid, mp 55–57° C.; $^1$H NMR (CDCl$_3$) δ 4.53–4.70 (bs, 1H), 6.67 (d, J=0.66, 2.0 Hz, 1H), 6.81 (dd, J=2.6, 8.8 Hz, 1H), 7.01 (d, J=2.4 Hz, 1H), 7.36 (d, J=8.8 Hz, 1H), 7.59 (d, J=2.2 Hz, 1H); IR (KBr) 3240, 2960, 1625, 1610, 1545, 1460, 1410, 1385, 1290, 1195, 1125, 1110, 1030, 865, 810, 765, 735, and 620 cm$^{-1}$; mass spectrum [EI], m/z 134 (M)$^+$; Anal. Calcd. for $C_8H_6O_2$: C, 71.63; H, 4.51; N, 0.00, Found: C, 71.19; H, 4.72; N, 0.05.

Step 2 2-Benzoylbenzofuran-5-ol

To a flamed dried round bottom flask with benzofuran-5-ol (0.100 g, 0.754 mmol) and THF (10.0 mL) cooled to −10° C. was added n-BuLi (0.684 mL, 2.5 M in hexane, 1.71 mmol) dropwise over a 10 min. period. The resulting solution was allowed to stir 10 min. while warming to −5° C. After cooling the mixture back down to −20° C., N-methoxy-N-methylbenzamide (0.125 mL, 0.820 mmol) was added dropwise. The solution was stirred at this temperature for 0.5 h and then warmed to room temperature for an additional 3 h. At this point, the reaction mixture was quenched with sat. aq. NH$_4$Cl (10 mL) and diluted with EtOAc (100 mL). The organic layer was washed with additional sat. aq. NH$_4$Cl (10 mL) and brine (10 mL) and then dried (MgSO$_4$). After concentration, the residue was purified by flash chromatography (10 to 30% EtOAc/ petroleum ether gradient) to afford the product (0.089 g, 50%) as a yellow powder, mp 159–160° C.; $^1$H NMR (DMSO-d$_6$) δ 7.02 (d, J=2.4, 8.8 Hz, 1H), 7.11 (d, J=2.4 Hz, 1H), 7.54–7.62 (m, 3H), 7.64 (d, J=0.66 Hz, 1H), 7.68–7.73 (m, 1H), 7.94–7.99 (m, 2H), 9.51 (s, 1H); IR (KBr) 3380, 2920, 1630, 1600, 1580, 1545, 1470, 1430, 1360, 1335, 1325, 1260, 1200, 1170, 1125, 980, 890, 860, 820, 725, and 630 cm$^{-1}$; mass spectrum [EI], m/z 238 (M)$^+$; Anal. Calcd. for $C_{15}H_{10}O_3 \cdot 0.25H_2O$: C, 74.22; H, 4.36; N, 0.00, Found: C, 73.99; H, 4.48; N, 0.13.

Step 3 (2-Benzoyl-4,6-dibromobenzofuran-5-yloxy)acetic Acid Methyl Ester

The title compound was prepared as a solid (0.072 g, 58%) using 2-benzoylbenzofuran-5-ol and a procedure similar to steps 1 and 3 of Example 39; $^1$H NMR (CDCl$_3$) δ 3.92 (s, 3H), 4.68 (s, 2H), 7.47 (s, 1H), 7.57 (t, J=9.3 Hz, 2H), 7.68 (t, J=9.3 Hz, 1H), 7.86 (s, 1H), 8.04 (d, J=8.5 Hz, 2H); mass spectrum [(+) ESI], m/z 469 (M+H)$^+$.

Step 4 (2-Benzoyl-4,6-dibromobenzofuran-5-yloxy)acetic Acid

The title compound was prepared as an off white solid (0.060 g, 88%) from (2-benzoyl-4,6-dibromobenzofuran-5-yloxy)acetic acid methyl ester using a procedure similar to step 2 of Example 36, mp 179–181° C.; $^1$H NMR (DMSO-d$_6$) δ 4.54 (s, 2H), 7.58 (d, J=0.88 Hz, 1H), 7.60–7.65 (m, 2H), 7.74 (tt, J=1.3, 6.8 Hz, 1H), 7.99–8.03 (m, 2H), 8.31 (d, J=0.88 Hz, 1H), 12.98–13.32 (bs, 1H); IR (KBr) 3420, 3080, 2910, 2580, 1740, 1645, 1610, 1540, 1440, 1410, 1330, 1290, 1250, 1175, 1125, 1070, 1000, 970, 915, 860, 800, 715, and 675 cm$^{-1}$; mass spectrum [(−) ESI], m/z 451 (M−H)$^-$; Anal. Calcd. for $C_{17}H_{10}Br_2O_5$: C, 44.97; H, 2.22; N, 0.00, Found: C, 44.71; H, 2.13; N, 0.04.

EXAMPLE 44

(5'-Butoxy-[1,1';3',1"]terphenyl-2'-yloxy)acetic Acid

Step 1 3,5-Diiodo-4-methoxyethoxymethoxybenzaldehyde

To a stirred solution of 3,5-diiodo-4-hydroxybenzaldehyde (10.0 g, 26.7 mmol) in THF (267 mL) at 0° C. was added NaH (1.39 g, 34.7 mmol). After 0.5 h at this temperature, MEMCl (4.88 mL, 42.7 mmol) was added dropwise. The reaction mixture was stirred for another 15 min. at 0° C. and then at room temperature for 18 h. The resulting mixture was quenched with 0.1 N NaOH and extracted with Et$_2$O (1000 mL). The organic layer was washed with 0.1 N NaOH (3×100 mL) and brine (100 mL) and then dried (MgSO$_4$). After concentration, the residue was purified by flash chromatography (5 to 15% EtOAc/ petroleum ether gradient) to afford the product (8.60 g, 69%) as a solid; $^1$H NMR (CDCl$_3$) δ 3.44 (s, 3H), 3.67 (t, J=5.5 Hz, 2H), 4.16 (t, J=5.5 Hz, 2H), 5.34 (s, 2H), 8.29 (s, 2H), 9.82 (s, 1H).

Step 2 2'-Methoxyethoxymethoxy-[1,1';3',1"]terphenyl-5'-carboxaldehyde

The title compound was prepared as a solid (0.995 g, 84%) from 3,5-diiodo-4-methoxyethoxymethoxybenzaldehyde using a procedure similar to step 1 of Example 37; $^1$H NMR (CDCl$_3$) δ 2.83–2.90 (m, 2H), 2.93–2.99 (m, 2H), 3.17 (s, 3H), 4.52 (s, 2H), 7.33–7.49 (m, 6H), 7.62 (d, J=8.3 Hz, 4H), 7.90 (s, 2H), 10. 06 (s, 1H).

Step 3 2'-Methoxyethoxymethoxy-[1,1';3',1"]terphenyl-5'-ol

To a stirred solution of 2'-methoxyethoxymethoxy-[1, 1';3',1"]terphenyl-5'-carboxaldehyde (0.836 g, 2.31 mmol) in CH$_2$Cl$_2$ (25 mL) at room temperature was added MCPBA (0.598 g, 3.46 mmol). The reaction mixture was refluxed for 48 h. After concentration, the residue was dissolved in EtOAc (300 mL). The organic layer 15 was washed with sat. aq. NaHCO$_3$ until effervescence ceased followed brine (30 mL) and then dried (Na$_2$SO$_4$). After concentration, the residue was dissolved in THF:MeOH (3:2, 45 mL) followed by the dropwise addition of 1 N KOH (11.6 mL, 11.6 mmol). The reaction mixture was stirred at room temperature for 1.5 h and then concentrated. The residue was diluted with H$_2$O (30 mL) and then acidified to pH 4 with 1 N HCl followed by extraction with EtOAc (300 mL). This organic layer was washed with brine (30 mL) and then dried (MgSO$_4$). After concentration, the residue was purified by the Biotage Flash 40 apparatus (5 to 15% acetone/hexane gradient) to afford the product (0.490 g, 61%) as a solid; $^1$H NMR (CDCl$_3$) δ 2.73–2.86 (m, 2H), 2.90–2.98 (m, 2H), 3.17 (s, 3H), 4.35 (s, 2H), 4.67 (s, 1H), 6.82 (s, 2H), 7.27–7.47 (m, 6H), 7.57 (d, J=9.3 Hz, 4H); mass spectrum [(+) ESI], m/z 373 (M+Na)$^+$.

Step 4 (2'-Methoxyethoxymethoxy-[1,1';3',1"]terphenyl-5'-yloxy)butane

To a stirred solution of 2'-methoxyethoxymethoxy-[1, 1';3',1"]terphenyl-5'-ol (0.240 g, 0.685 mmol) in DMF (10 mL) at room temperature was added K$_2$CO$_3$ (0.123 g, 0.890 mmol) followed by dropwise addition of 1-bromobutane (0.147 mL, 1.37 mmol). The reaction mixture was then heated to 60° C. After 4 days at this temperature, the resulting solution was diluted with H$_2$O (10 mL) and excess EtOAc (100 mL). The organic layer was washed with 1 N HCl (10 mL), sat. aq. NaHCO$_3$ (10 mL), and brine (10 mL) and then dried (MgSO$_4$). After concentration, the residue was purified by preparatory plate chromatography (20% EtOAc/petroleum ether) to afford the product (0.257 g, 92%) as a solid; $^1$H NMR (CDCl$_3$) δ 0.97 (t, J=8.1 Hz, 3H), 1.46–1.57 (m, 2H), 1.72–1.82 (m, 2H), 2.80 (t, J=5.6 Hz, 2H), 2.95 (t, J=5.6 Hz, 2H), 3.17 (s, 3H), 3.99 (t, J=6.9 Hz, 2H), 4.37 (s, 2H), 6.87 (s,;2H), 7.28–7.46 (m, 6H), 7.58 (d, J=7.5 Hz, 4H); mass spectrum [(+) ESI], m/z 429 (M+Na)$^+$.

Step 5 5'-Butoxy-[1,1';3',1"]terphenyl-2'-ol

To a stirred solution of (2'-methoxyethoxymethoxy-[1, 1';3',1"]terphenyl-5'-yloxy)butane (0.237 g, 0.583 mmol) in CH$_2$Cl$_2$ (6 mL) at room temperature was added anhydrous ZnBr$_2$ (0.656 g, 2.92 mmol). After 18 h at this temperature, the resulting mixture was diluted with EtOAc (100 mL). The organic layer was washed with sat. aq. NaHCO$_3$ (10 mL) and brine (10 mL) and then dried (MgSO$_4$). After concentration, the residue was purified by preparatory plate chromatography (10% EtOAc/petroleum ether) to afford the product (0.172 g, 92%) as a solid; $^1$H NMR (CDCl$_3$) δ 0.97 (t, J=10.9 Hz, 3H), 1.39–1.60 (m, 2H), 1.68–1.87 (m, 2H), 3.97 (t, J=9.5 Hz, 2H), 5.05 (s, 1H), 6.87 (s, 2H), 7.32–7.62 (m, 10H); mass spectrum [(+) ESI], m/z 319 (M+H)$^+$, 341 (M+Na)$^+$.

Step 6 (5'-Butoxy-[1,1';3',1"]terphenyl-2'-yloxy)acetic Acid Methyl Ester

The title compound was prepared as a solid (0.203 g, 96%) from 5'-butoxy-[1,1';3',1"]terphenyl-2'-ol using a procedure similar to step 1 of Example 36; $^1$H NMR (CDCl$_3$) δ 0.98 (t, J=10.7 Hz, 3H), 1.41–1.62 (m, 2H), 1.68–1.89 (m, 2H), 3.46 (s, 3H), 3.77 (s, 2H), 4.00 (t, J=9.3 Hz, 2H), 6.89 (s, 2H), 7.28–7.48 (m, 6H), 7.63 (d, J=8.6 Hz, 4H); mass spectrum [(+) ESI], m/z 391 (M+H)$^+$, 413 (M+Na)$^+$.

Step 7 (5'-Butoxy-[1,1';3',1"]terphenyl-2'-yloxy)acetic Acid

The title compound was prepared as an off white solid (0.167 g, 85%) from (5'-butoxy-[1,1';3',1"]terphenyl-2'-yloxy)acetic acid methyl ester using a procedure similar to step 2 of Example 36, mp 92–94° C.; $^1$H NMR (DMSO-d$_6$) δ 0.92 (t, J=7.5 Hz, 3H), 1.38–1.49 (m, 2H), 1.65–1.74 (m, 2H), 3.64 (s, 2H), 4.02 (t, J=6.6 Hz, 2H), 6.87 (s, 2H), 7.33–7.39 (m, 2H), 7.39–7.44 (m, 4H), 7.57–7.61 (m, 4H), 12.30–12.55 (bs, 1H); IR (KBr) 3420, 3060, 2930, 2860, 2770, 2590, 1725, 1590, 1570, 1460, 1420, 1360, 1260, 1235, 1215, 1195, 1075, 1050, 1010, 925, 760, 750, 700, and 620 cm$^{-1}$; mass spectrum [(+) ESI], m/z 394 (M+NH$_4$)$^+$; Anal. Calcd. for C$_{24}$H$_{24}$O$_4$: C, 76.57; H, 6.43; N, 0.00, Found: C, 76.33; H, 6.55; N, −0.04.

EXAMPLE 45

(5'-Octyloxy-[1,1';3',1"]terphenyl-2'-yloxy)acetic Acid

Step 1 (2'-Methoxyethoxymethoxy-[1,1';3',1"]terphenyl-5'-yloxy)octane

The title compound was prepared as a solid (0.305 g, 97%) from 2'-methoxyethoxymethoxy-[1,1';3',1"]terphenyl-5'-ol using a procedure similar to step 4 of Example 44; $^1$H NMR (CDCl$_3$) δ 0.87 (t, J=7.7 Hz, 3H), 1.22–1.53 (m, 10H), 1.72–1.96 (m, 2H), 2.81 (t, J=5.8 Hz, 2H), 2.96 (t, J=5.8 Hz, 2H), 3.16 (s, 3H), 3.98 (t, J=7.0 Hz, 2H), 4.36 (s, 2H), 6.88 (s, 2H), 7.27–7.46 (m, 6H), 7.59 (d, J=7.7 Hz, 4H); mass spectrum [(+) ESI], m/z 485 (M+Na)$^+$.

Step 2 (5'-Octyloxy-[1,1';3',1"]terphenyl-2'-yloxy)acetic Acid

The title compound was prepared as a white solid (0.130 g, 52%) from (2'-methoxyethoxymethoxy-[1,1';3',1"]terphenyl-5'-yloxy)octane using a procedure similar to steps 5–7 of Example 44, mp 82–84° C.; $^1$H NMR (DMSO-d$_6$) δ 0.84 (t, J=7.0 Hz, 3H), 1.20–1.35 (m, 8H), 1.35–1.45 (m, 2H), 1.65–1.74 (m, 2H), 3.64 (s, 2H), 4.01 (t, J=6.6 Hz, 2H), 6.86 (s, 2H), 7.33–7.38 (m, 2H), 7.39–7.44 (m, 4H), 7.56–7.60 (m, 4H), 12.28–12.64 (bs, 1H); IR (KBr) 3420, 3060, 2920, 2850, 2580, 1725, 1620, 1460, 1420, 1360, 1265, 1220, 1200, 1095, 1050, 1030, 860, 845, 750, and 700 cm$^{-1}$; mass spectrum [(+) ESI], m/z 450 (M+NH$_4$)$^+$; Anal. Calcd. for C$_{28}$H$_{32}$O$_4$: C, 77.75; H, 7.46; N, 0.00, Found: C, 77.37; H, 7.47; N, −0.03.

EXAMPLE 46

(3,3"-Dichloro-5'-octyloxy-[1,1';3',1"]terphenyl-2'-yloxy)acetic Acid

The title compound was prepared as a white solid (0.233 g, 39%) from 3,5-diiodo-4-hydroxybenzaldehyde using 3-chlorophenylboronic acid and procedures similar to Examples 44 and 45, mp 113–115.5° C.; $^1$H NMR (DMSO-d$_6$) δ 0.84 (t, J=7.0 Hz, 3H), 1.20–1.36 (m, 8H), 1.36–1.45 (m, 2H), 1.66–1.74 (m, 2H), 3.67 (s, 2H), 4.03 (t, J=6.4 Hz, 2H), 6.94 (s, 2H), 7.41–7.48 (m, 4H), 7.56 (dt, J=2.0, 6.6 Hz, 2H), 7.65–7.68 (m, 2H), 12.45–12.66 (bs, 1H); IR (KBr) 3420, 2920, 2860, 2590, 1720, 1590, 1560, 1475, 1460, 1425, 1395, 1350, 1320, 1270, 1240, 1200, 1150, 1070, 1050, 860, 780, and 695 cm$^{-1}$; mass spectrum [EI], m/z 500 (M)$^+$; Anal. Calcd. for C$_{28}$H$_{30}$Cl$_2$O$_4$: C, 67.07; H, 6.03; N, 0.00, Found: C, 67.07; H, 6.16; N, 0.10.

EXAMPLE 47

(3,3"-Bis-acetylamino-5'-octyloxy-[1,1';3',1"]terphenyl-2'-yloxy)acetic Acid

The title compound was prepared as a tan solid (0.065 g, 7%) from 3,5-diiodo-4-hydroxybenzaldehyde using 3-acetamidobenzeneboronic acid and procedures similar to Examples 44 and 45, mp>100° C. (decomp.); $^1$H NMR (DMSO-d$_6$) δ 0.86 (t, J=6.8 Hz, 3H), 1.23–1.37 (m, 8H), 1.37–1.46 (m, 2H), 1.68–1.76 (m, 2H), 2.06 (s, 6H), 3.72 (s, 2H), 4.01 (t, J=6.4 Hz, 2H), 6.83 (s, 2H), 7.24 (d, J=7.7 Hz, 2H), 7.33 (t, J=7.7 Hz, 2H), 7.64 (d, J=8.1 Hz, 2H), 7.72 (d, J=1.8 Hz, 2H), 10.01 (s, 2H), 12.33–12.61 (bs, 1H); IR (KBr) 3320, 2930, 2860, 1740, 1670, 1585, 1555, 1485, 1455, 1420, 1375, 1360, 1320, 1250, 1200, 1075, 860, 785, 710, and 540 cm$^{-1}$; mass spectrum [(+) ESI], m/z 547

(M+H)⁺, 564 (M+NH₄)⁺; Anal. Calcd. for C₃₂H₃₈N₂O₆.0.5H₂O: C, 69.17; H. 7.07; N, 5.04, Found: C, 69.34; H, 7.19; N, 4.78.

EXAMPLE 48

(5'-Octyloxy-3,3''-bis-trifluoromethyl-[1,1';3',1''] terphenyl-2'-yloxy)acetic Acid The title compound was prepared as a white solid (0.136 g, 16%) from-3,5-diiodo-4-hydroxybenzaldehyde using 3-(trifluoromethyl)phenylboronic acid and procedures similar to Examples 44 and 45, mp 75–77° C.; ¹H NMR (CDCl₃) δ 0.88 (t, J=6.8 Hz, 3H), 1.23–1.41 (m, 8H), 1.43–1.52 (m, 2H), 1.76–1.85 (m, 2H), 3.75 (s, 2H), 4.01 (t, J=6.6 Hz, 2H), 6.91 (s, 2H), 7.57 (t, J=7.9 Hz, 2H), 7.65 (d, J=7.9 Hz, 2H), 7.80 (d, J=7.7 Hz, 2H), 7.85 (s, 2H); IR (KBr) 3440, 2930, 2860, 2690, 2580, 1725, 1605, 1590, 1470, 1440, 1410, 1370, 1335, 1270, 1245, 1210, 1170, 1125, 1090, 1070, 1045, 910, 800, and 710 cm⁻¹; mass spectrum [(–) ESI], m/z 567 (M–H)⁻; Anal. Calcd. for C₃₀H₃₀F₆O₄: C, 63.38; H, 5.32; N, 0.00, Found: C, 63.41; H, 5.47; N, 0.00.

EXAMPLE 49

(3,3''-Dinitro-5'-octyloxy-[1,1';3',1'']terphenyl-2'-yloxy)acetic Acid

The title compound was prepared as an off white solid (0.143 g, 20%) from 3,5-diiodo-4-hydroxybenzaldehyde using 3-nitrophenylboronic acid and procedures similar to Examples 44 and 45, mp 129–132° C.; ¹H NMR (DMSO-d₆) δ 0.86 (t, J=7.0 Hz, 3H), 1.24–1.38 (m, 8H), 1.38–1.48 (m, 2H), 1.69–1.78 (m, 2H), 3.70 (s, 2H), 4.08 (t, J=6.4 Hz, 2H), 7.11 (s, 2H), 7.75 (t, J=8.1 Hz, 2H), 8.09 (dt, J=1.3, 7.9 Hz, 2H), 8.26 (ddd, J=0.88, 2.4, 8.3 Hz, 2H), 8.47 (t, J=2.0 Hz, 2H), 12.43–12.58 (bs, 1H); IR (KBr) 3420, 3220, 3120, 2940, 2860, 1745, 1670, 1600, 1570, 1530, 1460, 1410, 1350, 1310, 1235, 1205, 1080, 1070, 865, 815, 735, 720, and 695 cm⁻¹; mass spectrum [(–) ESI], m/z 521 (M–H)⁻; Anal. Calcd. for C₂₈H₃₀N₂O₈.0.25H₂O: C, 63.81; H, 5.83; N, 5.32, Found: C, 63.90; H, 5.73; N, 5.24.

EXAMPLE 50

(3,3''-Dimethoxy-5'-octyloxy-[1,1';3',1'']terphenyl-2'-yloxy)acetic Acid

The title compound was prepared as a clear oil (0.191 g, 35%) from 3,5-diiodo-4-hydroxybenzaldehyde using 3-methoxyphenylboronic acid and procedures similar to Examples 44 and 45; ¹H NMR (DMSO-d₆) δ 0.84 (t, J=7.0 Hz, 3H), 1.21–1.35 (m, 8H), 1.35–1.45 (m, 2H), 1.66–1.75 (m, 2H), 3.71 (s, 2H), 3.78 (s, 6H), 4.01 (t, J=6.6 Hz, 2H), 6.87 (s, 2H), 6.92 (dd, J=2.4, 8.1 Hz, 2H), 7.11–7.17 (m, 4H), 7.33 (t, J=7.9 Hz, 2H), 12.45–12.55 (bs, 1H); IR (film) 2930, 2880, 2590, 1730, 1595, 1495, 1465, 1415, 1360, 1300, 1240, 1200, 1075, 1050, 870, 780, 750, 710, and 500 cm⁻¹; mass spectrum [(–) ESI], m/z 491 (M–H)⁻; Anal. Calcd. for C₃₀H₃₆O₆.0.5H₂O: C, 71.83; H, 7.43; N, 0.00, Found: C, 72.17; H, 7.58; N, 0.05.

EXAMPLE 51

[3,3''-Dichloro-5'-(3-phenyl-propylcarbamoyl)-[1, 1';3'1'']terphenyl-2'-yloxy]acetic Acid
Step 1 N-(3-Phenylpropyl)-3,5-bis(m-chlorophenyl)-4-(2-hydroxyethoxy)-benzamide To a flamed dried round bottom flask with 3-phenyl-1-propylamine (0.404 mL, 2.84 mmol) and THF (5 mL) cooled to –78° C. was added n-BuLi (1.14 mL, 2.5 M in hexane, 2.84 mmol) dropwise over a 5 min. period. The resulting solution was stirred at this temperature for 0.5 h, warmed to 0° C. for 10 min., and then cooled back to –40° C. This lithiated amine solution was added dropwise to a solution (at –40° C.) of 3,5-bis-(m-chlorophenyl)-4-(2-hydroxyethoxy)benzoic acid ethyl ester (0.350 g, 0.811 mmol) in THF (15 mL) over 5 min. The final mixture was stirred at 40° C. for 15 min. and then warmed to room temperature for 15 min. At this point, the reaction mixture was quenched with H₂O (20 mL) and diluted with EtOAc (200 mL). The organic layer was washed with 1 N HCl (20 mL), sat. aq. NaHCO₃ (20 mL), and brine (20 mL) and then dried (MgSO₄). After concentration, the residue was purified by the Biotage Flash 40 apparatus (20 to 40% EtOAc/hexane gradient) to afford the product (0.347 g, 82%) as a solid; ¹H NMR (CDCl₃) δ 1.44–1.68 (bs, 1H), 2.01 (t, J=7.0 Hz, 2H), 2.74 (t, J=7.7 Hz, 2H), 3.27–3.46 (m, 4H), 3.53 (dd, J=7.7, 14.7 Hz, 2H), 5.94–6.08 (bs, 1H), 7.02–7.13 (m, 1H), 7.13–7.33 (m, 4H), 7.33–7.46 (m, 4H), 7.46–7.54 (m, 2H), 7.61 (s, 4H); mass spectrum [(+) APCI], m/z 520/522 (M+H)⁺.
Step 2 [3,3''-Dichloro-5'-(3-phenyl-propylcarbamoyl)-[1, 1';3'1'']terphenyl-2'-yloxy]acetic Acid To a stirred solution of N-(3-phenylpropyl)-3,5-bis(m-chlorophenyl)-4-(2-hydroxyethoxy)benzamide (0.330 g, 0.634 mmol) in CH₃CN (6 mL) at room temperature was added NMMO (0.149 g, 1.27 mmol) followed by TPAP (0.022 g, 0.0634 mmol). After 2 h, the reaction mixture still showed presence of intermediate aldehyde. Another 0.3 eq. of NMMO (0.022 g) and 0.015 eq. TPAP (0.003 g) was added, and the reaction was stirred for an additional 1 h. The mixture was quenched with 1 N HCl (2 mL) followed by aq. 10% NaHSO₃ (15 mL). After stirring for ~10 min., the mixture was diluted with EtOAc (100 mL). The resulting organic layer was washed with 1 N HCl (10 mL), sat. aq. NaHCO₃ (10 mL) and brine (10 mL) and then dried (MgSO₄). After concentration, the residue was purified by preparatory plate chromatography (10% MeOH/CHCl₃) to afford the product (0.135 g, 40%) as a gray solid, mp>79° C. (decomp.); ¹H NMR (DMSO-d₆) δ 1.79–1.87 (m, 2H), 2.62 (t, J=7.5 Hz, 2H), 3.27–3.35 (m, 2H), 3.77–3.83 (m, 2H), 7.13–7.18 (m, 1H), 7.19–7.23 (m, 2H), 7.24–7.29 (m, 2H), 7.44–7.51 (m, 4H), 7.56–7.60 (m, 2H), 7.68–7.70 (m, 2H), 7.86 (s, 2H), 8.49 (t, J=5.5 Hz, 1H), 11.90–13.20 (bs, 1H); IR (KBr) 3430, 3080, 3020, 2920, 2320, 1735, 1635, 1620, 1570, 1545, 1470, 1450, 1425, 1390, 1350, 1210, 1080, 1055, 875, 755, and 700 cm⁻¹; mass spectrum [(–) ESI], m/z 532/534/536 (M–H)⁻; Anal. Calcd. for C₃₀H₂₅Cl₂NO₄.H₂O: C, 65.22; H, 4.93; N, 2.54, Found: C, 65.33; H, 4.43; N, 2.61.

EXAMPLE 52

[3,3''-Dichloro-5'-(2-pyridin-2-yl-ethylcarbamoyl)-[1,1';3'1'']terphenyl-2'-yloxy]acetic Acid The title compound was prepared as an off white solid (0.128 g, 32%) from 3,5-bis-(m-chlorophenyl)-4-(2-hydroxyethoxy)benzoic acid ethyl ester using 2-(2-aminoethyl)pyridine and a procedure similar to Example 51, mp>94° C. (decomp.); ¹H NMR (DMSO-d₆) δ 3.01 (t, J=7.5 Hz, 2H), 3.64 (dd, J=6.6, 14.3 Hz, 2H), 3.82 (s, 2H), 7.22 (ddd, J=0.9, 4.8, 7.5 Hz, 1H), 7.28 (d, J=7.9 Hz, 1H), 7.46–7.53 (m, 4H), 7.58–7.62 (m, 2H), 7.68–7.73 (m, 3H), 7.85 (s, 2H), 8.51 (ddd, J=0.9, 1.8, 4.8 Hz, 1H), 8.72 (t, J=5.9 Hz, 1H), 11.70–13.15 (bs, 1H); IR (KBr) 3440, 3090, 2920, 2350, 2340, 1725, 1640, 1610, 1570, 1550, 1475, 1450, 1435, 1400, 1300, 1320, 1245, 1210, 1170, 1100, 1080, 1050, 880, 760, and 700 cm$^{-1}$; mass spectrum [(−) ESI], m/z 519/521/523 (M−H)$^-$; Anal. Calcd. for $C_{28}H_{22}Cl_2N_2O_4 \cdot 2.0H_2O$: C, 60.33; H, 4.70; N, 5.03, Found: C, 60.06; H, 3.98; N, 4.84.

EXAMPLE 53

[5'-(Benzyl-phenethyl-carbamoyl)-3,3"-Dichloro-[1,1';3'1"]terphenyl-2'-yloxy]acetic Acid The title compound was prepared as an off white foamy solid (0.181 g, 37%) from 3,5-bis-(m-chlorophenyl)-4-(2-hydroxyethoxy)benzoic acid ethyl ester using N-benzyl-2-phenethylamine and a procedure similar to Example 51, mp>67° C. (decomp.);, $^1$H NMR (DMSO-d$_6$) δ 2.73–2.98 (m, 2H), 3.16–3.67. (m, 2H), 3.67–3.80 (m, 2H), 4.42–4.87 (m, 2H), 6.86–6.93 (m, 1H), 6.98–7.14 (m, 3H), 7.14–7.32 (m, 6H), 7.32–7.64 (m, 10H), 12.30–13.40 (bs, 1H); IR (KBr) 3420, 3070, 3020, 2920, 2320, 2300, 1750, 1730, 1630, 1600, 1570, 1475, 1450, 1430, 1400, 1370, 1350, 1240, 1210, 1150, 1090,1075, 1025, 875, 780, 750, 730, and 705 cm$^{-1}$; mass spectrum [(−) ESI], m/z 608/610/612 (M−H)$^-$; Anal: Calcd. for $C_{36}H_{29}Cl_2NO_4 \cdot 2.0H_2O$: C, 66.88; H, 5.14; N, 2.17, Found: C, 66.41; H, 4.50; N, 2.28.

EXAMPLE 54

[3,3"-Dichloro-5'-(4-phenyl-butylcarbamoyl)-[1,1';3'1"]terphenyl-2'-yloxy]acetic Acid The title compound was prepared as an off white solid (0.128 g, 48%) from 3,5-bis-(m-chlorophenyl)-4-(2-hydroxyethoxy)benzoic acid ethyl ester using 4-phenylbutylamine and a procedure similar to Example 51, mp>164° C. (decomp.); $^1$H NMR (DMSO-d$_6$) δ 1.48–1.65 (m, 4H), 2.59 (t, J=7.2 Hz, 2H), 3.29 (dd, J=6.6, 12.5 Hz, 2H), 3.79 (s, 2H), 7.12–7.20 (m, 3H), 7.22–7.27 (m, 2H), 7.43–7.50 (m, 4H), 7.56–7.60 (m, 2H), 7.68 (s, 2H), 7.85 (s, 2H), 8.57 (t, J=5.7 Hz, 1H), 12.25–13.25 (bs, 1H); IR (KBr) 3420, 3080, 3020, 2930, 2820, 2320, 1735, 1635, 1620, 1570, 1560, 1475, 1455, 1420, 1390, 1360, 1330, 1245, 1215, 1100, 1080, 1050, 890, 810, 780, 755, and 700 cm$^{-1}$; mass spectrum [(−) ESI], m/z 546/548/550 (M−H)$^-$; Anal. Calcd. for $C_{31}H_{27}Cl_2NO_4 \cdot H_2O$: C, 65.73; H, 5.16; N, 2.47, Found: C, 65.53; H, 4.40; N, 2.59.

EXAMPLE 55

[5-(Benzyl-phenethyl-carbamoyl)-3-bromo-3'-chloro-biphenyl-2-yloxy]acetic Acid

The title compound was prepared as an off white glass (0.043 g, 12%) from 3-bromo-5-(m-chlorophenyl)-4-(2-hydroxyethoxy)benzoic acid ethyl ester using N-benzyl-2-phenethylamine and a procedure similar to Example 51, mp>72° C. (decomp.); $^1$H NMR (DMSO-d$_6$) δ 2.74–2.96 (m, 2H), 3.20–3.63 (m, 2H), 3.94–4.05 (m, 2H); 4.40–4.84 (m, 2H), 6.90–7.62 (m, 16H), 12.50–13.85 (bs, 1H); IR (KBr) 3440, 3070, 3020, 2920, 2320, 1755, 1725, 1630, 1600, 1475, 1450, 1420, 1370, 1330, 1220, 1190, 1080, 1030, 885, 755, and 700 cm$^{-1}$; mass spectrum [(−) ESI], m/z 576/578/580 (M−H)$^-$; Anal. Calcd. for $C_{30}H_{25}BrClNO_4 \cdot 2.5H_2O$: C, 57.75; H, 4.85; N, 2.24, Found: C, 57.45; H, 3.85; N, 2.23.

EXAMPLE 56

[3-Bromo-3'-chloro-5-(2-pyridin-2-yl-ethylcarbamoyl)-biphenyl-2-yloxy]acetic Acid The title compound was prepared as a white solid (0.028 g, 9%) from 3-bromo-5-(m-chlorophenyl)-4-(2-hydroxyethoxy)benzoic acid ethyl ester using 2-(2-aminoethyl)pyridine and a procedure similar to Example 51, mp>102° C. (decomp.); $^1$H NMR (DMSO-d$_6$) δ 3.00 (t, J=7.5 Hz, 2H), 3.63 (dd, J=7.5, 13.6 Hz, 2H), 4.02 (s, 2H), 7.23 (dd, J=6.3, 9.0 Hz, 1H), 7.28 (d, J=7.9 Hz, 1H), 7.47–7.51 (m, 2H), 7.55–7.60 (m, 1H), 7.67 (s, 1H), 7.71 (td, J=1.8, 9.6 Hz, 1H), 7.83 (d, J=2.2 Hz, 1H), 8.08 (d, J=2.2 Hz, 1H), 8.50–8.53 (m, 1H), 8.73 (t, J=7.7 Hz, 1H), 11.80–13.30 (bs, 1H); IR (KBr) 3430, 3080, 2910, 2330, 1725, 1635, 1605, 1560, 1480, 1450, 1420, 1370, 1330, 1225, 1190, 1140, 1120, 1080, 1030, 890, 755, and 700 cm$^{-1}$; mass spectrum [(+) ESI], m/z 489/491 (M+H)$^+$; Anal. Calcd. for $C_{22}H_{18}BrClN_2O_4 \cdot 0.6CHCl_3$: C, 48.35; H, 3.34; N, 4.99, Found: C, 47.99; H, 3.30; N, 4.87.

EXAMPLE 57

[5'-(Benzyl-phenethyl-carbamoyl)-3"-chloro-3-trifluoromethyl-[1,1';3'1"]-terphenyl-2'-yloxy]acetic Acid The title compound was prepared as an off white glass (0.089 g, 29%) from 3-(m-chlorophenyl)-4-(2-hydroxyethoxy)-5-(m-trifluoromethylphenyl)-benzoic acid ethyl ester using N-benzyl-2-phenethylamine and a procedure similar to Example 51, mp>75° C. (decomp.); $^1$H NMR (DMSO-d$_6$) δ 2.77–2.98 (m, 2H), 3.25–3.67 (m, 2H), 3.70–3.80 (m, 2H), 4.45–4.85 (m, 2H), 6.87–7.92 (m, 20H), 12.45–13.05 (bs, 1H); IR (KBr) 3430, 3070, 3020, 2920, 1755, 1740, 1635, 1610, 1495, 1475, 1450, 1425, 1365, 1330, 1290, 1240, 1210, 1170, 1130, 1100, 1080, 1030, 890, 800, 755, and 700 cm$^{-1}$; mass spectrum [(−) ESI], m/z 642/644 (M−H)$^-$; Anal. Calcd. for $C_{37}H_{29}ClF_3NO_4 \cdot 1.5H_2O$: C, 66.22; H, 4.81; N, 2.09, Found: C, 66.07; H, 4.19; N, 2.10.

EXAMPLE 58

[3"-Chloro-5'-(2-pyridin-2-yl-ethylcarbamoyl)-3-trifluoromethyl-[1,1';3'1"]-terphenyl-2'-yloxy]acetic Acid The title compound was prepared as a light brown glass (0.075 g, 29%) from 3-(m-chlorophenyl)-4-(2-hydroxyethoxy)-5-(m-trifluoromethylphenyl)-benzoic acid ethyl ester using 2-(2-aminoethyl)pyridine and a procedure similar to Example 51, mp>92° C. (decomp.); $^1$H NMR (DMSO-d$_6$) δ 3.01 (t, J=7.7 Hz, 2H), 3.64 (dd, J=6.6, 13.0 Hz, 2H), 3.78 (s, 2H), 7.22 (ddd, J=0.9, 4.8, 7.5 Hz, 1H), 7.28 (d, J=7.9 Hz, 1H), 7.46–7.53 (m, 2H), 7.59–7.62 (m, 1H), 7.67–7.74 (m, 3H), 7.77 (d, J=7.9 Hz, 1H), 7.87 (dd, J=2.2, 5.1 Hz, 2H), 7.94 (d, J=7.9 Hz, 1H), 7.98 (s, 1H), 8.49–8.52 (m, 1H), 8.73 (t, J=5.3 Hz, 1H), 11.90–13.70 (bs, 1H); IR (KBr) 3440, 3080, 2920, 1730, 1640, 1605, 1570, 1545, 1475, 1460, 1430, 1410, 1400, 1355, 1325, 1275, 1245, 1210, 1160, 1130, 1110, 1090, 890, 810, 760, and 700 cm$^{-1}$; mass spectrum [(−) ESI], m/z 553/555 (M−H)$^-$; Anal. Calcd. for $C_{29}H_{22}ClF_3N_2O_4 \cdot 0.5CHCl_3$: C, 57.65; H, 3.69; N, 4.56, Found: C, 57.44; H. 3.54; N, 4.41.

EXAMPLE 59

[3"-Chloro-5'-(3-phenyl-propylcarbamoyl)-3-trifluoromethyl-[1,1';3'1"]terphenyl-2'-yloxy]acetic Acid The title compound was prepared as an off white solid (0.073 g, 27%) from 3-(m-chlorophenyl)-4-(2-hydroxyethoxy)-5-(m-trifluoromethylphenyl)-benzoic acid ethyl ester using 3-phenyl-1-propylamine and a procedure similar to Example 51, mp>106° C. (decomp.); $^1$H NMR (DMSO-d$_6$) δ 1.80–1.88 (m, 2H), 2.64 (t, J=7.5 Hz, 2H), 3.28–3.37 (m, 2H), 3.78 (s, 2H), 7.14–7.19 (m, 1H), 7.20–7.31 (m, 4H), 7.46–7.53 (m, 2H), 7.59–7.63 (m, 1H), 7.68–7.74 (m, 2H), 7.77 (d, J=7.7 Hz, 1H), 7.90 (dd,J=2.2, 5.1 Hz, 2H), 7.94 (d, J=7.7 Hz, 1H), 7.99 (s, 1H), 8.62 (t, J=5.3 Hz, 1H), 11.80–13.50 (bs, 1H); IR (KBr) 3330, 3080, 3020, 2920, 2860, 1740, 1635, 1620, 1555, 1495, 1455, 1425, 1360, 1325, 1280, 1245, 1210, 1165, 1130, 1095, 1080, 1055, 880, 820, 790, 750, 700, and 670 cm$^{-1}$; mass spectrum [(+) APCI], m/z 568 (M+H)$^+$; Anal. Calcd. for $C_{31}H_{25}ClF_3NO_4 \cdot 1.5H_2O$: C, 62.58; H, 4.74; N, 2.35, Found: C, 62.32; H, 4.20; N, 2.35.

EXAMPLE 60

[3"-Chloro-5'-(4-phenyl-burylcarbamoyl)-3-trifluoromethyl-[1,1';3'1"]terphenyl-2'-yloxy]acetic Acid The title compound was prepared as an off white solid (0.105 g, 38%) from 3-(m-chlorophenyl)-4-(2-hydroxyethoxy)-5-(m-trifluoromethylphenyl)-benzoic acid ethyl ester using 4-phenylbutylamine and a procedure similar to Example 51, mp 187–190° C.; $^1$H NMR (DMSO-d$_6$) δ 1.50–1.67 (m, 4H), 2.61 (t, J=7.2 Hz, 2H), 3.31 (dd, J=6.6, 12.7 Hz, 2H), 3.79 (s, 2H), 7.13–7.23 (m, 3H), 7.23–7.29 (m, 2H), 7.45–7.53 (m, 2H), 7.58–7.62 (m, 1H), 7.67–7.74 (m, 2H), 7.77 (d, J=8.1 Hz, 1H), 7.89 (dd, J=2.0, 5.1 Hz, 2H), 7.93 (d, J=7.5 Hz, 1H), 7.98 (s, 1H), 8.60 (t, J=5.5 Hz, 1H), 11.40–14.10 (bs, 1H); IR (KBr) 3380, 3080, 3020, 2930, 2850, 1730, 1620, 1570, 1495, 1450, 1400, 1360, 1330, 1280, 1245, 1205, 1165, 1130, 1095, 1080 1050, 890, 815, 790, 750, and 700 cm$^{-1}$; mass spectrum [(+) APCI], m/z 582 (M+H)$^+$; Anal. Calcd. for $C_{32}H_{27}ClF_3NO_4 \cdot H_2O$: C, 64.06; H, 4.87; N, 2.33, Found: C, 63.86; H, 5 4.45; N, 2.39.

EXAMPLE 61

[3"-Chloro-5'-(3-cyclopentyl-propylcarbamoyl)-3-trifluoromethyl-[1,1';3'1"]-terphenyl-2'-yloxy]acetic Acid Step 1 3-Cyclopentylpropylamine To a stirred solution of condensed liquid ammonia (excess, saturated at −40° C.) in Et$_2$O (60 mL) at −40° C. was added 3-cyclopentylpropionyl chloride (10.0 mL, 65.3 mmol) in Et$_2$O (60 mL) dropwise. The reaction mixture was warmed to room temperature and stirred at this temperature for 18 h. The solid that formed was filtered off and washed with excess Et$_2$O. After concentration, the residue was used directly in the next part without further purification. This intermediate amide was dissolved in Et$_2$O:THF (5:2, 140 mL) and added dropwise to a slurry of LAH (6.36 g, 45.0 mmol) in anhydrous Et$_2$O (75 mL) at 0° C. After stirring at this temperature for 1 h, the mixture (with efficient stirring) was quenched with the dropwise addition of H$_2$O (5.12 mL), 15% aq. NaOH (5.12 mL), and H$_2$O (15.36 mL) and then stirred an additional 18 h at room temperature. The resulting slurry was dried (Na$_2$SO$_4$) and then filtered. After concentration, the residue was taken up in hexane. The white solid that formed (excess amide SM) was filtered off, and the resulting filtrate was concentrated. The liquid amine product (4.31 g, 52%) was used directly in subsequent reactions without further purification; $^1$H NMR (DMSO-d$_6$) δ 0.95–1.13 (m, 2H), 1.21–1.38 (m, 4H), 1.41–1.62 (m, 4H), 1.63–1.88 (m, 3H), 2.47–2.54 (m, 2H, overlapping with DMSO peak); mass spectrum [(+) ESI], m/z 128 (M+H)$^+$.

Step 2 [3"-Chloro-5'-(3-cyclopentyl-propylcarbamoyl)-3-trifluoromethyl-[1,1';3'1"]-terphenyl-2'-yloxy]acetic Acid The title compound was prepared as an off white solid (0.064 g, 25%) from 3-(m-chlorophenyl)-4-(2-hydroxyethoxy)-5-(m-trifluoromethylphenyl)-benzoic acid ethyl ester using 3-cyclopentylpropylamine and a procedure similar to Example 51, mp 173–175° C.; $^1$H NMR (DMSO-d$_6$) δ 0.97–1.10 (m, 2H), 1.27–1.36 (m, 2H), 1.42–1.59 (m, 6H), 1.67–1.79 (m, 3H), 3.25 (dd, J=6.6, 12.7 Hz, 2H), 3.75 (s, 2H), 7.44–7.51 (m, 2H), 7.59 (d, J=6.4 Hz, 1H), 7.66–7.71 (m, 2H), 7.75 (d, J=7.7 Hz, 1H), 7.88 (d, J=2.6 Hz, 2H), 7.92 (d, J=7.7 Hz, 1H), 1.97 (s, 1H), 8.57 (t, J=5.7 Hz, 1H), 12.00–13.90 (bs, 1H); IR (KBr) 3330, 3090, 2960, 2890, 1735, 1635, 1555, 1460, 1400, 1350, 1325, 1275, 1250, 1220, 1170, 1125, 1095, 1080, 1060, 890, 875, 820, 790, 770, 730, 700, and 675 cm$^{-1}$; mass spectrum. [(−) ESI], m/z 558 (M−H)$^-$; Anal. Calcd. for $C_{30}H_{29}ClF_3NO_4 \cdot 0.75H_2O$: C, 62.83; H, 5.36; N, 2.44, Found: C, 62.87; H, 5.04; N, 2.40.

EXAMPLE 62

[3-Bromo-3'-chloro-5-(3-cyclopentyl-propylcarbamoyl)-biphenyl-2-yloxy]acetic Acid The title compound was prepared as an off white solid (0.057 g, 18%) from 3-bromo-5-(m-chlorophenyl)-4-(2-hydroxyethoxy)benzoic acid ethyl ester using 3-cyclopentylpropylamine and a procedure similar to Example 51, mp>135° C. (decomp.); $^1$H NMR (DMSO-d$_6$) δ 0.98–1.09 (m, 2H), 1.25–1.34 (m, 2H), 1.42–1.60 (m, 6H), 1.66–1.79 (m, 3H), 3.23 (dd, J=6.8, 12.7 Hz, 2H), 4.00 (s, 2H), 7.44–7.49 (m, 2H), 7.53–7.58 (m, 1H), 7.65 (s, 1H), 7.84 (d, J=2.2 Hz, 1H), 8.08 (d, J=2,2 Hz, 1H), 8.58 (t, J=5.5 Hz, 1H), 12.60–14.10 (bs, 1H); IR (KBr) 3330, 3090, 2950, 2860, 1740, 1635, 1595,1555,1455, 1430, 1325, 1225, 1200, 1080, 1040, 880, 795, 760, and 700 cm$^{-1}$; mass spectrum [(−) ESI], m/z 492 (M−H)$^-$; Anal. Calcd. for $C_{23}H_{25}BrClNO_4 \cdot 0.5H_2O$: C, 54.83; H, 5.20; N, 2.78, Found: C, 54.87; H, 5.03; N, 2.74.

EXAMPLE 63

{5'-[2-(4-Bromo-phenyl)-ethylcarbamoyl]-3"-chloro-3-trifluoromethyl-[1,1';3'1"]-terphenyl-2'-yloxy}acetic Acid The title compound was prepared as an off white solid (0.068 g, 24%) from 3-(m-chlorophenyl)-4-(2-hydroxyethoxy)-5-(m-trifluoromethylphenyl)-benzoic acid ethyl ester using 4-bromophenethylamine and a procedure similar to Example 51, mp>102° C. (decomp.); $^1$H NMR (DMSO-d$_6$) δ 2.82 (t, J=6.8 Hz, 2H), 3.48 (dd, J=6.8, 13.0 Hz, 2H), 3.79 (s, 2H), 7.20 (d, J=8.3 Hz, 2H), 7.44–7.52 (m, 4H), 7.57–7.60 (m, 1H), 7.67–7.73 (m, 2H), 7.76 (d, J=7.0 Hz, 1H), 7.84 (d, J=3.3 Hz, 2H), 7.92 (d, J=7.7 Hz, 1H), 7.97 (s, 1H), 8.67 (t, J=7.5 Hz, 1H), 12.40–13.05 (bs, 1H); IR (KBr) 3400, 3090, 2930, 1740, 1635, 1610, 1545, 1485, 1460, 1390, 1350, 1325, 1275, 1245, 1215, 1160, 1130, 1100, 1080, 1010, 880, 810, 790, 760, and 700 cm$^{-1}$; mass spectrum [(−) ESI], m/z 630/632/634 (M−H); Anal. Calcd. for $C_{30}H_{22}BrClF_3NO_4 \cdot H_2O$: C, 55.36; H, 3.72; N, 2.15, Found: C, 55.58; H, 3.29; N, 2.17.

EXAMPLE 64

[3,3"-Dichloro-5'-(3cyclopentyl-propylcarbamoyl)-[1,1';3'1"]terphenyl-2'-yloxy]acetic Acid The title compound was prepared as an off white solid (0.114 g, 27%) from 3,5-bis-(m-chlorophenyl)-4-(2- hydroxyethoxy)benzoic acid ethyl ester using 3-cyclopentylpropylamine and a procedure similar to Example 51, mp>173° C. (decomp.); $^1$H NMR (DMSO-d$_6$) δ 0.99–1.09 (m, 2H), 1.27–1.34 (m, 2H), 1.41–1.60 (m, 6H), 1.67–1.80 (m, 3H), 3.25 (dd, J=6.6, 13.0 Hz, 2H), 3.81 (s, 2H), 7.44–7.51 (m, 4H), 7.56–7.60 (m, 2H), 7.68–7.70 (m, 2H), 7.86 (s, 2H), 8.56 (t, J=5.9 Hz, 1H), 12.15–13.15 (bs, 1H); IR (KBr) 3390, 3080, 2950, 2870, 1740, 1640, 1610, 1570, 1555, 1475, 1450, 1430, 1400, 1360, 1310, 1245, 1215, 1160, 1110, 1080, 1045, 880, 800, 760, and 700 cm$^{-1}$; mass spectrum [(−) ESI], m/z 524/526/528 (M−H)$^−$; Anal. Calcd. for C$_{29}$H$_{29}$Cl$_2$NO$_4$·H$_2$O: C, 63.97; H, 5.74; N, 2.57, Found: C, 63.67; H, 5.38; N, 2.63.

EXAMPLE 65

[4"-Methoxy-5'-(2-pyridin-2-yl-ethylcarbamoyl)-3-trifluoromethyl-[1,1';3'1"]-terphenyl-2'-yloxy]acetic Acid The title compound was prepared as an off white solid (0.067 g, 28%) from 4-(2-hydroxyethoxy)-3-(p-methoxyphenyl)-5-(m-trifluoromethylphenyl)-benzoic acid ethyl ester using 2-(2-aminoethyl)pyridine and a procedure similar to Example 51, mp>105° C. (decomp.); $^1$H NMR (DMSO-d$_6$) δ 2.99 (t, J=7.7 Hz, 2H), 3.62 (dd, J=6.4, 13.2 Hz, 2H), 3.72 (s, 2H), 3.80 (s, 3H), 7.01 (d, J=8.6 Hz, 2H), 7.20 (dd, J=4.8, 7.5 Hz, 1H), 7.26 (d, J=7.7 Hz, 1H), 7.56 (d, J=8.6 Hz, 2H), 7.64–7.74 (m, 3H), 7.80 (dd, J=2.0, 7.9 Hz, 2H), 7.92 (d, J=7.7 Hz, 1H), 7.96 (s, 1H), 8.47–8.50 (m, 1H), 8.68 (t, J=5.5 Hz, 1H), 11.70–13.45 (bs, 1H); IR (KBr) 3400, 3080, 3000, 2920, 2810, 1730, 1640, 1620, 1560, 1510, 1495, 1455, 1435, 1415, 1360, 1325, 1305, 1280, 1250, 1215, 1160, 1130, 1080, 1030, 890, 835, 800, 755, and 710 cm$^{-1}$; mass spectrum [(−) ESI], m/z 549 (M−H)$^−$; Anal. Calcd. for C$_{30}$H$_{25}$F$_3$N$_2$O$_5$·2.5H$_2$O: C, 60.50; H, 5.08; N, 4.70, Found: C, 60.65; H, 4.36; N, 4.64.

EXAMPLE 66

[5'-(3-Cyclopentyl-propylcarbamoyl)-4"-methoxy-3-trifluoromethyl-[1,1';3'1"]-terphenyl-2'-yloxy]acetic Acid The title compound was prepared as an off white solid (0.085 g, 35%) from 4-(2-hydroxyethoxy)-3-(p-methoxyphenyl)-5-(m-trifluoromethylphenyl)-benzoic acid ethyl ester using 3-cyclopentylpropylamine and a procedure similar to Example 51, mp>114° C. (decomp.); $^1$H NMR (DMSO-d$_6$) δ 0.98–1.07 (m, 2H), 1.27–1.34 (m, 2H), 1.42–1.59 (m, 6H), 1.66–1.79 (m, 3H), 3.25 (dd, J=6.8, 13.0 Hz, 2H), 3.73 (s, 2H), 3.80 (s, 3H), 7.01 (d, J=8.8 Hz, 2H), 7.56 (d, J=8.8 Hz, 2H), 7.66 (t, J=7.7 Hz, 1H), 7.72 (d, J=7.5 Hz, 1H), 7.82 (dd, J=2.0, 6.8 Hz, 2H), 7.92 (d, J=7.7 Hz, 1H), 7.96 (s, 1H), 8.54 (t, J=5.7 Hz, 1H), 12.10–13.50 (bs, 1H); IR (KBr) 3430, 3090, 2950, 2860, 1740, 1640, 1620, 1590, 1560, 1510, 1495, 1455, 1360, 1330, 1310, 1290, 1250, 1220, 1170, 1135, 1100, 1080, 1030, 890, 840, 800, and 705 cm$^{-1}$; mass spectrum [(−) ESI], m/z 554 (M−H)$^−$; Anal. Calcd. for C$_{31}$H$_{32}$F$_3$NO$_5$·0.75H$_2$O: C, 65.43; H, 5.93; N, 2.46, Found: C, 65.38; H, 5.57; N, 2.49.

EXAMPLE 67

[5'-(Benzyl-phenethyl-carbamoyl)-4"-methoxy-3-trifluoromethyl-[1,1';3'1"]-terphenyl-2'-yloxy]acetic Acid The title compound was prepared as an off white solid (0.101 g, 36%) from 4-(2-hydroxyethoxy)-3-(p-methoxyphenyl)-5-(m-trifluoromethylphenyl)-benzoic acid ethyl ester using N-benzyl-2-phenethylamine and a procedure similar to Example 51, mp>82° C. (decomp.); $^1$H NMR (DMSO-d$_6$) δ 2.74–2.97 (m, 2H), 3.23–3.64 (m, 2H), 3.66–3.76 (m, 2H), 3.79 (s, 3H), 4.45–4.83 (m, 2H), 6.84–7.92 (m, 20H), 11.90–13.40 (bs, 1H); IR (KBr) 3340, 3070, 320, 2920, 2820, 1755, 1740, 1635, 1605, 1510, 1495, 1450, 1420, 1360, 1325, 1300, 1275, 1250, 1210, 1170, 1160, 1125, 1100, 1080, 1030, 890, 830, 800, 750, and 700 cm$^{-1}$; mass spectrum [(−) ESI], m/z 638 (M−H)$^−$; Anal. Calcd. for C$_{38}$H$_{32}$F$_3$NO$_5$·1.25H$_2$O: C, 68.93; H, 5.25; N, 2.12, Found: C, 68.65; H, 5.04; N, 2.11.

EXAMPLE 68

[5'-(Benzyl-phenethyl-carbamoyl)-2-fluoro-4"-methoxy-[1,1';3'1"]-terphenyl-2'-yloxy]acetic Acid The title compound was prepared as an off white solid (0.089 g, 27%) from 3-(o-fluorophenyl)-4-(2-hydroxyethoxy)-5-(p-methoxyphenyl)benzoic acid ethyl ester using N-benzyl-2-phenethylamine and a procedure similar to Example 51, mp>73° C. (decomp.); $^1$H NMR (DMSO-d$_6$) δ 2.73–2.94 (m, 2H), 3.20–3.63 (m, 2H), 3.70–3.79 (m, 2H), 3.79 (s, 3H), 4.43.4.83 (m, 2H), 6.84–7.53 (m, 20H), 11.30–13.50 (bs, 1H); IR (KBr) 3440, 3070, 3020, 2920, 1755, 1735, 1630, 1610, 1510, 1495, 1440, 1420, 1340, 1300, 1250, 1215, 1180, 1100, 1070, 1030, 890, 840, 810, 755, and 700 cm$^{-1}$; mass spectrum [(+) ESI], m/z 590 (M+H)$^+$, 622 (M+Na)$^+$; Anal. Calcd. for C$_{37}$H$_{32}$FNO$_5$·1.5H$_2$O: C, 72.06; H, 5.72; N, 2.27, Found: C, 72.32; H, 5.32; N, 2.33.

EXAMPLE 69

[5-(Benzylphenethyl-carbamoyl)-3-bromo-2'-fluoro-biphenyl-2-yloxy]acetic Acid

The title compound was prepared as an off white solid (0.029 g, 8%) from 3-bromo-5-(o-fluorophenyl)-4-(2-hydroxyethoxy)benzoic acid ethyl ester using N-benzyl-2-phenethylamine and a procedure similar to Example 51, mp>85° C. (decomp.); $^1$H NMR (DMSO-d$_6$) δ 2.72–2.93 (m, 2H), 3.15–3.63 (m, 2H), 3.88–4.03 (m, 2H), 4.36–4.84 (m, 2H), 6.84–7.00 (m, 2H), 7.00–7.60 (m, 14H), 11.60–13.10 (bs, 1H); IR (KBr) 3430, 3060, 3020, 2920, 1740, 1635, 1495, 1450, 1420, 1360, 1330, 1260, 1240, 1220, 1120, 1070, 1030, 930, 890, 830, 755, and 700 cm$^{-1}$; mass spectrum [(−) ESI], m/z 560 (M−H)$^−$; Anal. Calcd. for C$_{30}$H$_{25}$BrFNO$_4$·1.75H$_2$O: C, 60.67; H, 4.84; N, 2.36, Found: C, 60.64; H, 4.41; N, 2.41.

EXAMPLE 70

[2-Fluoro-4"-methoxy-5'-(2-pyridin-2-yl-ethylcarbamoyl)-[1,1';3'1"]-terphenyl-2'-yloxy]acetic Acid The title compound was prepared as a white solid (0.121 g, 39%) from 3-(o-fluorophenyl)-4-(2-hydroxyethoxy)-5-(p-methoxyphenyl)benzoic acid ethyl ester using 2-(2-aminoethyl)pyridine and a procedure similar to Example 51, mp>102° C. (decomp.); $^1$H NMR (DMSO-d$_6$) δ 3.00 (t, J=7.7 Hz, 2H), 3.62 (dd, J=6.6, 12.7 Hz, 2H), 3.79 (s, 2H), 3.81 (s, 3H), 7.01–7.06 (m, 2H), 7.22 (ddd, J=1.1, 4.8, 7.5 Hz, 1H), 7.26–7.32 (m, 3H), 7.42–7.50 (m, 2H), 7.54–7.60 (m, 2H), 7.67–7.73 (m, 2H), 7.85 (d, J=2.4 Hz, 1H), 8.50 (ddd, J=0.9, 1.8, 4.8 Hz, 1H), 8.66 (t, J=5.7 Hz, 1H), 11.75–13.45 (bs, 1H); IR (KBr) 3420, 3080, 3000, 2930, 2820, 1735, 1640, 1615, 1580, 1550, 1510, 1495, 1450, 1430, 1410, 1370, 1310, 1250, 1215, 1175, 11100, 1070, 1025, 900, 840, 810, 755, and 710 cm$^{-1}$; mass spectrum [(–) ESI], m/z 499 (M–H)$^-$; Anal. Calcd. for $C_{29}H_{25}FN_2O_5 \cdot 2.5H_2O$: C, 63.85; H, 5.54; N, 5.13, Found: C, 63.40; H, 4.79; N, 4.93.

EXAMPLE 71

[2-Fluoro-4"-methoxy-5'-(3-phenyl-propylcarbamoyl)-[1,1';3'1"]-terphenyl-2'-yloxy]acetic Acid The title compound was prepared as an off white solid (0.130 g, 42%) from 3-(o-fluorophenyl)-4-(2-hydroxyethoxy)-5-(p-methoxyphenyl)benzoic acid ethyl ester using 3-phenyl-1-propylamine and a procedure similar to Example 51, mp>89° C. (decomp.); $^1$H NMR (DMSO-d$_6$) δ 1.77–1.87 (m, 2H), 2.61 (t, J=7.2 Hz, 2H), 3.27 (dd, J=6.8, 13.0 Hz, 2H), 3.78 (s, 2H), 3.79 (s, 3H), 6.99–7.04 (m, 2H), 7.13–7.18 (m, 1H), 7.19–7.23 (m, 2H), 7.24–7.30 (m, 4H), 7.41–7.50 (m, 2H), 7.54–7.58 (m, 2H), 7.72 (d, J=2.2 Hz, 1H), 7.87 (d, J=2.4 Hz, 1H), 8.54 (t, J=5.7 Hz, 1H), 11.85–13.30 (bs, 1H); IR (KBr) 3420, 3070, 3020, 2940, 1740, 1640, 1620, 1590, 1560, 1510, 1495, 1450, 1415, 1350, 1310, 1250, 1215, 1180, 1100, 1080, 1030, 900, 840, 805, 755, and 700 cm$^{-1}$; mass spectrum [(–) ESI], m/z 512 (M–H)$^-$; Anal. Calcd. for $C_{31}H_{28}FNO_5 \cdot 1.25H_2O$: C, 69.46; H, 5.73; N, 2.61, Found: C, 69.36; H, 5.40; N, 2.56.

EXAMPLE 72

[3-Bromo-2'-fluoro-5-(2-pyridin-2-yl-ethylcarbamoyl)-biphenyl-2-yloxy]acetic Acid The title compound was prepared as a white solid (0.041 g, 15%) from 3-bromo-5-(o-fluorophenyl)-4-(2-hydroxyethoxy)benzoic acid ethyl ester using 2-(2-aminoethyl)pyridine and a procedure similar to Example 51, mp>154° C. (decomp.); $^1$H NMR (DMSO-d$_6$) δ 2.97 (t, J=7.7 Hz, 2H), 3.59 (dd, J=6.6, 12.7 Hz, 2H), 3.97 (s, 2H), 7.20 (ddd, J=0.9, 4.8, 7.5. Hz, 1H), 7.24–7.32 (m, 3H), 7.42–7.50 (m, 2H), 7.68 (td, J=1.8, 7.7 Hz, 1H), 7.74 (d, J=2.0 Hz, 1H), 8.10 (d, J=2.0 Hz, 1H), 8.48 (dd, J=0.9, 4.8 Hz, 1H), 8.67 (t, J=5.3 Hz, 1H), 11.40–13.20 (bs, 1H); IR (KBr) 3420, 3080, 2930, 1725, 1630, 1600, 1550, 1495, 1460, 1450, 1435, 1370, 1330, 1245, 1225, 1150, 1120, 1080, 1030, 890, 830, 755, and 710 cm$^{-1}$; mass spectrum [(–) ESI], m/z 471/473 (M–H)$^-$; Anal. Calcd. for $C_{22}H_{18}BrFN_2O_4 \cdot 2.5H_2O$: C, 50.98; H, 4.47; N, 5.40, Found: C, 50.96; H, 3.81; N, 5.06.

EXAMPLE 73

[3-Bromo-2'-fluoro-5-(3-phenyl-propylcarbamoyl)-biphenyl-2-yloxy]acetic Acid

The title compound was prepared as an off white solid (0.091 g, 32%) from 3-bromo-5-(o-fluorophenyl)-4-(2-hydroxyethoxy)benzoic acid ethyl ester using 3-phenyl-1-propylamine and a procedure similar to Example 51, mp>90° C. (decomp.); $^1$H NMR (DMSO-d$_6$) δ 1.77–1.85 (m, 2H), 2.61 (t, J=7.5 Hz, 2H), 3.26 (dd, J=6.8, 12.5 Hz, 2H), 4.08 (s, 2H), 7.13–7.23 (m, 3H), 7,23–7.33 (m, 4H), 7.42–7.51 (m, 2H), 7.78 (d, J=2.2 Hz, 1H), 8.14 (d, J=2.0 Hz, 1H), 8.58 (t, J=5.5 Hz, 1H), 11.70–13.90 (bs, 1H); IR 3350, 3080, 3020, 2940, 2860, 1740, 1630, 1590, 1550, 1495, 1450, 1430, 1325, 1220, 1200, 1100, 1080, 1050, 890, 830, 755, and 695 (KBr) cm$^{-1}$; mass spectrum [(–) ESI], m/z 484/486 (M–H)$^-$; Anal. Calcd. for $C_{24}H_{21}BrFNO_4 \cdot 1.25H_2O$: C, 56.65; H, 4.65; N, 2.75, Found: C, 56.61; H, 4.26; N, 2.65.

EXAMPLE 74

[5'-(3-Cyclopentyl-propylcarbamoyl)-2-fluoro-4"-methoxy-[1,1';3'1"]-terphenyl-2'-yloxy]acetic Acid The title compound was prepared as an off white solid (0.100 g, 33%) from 3-(o-fluorophenyl)-4-(2-hydroxyethoxy)-5-(p-methoxyphenyl)benzoic acid ethyl ester using 3-cyclopentylpropylamine and a procedure similar to Example 51, mp>97° C. (decomp.); $^1$H NMR (DMSO-d$_6$) δ 1.00–1.09 (m, 2H), 1.28–1.36 (m, 2H), 1.42–1.61 (m, 6H), 1.68–1.81 (m, 3H), 3.25 (dd, J=6.4, 12.7 Hz, 2H), 3.78 (s, 2H), 3.81 (s, 3H), 7.03 (d, J=9.0 Hz, 2H), 7.25–7.32 (m, 2H), 7.42–7.51 (m, 2H), 7.57 (d, J=8.6 Hz, 2H), 7.73 (d, J=2.2 Hz, 1H), 7.87 (d, J=2.2 Hz, 1H), 8.52 (t, J=5.7 Hz, 1H), 11.85–13.40. (bs, 1H); IR (KBr) 3390, 3090, 2950, 2880, 1740, 1635, 1620, 1585, 1565, 1515, 1495, 1450, 1440, 1420, 1360, 1295, 1250, 1215, 1180, 1100, 1075, 1030, 900, 830, 810, 755, and 710 cm$^{-1}$; mass spectrum [(–) ESI], m/z 504 (M–H)$^-$; Anal. Calcd. for $C_{30}H_{32}FNO_5 \cdot H_2O$: C, 68.82; H, 6.55; N, 2.68, Found: C, 68.63; H, 6.14; N, 2.73.

EXAMPLE 75

[3-Bromo-5-(3-cyclopentyl-propylcarbamoyl)-2'-fluoro-biphenyl-2-yloxy]acetic Acid The title compound was prepared as an off white solid (0.041 g, 14%) from 3-bromo-5-(o-fluorophenyl)-4-(2-hydroxyethoxy)benzoic acid ethyl ester using 3-cyclopentylpropylamine and a procedure similar to Example 51, mp>127° C. (decomp.); $^1$H NMR (DMSO-d$_6$) δ 1.00–1.09 (m, 2H), 1.27–1.34 (m, 2H), 1.43–1.62 (m, 6H), 1.68–1.79 (m, 3H), 3.23 (dd, J=6.8, 12.7 Hz, 2H), 3.98 (s, 2H), 7.27–7.34 (m, 2H), 7.42–7.52 (m, 2H), 7.78 (d, J=2.0 Hz, 1H), 8.14 (d, J=2.2 Hz, 1H), 8.55 (t, J=5.7 Hz, 1H), 11.40–13.50 (bs, 1H); IR (KBr) 3390, 3090, 2950, 2870, 1735, 1630, 1555, 1495, 1435, 1425, 1330, 1225, 1100, 1070, 1030, 890, 830, 755, and 705 cm$^{-1}$; mass spectrum [(–) ESI], m/z 476/478 (M–H); Anal. Calcd. for $C_{23}H_{25}BrFNO_4 \cdot 1.5H_2O$: C, 54.66; H, 5.58; N, 2.77, Found: C, 54.36; H, 4.78; N, 2.75.

EXAMPLE 76

[2-Fluoro-4"-methoxy-5'-(8-phenyl-octylcarbamoyl)-[1,1';3'1"]-terphenyl-2'-yloxy]acetic Acid The title compound was prepared as an off white solid (0.150 g, 41%) from 3-(o-fluorophenyl)-4-(2-hydroxyethoxy)-5-(p-methoxyphenyl)benzoic acid ethyl ester using, 8-phenyloctylamine and a procedure similar to Example 51, mp>84° C. (decomp.); $^1$H NMR (DMSO-d$_6$) δ 1.23–1.34 (m, 8H), 1.47–1.58 (m, 4H), 2.54 (t, J=7.5 Hz, 2H), 3.24 (dd, J=6.8, 12.7 Hz, 2H), 3.81 (s, SH), 7.03 (d, J=8.1 Hz, 2H), 7.12–7.18 (m, 3H), 7.22–7.31 (m, 4H), 7.42–7.50 (m, 2H), 7.57 (d, J=8.1 Hz, 2H), 7.74 (d, J=2.0 Hz, 1H), 7.87 (d, J=2.2 Hz, 1H), 8.51 (t, J=5.5 Hz, 1H), 11.40–13.40 (bs, 1H); IR (KBr) 3400, 3080, 3020, 2930, 2860, 1735, 1640, 1615, 1590, 1550, 1510, 1495, 1440, 1430, 1400, 1355, 1300, 1250, 1210, 1180, 1100, 1080, 1030, 900, 830, 810, 755, and 695 cm$^{-1}$; mass spectrum [(–) ESI], m/z 584 (M–H)$^-$; Anal. Calcd. for

EXAMPLE 77

[3-Bromo-2'-fluoro-5-(8-phenyl-octylcarbamoyl)-biphenyl-2-yloxy]acetic Acid

The title compound was prepared as an off white solid (0.062 g, 18%) from 3-bromo-5-(o-fluorophenyl)-4-(2-hydroxyethoxy)benzoic acid ethyl ester using 8-phenyloctylamine and a procedure similar to Example 51, mp>79° C. (decomp.); $^1$H NMR (DMSO-d$_6$) δ 1.23–1.33 (m, 8H), 1.45–1.59 (m, 4H), 2.55 (t, J=7.2 Hz, 2H), 3.23 (dd, J=6.2, 12.3 Hz, 2H), 4.03 (s, 2H), 7.12–7.19 (m, 3H), 7.23–7.34 (m, 4H), 7.42–7.52 (m, 2H), 7.78 (s, 1H), 8.13–8.17 (m, 1H), 8.55 (t, J=5.7 Hz, 1H), 11.70–13.60 (bs, 1H); IR (KBr) 3360, 3080, 3020, 2930, 2860, 2340, 1740, 1635, 1560, 1495, 1450, 1430, 1370, 1325, 1220, 1100, 1080, 1035, 900, 830, 755, and 700 cm$^{-1}$; mass spectrum [(+) ESI], m/z 5561558 (M+H)$^+$; Anal. Calcd. for C$_{29}$H$_{31}$BrFNO$_4$.0.75H$_2$O: C, 61.11; H, 5.75; N, 2.46, Found: C, 61.14; H, 5.19; N, 2.45.

EXAMPLE 78

[2-Fluoro-4"-methoxy-5'-(6-phenyl-hexylcarbamoyl)-[1,1';3'1"]-terphenyl-2'-yloxy]acetic Acid The title compound was prepared as an off white solid (0.155 g, 47%) from 3-(o-fluorophenyl)-4-(2-hydroxyethoxy)-5-(p-methoxyphenyl)benzoic acid ethyl ester using 6-phenylhexylamine and a procedure similar to Example 51, mp>72° C. (decomp.); $^1$H NMR (DMSO-d$_6$) δ 1.26–1.37 (m, 4H), 1.45–1.59 (m, 4H), 2.54 (t, J=7.9 Hz, 2H), 3.23 (dd, J=6.8, 13.0 Hz, 2H), 3.79 (s, 5H), 6.98–7.04 (m, 2H), 7.10–7.18 (m, 3H), 7.20–7.30 (m, 4H), 7.40–7.49 (m, 2H), 7.53–7.57 (m, 2H), 7.72 (d, J=2.2 Hz, 1H), 7.86 (d, J=2.4 Hz, 1H), 8.49 (t, J=5.5 Hz, 1H), 12.65–13.30 (bs, 1H); IR (KBr) 3400, 3070, 3020, 2940, 2860, 1740, 1635, 1615, 1580, 1550, 1510, 1495, 1445, 1410, 1350, 1305, 1250, 1215, 1185, 1100, 1070, 1030, 900, 830, 810, 755, and 700 cm$^{-1}$; mass spectrum [(+) ESI], m/z 556 (M+H)$^+$; Anal. Calcd. for C$_{34}$H$_{34}$FNO$_5$.0.75H$_2$O: C, 71.75; H, 6.29; N, 2.46, Found: C, 71.72; H, 6.09; N, 2.46.

EXAMPLE 79

[3-Bromo-2'-fluoro-5-(6-phenyl-hexylcarbamoyl)-biphenyl-2-yloxy]acetic Acid

The title compound was prepared as a white solid (0.077 g, 26%) from 3-bromo-5-(o-fluorophenyl)-4-(2-hydroxyethoxy)benzoic acid ethyl ester using 6-phenylhexylamine and a procedure similar to Example 51, mp>84° C. (decomp.); $^1$H NMR (DMSO-d$_6$) δ 1.27–1.36 (m, 4H), 1.44–1.59 (m, 4H), 2.54 (t, J=7.2 Hz, 2H), 3.21 (dd, J=6.4, 12.5 Hz, 2H), 4.01 (s, 2H), 7.11–7.18 (m, 3H), 7.21–7.32 (m, 4H), 7.41–7.50 (m, 2H), 7.77 (d, J=1.8 Hz, 1H), 8.13 (d, J=2.0 Hz, 1H), 8.53 (t, J=5.3 Hz, 1H), 11.80–13.50 (bs, 1H); IR (KBr) 3410, 3070, 3020, 2940, 2850, 1740, 1635, 1550, 1495, 1450, 1425, 1330, 1300, 1220, 1115, 1070, 1030, 900, 830, 755, and 700 cm$^{-1}$; mass spectrum [(+) ESI], m/z 528/530 (M+H)$^+$; Anal. Calcd. for C$_{27}$H$_{27}$BrFNO$_4$.2.5H$_2$O: C, 56.55; H, 5.62; N, 2.44, Found: C, 56.23; H, 4.43; N, 2.56.

EXAMPLE 80

[3,3"-Dichloro-5'-(6-phenyl-hexylcarbamoyl)-[1,1';3'1"]terphenyl-2'-yloxy]acetic Acid The title compound was prepared as an off white solid (0.065 g, 19%) from 3,5-bis-(m-chlorophenyl)-4-(2-hydroxyethoxy)benzoic acid ethyl ester using 6-phenylhexylamine and a procedure similar to Example 51, mp 178–181° C.; $^1$H NMR (DMSO-d$_6$) δ 1.27–1.37 (m, 4H), 1.48–1.59 (m, 4H), 2.55 (t, J=7.5 Hz, 2H), 3.25 (dd, J=6.4, 13.0 Hz, 2H), 3.81 (s, 2H), 7.10–7.17 (m, 3H), 7.21–7.26 (m, 2H), 7.44–7.51 (m, 4H), 7.56–7.60 (m, 2H), 7.68–7.70 (m, 2H), 7.85 (s, 2H), 8.55 (t, J=5.3 Hz, 1H), 11.60–13.35 (bs, 1H); IR (KBr) 3380, 3070, 3020, 2930, 2860, 2510, 1725, 1620, 1565, 1475, 1450, 1400, 1340, 1320, 1240, 1200, 1170, 1100, 1080, 1050, 880, 790, 770, 750, and 700 cm$^{-1}$; mass spectrum [(+) ESI], m/z 576 (M+H)$^+$; Anal. Calcd. for C$_{33}$H$_{31}$Cl$_2$NO$_4$.0.75H$_2$O: C, 67.18; H, 5.55; N, 2.37, Found: C, 67.35; H, 5.51; N, 2.36.

EXAMPLE 81

{4"-Methoxy-5'-[methyl-(8-phenyl-octyl)-carbamoyl]-3-trifluoromethyl-[1,1';3'1"]-terphenyl-2'-yloxy}acetic Acid The title compound was prepared as a gray foam (0.399 g, 71%) from 4-(2-hydroxyethoxy)-3-(p-methoxyphenyl)-5-(m-trifluoromethylphenyl)benzoic acid ethyl ester using N-methyl-8-phenyloctylamine and a procedure similar to Example 51, mp>39° C. (decomp.); $^1$H NMR (DMSO-d$_6$) δ 1.02–1.18 (m, 4H), 1.20–1.36 (m, 4H), 1.40–1.60 (m, 4H), 2.44–2.57 (m, 2H), 2.96 (s, 3H), 3.22–3.47 (m, 2H), 3.79 (s, 5H), 7.01 (d, J=8.6 Hz, 2H), 7.10–7.19 (m, 3H), 7.22–7.28 (m, 2H), 7.36 (d, J=10.5 Hz, 2H), 7.55 (d, J=8.3 Hz, 2H), 7.67 (t, J=7.7 Hz, 1H), 7.74 (d, J=7.9 Hz, 1H), 7.89 (d, J=7.5 Hz, 1H), 7.96 (s, 1H), 11.25–13.50 (bs, 1H); IR (KBr) 3440, 3070, 3020, 2930, 2860, 1755, 1735, 1610, 1510, 1495, 1455, 1400, 1345, 1330, 1300, 1270, 1250, 1180, 1165, 1125, 1100, 1080, 1060, 1030, 890, 830, 800, 750, and 705 cm$^{-1}$; mass spectrum [(+) APCI], m/z 648 (M+H)$^+$; Anal. Calcd. for C$_{38}$H$_{40}$F$_3$NO$_5$.0.5H$_2$O: C, 69.50; H, 6.29; N, 2.13, Found: C, 69.09; H, 6.11; N, 2.17.

EXAMPLE 82

{3,3"-Dichloro-5'-[methyl-(8-phenyl-octyl)-carbamoyl]-[1,1';3'1"]terphenyl-2'-yloxy}acetic Acid The title compound was prepared as an off white foam (0.231 g, 43%) from 3,5-bis-(m-chlorophenyl)-4-(2-hydroxyethoxy)benzoic acid ethyl ester using N-methyl-8-phenyloctylarmine and a procedure similar to Example 51, mp>44° C. (decomp.); $^1$H NMR (DMSO-d$_6$) δ 1.03–1.22 (m, 4H), 1.22–1.37 (m, 4H), 1.41–1.63 (m, 4H), 2.44–2.58 (m, 2H), 2.95 (s, 3H), 3.17–3.54 (m, 2H), 3.79 (s, 2H), 7.12–7.18 (m, 3H), 7.22–7.28 (m, 2H), 7.39 (s, 2H), 7.43–7.50 (m, 4H), 7.54–7.59 (m, 2H), 7.67 (s, 2H), 10.95–14.15 (bs, 1H); IR (KBr) 3440, 3080, 3020, 2930, 2870, 1755, 1730, 1630, 1605, 1565, 1495, 1480, 1445, 1400, 1340, 1310, 1215, 1170, 1100, 1085, 1050, 880, 775, 755, and 695 cm$^{-1}$; mass spectrum [(+) APCI], m/z 618 (M+H)$^+$; Anal. Calcd. for C$_{36}$H$_{37}$Cl$_2$NO$_4$.0.5H$_2$O: C, 68.90; H, 6.10; N, 2.23, Found: C, 68.76; H, 5.98; N, 2.25.

EXAMPLE 83

[3,3"-Difluoro-5'-(8-phenyl-octylcarbamoyl)-[1,1';3'1"]terphenyl-2'-yloxy]acetic Acid The title compound was prepared as an off white foam (0.207 g, 37%) from 3,5-bis-(m-fluorophenyl)-4-(2-hydroxyethoxy)benzoic acid ethyl ester using 8-phenyloctylamine and a procedure similar to Example 51, mp>58° C.(decomp.); $^1$H NMR (DMSO-d$_6$) δ 1.22–1.34 (m,

---

C$_{36}$H$_{38}$FNO$_5$.0.5H$_2$O: C, 72.95; H, 6.63; N, 2.36, Found: C, 73.04; H, 6.42; N. 2.41.

8H), 1.47–1.59 (m, 4H), 2.54 (t, J=7.5 Hz, 2H), 3.26 (dd, J=6.8, 13.0 Hz, 2H), 3.80 (s, 2H), 7.12–7.19 (m, 3H), 7.20–7.28 (m, 4H), 7.44–7.54 (m, 6H), 7.88 (s, 2H), 8.56 (t, J=5.3 Hz, 1H), 11.85–13.60 (bs, 1H); IR (KBr) 3390, 3080, 3020, 2930, 2850, 1740, 1640, 1620, 1585, 1550, 1490, 1455, 1435, 1410, 1340, 1260, 1215, 1195, 1060, 940, 875, 775, 750, and 705 cm$^{-1}$; mass spectrum [(+) APCI], m/z 572 (M+H)$^+$; Anal. Calcd. for $C_{35}H_{35}F_2NO_4 \cdot 0.5H_2O$: C, 72.40; H, 6.25; N, 2.41, Found: C, 72.14; H, 6.11; N, 2.45.

EXAMPLE 84

{3,3''-Difluoro-5'-[methyl-(8-phenyl-octyl)-carbamoyl]-[1,1';3'1'']terphenyl-2'-yloxy}acetic Acid The title compound was prepared as a grayish foam (0.240 g, 41%) from 3,5-bis-(m-fluorophenyl)-4-(2-hydroxyethoxy)benzoic acid ethyl ester using N-methyl-8-phenyloctylamine and a procedure similar to Example 51, mp>43° C. (decomp.); $^1$H NMR (DMSO-d$_6$) δ 1.02–1.21 (m, 4H), 1.21–1.37 (m, 4H), 1.40–1.63 (m, 4H), 2.44–2.58 (m, 2H), 2.96 (s, 3H), 3.22–3.47 (m, 2H), 3.77 (s, 2H), 7.11–7.18 (m 3H), 7.18–7.28 (m, 4H), 7.36–7.51 (m, 8H), 11.25–14.35 (bs, 1H); IR (KBr) 3430, 3070, 3020, 2930, 2860, 1755, 1740, 1635, 1615, 1585, 1490, 1445, 1410, 1335, 1260, 1210, 1180, 1120, 1080, 1050, 930, 875, 780, 750, and 700 cm$^{-1}$; mass spectrum [(–) ESI], m/z 584 (M–H)$^-$; Anal. Calcd. for $C_{36}H_{37}F_2NO_4 \cdot 1.25H_2O$: C, 71.09; H, 6.55; N, 2.30, Found: C, 71.15; H, 6.09; N, 2.31.

EXAMPLE 85

[3,3''-Dichloro-5'-(8-morpholin-4-yl-octylcarbamoyl)-[1,1';3'1'']terphenyl-2'-yloxy]acetic Acid Step 1 8-Morpholin-4-yloctylamine To a solution of N-(8-bromooctyl)phthalimide (8.46 g, 25.0 mmol) in CH$_3$CN (70 mL) at room temperature was added morpholine (4.80 g, 55.0 mmol). After 18 h at this temperature, the reaction mixture was concentrated and then diluted with EtOAc (100 mL). The organic layer was washed with 10% aq. Na$_2$CO$_3$ (3×30 mL), H$_2$O (2×20 mL), and brine (2×20 mL) and then dried (Na$_2$SO$_4$). After concentration, the residue was purified by the flash chromatography (5 to 10% MeOH/CH$_2$Cl$_2$ gradient) to afford the substituted morpholine intermediate.

To this substituted morpholine intermediate (7.40 g, 21.5 mmol) in MeOH (70 mL) at room temperature was added hydrazine monohydrate (1.28 mL, 25.8 mmol) and the resulting mixture was heated to reflux. After 2 h at this temperature, the reaction was concentrated and then diluted with 1N HCl (100 mL). The mixture was stirred for 1 h, and the precipitate that formed during this time was filtered and washed with excess 0.5 N HCl. The filtrate was basified with 50% aq. NaOH (~7 mL) and stirred about 15 min. This aqueous solution was extracted with CHCl$_3$ (4×50 mL) and the combined organic layers were washed with H$_2$O (3×50 mL) and brine (1×50 mL). The organic layer was then dried (Na$_2$SO$_4$) and concentrated to afford the product (4.16 g, 77%) as an oil; $^1$H NMR (DMSO-d$_6$) δ 1.18–1.34 (m, 12H), 1.34–1.43 (m, 2H), 2.21 (t, J=7.0 Hz, 2H), 2.26–2.33 (m, 4H), 2.46–2.52 (m, 2H), 3.53 (t, J=4.6 Hz, 4H); IR (film) 3390, 2930, 2860, 2820, 2790, 2710, 2180, 1640, 1610, 1460, 1390, 1375, 1360, 1320, 1300, 1275, 1200, 1135, 1120, 1080, 1040, 1010, 900, 870, 815, 800, and 725 cm$^{-1}$; mass spectrum [(+) APCI], m/z 215 (M+H)$^+$.

Step 2 [3,3''-Dichloro-5'-(8-morpholin-4-yl-octylcarbamoyl)-[1,1';3'1'']terphenyl-2'-yloxy]acetic Acid The title compound was prepared as an off white foam (0.147 g, 21%) from 3,5-bis-(m-chlorophenyl)-4-(2-hydroxyethoxy)benzoic acid ethyl ester using 8-morpholin-4'-yloctylamine and a procedure similar to Example 51, mp>91° C. (decomp.); $^1$H NMR (DMSO-d$_6$) δ 1.16–1.32 (m, 8H), 1.32–1.43 (m, 2H), 1.43–1.56 (m, 2H), 2.20 (t, J=7.2 Hz, 2H), 2.25–2.34 (m, 4H), 3.25 (dd, J=6.8, 13.0 Hz, 2H), 3.52 (t, J=4.6 Hz, 4H), 3.76 (s, 2H), 7.43–7.50 (m, 4H), 7.58 (dt, J=1.8, 6.6 Hz, 2H), 7.68–7.70 (m, 2H), 7.85 (s, 2H), 8.54 (t, J=5.7 Hz, 1H), 10.75–13.35 (bs, 1H); IR (KBr) 3430, 3080, 2940, 2860, 2330, 1720, 1640, 1605, 1560, 1545, 1480, 1460, 1400, 1345, 1310, 1255, 1215, 1160, 1120, 1080, 1030, 875, 755, and 700 cm$^{-1}$; mass spectrum [(+) ESI], m/z 613/615 (M+H)$^+$; Anal. Calcd. for $C_{33}H_{38}Cl_2N_2O_5 \cdot 0.8CHCl_3$: C, 57.25; H, 5.52; N, 3.95, Found: C, 57.15; H, 5.41; N, 3.87.

EXAMPLE 86

{3,3''-Dichloro-5'-[8-(2,6-dimethoxy-phenoxy)-octylcarbamoyl]-[1,1';3'1'']-terphenyl-2'-yloxy}acetic Acid Step 1 8-(240,6'-Dimethoxyphenoxy)octylamine To a round bottom flask with NaH (0.260 g, 6.49 mmol) and THF (120 mL) cooled to 0° C. was added 2,6-dimethoxyphenol (1.00 g, 6.49 mmol). The resulting solution was heated to reflux for 10 min. and then cooled back to room temperature. To this solution was added 15-crown-5 (0.117 mL, 0.589 mmol), tetrabutylammonium iodide (0.220 g, 0.589 mmol), and finally N-(8-bromo-octyl) phthalimide (2.00 g, 5.89 mmol). The final mixture was heated to reflux for 18 h. At this point, the reaction mixture was filtered, and the filtrate was diluted with EtOAc (400 mL). The organic layer was washed with 1 N HCl (40 mL), sat. aq. NaHCO$_3$ (40 mL), and brine (40 mL) and then dried (MgSO$_4$). After concentration, the residue was purified by the Biotage Flash 40 apparatus (5 to 10% EtOAc/petroleum ether gradient) to afford the ether intermediate.

To this ether intermediate (1.23 g, 2.99 mmol) in MeOH (20 mL) at room temperature was added hydrazine monohydrate (0.348 mL, 7.18 mmol) and the resulting mixture was heated to reflux. After 5 h at this temperature, the reaction was concentrated, taken up in EtOAc (200 mL), and filtered to remove insoluble materials. This phthalimide byproduct was washed with excess EtAOc, and the filtrate was washed with H$_2$O (30 mL) and brine (30 mL). The organic layer was then dried (Na$_2$SO$_4$) and concentrated to afford the product (0.833 g, 50%) as an oil; $^1$H NMR (CDCl$_3$) δ 1.28–1.68 (m, 12H), 1.68–1.82 (m, 2H), 2.69 (t, J=6.9 Hz, 2H), 3.86 (s, 6H), 3.96 (t, J=6.9 Hz, 2H), 6.58 (d, J=8.2 Hz, 2H), 6.97 (t, J=8.2 Hz, 1H); mass spectrum [(+) ESI], m/z 282 (M+H)$^+$, 304 (M+Na)$^+$.

Step 2 {3,3''-Dichloro-5'-[8-(2,6-dimethoxy-phenoxy)-octylcarbamoyl]-[1,1';3'1'']-terphenyl-2'-yloxy}acetic Acid The title compound was prepared as an off white solid (0.059 g, 11%) from 3,5-bis-(m-chlorophenyl)-4-(2-hydroxyethoxy)benzoic acid ethyl ester using 8-(2',6'-dimethoxyphenoxy)octylamine and a procedure similar to Example 51, mp>70° C. (decomp.); $^1$H NMR (DMSO-d$_6$) δ 1.24–1.34 (m, 6H), 1.34–1.44 (in, 2H), 1.48–1.63 (m, 4H), 3.23–3.38 (m, 2H), 3.72 (s, 6H), 3.77 (s, 2H), 3.79 (t, J=6.4 Hz, 2H), 6.61 (d, J=8.6 Hz, 2H), 6.94 (t, J=8.6 Hz, 1H), 7.43–7.50 (m, 4H), 7.56–7.60 (m, 2H), 7.69 (s, 2H), 7.85 (s, 2H), 8.54 (t, J=5.5 Hz, 1H), 10.95–14.75 (bs, 1H); IR (KBr) 3375, 3080, 3000, 2930, 2860, 1730, 1595, 1570, 1545, 1495, 1480, 1465, 1430, 1395, 1330, 1295, 1255, 1210, 1110, 1035, 1000, 880, 780, 725, and 700 cm$^{-1}$; mass spectrum [(+) ESI], m/z 680 (M+H)$^+$; Anal. Calcd. for $C_{37}H_{39}Cl_2NO_7 \cdot 0.25CHCl_3$: C, 62.97; H, 5.57; N, 1.97, Found: C, 62.76; H, 5.24; N, 1.87.

EXAMPLE 87

{5'-[8-(Benzoxazol-2-ylsulfanyl)-octylcarbamoyl]-3,3"-dichloro-[1,1';3'1"]-terphenyl-2'-yloxy}acetic Acid Step 1 8-(Benzoxazol-2-ylsulfanyl)-octylamine To a round bottom flask with 2-mercaptobenzoxazole (2.14 g, 14.2 mmol) and DMF (100 mL) at room temperature was added $K_2CO_3$ (2.61 g, 18.9 mmol) followed by N-(8-bromooctyl)phthalimide (4.00 g, 11.8 mmol). The resulting solution was heated to 60° C. for 0.5 h and then cooled back to room temperature. At this point, the reaction mixture was quenched with $H_2O$ (100 mL) and then diluted with EtOAc (600 mL). The organic layer was washed with 1 N HCl (60 mL), sat. aq. $NaHCO_3$ (60 mL), and brine (60 mL) and then dried ($MgSO_4$). After concentration, the residue was purified by the Biotage Flash 40 apparatus (10 to 20% EtOAc/petroleum ether gradient) to afford the thioether intermediate.

To this thioether intermediate (3.02 g, 7.39 mmol) in MeOH (40 mL) at room temperature was added hydrazine monohydrate (0.860 mL, 17.7 mmol) and the resulting mixture was heated to reflux. After 18 h at this temperature, the reaction was concentrated, taken up in EtOAc (300 mL), and filtered to remove insoluble materials. This phthalimide byproduct was washed with excess EtAOc, and the filtrate was washed with $H_2O$ (40 mL) and brine (40 mL). The organic layer was then dried ($Na_2SO_4$) and concentrated to afford the product (1.87 g, 57%) as an oil; $^1$H NMR (CDCl$_3$) δ 1.14–1.67 (m, 12H), 1.72–1.92 (m, 2H), 2.69 (t, J=9.6 Hz, 2H), 3.32 (t, J=8.5 Hz, 2H), 7.16–7.34 (m, 2H), 7.38–7.47 (m, 1H), 7.54–7.66 (m, 1H); mass spectrum [(+) ESI], m/z 279 (M+H)$^+$.

Step 2 {5'-[8-(Benzoxazol-2-ylsulfanyl)-octylcarbamoyl]-3,3"-dichloro-[1,1';3'1"]-terphenyl-2'-yloxy}-ethanol To a stirred solution of 3,5-bis-(m-chlorophenyl)-4-(2-hydroxyethoxy)benzoic acid ethyl ester (0.620 g, 1.44 mmol) in THF:EtOH (3:2, 30 mL) at room temperature was added 1 N KOH (7.20 mL, 7.20 mmol) dropwise. After 18 h at this temperature, the reaction mixture was concentrated and diluted with $H_2O$ (100 mL). The aqueous solution was acidified to pH 1 with 2 N HCl. The solid [3,5-bis-(m-chlorophenyl)-4-(2-hydroxyethoxy)benzoic acid] that formed was filtered off, washed with excess $H_2O$, and then dried on the high vacuum pump (0.450 g, 78%).

To a flame dried round bottom flask with 8-(benzoxazol-2-ylsulfanyl)octylamine (0.155 g, 0.558 mmol) in benzene:EtOH (1:1, 6 mL) at room temperature was added 3,5-bis-(m-chlorophenyl)-4-(2-hydroxyethoxy)benzoic acid (0.150 g, 0.372 mmol) followed by EEDQ (0.258 g, 1.04 mmol). After 3 days at this temperature, it was diluted with EtOAc (200 mL). This solution was washed with 1 N HCl (20 mL), sat. aq. $NaHCO_3$ (20 mL), and brine (20 mL) and then dried ($MgSO_4$). After concentration, the residue was purified by preparatory plate chromatography (30% EtOAc/petroleum ether) to afford the product (0.183 g, 74%) as a solid; $^1$H NMR (CDCl$_3$) δ 1.28–1.42 (m, 6H), 1.42–1.68 (m, 5H), 1.77–1.97 (m, 2H), 3.27–3.41 (m, 6H), 3.46 (dd, J=6.1, 13.5 Hz, 2H), 6.09–6.17 (m, 1H), 7.22–7.47 (m, 7H), 7.47–7.54 (m, 2H), 7.54–7.66 (m, 3H), 7.74 (s, 2H); mass spectrum [(+) ESI], m/z 664 (M+H)$^+$.

Step 3 {5'-[8-(Benzoxazol-2-ylsulfanyl)-octylcarbamoyl]-3,3"-dichloro-[1,1';3'1"]-terphenyl-2'-yloxy}acetic Acid The title compound was prepared as a white foamy solid (0.087 g, 47%) from {5'-[8-(benzoxazol-2-ylsulfanyl)-octylcarbamoyl]-3,3"-dichloro-[1,1';3'1"]-terphenyl-2'-yloxy}ethanol using a procedure similar to step 2 of Example 51, mp>68° C. (decomp.); $^1$H NMR (DMSO-d$_6$) δ 1.27–1.34 (m, 6H), 1.36–1.44 (m, 2H), 1.46–1.55 (m, 2H), 1.71–1.80 (m, 2H), 3.22–3.36 (m, 4H), 3.79 (s, 2H), 7.26–7.33 (m, 2H), 7.43–7.50 (m, 4H), 7.56–7.63 (m, 4H), 7.68 (s, 2H), 7.85 (s, 2H), 8.54 (t, J=5.3 Hz, 1H), 11.55–13.75 (bs, 1H); IR (KBr) 3410, 3080, 2930, 2860, 1730, 1630, 1600, 1565, 1545, 1500, 1480, 1455, 1430, 1395, 1335, 1300, 1230, 1210, 1170, 1130, 1100, 1080, 1040, 1000, 925, 885, 800, 740, and 700 cm$^{-1}$; mass spectrum [(+) APCI], m/z 677/679 (M+H)$^+$; Anal. Calcd. for $C_{36}H_{34}Cl_2N_2O_5S \cdot 1.5H_2O$: C, 61.36; H, 5.29; N, 3.98, Found: C, 61.37; H, 4.74; N, 4.04.

EXAMPLE 88

[3,3"-Dichloro-5'-(8-indol-1-yl-octylcarbamoyl)-[1,1';3'1"]terphenyl-2'-yloxy]acetic Acid Step 1 [3,3"-Dichloro-5'-(8-indol-1-yl-octylcarbamoyl)-[1,1';3'1"]terphenyl-2'-yloxy]-ethanol To a flame dried round bottom flask-with 8-indol-1-yloctylamine (0.227 g, 0.930 mmol, preparation similar to step 1 of Example 54) in $CH_2Cl_2$ (10 mL) at room temperature was added 3,5-bis-(m-chlorophenyl)-4-(2-hydroxyethoxy)-benzoic acid (0.250 g, 0.620 mmol, prepared in step 2 of Example 55) followed by Et3N (0.259 mL, 1.86 mmol), HOBt (0.092 g, 0.682 mmol), and finally DCC (0.153 g, 0.744 mmol). After 3 days at this temperature, it was concentrated and then diluted with EtOAc (200 mL). The white solid (DCU) that formed was filtered off and washed with excess EtOAc. The organic layer was washed with 1 N HCl (20 mL), sat. aq. $NaHCO_3$ (20 mL), and brine (20 mL) and then dried ($MgSO_4$). After concentration, the residue was purified by the Biotage Flash 40 apparatus (30 to 50% EtOAc/petroleum ether) to afford the product (0.341 g, 87%) as a solid; $^1$H NMR (CDCl$_3$) δ 1.21–1.38 (m, 8H), 1.46–1.63 (m, 3H), 1.75–1.89 (m, 2H), 3.27–3.49 (m, 6H), 4.11 (t, J=8.1 Hz, 2H), 6.01–6.13 (m, 1H), 6.47 (d, J=2.2 Hz, 1H), 7.05–7.13 (m, 2H), 7.19 (t, J=8.8 Hz, 1H), 7.39–7.46 (m, 5H), 7.48–7.55 (m, 2H), 7.58–7.66 (m, 3H), 7.74 (s, 2H); mass spectrum [(+) ESI], m/z 629 (M)$^+$.

Step 2 [3,3"-Dichloro-5'-(8-indol-1-yl-octylcarbamoyl)-[1,1';3'1"]terphenyl-2'-yloxy]acetic Acid The title compound was prepared as an off white foamy solid (0.051 g, 37%) from [3,3"-dichloro-5'-(8-indol-1-yl-octylcarbamoyl)-[1,1';3'1"]terphenyl-2'-yloxy]ethanol using a procedure similar to step 2 of Example 51, mp>84° C. (decomp.); $^1$H NMR (DMSO-d$_6$) δ 1.16–1.33 (m, 8H), 1.44–1.54 (m, 2H), 1.68–1.77 (m, 2H), 3.18–3.31 (m, 2H), 3.77 (s, 2H), 4.12 (t, J=6.8 Hz, 2H), 6.37 (d, J=2.9 Hz, 1H), 6.97 (t, J=7.2 Hz, 1H), 7.08 (t, J=7.2 Hz, 1H), 7.31 (d, J=2.9 Hz, 1H), 7.40–7.52 (m, 6H), 7.58 (d, J=6.6 Hz, 2H), 7.68 (s, 2H), 7.84 (s, 2H), 8.52 (t, J=5.9 Hz, 1H), 11.65–13.65 (bs, 1H); IR (KBr) 3410, 3070, 2930, 2860, 1730, 1635, 1600, 1580, 1570, 1545, 1480, 1460, 1430, 1400, 1330, 1310, 1240, 1210, 1170, 1100, 1080, 1045, 880, 795, 760, 740, and 700 cm$^{-1}$; mass spectrum [(+) APCI], m/z 643/645 (M+H)$^+$; Anal. Calcd. for $C_{37}H_{36}Cl_2N_2O_4 \cdot 1.5H_2O$: C, 66.27; H, 5.86; N, 4.18, Found: C, 66.30; H, 5.12; N, 4.14.

EXAMPLE 89

{3,3"-Dichloro-5'-[8-(3-cyano-phenoxy)-octylcarbamoyl]-[1,1';3'1"]terphenyl-2'-yloxy}acetic Acid The title compound was prepared as an off white foam (0.169 g, 50%) from 3,5-bis-(m-chlorophenyl)-4-(2- hydroxyethoxy)benzoic acid using 8-(3-cyano-phenoxy) octylamine (preparation similar to step 1 of Example 86) and a procedure similar to Example 88, mp>61° C. (decomp.); $^1$H NMR (DMSO-d$_6$) δ 1.28–11.43 (m, 8H), 1.47–1.56 (m, 2H), 1.65–1.74 (m, 2H), 3.23–3.32 (m, 2H), 3.78 (s, 2H), 3.99 (t, J=6.6 Hz, 2H), 7.25 (dd, J=2.6, 8.3 Hz, 1H), 7.34–7.39 (m, 2H), 7.42–7.50 (m, 5H), 7.56–7.60 (m, 2H), 7.68 (s, 2H), 7.85 (s, 2H), 8.56 (t, J=5.5 Hz, 1H), 12.25–13.55 (bs, 1H); IR (KBr) 3380, 3080, 2930, 2860, 2240, 1730, 1630, 1600, 1580, 1560, 1535, 1480, 1465, 1430, 1395, 1325, 1290, 1265, 1205, 1160, 1140, 1000, 875, 790, 780, 765, 700, and 680 cm$^{-1}$; mass spectrum [(+) ESI], m/z 645 (M+H)$^+$; Anal. Calcd. for $C_{36}H_{34}Cl_2N_2O_5 \cdot 1.5H_2O$: C, 64.29; H, 5.54; N, 4.16, Found: C, 64.05; H, 5.01; N, 4.08.

EXAMPLE 90

{3,3''-Dichloro-5'-[8-(4-chloro-benzyloxy)-octylcarbamoyl]-[1,1';3'1'']terphenyl-2'-yloxy}acetic Acid The title compound was prepared as an off white solid (0.161 g, 51%) from 3,5-bis-(m-chlorophenyl)-4-(2-hydroxyethoxy)benzoic acid using 8-(4-chlorobenzyloxy) octylamine (preparation similar to step 1 of Example 86) and a procedure similar to Example 88, mp 128–131° C.; $^1$H NMR (DMSO-d$_6$) δ 1.32–1.34 (m, 8H), 1.47–1.56 (m, 4H), 3.26 (dd, J=6.8, 13.0 Hz, 2H), 3.39 (t, J=6.6 Hz, 2H), 3.78 (s, 2H), 4.41 (s, 2H), 7.29–7.33 (m, 2H), 7.36–7.40 (m, 2H), 7.42–7.51 (m, 4H), 7.58 (dt, J=2.2, 6.4 Hz, 2H), 7.68–7.71 (m, 2H), 7.86 (s, 2H), 8.56 (t, J=5.5 Hz, 1H), 11.75–13.85 (bs, 1H); IR (KBr) 3320, 3070, 2930, 2860, 1725, 1620, 1600, 1570, 1490, 1480, 1460, 1425, 1400, 1340, 1300, 1280, 1240, 1200, 1170, 1155, 1090, 1050, 1015, 885, 800, 780, 755, and 700 cm$^{-1}$; mass spectrum [(+) ESI], m/z 668/670/672 (M+H)$^+$; Anal. Calcd. for $C_{36}H_{36}Cl_3NO_5 \cdot H_2O$: C, 62.93; H, 5.57; N, 2.04, Found: C, 62.95; H, 5.13; N, 1.96.

EXAMPLE 91

{3,3''-Dichloro-5'-[8-(4-fluoro-3-methyl-phenoxy)-octylcarbamoyl]-[1,1';3'1'']-terphenyl-2'-yloxy}acetic Acid The title compound was prepared as a white solid (0.193 g, 48%) from 3,5-bis-(m-chlorophenyl)-4-(2-hydroxyethoxy)benzoic acid using 8-(4-fluoro-3-methylphenoxy)octylamine (preparation similar to step 1 of Example 86) and a procedure similar to Example 88, mp 138–140° C.; $^1$H NMR (DMSO-d$_6$) δ 1.26–1.33 (m, 8H), 1.48–1.57 (m, 2H), 1.63–1.71 (m, 2H), 2.17 (d, J=1.8 Hz, 3H), 3.27 (dd, J=6.6, 12.7 Hz, 2H), 3.81 (s, 2H), 3.88 (t, J=6.4 Hz, 2H), 6.68–6.73 (m, 1H), 6.81 (dd, J=3.1, 6.4 Hz, 1H), 6.99 (t, J=9.2 Hz, 1H), 7.45–7.52 (m, 4H), 7.57–7.60 (m, 2H), 15 7.69 (s, 2H), 7.87 (s, 2H), 8.57 (t, J=5.5 Hz, 1H), 12.00–13.45 (bs, 1H); IR (KBr) 3330, 3080, 2930, 2860, 1725, 1625, 1570, 1500, 1485, 1460, 1430, 1395, 1330, 1300, 1280; 1245, 1205, 1165, 1100, 1075, 1050, 885, 795, 770, and 700 cm$^{-1}$; mass spectrum [(−) ESI], m/z 650 (M−H)$^-$; Anal. Calcd. for $C_{36}H_{36}Cl_2FNO_5 \cdot 0.5H_2O$: C, 65.36; H, 5.64; N, 2.12, Found: C, 65.22; Hi 5.56; N, 2.13.

EXAMPLE 92

[3,3''-Dichloro-5'-(8-imidazol-1-yl-octylcarbamoyl)-[1,1';3'1'']terphenyl-2'-yloxy]acetic Acid The title compound was prepared as an off white solid (0.010 g, 2%) from 3,5-bis-(m-chlorophenyl)-4-(2-hydroxyethoxy)benzoic acid using 8-imidazol-1-yl-octylamine (preparation similar to step 1 of Example 86) and a procedure similar to Example 88, mp>109° C. (decomp.); $^1$H NMR (DMSO-d$_6$) δ 1.13–1.32 (m, 8H), 1.44–1.54 (m, 2H), 1.62–1.70 (m, 2H), 3.20–3.36 (m, 2H), 3.64 (s, 2H), 3.90 (t, J=7.0 Hz, 2H), 6.84 (s, 1H), 7.12 (s, 1H), 7.41–7.48 (m, 4H), 7.56–7.62 (m, 3H), 7.71 (s, 2H), 7.82 (s, 2H), 8.51 (t, J=5.3 Hz, 1H), 10.75–13.45 (bs, 1H); IR (KBr) 3420, 3125, 3080, 2930, 2860, 1735, 1630, 1600, 1580, 1565, 1480, 1460, 1425, 1400, 1330, 1300, 1275, 1260, 1240, 1210, 1165, 1085, 1030, 880, 780, 770, and 700 cm$^{-1}$; mass spectrum [(+) ESI], m/z 594 (M+H)$^+$; Anal. Calcd. for $C_{32}H_{33}Cl_2N_3O_4 \cdot 6H_2O$: C, 54.70; H, 6.46; N, 5.98, Found: C, 54.60; H, 5.34; N, 5.23.

EXAMPLE 93

{3,3''-Dichloro-5'-[6-(naphthalen-1-ylcarbamoyloxy)-hexylcarbamoyl]-[1,1';3'1'']-terphenyl-2'-yloxy}acetic Acid Step 1 6-(Naphthalen-1-ylcarbamoyloxy)hexylamine To a round bottom flask with 6-bromo-1-hexanol (0.500 g, 2.76 mmol) and $CH_2Cl_2$ (25 mL) at room temperature was added 1-naphthyl isocyanate (0.595 mL, 4.14 mmol) followed by bis(chloro-dibutyltin) oxide (0.076 g, 0.138 mmol). After stirring at this temperature for 2 h, the reaction mixture was quenched with MeOH (15 mL) and then diluted with EtOAc (300 mL). The organic layer was washed with 1 N HCl (30 mL), sat. aq. NaHCO$_3$ (30 mL), and brine (30 mL) and then dried (MgSO$_4$). After concentration, the residue was diluted with CHCl$_3$ (200 mL), and the white polymeric solid which formed was filtered off. After a second concentration, the residue was purified by the Biotage Flash 40 apparatus (10 to 15% EtOAc/petroleum ether gradient) to afford the carbamate-bromide intermediate.

To a round bottom flask with the above carbamate-bromide intermediate (0.741 g, 2.12 mmol) and DMF (20 mL) at room temperature was added sodium azide (0.689 g, 10.6 mmol) followed by tetrabutylammonium iodide (0.078 g, 0.212 mmol). The mixture was heated to 100° C. for 3 h. At this point, the reaction mixture was concentrated and then diluted with EtOAc (300 mL). The organic layer was washed with 1 N HCl (30 mL), sat. aq. NaHCO$_3$ (30 mL), and brine (30 mL) and then dried (Na$_2$SO$_4$). After concentration, the residue was purified by the Biotage Flash 40 apparatus (5 to 15% EtOAc/petroleum ether gradient) to afford the carbamate-azide intermediate.

To this carbamate-azide intermediate (0.439 g, 1.41 mmol) in THF (14 mL) at room temperature was added H$_2$O (0.028 mL, 1.55 mmol) followed by triphenyl phosphine (0.407 g, 1.55 mmol). After stirring at this temperature for 18 h, the reaction was about half done by TLC. A few boiling chips were added and the stirring was continued at room temperature for another 3 days. The solution was diluted with excess EtOAc (200 mL), dried (Na$_2$SO$_4$), and concentrated to afford the product (0.398 g, 65%) as an oil (contaminated with triphenyl phosphine oxide which did not cause a problem in subsequent steps); $^1$H NMR (CDCl$_3$) δ 1.31–1.54 (m, 8H), 1.86–1.98 (m, 2H), 2.70 (t, J=6.8 Hz, 2H), 4.25 (t, J=6.8 Hz, 2H), 6.98–7.12 (bs, 1H), 7.26–7.97 (m, 7H); mass spectrum [(+) ESI], m/z 287 (M+H)$^+$.

Step 2 2,6-Diiodo-4-[6'-(naphthalen-1'-ylcarbamoyloxy)-hexylcarbamoyl]-phenol

To a round bottom flask with 3,5-diiodo-4-hydroxybenzoic acid (0.420 g, 1.08 mmol) was added SOCl$_2$ (3 mL). After 2 h at reflux, the solution was concentrated and pumped on the high vacuum for 0.5 h. This acid chloride was then dissolved in THF (3 mL) and added dropwise to a solution of 6-(naphthalen-1-ylcarbamoyloxy) hexylamine (0.402 g, 1.40 mmol) and Et$_3$N (0.452 mL, 3.24 mmol) in THF (7 mL). After stirring for 1 h at room temperature, the reaction mixture was diluted with EtOAc (250 mL). The organic layer was washed with 1 N HCl (25 mL), sat. aq. NaHCO$_3$ (25 mL), and brine (25 mL) and then dried (MgSO$_4$). After concentration, the residue was purified by the Biotage Flash 40 apparatus (30 to 50% EtOAc/ petroleum ether) to afford the product (0.394 g, 55%) as a solid; $^1$H NMR (DMSO-d$_6$) δ 1.27–1.46 (m, 4H), 1.46–1.58 (m, 2H), 1.58–1.71 (m, 2H), 3.22 (dd, J=5.7, 13.8 Hz, 2H), 4.12 (t, J=6.1 Hz, 2H), 7.45–7.62 (m, 4H), 7.73 (d, J=8.9 Hz, 1H), 7.88–7.94 (m, 1H), 8.03–8.10 (m, 1H), 8.23 (s, 2H), 8.43 (t, J=5.4 Hz, 1H), 9.49 (s, 1H), 10.03 (s, 1H); mass spectrum [(–) ESI], m/z 657 (M–H)$^-$.

Step 3 3,3''-Dichloro-5'-[6-(naphthalen-1-ylcarbamoyloxy)-hexylcarbamoyl]-[1,1';3'1'']-terphenyl-2'-ol To a flask with 2,6-diiodo-4-[6'-(naphthalen-1'-ylcarbamoyloxy)-hexylcarbamoyl]phenol (0.394 g, 0.599 mmol) was added 1 M solution of K$_2$CO$_3$ (1.80 mL, 1.80 mmol) followed by dioxane (18 mL). To this mixture was added 3-chlorophenylboronic acid (0.225 g, 1.44 mmol) and then PdCl$_2$(dppf) (0.010 g, 0.0120 mmol). The mixture was stirred at room temperature for 0.5 h then heated at 65° C. for 3 h. At this point, the reaction was cooled to room temperature, concentrated, and then diluted with EtOAc (250 mL). The organic layer was washed with 1 N HCl (25 mL), sat. aq. NaHCO$_3$ (25 mL), and brine (25 mL) and then dried (MgSO$_4$). After concentration, the residue was purified by the Biotage Flash 40 apparatus (30 to 50% EtAOc/ petroleum ether gradient) to afford the product (0.337 g, 90%) as a solid; $^1$H NMR (DMSO-d$_6$) δ 1.30–1.50 (m, 4H), 1.50–1.61 (m, 2H), 1.61–1.72 (m, 2H), 3.19–3.35 (m, 2H), 4.11 (t, J=6.7 Hz, 2H), 7.43–7.62 (m, 10H), 7.65 (s, 2H), 7.73 (d, J=7.8 Hz, 1H), 7.79 (s, 2H), 7.88–7.94 (m, 1H), 8.03–8.09 (m, 1H), 8.46 (t, J=5.6 Hz, 1H), 9.18 (s, 1H), 9.50 (s, 1H); mass spectrum [(+) ESI], m/z 628 (M+H)$^+$, 650 (M+Na)$^+$.

Step 4 {3,3''-Dichloro-5'-[6-(naphthalen-1-ylcarbamoyloxy)-hexylcarbamoyl]-[1,1';3'1'']-terphenyl-2'-yloxy}acetic Acid Methyl Ester To a stirred solution of 3,3''-dichloro-5'-[6-(naphthalen-1-ylcarbamoyloxy)-hexylcarbamoyl]-[1,1';3'1'']-terphenyl-2'-ol (0.320 g, 0.510 mmol) and K$_2$CO$_3$ (0.078 g, 0.561 mmol) in DMF (10 mL) at room temperature was added dropwise methyl bromoacetate (0.097 mL, 1.02 mmol). After 18 h at this temperature, it was concentrated and then diluted with excess EtOAc (250 mL). The organic layer was washed with 1 N HCl (25 mL), sat. aq. NaHCO$_3$ (25 mL), and brine (25 mL) and then dried (MgSO$_4$). After concentration, the residue was purified by flash chromatography (30 to 50% EtOAc/petroleum ether gradient) to afford the product (0.231 g, 65%) as a solid; $^1$H NMR (DMSO-d$_6$) δ 1.32–1.49 (m, 4H), 1.49–1.73 (m, 4H), 3.23–3.35 (m, 2H), 3.44 (s, 3H), 3.99 (s, 2H), 4.11 (t, J=6.3 Hz, 2H), 7.45–7.63 (m, 10H), 7.69 (s, 2H), 7.73 (d, J=9.4 Hz, 1H), 7.87–7.94 (m, 3H), 8.02–8.12 (m, 1H), 8.61 (t, J=5.5 Hz, 1H), 9.49 (s, 1H); mass spectrum [(+) ESI], m/z 700 (M+H)$^+$.

Step 5 {3,3''-Dichloro-5'-[6-(naphthalen-1-ylcarbamoyloxy)-hexylcarbamoyl]-[1,1';3'1'']-terphenyl-2'-yloxy }acetic Acid To a stirred solution of {3,3''-dichloro-5'-[6-(naphthalen-1-ylcarbamoyloxy)-hexylcarbamoyl]-[1,1';3'1'']-terphenyl-2'-yloxy}acetic acid methyl ester (0.182 g, 0.310 mmol) in THF:MeOH (3:2, 10 mL) at 0° C. was added dropwise 1 N KOH (1.55 mL, 1.55 mmol). After 0.5 h at this temperature, it was warmed to room temperature for 0.5 h. It was then concentrated and diluted with H$_2$O. The solution was then acidified to pH 1 with 2 N HCl. The cloudy-white precipitate was filtered off and washed with H$_2$O. The resulting solid was purified by preparatory plate chromatography (10% MeOH:CHCl$_3$) to afford the product (0.151 g, 72%) as an off white solid, mp 201–204° C.; $^1$H NMR (DMSO-d$_6$) δ 1.32–1.45 (m, 4H), 1.51–1.58 (m, 2H), 1.61–1.68 (m, 2H), 3.24–3.35 (m, 2H), 3.77 (s, 2H), 4.10 (t, J=6.6 Hz, 2H), 7.43–7.53 (m, 7H), 7.55–7.60 (m, 3H), 7.68–7.74 (m, 3H), 7.86 (s, 2H), 7.88–7:92 (m, 1H), 8.02–8.06 (m, 1H), 8.58 (t, J=5.5 Hz, 1H), 9.48 (s, 1H), 11.65–13.45 (bs, 1H); IR (KBr) 3430, 3260, 3060, 2930, 2870, 2720, 2670, 2600, 2510, 2320, 1765, 1690, 1610, 1570, 1535, 1505, 1480, 1465, 1430, 1415, 1390, 1390, 1335, 1300, 1240, 1220, 1195, 1165, 1105, 1080, 1070, 1030, 1010, 900, 895, 785, 780, 765, and 700 cm$^{-1}$; mass spectrum [(–) ESI], m/z 683 (M–H)$^+$; Anal. Calcd. for C$_{38}$H$_{34}$Cl$_2$N$_2$O$_6$.2.25H$_2$O: C, 62.86; H, 5.34; N, 3.86, Found: C, 62.69; H, 4.58; N, 3.79.

EXAMPLE 94

{3,3''-Dichloro-5'-[6-(2,4-difluoro-phenylcarbamoyloxy)-hexylcarbamoyl]-[1,1';3'1''] terphenyl-2'-yloxy}acetic Acid The title compound was prepared as a white foamy solid (0.203 g, 30%) from 3,5-diiodo-4-hydroxybenzoic acid using 6-(2,4-difluorophenyl-carbamoyloxy)-hexylamine and a procedure similar to Example 93, mp>80° C. (decomp.); $^1$H NMR (DMSO-d$_6$) δ 1.30–1.42 (m, 4H), 1.48–1.64 (m, 4H), 3.23–3.33 (m, 2H), 3.82 (s, 2H), 4.04 (t, J=6.8 Hz, 2H), 6.99–7.05 (m, 1H), 7.22–7.29 (m, 1H), 7.44–7.60 (m, 7H), 7.67–7.70 (m, 2H), 7.87 (s, 2H), 8.58 (t, J=5.5 Hz, 1H), 9.22 (s, 1H), 11.65–13.45 (bs, 1H); IR (KBr) 3320, 3070, 2930, 2860, 1725, 1620, 1530, 1480, 1460, 1425, 1400, 1330, 1290, 1225, 1200, 1170, 1145, 1100, 1070, 970, 880, 845, 795, 775, and 700 cm$^{-1}$; mass spectrum [(–) ESI], m/z 669 (M–H)$^-$; Anal. Calcd. for C$_{34}$H$_{30}$Cl$_2$F$_2$N$_2$O$_6$.0.75H$_2$O: C, 59.61; H, 4.63; N, 4.09, Found: C, 59.53; H, 4.12; N, 3.99.

EXAMPLE 95

{3,3''-Dichloro-5'-[6-(4-phenoxy-phenylcarbamoyloxy)-hexylcarbamoyl]-[1,1';3'1''] terphenyl-2'-yloxy}acetic Acid The title compound was prepared as a white foamy solid (0.494 g, 45%) from 3,5-diiodo-4-hydroxybenzoic acid using 6-(4-phenoxy-phenylcarbamoyloxy)hexylamine and a procedure similar to Example 93, mp>75° C. (decomp.); $^1$H NMR (DMSO-d$_6$) δ 1.32–1.43 (m, 4H), 1.50–1.66 (m, 4H), 3.24–3.33 (m, 2H), 3.84 (s, 2H), 4.06 (t, J=6.6 Hz, 2H), 6.90–6.97 (m, 4H), 7.06 (t, J=7.2 Hz, 1H), 7.30–7.37 (m, 2H), 7.42–7.52 (m, 6H), 7.58 (dt, J=2.0, 6.6 Hz, 2H), 7.67–7.71 (m, 2H), 7.87 (s, 2H), 8.58 (t, J=5.8 Hz, 1H), 9.59 (s, 1H), 11.50–12.75 (bs, 1H); IR (KBr) 3320, 3060, 2930, 2860, 1725, 1705, 1640, 1600, 1545, 1505, 1490, 1465, 1430, 1410, 1330, 1305, 1215, 1170, 1100, 1075, 1010, 980, 835, 795, 765, and 695 cm$^{-1}$; mass spectrum [(–) ESI], m/z 725 (M–H)$^-$; Anal. Calcd. for C$_{40}$H$_{36}$Cl$_2$N$_2$O$_7$.H$_2$O: C, 64.43; H, 5.14; N, 3.76, Found: C, 64.44; H, 4.69; N, 3.53.

EXAMPLE 96

{3,3''-Dichloro-5'-[8-(5-fluoro-indol-1-yl)-octylcarbamoyl]-[1,1';3'1'']terphenyl-2'-yloxy}acetic Acid The title compound was prepared as an offwhite solid (0.373 g, 48%) from 3,5-diiodo-4-hydroxybenzoic acid using 8-(5-fluoro-indol-1-yl)octylamine (preparation similar to step 1 of Example 86) and a procedure similar to Example 93, mp 141–144° C.; $^1$H NMR (DMSO-$d_6$) δ 1.16–1.31 (m, 8H), 1.44–1.53 (m, 2H), 1.67–1.76 (m, 2H), 3.23 (dd, J=6.8, 13.2 Hz, 2H), 3.82 (s, 2H), 4.12 (t, J=7.0 Hz, 2H), 6.37 (dd, J=0.7, 3.1 Hz, 1H), 6.93 (td, J=2.4, 9.2 Hz, 1H), 7.26 (dd, J=2.2, 9.7 Hz, 1H), 7.40 (d, J=3.1 Hz, 1H), 7.41–7.51 (m, 5H), 7.57 (dt, J=2.2, 6.6 Hz, 2H), 7.67–7.69 (m, 2H), 7.85 (s, 2H), 8.53 (t, J=5.7 Hz, 1H), 11.55–13.30 (bs, 1H); IR (KBr) 3340, 3070, 2930, 2860, 2520, 1725, 1625, 1580, 1565, 1490, 1445, 1400, 1375, 1340, 1300, 1280, 1230, 1205, 1150, 1140, 1110, 1100, 1085, 1050, 945, 890, 860, 795, 780, 750, 715, and 695 cm$^{-1}$; mass spectrum [(+) APCI], m/z 661 (M+H)$^+$; Anal. Calcd. for $C_{37}H_{35}Cl_2FN_2O_4 \cdot H_2O$: C, 65.39; H, 5.49; N, 4.12, Found: C, 65.44; H, 5.21; N, 3.98.

EXAMPLE 97

{3,3"-Dichloro-5'-[8-(5-methoxy-indol-1-yl)-octylcarbamoyl]-[1,1';3'1"]terphenyl-2'-yloxy}acetic Acid The title compound was prepared as a white foamy solid (0.288 g, 37%) from 3,5-diiodo-4-hydroxybenzoic acid using 8-(5-methoxy-indol-1-yl)octylamine (preparation similar to step 1 of Example 86) and a procedure similar to Example 93, mp>70° C. (decomp.); $^1$H NMR (DMSO-$d_6$) δ 1.15–1.29 (m, 8H), 1.43–1.53, (m, 2H), 1.65–1.74 (m, 2H), 3.23 (dd, J=6.8, 13.0 Hz, 2H), 3.72 (s, 3H), 3.82 (s, 2H), 4.07 (t, J=7.0 Hz, 2H), 6.28 (dd, J=0.7, 3.1 Hz, 1H), 6.73 (dd, J=2.4, 8.8 Hz, 1H), 7.00 (d, J=2.2 Hz, 1H), 7.26 (d, J=3.1 Hz, 1H), 7.30 (d, J=9.0 Hz, 1H), 7.44–7.51 (m, 4H), 7.57 (dt, J=2.2, 6.6 Hz, 2H), 7.67–7.69 (m, 2H), 7.86 (s, 2H), 8.53 (t, J=5.7 Hz, 1H), 11.65–13.50 (bs, 1H); IR (KBr) 3360, 3070, 2930, 2860, 2520, 1730, 1620, 1600, 1575, 1550, 1490, 1445, 1430, 1395, 1335, 1300, 1230, 1205, 1160, 1145, 1100, 1080, 1050, 1025, 885, 795, 780, 760, and 695 cm$^{-1}$; mass spectrum [(+) APCI], m/z 673 (M+H)$^+$; Anal. Calcd. for $C_{38}H_{38}Cl_2N_2O_5 \cdot 2.0H_2O$: C, 64.31; H, 5.97; N, 3.95, Found: C, 64.29; H, 5.56; N, 3.81.

EXAMPLE 98

{3,3"-Dichloro-5'-[8-(2,5-dimethyl-indol-1-yl)-octylcarbamoyl]-[1,1';3'1"]-terphenyl-2'-yloxy}acetic Acid The title compound was prepared as a light orange solid (0.138 g, 19%) from 3,5-diiodo-4-hydroxybenzoic acid using 8-(2,5-dimethyl-indol-1-yl)octylamine (preparation similar to step 1 of Example 86) and a procedure similar to Example 93, mp>172° C. (decomp.); $^1$H NMR (DMSO-$d_6$) δ 1.18–1.32 (m, 8H), 1.44–1.53 (m, 2H), 1.55–1.64 (m, 2H), 2.31 (s, 3H), 2.33 (s, 3H), 3.24 (dd, J=7.0, 13.4 Hz, 2H), 3.81 (s, 2H), 4.01 (t, J=7.2 Hz, 2H), 6.03–6.05 (m, 1H), 6.82 (dd, J=1.5, 8.6 Hz, 1H), 7.14–7.16 (m, 1H), 7.19 (d, J=8.3 Hz, 1H), 7.43–7.51 (m, 4H), 7.57 (dt, J=2.2, 6.6 Hz, 2H), 7.67–7.69 (m, 2H), 7.86 (s, 2H), 8.53 (t, J=5.7 Hz, 1H), 11.80–13.30 (bs, 1H); IR (KBr) 3340, 3070, 3010, 2930, 2860, 2740, 2510, 1725, 1620, 1580, 1560, 1485, 1455, 1400, 1345, 1330, 1300, 1240, 1200, 1165, 1100, 1080, 1050, 885, 870, 795, 780, 770, 760, and 700 cm$^{-1}$; mass spectrum [(+) APCI], m/z 671 (M+H)$^+$; Anal. Calcd. for $C_{39}H_{40}Cl_2N_2O_4 \cdot 1.5H_2O$: C, 67.04; H, 6.20; N, 4.01, Found: C, 66.83; H, 5.94; N, 3.85.

EXAMPLE. 99

{3,3"-Dichloro-5'-[8-(5-methoxy-2-methyl-indol-1-yl)-octylcarbamoyl]-[1,1';3'1"]-terphenyl-2'-yloxy}acetic Acid The title compound was prepared as a light orange foamy solid (0.310 g, 41%) from 3,5-diiodo-4-hydroxybenzoic acid using 8-(5-methoxy2-methyl-indol-1-yl)octylamine (preparation similar to step 1 of Example 86) and a procedure similar to Example 93, mp>75° C. (decomp.); $^1$H NMR (DMSO-$d_6$) δ 1.22–1.32 (m, 8H), 1.44–1.54 (m, 2H), 1.54–1.64 (m, 2H), 2.33 (s, 3H), 3.24 (dd, J=6.4, 12.5 Hz, 2H), 3.70 (s, 3H), 3.85 (s, 2H), 4.00 (t, J=7.2 Hz, 2H), 6.05–6.07 (m, 1H), 6.64 (dd, J=2.4, 8.8 Hz, 1H), 6.90 (d, J=2.2 Hz, 1H), 7.20 (d, J=8.8 Hz, 1H), 7.44–7.52 (m, 4H), 7.57 (dt, J=2.2, 6.6 Hz, 2H), 7.67–7.69 (m, 2H), 7.86 (s, 2H), 8.54 (t, J=6.9 Hz, 1H), 12.20–12.85 (bs, 1H); IR (KBr) 3410, 3070, 2930, 2860, 1735, 1635, 1615, 1600, 1580, 1570, 1555, 1490, 1455, 1430, 1400, 1330, 1300, 1210, 1165, 1100, 1075, 1050, 1030, 880, 830, 795, 775, and 700 cm$^{-1}$; mass spectrum [(+) APCI], m/z 687 (M+H)$^+$; Anal. Calcd. for $C_{39}H_{40}Cl_2N_2O_5 \cdot H_2O$: C, 66.38, H, 6.00; N, 3.97, Found: C, 66.62; H, 5.70; N, 3.93.

EXAMPLE 100

(3,3"-Dichloro-5'-{[1-(4-phenyl-butoxymethyl)-cyclopropylmethyl]-carbamoyl}-[1,1';3'1"]terphenyl-2'-yloxy)acetic Acid Step 1 3-Hydroxy-2-cyclopropylpropylamine To a slurry of LAH (16.14 g, 425 mmol) in THF (300 mL) cooled to 0° C. was added a slurry of 1-(aminocarbonyl)-1-cyclopropanecarboxylic acid (9.15 g, 70.9 mmol) in THF (100 mL) dropwise. After 15 min. at this temperature, it was warmed to room temperature and stirred for 2.5 h. At this point, the mixture was cooled back down to 0° C. and quenched with efficient stirring by dropwise addition of $H_2O$ (16.14 mL), 15% aq. NaOH (16.14 mL), and $H_2O$ (48.42 mL). It was then stirred an additional 18 h at room temperature. At this time, the solvent was dried ($Na_2SO_4$), filtered, and concentrated. The residue was purified by vacuum distillation (~5 mm Hg, 95–100° C. head temperature) to afford the product (1.40 g, 20%) as an oil; $^1$H NMR (DMSO-$d_6$) δ 0.24–0.28 (m, 4H), 2.49 (s, 2H), 3.30 (m, 2H); IR (film) 3365, 3300, 3080, 3000, 2920, 2870, 1650, 1595, 1465, 1430, 1395, 1310, 1210, 1035, 980, 925, 895, 865, and 720 cm$^{-1}$; mass spectrum [(+) ESI], m/z 102 (M+H)$^+$.

Step 2 (3,3"-Dichloro-5'-{[1-(hydroxymethyl)-cyclopropylmethyl]-carbamoyl}-[1,1';3'1"]terphenyl-2'-yloxy)-methyl methyl Ether To a stirred solution of 3,5-bis-(m-chlorophenyl)-4-(2-methoxymethoxy)benzoic acid ethyl ester (3.18 g, 7.37 mmol) in THF:EtOH (3:2, 100 mL) at room temperature was added 1 N KOH (37 mL, 36.9 mmol) dropwise. After 18 h at this temperature, the reaction mixture was concentrated and diluted with $H_2O$ (200 mL). The aqueous solution was acidified to pH 1 with 2 N HCl. The solid that formed was filtered off and washed with excess $H_2O$. It was then dissolved in EtOAc (300 mL), washed with brine (30 mL), and dried (MgSO$_4$). After concentration, the residue was purified by the Biotage Flash 40 apparatus (1 to 5% MeOH/CHCl3 ether gradient) to afford the product [2.45 g, 82%, 3,5-bis-(m-chlorophenyl)-4-(2-methoxymethoxy)benzoic acid] as a solid.

To a flame dried round bottom flask with 3-hydroxy-2-cyclopropylpropylamine (0.842 g, 8.33 mmol) in $CH_2Cl_2$ (80 mL) at room temperature was added 3,5-bis-(m-chlorophenyl)-4-(2-hydroxyethoxy)benzoic acid (2.24 g, 5.55 mmol) followed by Et$_3$N (2.32 mL, 16.7 mmol), HOBt (0.825 g, 6.11 mmol), and finally DCC (1.37 g, 6.66 mmol). After 18 h at this temperature, it was concentrated and then diluted with EtOAc (400 mL). The white solid (DCU) that formed was filtered off and washed with excess EtOAc. The organic layer was washed with 1 N HCl (40 mL), sat. aq.

NaHCO$_3$ (40 mL), and brine (40 mL) and then dried (MgSO$_4$). After concentration, the residue was purified by the Biotage Flash 40 apparatus (30 to 50% EtOAc/petroleum ether) to afford the product (2.28 g, 84%) as a solid; $^1$H NMR (DMSO-d$_6$) δ 0.34–0.40 (m, 2H), 0.43–0.50 (m, 2H), 2.66 (s, 3H), 3.22–3.42 (m, 4H), 4.38 (s, 2H), 4.53 (s, 1H), 7.43–7.66 (m, 6H), 7.72 (s, 2H), 7.89 (s, 2H), 8.61 (t, J=5.4 Hz, 1H); mass spectrum [(+) ESI], m/z 486 (M)$^+$.

Step 3 (3.3"-Dichloro-5'-{[1-(4-phenyl-butoxymethyl)-cyclopropylmethyl]-carbamoyl}-[1,1';3'1"]terphenyl-2'-yloxy)-methyl Methyl Ether To a solution of 4-phenyl-1-butanol (5.00 g, 33.3 mmol) and CH$_2$Cl$_2$ (250 mL) at 0° C. was added triphenylphosphine (13.1 g, 50.0 mmol) followed by NBS (8.90 g, 50.0 mmol). After stirring at this temperature for 2 h, the mixture was quenched with H$_2$O (50 mL) and extracted with CH$_2$Cl$_2$ (150 mL) The organic layer was washed with brine (40 mL) and dried (Na$_2$SO$_4$). After concentration, the residue was flushed through two quick columns of silica gel using 2% EtOAc/petroleum ether as an eluant to afford 4-phenylbutyl bromide (6.22 g, 88%) as an intermediate.

To a round bottom flask with NaH (0.201 g, 5.03 mmol) and THF (50 mL) cooled to 0° C. was added (3,3"-dichloro-5'-{[1-(hydroxymethyl)-cyclopropylmethyl]-carbamoyl}-[1,1';3'1"]terphenyl-2'-yloxy)methyl methyl ether (1.88 g, 3.87 mmol). The resulting solution was heated to reflux for 10 min. and then cooled back to room temperature. To this solution was added 15-crown-5 (0.308 mL, 1.55 mmol), tetrabutylammonium iodide (0.573 g, 1.55 mmol), and finally 4-phenyl-butylbromide (3.30 g, 15.5 mmol) in THF (10 mL). The final mixture was heated to reflux for 18 h. At this point, the reaction mixture was quenched with MeOH (10 mL) and then diluted with EtOAc (400 mL). The organic layer was washed with 1 N HCl (40 mL), sat. aq. NaHCO$_3$ (40 mL), and brine (40 mL) and then dried (MgSO$_4$). After concentration, the residue was purified by the Biotage Flash 40 apparatus (10 to 30% EtOAc/petroleum ether gradient) to afford the product (0.777 g, 33%) as a solid; $^1$H NMR (CDCl$_3$) δ 0.48–0.58 (m, 2H), 0.58–0.67 (m, 2H), 1.47–1.56 (m, 4H), 2.40 (t, J=7.5 Hz, 2H), 2.73 (s, 3H), 3.38 (s, 2H), 3.38–3.48 (m, 4H), 4.40 (s, 2H), 7.07 (d, J=7.5 Hz, 2H), 7.12–7.26 (m, 3H), 7.31–7.42 (m, 4H), 7.42–7.53 (m, 3H), 7.62 (s, 2H), 7.7 (s, 2H); mass spectrum [(+) ESI], m/z 618 (M)$^+$.

Step 4 3.3"-Dichloro-5'-{[1-(4-phenyl-butoxymethyl)-cyclopropylmethyl]-carbamoyl}-[1,1';3'1"]terphenyl-2'-ol To a solution of (3,3"-dichloro-5'-{[1-(4-phenylbutoxymethyl)-cyclopropylmethyl]-carbamoyl}-[1,1';3'1"]terphenyl-2'-yloxy)methyl methyl ether (0.681 g, 1.10 mmol) in CH$_2$Cl$_2$ (15 mL) at –30° C. containing 4 Å molecular sieves was added trimethylsilyl bromide (0.581 mL, 4.40 mmol). After stirring at this temperature for 1 h, it was warmed to 0° C. and stirred an additional 5 h. Only slight conversion to product so warmed to room temperature and stirred at this temperature for 18 h. At this point, the mixture was quenched with sat. aq. NaHCO$_3$ (10 mL) and extracted with EtOAc (250 mL). The organic layer was washed with brine (25 mL) and dried (MgSO$_4$). After concentration, the residue was purified by the Biotage Flash 40 apparatus (10 to 30% EtOAc/petroleum ether gradient) to afford the product (0.455 g, 72%) as a solid; $^1$H NMR (DMSO-d$_6$) δ 0.32–0.41 (m, 2H), 0.47–0.55 (m, 2H), 1.40–1.62 (m, 4H), 2.46–2.58 (m, 2H), 3.28 (s, 2H), 3.28–3.42 (m, 4H), 7.11–7.20 (m, 3H), 7.20–7.29 (m, 2H), 7.42–7.55 (m, 6H), 7.65 (s, 2H), 7.79 (s, 2H), 8.34 (t, J=6.3 Hz, 1H), 9.19 (s, 1H); mass spectrum [(+) ESI], m/z 574 (M)$^+$.

Step 5 (3.3"-Dichloro-5'-{[1-(4-phenyl-butoxymethyl)-cyclopropylmethyl]-carbamoyl}-[1,1';3'1"]terphenyl-2'-yloxy)acetic Acid The title compound was prepared as a white foamy solid (0.202 g, 47%) from 3,3"-dichloro-5'-{[1-(4-phenyl-butoxymethyl)-cyclopropylmethyl]-carbamoyl-[1,1';3'1'] terphenyl-2'-ol using a procedure similar to steps 4–5 of Example 93, mp>52° C. (decomp.); $^1$H NMR (DMSO-d$_6$) δ 0.36 (dd, J=4.0, 5.5 Hz, 2H), 0.52 (dd, J=4.6, 6.2 Hz, 2H), 1.42–1.51 (m, 2H), 1.51–1.59 (m, 2H), 2.47–2.54 (m, 2H), 3.24–3.39 (m, 6H), 3.83 (s, 2H), 7.10–7.15 (m, 3H), 7.20–7.25 (m, 2H), 7.42–7.51 (m, 4H), 7.57 (dt, J=2.2, 6.8 Hz, 2H), 7.67–7.69 (m, 2H), 7.86 (s, 2H), 8.47 (t, J=5.7 Hz, 1H), 11.55–13.35 (bs, 1H); IR (KBr) 3380, 3070, 3020, 2930, 2860, 1755, 1735, 1630, 1600, 1585, 1570, 1540, 1495, 1485, 1460, 1430, 1395, 1370, 1340, 1300, 1245, 1205, 1165, 1095, 1085, 1050, 885, 795, 780, 770, 755, and 700 cm$^{-1}$; mass spectrum [(+) APCI], m/z 632 (M+H)$^+$; Anal. Calcd. for C$_{36}$H$_{35}$Cl$_2$NO$_5$.0.25H$_2$O: C, 67.87; H, 5.62; N, 2.20, Found: C, 67.77; H, 5.51; N, 2.14.

EXAMPLE 101

[5'-(Benzofuran-2-carbonyl)-[1,1';3'1"]terphenyl-2'-yloxy]acetic Acid

Step 1 [5'-(Benzofuran-2-carbonyl)-[1,1';3'1"]terphenyl-2'-yl]methoxyethoxymethyl Ether To a flamed dried round bottom flask with 2,3-benzofuran (0.277 mL, 2.51 mmol) and DME (30 mL) cooled to –10° C. was added n-BuLi (1.10 mL, 2.5 M in hexane, 2.76 mmol) dropwise over a 10 min. period. The resulting solution was stirred for 10 min. while warming to –5° C., and then cooled back to –20 ° C. To this solution was added 2'-methoxyethoxymethoxy-[1,1';3',1"]terphenyl-5'-carboxaldehyde (1.00 g, 2.76 mmol) in DME (5 mL) dropwise. The final mixture was stirred at –20° C. for 0.5 h and then warmed to room temperature for 15 min. At this point, the reaction mixture was quenched by pouring into sat. aq. NH$_4$Cl (100 mL) and diluted with EtOAc (350 mL). The organic layer was washed with additional sat. aq. NH$_4$Cl (40 mL) and brine (40 mL) and then dried (MgSO$_4$). After concentration, the residue was purified by the Biotage Flash 40 apparatus (10 to 30% EtOAc/petroleum ether gradient) to afford the alcohol intermediate.

To this alcohol intermediate (0.478 g, 0.995 mmol) in CH$_2$Cl$_2$ (20 mL) at room temperature was added NMMO (0.152 g, 1.29 mmol) followed by TPAP (0.105 g, 0.299 mmol). After 1 h at this temperature, the reaction was filtered through a 1" column of silica gel. After concentration of the filtrate, the residue was purified by the Biotage Flash 40 apparatus (5 to 15% EtOAc/petroleum ether gradient) to afford the product (0.430 g, 42%) as a solid; $^1$H NMR (CDCl$_3$) δ 2.85–2.92 (m, 2H), 2.94–3.00 (m, 2H), 3.18 (s, 3H), 4.53 (s, 2H), 7.30–7.42 (m, 3H), 7.42–7.54 (m, 5H), 7.58 (s, 1H), 7.61–7.71 (m, 5H), 7.75 (d, J=8.0 Hz, 1H), 8.07 (s, 2H); mass spectrum [(+) ESI], m/z 479 (M +H)$^+$, 501 (M+Na)$^+$.

Step 2 [5'-(Benzofuran-2-carbonyl)-[1,1';3'1"]terphenyl-2'-yloxy]acetic Acid

The title compound was prepared as a white foam (0.280 g, 79%) from [5'-(benzofuran-2-carbonyl)-[1,1';3'1"] terphenyl-2'-yl]methoxyethoxymethyl ether using a procedure similar to steps 5–7 of Example 44, mp>73° C. (decomp.); $^1$H NMR (DMSO-d$_6$) δ 3.90 (s, 2H), 7.36–7.44 (m, 3H), 7.45–7.50 (m, 4H), 7.53–7.59 (m, 1H), 7.65–769 (m, 4H), 7.77 (d, J=8.3 Hz, 1H), 7.87 (d, J=7.9 Hz, 1H), 7.91 (d, J=0.7 Hz, 1H), 7.93 (s, 2H), 11.80–13.40 (bs, 1H); IR (ATR) 3120, 3060, 3030, 2910, 1770, 1730, 1640, 1610, 1585, 1545, 1495, 1475, 1465, 1440, 1420, 1410, 1355, 1340, 1290, 1275, 1255, 1205, 1180, 1140, 1125, 1110, 1070, 1055, 1030, 1000, 985, 910, 890, 830, 750, 730, and 700cm$^{-1}$; mass spectrum [(−) APCI], m/z 447 (M−H)$^-$; Anal. Calcd. for $C_{29}H_{20}O_5 \cdot 0.35CHCl_3$: C, 71.91; H, 4.18; N, 0.00, Found: C, 71.71; H, 3.91; N, 0.16.

EXAMPLE 102

3-[3"-(2-Carboxy-vinyl)-2'-methoxy-5'-(8-phenyl-octylcarbamoyl)-[1,1';3'1"]-terphenyl-3-yl]-acrylic Acid Step 1 2,6-Diiodo-4-(8-phenyl-octylcarbamoyl)phenol The title compound was prepared as a solid (0.718 g, 66%) from 3,5-diiodo-4-hydroxybenzoic acid using 8-phenyloctylamine and a procedure similar to step 2 of Example 93; $^1$H NMR (DMSO-d$_6$) δ 1.17–1.36 (m, 8H), 1.41–1.61 (m, 4H), 2.48–2.60 (m, 2H), 3.20 (dd, J=5.9, 8.8 Hz, 2H), 7.10–7.21 (m, 3H), 7.21–7.30 (m, 2H), 8.21 (s, 2H), 8.40 (t, J=4.4 Hz, 1H), 10.06 (s, 1H); mass spectrum [(+) ESI], m/z 578 (M+H)$^+$.

Step 2 2.6-Diiodo-4-(8-phenyl-octylcarbamoyl)phenyl Methyl Ether

The title compound was prepared as a solid (0.691 g, 94%) from 2,6-diiodo-4-(8-phenyl-octylcarbamoyl)phenol using methyl iodide and a procedure similar to step 4 of Example 93; $^1$H NMR (DMSO-d$_6$) δ 1.19–1.34 (m, 8H), 1.41–1.61 (m, 4H), 2.48–2.59 (m, 2H), 3.21 (dd, J=6.4, 14.1 Hz, 2H), 3.78 (s, 3H), 7.10–7.21 (m, 3H), 7.21–7.31 (m 2H), 8.28 (s, 2H), 8.53 (t, J=5.6 Hz, 1H); mass spectrum [(+) ESI], m/z 592 (M+H)$^+$, 614 (M+Na)$^+$.

Step 3 [3,3"-Diformyl-5'-(8-phenyl-octylcarbamoyl)-[1,1';3'1"]terphenyl-2'-yl]methyl Ether The title compound was prepared as a solid (0.479 g, 75%) from 2,6-diiodo-4-(8-phenyl-octylcarbamoyl)phenyl methyl ether using 3-formylbenzeneboronic acid and a procedure similar to step 3 of Example 93; $^1$H NMR (DMSO-d$_6$) δ 1.21–1.35 (m, 8H), 1.46–1.60 (m, 4H), 2.47–2.58 (m, 2H), 3.13 (s, 3H), 3.21–3.32 (m, 2H), 7.09–7.19 (m, 3H), 7.21–7.30 (m, 2H), 7.54 (t, J=7.5 Hz, 2H), 7.94–8.03 (m, 6H), 8.17 (s, 2H), 8.61 (t, J=5.6 Hz, 1H), 10.14 (s, 2H); mass spectrum [(+) ESI], m/z 548 (M+H)$^+$, 570 (M+Na)$^+$.

Step 4 3-[3"-(2-Methoxy-carbonyl-vinyl)-2'-methoxy-5'-(8-phenyl-octylcarbamoyl)-[1,1';3'1']-terphenyl-3-yl]acrylic Acid Methyl Ester To a round bottom flask with [3,3"-diformyl-5'-(8-phenyl-octylcarbamoyl)-[1,1';3'1"]terphenyl-2'-yl]methyl ether (0.422 g, 0.770 mmol) in CH$_3$CN (20 mL) at room temperature was added methyl (triphenylphosphoranylidene) acetate (1.29 g, 3.86 mmol). After 5 h at this temperature, it was concentrated and then diluted with EtOAc (250 mL). The organic layer was washed with 1 N HCl (25 mL), sat. aq. NaHCO$_3$ (25 mL), and brine (25 mL) and then dried (Na2SO$_4$). After concentration, the residue was purified by the Biotage Flash 40 apparatus (15 to 35% EtOAc/petroleum ether) to afford the product (0.485 g, 89%) as a solid; $^1$H NMR (DMSO-d$_6$) δ 1.23–1.38 (m, 8H), 1.46–1.62 (m, 4H), 2.47–2.58 (m, 2H), 3.17 (s, 3H), 3.21–3.35 (m, 2H), 3.75 (s, 6H), 6.74 (d, J=16.5 Hz, 2H), 7.10–7.20 (m, 3H), 7.20–7.29 (m, 2H), 7.55 (t, J=7.2 Hz, 2H), 7.67 (d, J=7.2 Hz, 2H), 7.72–7.85 (m, 4H), 7.92 (d, J=11.5 Hz, 2H), 8.52 (t, J=5.7 Hz, 1H); mass spectrum [(+) ESI], m/z 660 (M+H)+.

Step 5 3-[3"-(2-Carboxy-vinyl)-2'-methoxy-5'-(8-phenyl-octylcarbamoyl)-[1,1';3'1"]-terphenyl-3-yl]acrylic Acid The title compound was prepared as an off white foam (0.094 g, 98%) from 3-[3"-(2-methoxy-carbonyl-vinyl)-2'-methoxy-5'-(8-phenyl-octylcarbamoyl)-[1,1';3'1"]-terphenyl-3-yl]-acrylic acid methyl ester using a procedure similar to step 5 of Example 93, mp>101° C. (decomp.); $^1$H NMR (DMSO-d$_6$) δ 1.20–1.33 (m, 8H), 1.45–1.58 (m, 4H), 2.45–2.56 (m, 2H), 3.15 (s, 3H), 3.20–3.29 (m, 2H), 6.61 (d, J=16.0 Hz, 2H), 7.10–7.18 (m, 3H), 7.20–7.26 (m, 2H), 7.48–7.57 (m, 3H), 7.60–7.78 (m, 5H), 7.87 (s, 4H), 8.47–8.55 (m, 1H), 12.10–12.75 (bs, 2H); IR (KBr) 3370, 3070, 3020, 2930, 2860, 2660, 2580, 1785, 1730, 1580, 1540, 1490, 1470, 1435, 1405, 1340, 1285, 1230, 1205, 1185, 1095, 1070, 1000, 985, 900, 870, 805, 790, 770, 750, and 700 cm$^{-1}$; mass spectrum [(+) APCI], m/z 632 (M+H)$^+$; Anal. Calcd. for $C_{40}H_{41}NO_6 \cdot 0.5H_2O$: C, 74.98; H, 6.61; N, 2.19, Found: C, 74.79; H, 6.62; N, 2.02.

EXAMPLE 103

3-[3"-(2-Carboxy-ethyl)-2'-methoxy-5'-(8-phenyl-octylcarbamoyl)-[1,1';3'1"]-terphenyl-3-yl]-propionic Acid Into a round flask with Pd/C (0.022 g, 1.05 mmol) and EtOAc:MeOH (1:1, 7 mL) was added 3-[3"-(2-methoxy-carbonyl-vinyl)-2'-methoxy-5'-(8-phenyl-octylcarbamoyl)-[1,1';3'1"]-terphenyl-3-yl]acrylic acid methyl ester (0.230 g, 0.349 mmol) in EtAOc:MeOH (1:1, 3 mL). The flask was flushed with H$_2$ (atmospheric) from a balloon, and the reaction stirred at room temperature for 2 h. The reaction mixture was then filtered through celite, and the celite washed with excess EtOAc:MeOH. This solution was concentrated to afford the saturated intermediate {3-[3"-(2-methoxycarbonyl-ethyl)-2'-methoxy-5'-(8-phenyl-octylcarbamoyl)-[1,1';3'1"]-terphenyl-3-yl]propionic acid methyl ester}.

The title compound was prepared as a white foamy solid (0.200 g, 88%) from the 3-[3"-(2-methoxy-carbonyl-ethyl)-2'-methoxy-5'-(8-phenyl-octylcarbamoyl)-[1,1';3'1"]-terphenyl-3-yl]propionic acid methyl ester using a procedure similar to step 5 of Example 61, mp>53° C. (decomp.); $^1$H NMR (DMSO-d6) δ 1.23–1.31 (m, 8H), 1.44–1.57 (m, 4H), 2.48–2.60 (m, 6H), 2.89 (t, J=7.5 Hz, 4H), 3.13 (s, 3H), 3.23 (dd, J=6.6, 13.0 Hz, 2H), 7.10–7.16 (m, 3H), 7.20–7.28 (m, 4H), 7.35–7.41 (m, 4), 7.43 (s 2H), 7.79 (s, 2H), 8.49 (t, J=5.7 Hz, 1H), 11.85–12.30 (bs, 2H); IR (KBr) 3380, 3020, 2930, 2860, 1710, 1625, 1575, 1540, 1490, 1470, 1465, 1405, 1340, 1280, 1230, 1180, 1155, 1095, 1070, 1005, 900, 805, 750, amd 705 cm$^{-1}$; mass spectrum [(+) APCI, m/z 636 (M+H)$^+$; Anal. Calcd. for $C_{40}H_{45}NO_6 \cdot 0.5H_2O$: C, 74.51; H, 7.19; N, 2.17, Found: C, 74.43; H, 7.16; N, 2.10.

EXAMPLE 104

5'-[(2-Butyl-benzofuran-3-ylmethyl)-amino]-[1,1';3',1"]terphenyl-2'-ylolxy}acetic Acid Methyl Ester Step 1 5'-[(2-Butyl-benzofuran-3-ylmethyl)-amino]-[1,1';3',1"]terphenyl-2'-ol A mixture of 2-N-Butyl-3-benzofurancarboxaldehyde (2.48 g, 13.3 mmol), and 4-amino-2,6-diphenol in 15 mls of anhydrous methanol was cooled to 0° C. 16.6 mls of 1N HCl in diethyl ether was added and sodium cyanoborohydride (0.92 g, 14.65 mmol) was added portion wise at such a rate as not to allow excess foaming. After addition was complete, the ice bath was removed, and the solution was allowed to warm to room temperature overnight. The reaction was quenched with 3N HCl until all precipitates dissolved and evolution of HCN ceased. The reaction was concentrated in vacuo and dissolved in methylene chloride, washed 2× with Saturated sodium bicarbonate and brine then dried (MgSO$_4$). Flash chromatography eluting with 5–15% ethyl acetate petroleum ether gave the title compound as a yellow gum. ¹H NMR (300 MHz, CDCl₃) δ 0.92 (t, 3H), 1.42–1.34 (m, 2H), 1.74–1.67 (m, 2H), 2.8 (t, 2H), 3.53 (s, 1H), 4.33 (s, 2H), 4.91 (s, 1H), 6.68 (s, 2H), 7.26–7.18 (m, 2H), 7.49–7.36 (m, 7H), 7.58–7.56 (m, 5H). mass spectrum (EI), m/z 447. Anal. Calcd. for $C_{31}H_{29}NO_2$ 0.2 EtOAc: C, 82.11; H, 6.63; N, 3.01. Found: C, 82.15; H, 6.92; N, 2.96.

Step 2 {5'-[(2-Butyl-benzofuran-3-ylmethyl)-amino]-[1,1';3',1"]terphenyl-2'-ylolxy}acetic Acid Methyl Ester To a mixture of 5'-[(2-Butylbenzofuran-3-ylmethyl)-amino]-[1,1';3',1"]terphenyl-2'-ol (0.81 g, 1.82 mmol) in 10 ml of dry acetonitrile was added methyl bromoacetate (0.22 mL, 2.27 mol) and a catalytic amount of 18-crown-6. The mixture was stirred at room temperature for 48 hrs. The reaction was diluted with diethyl ether and filtered. The organic layer was washed with water then saturated brine, dried over anhydrous $MgSO_4$, filtered, and concentrated in vacuo. Flash chromatography eluting with 5–10% acetone petroleum ether gave pure product as a yellow gum. ¹H NMR (300 MHz, DMSO) δ 0.82 (t, 3H), 1.3–1.25 (m, 2H), 1.61–1.53 (m, 2H), 2.81 (t, 2H), 3.32 (s, 2H), 3.68 (s, 3H), 4.34 (d, 2H), 6.09 (t, 1H), 6.6 (s, 2H) 7.49–7.16 (m 13H), 7.71–7.69 (m, 1H). mass spectrum (EI), m/z 519. Anal. Calcd. for $C_{34}H_{33}NO_4$: C, 78.59; H, 6.40; N, 2.70. Found: C, 78.14; H, 6.23; N, 2.68.

EXAMPLE 105

{5'-[(2-Butyl-benzofuran-3-ylmethyl)-amino]-[1,1';3',1"]terphenyl-2'-yloxy}acetic Acid To a stirred solution of {5'-[(2-Butyl-benzofuran-3-ylmethyl)-amino]-[1,1';3',1"]terphenyl-2'-ylolxy}acetic acid methyl ester in 2.5 ml THF and 2.5 ml MeOH was added 0.84 ml of 5N sodium hydroxide. The reaction was allowed to stir overnight. The solvents were removed in vacuo and the solids suspended in water and brought to a pH of 1 with 5N HCl. The water layer was extracted several times with ethyl acetate, dried over anhydrous $MgSO_4$, filtered, and concentrated in vacuo to give pure product as a brown solid. ¹H NMR (300 MHz, CDCl₃) δ 0.92 (t, 3H), 1.40–1.34 (m, 2H), 1.73–1.67 (m, 2H), 2.80 (t, 2H), 3.77 (s, 2H), 4.35 (s, 2H), 6.6 (d, 2H), 7.28–7.21 (m 2H), 7.48–7.37 (m, 7H), 7.56–7.54 (m, 5H). mass spectrum (EI), m/z 505. Anal. Calcd. for $C_{33}H_{31}NO_4$ 1.5 H₂O: C, 74.42; H, 6.43; N, 2.63. Found: C, 74.39; H, 5.96; N, 2.56.

EXAMPLE 106

{2,6-Dibromo-4-[(2-butyl-benzofuran-3-ylmethyl)-amino-phenoxy}Acetic Acid Methyl Ester Step 1 2,6-Dibromo-4-(2-butyl-benzofuran-3-ylmethyl)-amino-phenol The title compound was prepared according to the procedure of step 1 of Example 104 affording a light brown solid. ¹H NMR (300 MHz, DMSO) δ 0.90 (t, 3H), 1.39–1.33 (m, 2H), 1.68–1.61 (m, 2H), 2.82 (t, 2H), 4.24 (d, 2H), 5.95 (t, 1H), 6.81 (s, 2H), 7.23–7.16 (m, 2H), 7.46–7.44 (m, 1H), 7.64–7.62 (m, 1H), 8.74 (s 1H). mass spectrum (EI), m/z 451. Anal. Calcd. for $C_{19}H_{19}Br_2NO_2$: C, 50.36; H, 4.23; N, 3.09. Found: C, 49.93; H, 4.29; N, 3.05.

Step 2 {2,6-Dibromo-4-[(2-butyl-benzofuran-3-ylmethyl)-amino-phenoxy}acetic Acid Methyl Ester The title compound was prepared according to the procedure of step 2 of Example 104 affording a clear oil. ¹H NMR (300 MHz, DMSO) δ 0.92 (t, 3H), 1.40–1.35 (m, 2H), 1.69–1.65 (m, 2H), 2.85 (t, 2H), 3.72 (s, 3H), 4.29 (d, 2H) 2H), 6.44 (t, 1H), 6.86 (s, 2H), 7.25-7.19 (m, 2H), 7.49–7.47 (m, 1H), 7.65–7.62 (m, 1H). mass spectrum (EI), m/z 523.

EXAMPLE 107

{2,6-Dibromo-4-[(2-butyl-benzofuran-3-ylmethyl)-amino]-phenoxy}acetic Acid

The title compound was prepared according to the procedure of Example 105 affording a light brown solid. ¹H NMR (300 MHz, DMSO-d₆) δ 0.90 (t, 3H), 1.40–1.31 (m, 2H), 1.69–1.61 (m, 2H), 2.83 (t, 2H), 4.16 (2, 2H), 4.27 (d, 2H), 1H), 6.84 (s, 2H), 7.24–7.16 (m, 2H), 7.48–7.45 (m, 1H), 7.63–7.61 (m, 1H), mass spectrum (ESI), (M–H) m/z 508. Anal. Calcd. for $C_{21}H_{21}Br_2NO_4$ 0.5 H₂O: C, 48.49; H, 4.26; N, 2.69. Found: C, 48.37; H, 3.99; N, 2.56.

Examples 108 to 124 were prepared in a similar manner to Example 175. Examples 125 to 130 and Example 134 were prepared in a similar manner to Example 179. Examples 131 to 133 were prepared in a manner analogous to Examples 175, 179 and 192 using 4-hydroxy-4'-carboxymethyl diphenyl as a starting material, rather than 4-hydroxy benzoic acid. Physico-chemical properties of the compounds 108 to 134 are summarized in Table 1.

TABLE 1

| Ex. | Name | NMR ¹H(400MHz) | C H N Theory | C H N Found | MS (Mol. Ion) | M.p. °C. Yield, % |
|---|---|---|---|---|---|---|
| 108 | [2"-Fluoro-5'-(8-phenyl-octylcarbamoyl)-3-trifluoromethyl-[1,1';3',1"]terphenyl-2'-yloxy)-acetic acid | DMSO-d₆:_12.6(s, 1H), 8.6 (t, 1H), 7.0–8.0(m, 15H, arom), 3.84(s, 2H), 3.22 (m, 2H), 2.55(m, 2H)1.2–1.6 (m, 12H) | 68.56, 5.75, 2.22 $C_{36}H_{35}F_4NO_4x$ 0.5H₂O) | 68.77, 5.71, 2.17 | (−)ESI: [M-H]620 | Amorph 42% |
| 109 | (5'-Dodecylcarbamoyl-2"-fluoro-3-trifluoromethyl-[1,1';3',1"]terphenyl-2'-yloxy)-acetic acid | DMSO:_12.6(s, 1H), 8.6(t, 1H), 7.2–7.9(m, 10H, arom), 3.85(2, 2H), 3.22(m, 2H), 0.8–1.6(m, 23H) | 66.87, 6.60, 2.29 $(C_{34}H_{39}F_4NO_4x$ 0.5H₂O) | 66.68, 6.31, 2.22 | (−)ESI: [M-H]600 | Amorph 24% |
| 110 | (5'-Dodecylcarbamoyl-2,2"-difluoro-[1,1';3',1"]terphenyl-2'-yloxy)-acetic acid | DMSO:_12.6(s, 1H), 8.55(t, 1H), 7.2–7.9(m, 10H, arom), 3.85(s, 2H), 3.22(m, 2H), 0.8–1.6(m, 23H) | 71.61, 7.14, 2.53 $(C_{33}H_{39}F_2NO_4x$ 0.1H₂O) | 71.14, 7.03, 2.49 | (−)ESI: [M-H]550 | Amorph 46% |
| 111 | [2,2"-Difluoro-5'-(8-phenyl-octylcarbamoyl)-[1,1';3',1"]terphenyl-2'-yloxy)-acetic acid | DMSO:_12.5(s, 1H), 8.55(t, 1H), 7.1–7.95(m, 15H, arom), 3.85(s, 2H), 3.22(m, 2 H) 2.55(m, 2H), 1.2–1.6(m, 12H) | 73.54, 6.17, 2.45 $C_{35}H_{35}F_2NO_4$ | 73.09, 6.08, 2.40 | (−)ESI: [M-H]570 | Amorph 49% |
| 112 | [2,2"-Difluoro-5'-(6-phenyl- | DMSO:_12.5(s, 1H), 8.55(t, | 71.72, 5.84, 2.53 | 71.75, | (31 )ESI: | Amorph |

TABLE 1-continued

| Ex. | Name | NMR ¹H(400MHz) | C H N Theory | C H N Found | MS (Mol. Ion) | M.p. °C. Yield, % |
|---|---|---|---|---|---|---|
| | hexylcarbamoyl)-[1,1';3',1"]terphenyl-2'-yloxy]-acetic acid | 1H), 7.1–7.95(m, 15H, arom), 3.85(s, 2H), 3.22(m, 2H), 2.55(m, 2H), 1.2–1.6 (m, 8H) | (C₃₃H₃₁F₂NO₄x 0.5 H₂O) | 5.67, 2.43 | [M-H]542 | 41% |
| 113 | [5'-(6-(2,4-Difluoro-phenoxy)-hexylcarbamoyl]-2,2"-difluoro-[1,1';3',1"]terphenyl-2'-yloxy]-acetic acid | DMSO:_12.5(s, 1H), 8.55(t, 1H); 6.9–7.95(m, 13H, arom), 4.0(t, 2H), 3.85(s, 2 H), 3.22(m, 2H), 1.2–1.8(m, 8H) | 65.56, 5.00, 2.32 (C₃₃H₂₉F₂NO₅x 0.5 H₂O) | 65.15, 4.93, 2.27 | (-)ESI: [M-H]596 | Amorph 47% |
| 114 | (3"-Chloro-5'-dodecylcarbamoyl-2-fluoro-[1,1';3',1"]terphenyl-2'-yloxy]-acetic acid | DMSO:_12.5(s, 1H), _8.55(t, 1H), 7.1–7.0(m, 10H, arom), 3.85(s, 2H), 3.22(m, 2H), 0.8–1.6(m, 23H) | 69.77, 6.92, 2.47 C₃₃H₃₉ClFNO₄ | 69.67, 6.97, 2.43 | (-)ESI: [M-H]566 | Amorph 25% |
| 115 | [3"-Chloro-2-fluoro-5'-(8-phenyl-octylcarbamoyl)-[1,1';3',1"]terphenyl-2'-yloxy]-acetic acid | DMSO:_12.5(s, 1H), 8.55(t, 1H), 7.1–7.95(m, 15H, arom), 3.85(s, 2H), 3.22(m, 12H), 2.55(m, 2H), 1.2–1.8(m, 12H) | 71.48, 6.00, 2.38 C₃₅H₃₅ClF₄N₄ | 71.19, 6.04, 2.35 | (-)ESI: [M-H]586 | Amorph 27% |
| 116 | (3-Chloro-5'-[6-(2,4-difluoro-phenoxy)-hexylcarbamoyl]-2"-fluoro-[1,1';3',1"]terphenyl-2'-yloxy}-acetic acid | DMSO:_12.5(s, 1H), 8.55(t, 1H), 6.9–7.95(m, 13H, arom), 4.0(t, 2H), 3.85(s, 2H), 3.22(m, 2H), 1.2–1.8(m, 8H) | 64.76, 4.78, 2.29 C₃₃H₂₉ClF₃N₅ | 64.26, 4.61, 2.20 | (-)ESI: [M-H]612 | Amorph 29% |
| 117 | {3"-Chloro-2-fluoro-5'-[methyl-(8-phenyl-octyl)-carbamoyl]-[1,1';3',1"]terphenyl-2'-yloxy}-acetic acid | DMSO:_12.6(s, 1H), 6.9–7.7(m, 15H, arom), 3.8(s, 2 H), 3.4(m, 2H), 2.9(s, 3H), 1.0–1.6(m, 12H) | 70.75, 6.27, 2.29 (C₃₆H₃₇ClF₄NO₄x 0.5H₂O) | 70.43, 6.09, 2.27 | (-)ESI: [M-H]600 1CL | Amorph 27% |
| 118 | {2,2"-Difluoro-5'-[methyl-(8-phenyl-octyl)-carbamoyl]-[1,1';3',1"]terphenyl-2'-yloxy}-acetic acid | DMSO:_12.6(s, 1H), 7.1–7.7(m, 15H, arom), 3.8(s, 2 H), 3.4(m, 2H), 2.9(s, 3H), 1.0–1.6(m, 12H) | 72.71, 6.44, 2.36 (C₃₆H₃₇F₂NO₄x 0.5 H₂O) | 72.64, 6.53, 2.34 | (-)ESI: [M-H]584 | Amorph 44% |
| 119 | {3,3"-Difluoro-5'-[8-(4-chloro-benzenesulfinyl)-octylcarbamoyl]-[1,1';3',1"]terphenyl-2'-yloxy}-acetic acid | DMSO:_12.6(s, 1H), 8.5 (t, 2H), 7.4–8.0(m, 14H, arom), 3.8(s, 2H), 3.22(m, 2H, 1.0–1.6(m, 12H) | 60.71, 5.04, 2.02 (C₃₅H₃₄Cl₃NO₅S x 0.3 H₂O) | 60.95, 4.85, 1.95 | (-)ESI: [M-H]684 3CL | Amorph 41% |
| 120 | {3,3"-Dichloro-5'[8-(2,4-difluoro-phenoxy)-octylcarbamoyl]-[1,1';3',1"]terphenyl-2'-yloxy]-acetic acid | DMSO:_12.6(s, 1H), 8.55(t, 1H), 6.9–7.95(m, 13H, arom), 4.0(t, 2H), 3.85(s, 2 H), 3.22(m, 2H), 1.2–1.8(m, 12H) | 63.16, 5.15, 2.10 (C₃₅H₃₃Cl₂F₂NO₅ x 0.5 H₂O) | 62.9, 4.79, 2.12 | (-)ESI: [M-H]654 2CL | Amorph 44% |
| 121 | {3,3"-Dichloro-5'-[12 -(2,4-difluoro-phenoxy)-dodecylcarbamoyl]-[1,1';3',1"]terphenyl-2'-yloxy]-acetic acid | DMSO:_12.5(s, 1H), 8.55(t, 1H), 6.9–7.95(m, 13H, arom), 4.0(t, 2H), 3.85(s, 2 H),3.22(m, 2H), 1.2–1.8(m, 20H) | 65.73, 5.80, 1.97 C₃₉H₄₁Cl₂F₂NO₅ | 65.17, 5.73, 1.86 | (-)ESI: [M-H]710 2CL | Amorph 51% |
| 122 | {3,3"-Dichloro-5'-[8-(4-trifluoromethyl-benzyloxy)-octylcarbamoyl]-[1,1';3',1"]terphenyl-2'-yloxy]-acetic acid | DMSO:_12.6(s, 1H), 8.55(t, 1H), 7.4–7.9(m, 14H, arom), 4.6,(s, 2H), 3.85(s, 2H), 3.44 (t, 2H), 3.22(m, 2H), 1.2–1.6 (m, 12H) | 60.17, 5.46, 1.90 (C₃₇H₃₆Cl₂F₃NO₅ x 2 H₂O) | 59.62, 5.22, 1.64 | (-)ESI: [M-H]700 | Amorph 47% |
| 123 | [3,3"-Dichloro-5'-(8-{3-[3-(3-methoxy-propoxy)-propoxy]-propoxy}-octylcarbamoyl)-[1,1';3',1"]terphenyl-2'-yloxy]-acetic acid | DMSO:_12.6(s, 1H), 8.55(t, 1H), 7.4–7.9(m, 10H, arom), 3.85(s, 2H), 3.2–3.4(m, 19H), 0.9–1.6(m, 18H) | 63.93, 7.02, 1.91 C₃₉H₅₁Cl₂NO₈ | 63.56, 7.03, 1.82 | (-)ESI: [M-H]730 | Amorph 35% |
| 124 | (3,3"-Dichloro-5"-dicyclohexylcarbamoyl-[1,1';3',1"]terphenyl-2'-yloxy)-acetic acid | DMSO:_12.6(s, 1H), 7.2–7.7 (m, 10H, arom), 3.85(s, 2H), 0.8–1.8(m, 22H) | 68.27, 6.08, 2.41 C₃₃H₃₅Cl₂NO₄ | 68.58, 6.34, 2.18 | (-)ESI: [M-H]580 | Amorph 61% |
| 125 | 4-[4,4"-Dimethoxy-5'-(7-phenyl-heptylcarbamoyl)-[1,1';3',1"]terphenyl-2'-yloxy]-butyric acid | DMSO:_11.8(s, 1H), 8.55(t, 1H), 7.0–7.9(m, 15H, arom), 3.8(s, 6H), 3.22(m, 4H), 2.52 (t, 2H), 1.85(t, 2H), 1.0–1.6 (m, 12H) | 72.70, 7.23, 2.23 (C₃₉H₄₃NO₆ x 1 H₂O) | 72.52, 7.55, 2.11 | (-)ESI: [M-H]610 | Amorph 42% |
| 126 | 4-[3,3"-Dichloro-5'-(7-phenyl-heptylcarbamoyl)-[1,1';3',1"]terphenyl-2'-yloxy]-butyric acid | DMSO:_11.8(s, 1H), 8.55(t, 1H), 7.0–7.9)m, 15H, arom), 3.23(m, 4H), 2.52(t, 2H), 1.85 (t, 2H), 1.0–1.6(m, 12H) | 68.90, 6.10, 2.23 (C₃₆H₃₇Cl₂N₄ x 0.5 H₂O) | 68.80, 6.30, 2.28 | (-)ESI: [M-H]616 | Amorph 45% |
| 127 | [5'-(7-Phenyl-heptylcarbamoyl)-3,3"-bis-trifluoromethyl-[1,1';3',1"]terphenyl-2'-yloxymethyl]-phosphonic acid diethyl ester | DMSO:_8.55(t, 1H), 7.0–7.9 (m, 15H, arom) 3.23–3.7(m, 8 H), 2.52(t, 2H), 1.0–1.6(m, 16H) | 61.74, 5.71, 1.85 (C₃₉H₄₂F₆NO₃P x 0.5 H₂O) | 61.75, 5.57, 1.55 | (-)ESI: [M-H]748 | 84–85 41% |
| 128 | [5'-(7-Phenyl- | DMSO:_8.55(t, 1H), 7.0–8.1 | 56.23, 5.39, 1.87 | 56.23, | (-)ESI: | 160–165 |

TABLE 1-continued

| Ex. | Name | NMR ¹H(400MHz) | C H N Theory | C H N Found | MS (Mol. Ion) | M.p. °C. Yield, % |
|---|---|---|---|---|---|---|
| | heptylcarbamoyl)-3,3"-bis-trifluoromethyl-[1,1';3',1"]terphenyl-2'-yloxymethyl]-phosphonic acid | (m, 15H, arom), 1.1–1.6(m, 10H) | ($C_{35}H_{34}F_6NO_5P$ x 3 $H_2O$) | 4.72, 1.29 | [M-H]692 | 38% |
| 129 | 2,2-Dimethyl-3-[5'-(7-phenyl-heptylcarbamoyl)-3,3"-bis-trifluoromethyl-[1,1';3',1"]terphenyl-2'-yloxy]-propionic acid | DMSO:_12,0(s, _8.55(t, 1H), 7.0–7.9(m, 15H, arom), 3.3(m, 2H), 3.1(s, 2H), 2.52 (t, 2H), 0.6–1.6(m, 16H) | 66.94, 5.62, 2.00 $C_{39}H_{39}FNO_4$ | 67.08, 5.57, 1.59 | (−)ESI: [M-H]700 | 130–132 40% |
| 130 | 4-[5'-(7-Phenyl-heptylcarbamoyl)-3,3"-bis-trifluoromethyl-[1,1'3',1]terphenyl-2'-yloxymethyl]-benzenesulfonic acid | DMSO:_8.55(t, 1H), 6.5–8.0 (m, 19H, arom), 4.16(s, 2H), 3.25(m, 2H), 2.52(t, 2H), 0.8–1.6(m, 10H) | 62.51, 4.99, 1.78 ($C_{41}H_{37}F_6NO_5S$ x 1 $H_2O$) | 62.57, 5.58, 1.78 | (−)ESI [M-H]768 | Amorph 54% |
| 131 | [[4,4'-Dimethoxy-5'-[4-[[(7-phenylheptyl)amino]carbonyl]phenyl[[1,1';3',1'-terphenyl]-2'-yl]oxy]acetic acid | DMSO:_12.6(s, _8.55(t, 1H), 7.0–8.1(m, 19H, arom), 3.8(s, 2H), 3.22(m, 2H), 2.52 (t, 2H), 1.1–1.6(m, 10H) | 75.65, 6.65, 2.10 ($C_{42}H_{43}NO_{56}$ x 0.5 $H_2O$) | 75.59, 6.75, 2.02 | (−)ESI: [M-H]658 | Amorph 44% |
| 132 | [[5'-[4-[[(7-Phenylheptyl)amino]carbonyl]phenyl]-3,3'-bis(trifluoromethyl)[1,1':3',1'-terphenyl]-2'-yl]oxy]acetic acid | DMSO:_12.6(s, _8.55(t, 1H), 7.0–8.1(m, 19H, arom), 3.8(s, 2H), 3.22(m, 2H), 2.52 (t, 2H), 1.1–1.6(m, 10H) | 67.92, 5.16, 1.89 ($C_{42}H_{37}F_6NO_4$ x 0.5 $H_2O$) | 67.81, 5.16, 1.84 | (−)ESI: [M-H]734 | Amorph 38% |
| 133 | 4-[[[4,4'-Dimethoxy-5'-[4-[[(7-phenylheptyl)amino[carbonyl]phenyl[[1,1';3',1'-terphenyl]-2'-yloxymethyl]-benzoic acid | DMSO:_12.6(s, _8.55(t, 1H), 6.9–8.1(m, 23H, arom), 4.3(s, 2H), 3.8(s, 6H), 3.22 (m, 2H), 2.52(t, 2H), 1.1–1.6 (m, 10H) | 76.67, 6.57, 1.86 ($C_{48}H_{47}NO_6$ x 1 $H_2O$) | 76.19, 6.44, 1.79 | (−)ESI: [M-H]732 | '140–142 56% |
| 134 | 4-[5'-(7-Phenyl-heptylcarbamoyl)-3,3"-bis-trifluoromethyl-[1,1';3',1"]terphenyl-2'-yloxymethyl]-benzoic acid | DMSO:_12.8(s, _8.55(t, 1H), 6.7–8.0(m, 19H, arom), 4.3(s, 2H), 3.3(m, 2H), 2.52 (t, 2H), 1.1–1.6(m, 10H) | 67.51, 5.19, 1.87 ($C_{42}H_{37}F_6NO_4$0.75 $H_2O$) | 67.27, 5.17, 1.81 | (−)ESI: [M-H]734 | '89"91 52% |

EXAMPLE 135

(3-Bromo-3'-chloro-5-dodecylcarbamoyl-4'-fluoro-biphenyl-2-yloxy)acetic Acid

Step 1  3-Bromo-4-(2-hydroxyethoxy)-5-(3-chloro-4-fluorophenyl)benzoic Acid Ethyl Ester To a stirred solution of $K_2CO_3$ (4.99 g, 36.1 mmol) in 18 mL $H_2O$ was added 145 mL dioxane, 3-bromo-4-(2-hydroxyethoxy)-5-iodobenzoic acid ethyl ester (5.0 g, 12.04 mmol), and 3-chloro-4-fluorophenylboronic acid (2.1 g, 12.04 mmol) at room temperature. This mixture was stirred for 5 min then degassed twice. Then [1,1 i-bis(diphenylphosphino)ferrocene]dichloropalladium(II), complex with $CH_2Cl_2$ (49 mg, 0.06 mmol) was added. The reaction was stirred for three hours then 98 mg, 0.12 mmol, of the catalyst was added. The reaction was allowed to stir for five days at room temperature before being worked up in the following manner. The reaction was diluted with 1N HCl and $H_2O$ and extracting with EtOAc three times. The combined organic extracts were dried over $Na_2SO_4$ and filtered. Removal of the solvent in vacuo gave crude material which was subjected to prep HPLC to yield 2 g, 35.5% of the bis arylated product ¹H NMR (CDCl₃) δ 1.40 (t, J=8.18 Hz, 3H); 1.945 (s, 1H); 3.712 (m, 4H); 4.36 (q, J=8.18 Hz, 2H); 7.19–7.23 (m, 1H); 7.40–7.45 (m, 1H); 7.60–7.65 (dd, J=8.18 Hz, 2.73 Hz, 1H); 7.91 (d, J=2.73 Hz, 1H); 8.24 (d, J=2.73 Hz, 1H); and 860 mg, 17.1% of the mono arylated product ¹H NMR (CDCl₃) δ 1.29 (bs, 1H); 1.41 (t, J=8.18 Hz, 3H); 3.40 (m, 4H); 4.40 (q, J=8.18 Hz, 2H); 7.20–7.28, (m, 2H); 7.454–7.545 (m, 2H); 7.69 (dd, J=8.18 Hz, 2.73 Hz, 2H); 8.013 (s, 1H); and 38% recovered SM.

Step 2  N-Dodecyl-3-bromo-4-(2-hydroxyethoxy)-5-(3-chloro-4-fluorophenyl)benzamide Into a flamed dried round bottom flask charged with n-dodecylamine (586 mg, 3.16 mmol) in 7 mL THF at −20° C. was added n-BuLi (1.8 mL, 3.6 mmol) as a solution in hexanes. After the addition, the reaction was warmed up to room temperature and stirred for one-half hour. Then the solution was cooled to −20° C. and was added to solution of 3-bromo-4-(2-hydroxyethoxy)-5-(3-chloro-4-fluorophenyl)benzoic acid ethyl ester (400 mg, 0.957 mmol) in 8 mL THF that had been previously cooled to 40° C. The resulting mixture was stirred at 40° C. for 5 min after which point the reaction mixture was allowed to warm up to room temperature. The reaction was diluted with water and 2N HCl then extracted with EtOAc three times. The combined organic extracts were washed with sat $NaHCO_3$ then dried over $Na_2SO_4$. After filtering and removal of solvent in vacuo, there yielded a yellow oil that was subjected to column chromatography on silica gel (10% EtOAc:90% Hexanes followed by 25% EtOAc:75% Hexanes). There resulted 300 mg, 58% of the amide as a yellow oil. ¹H NMR (CDCl₃) 0.868 (t, J=8.13 Hz, t); 1.20–1.40 (m, 18H); 1.48–1.67 (m, 2H); 1.895–2.00 (bs, 1H); 3.427 (q, J=8.13 Hz, 2H); 3.636–7.71 (m, 4H); 6.014 (m, 1H); 7.20–7.24 (m, 1H); 7.40–7.454 (m, 1H); 7.586–7.668 (m, 2H); 7.868 (d, J=2.04 Hz, 1H).

Step 3  (3-Bromo-3'-chloro-5-dodecylcarbamoyl-4'-fluoro-biphenyl-2-yloxy)acetic Acid To a solution of N-dodecyl-3-bromo-4-(2-hydroxyethoxy)-5-(3-chloro-4-fluorophenyl)benzamide (340 mg, 0.61 mmol) in 5 mL $CH_2Cl_2$ was added $NMMO \cdot H_2O$ (165 mg, 1.22 mmol) and TPAP (22 mg, 0.061 mmol). The reaction mixture was stirred overnight and 2 mL $CH_3CN$ and 50 mg, 0.14 mmol TPAP were added. The reaction was stirred for ca 7 hours then 90 mg, 0.665 mmol NMNMO.H$_2$O was added and the reaction was stirred overnight. The reaction was worked up by adding H$_2$O and a mixture of sodium bisulfite/sodium dithionite and was stirred for 4 hours. The now grayish mixture was acidified with 2N HCl and extracted with EtOAc (3×). The combined organic layers were dried over Na$_2$SO$_4$ followed by filtration and removal of solvent in vacuo. There yielded a black semisolid that was subjected to column chromatography (40% EtOAc:60% Hexanes) on silica gel pretreated with HCOOH. Yield of the acid is 130 mg, 37% as a dark yellowish brown oil. $^1$H NMR (DMSO-d$_6$) δ 0.84 (t, J=6.81 Hz, 3H); 1.22–1.27 (m, 18H); 1.50 (t, J=6.37 Hz, 2H); 3.23 (q, J=6.81 Hz, 2H); 4.19 (s, 2H); 7.51 (t, J=8.57 Hz, 1H); 7.57–7.61 (m, 1H); 7.81 (dd, J=7.25 Hz, 2.20 Hz, 1H); 7.85 (d, J=2.2 Hz, 1H); 8.10 (d, J=2.20 Hz, 1H); 8.56 (t, J=5.49 Hz, 1H); 12.75 (bs, 1H); IR 3370, 2930, 1730, 1635, 1400, 1225, 1150, and 700 cm$^{-1}$; mass spectrum [(+)APCI], m/z 570 [M+H]$^+$; Anal. Calcd. for C$_{27}$H$_{34}$BrClFNO$_4$: C, 56.80; H, 6.00; N, 2.45, Found: C, 54.30; H, 5.73; N, 2.18.

EXAMPLE 136

[3'-Chloro-4'-fluoro-5-(8-phenyl-octylcarbamoyl)-biphenyl-2-yloxy]acetic Acid

Step 1 N-(8-Phenyloctyl)4-(2-hydroxyethoxy)-5-(3-chloro-4-fluorophenyl)benzamide To a flamed dried round bottom flask charged with 8-phenyloctylamine (688 mg, 3.35 mmol, 6.68 μL) in 5 mL THF at −78° C. was added n-BuLi (2.2 mL, 4.4 mmol) as a solution in hexanes. The solution was stirred at −78° C. for 30 min then stirred at room temperature for 15 min. The solution was cooled back down to−40° C. and a cooled (−40° C.) solution of 3-bromo-4-(2-hydroxyethoxy)-5-(3-chloro-4-fluorophenyl)benzoic acid ethyl ester (400 mg, 0.957 mmol) in 10 mL THF via cannula. After the addition was completed, the reaction was warmed up to room temperature, stirred for 10 min, then worked up as in Step 2 of Example 135. The crude yellow oil that was obtained was dissolved in 1:1 EtOAc/Hexanes and filtered through a pad of silica gel with the same solvent system to yield 200 mg, 43% of the amide as a yellow oil. $^1$H NMR (CDCl$_3$) δ 1.25–1.40 (m, 2H); 1.54–1.65 (m, 2H); 1.80 (bs, 1H); 2.57 (t, J=8.18 Hz, 2H); 3.41 (q, J=6.54 Hz, 2H); 3.90 (t, J=6.13, 2H); 4.12 (t, J=6.13 Hz, 2H); 6.07 (m, 1H); 6.99 (d, J=8.13 Hz, 1H); 7.08–7.18 (m, 3H); 7.20–7.27 (m, 2H); 7.33–7.40 (m, 1H); 7.56 (dd, J=6.54 Hz, 3.27 Hz, 1H); 7.65–7.69 (m, 1H); 7.73 (dd, J=8.13 Hz, 2.58 Hz, 1H).

Step 2 [3'-Chloro-4'-fluoro-5-(8-phenyl-octylcarbamoyl)-biphenyl-2-yloxy]acetic Acid To a solution of N-(8-phenyloctyl)-4-(2-hydroxyethoxy)-5-(3-chloro-4-fluorophenyl)benzamide (200 mg, 0.415 mmol) in 5 mL CH$_2$Cl$_2$ was added NMMO.H$_2$O (96 mg, 0.712 mmol) and TPAP (12.5 mg, 0.0356 mmol). The reaction was stirred overnight and 50 mg, 0.14 mmol TPAP, 2 mL CH$_3$CN, and 90 mg, 0.665 mmol NMMO.H$_2$O were added and the reaction was stirred overnight. The reaction was worked up as in Step 3 of Example 135. The crude material was subjected to column chromatography (40% EtOAc:660% Hexanes) on HCOOH pretreated silica gel to yield 70 mg, 34% of the acid as a dark yellow oil. $^1$H NMR (DMSO-d$_6$) 1.22–1.27 (m, 8H); 1.474–1.551 (m, 4H); 2.53 (t, J=7.47 Hz, t); 3.21 (q, J=6.59 Hz, 2H); 4.82 (s, 1H); 7.08–7.17 (m, 4H); 7.22–7.26 (m, 2H); 7.48 (t, J=8.79 Hz, 1H); 7.60–7.64 (m, 1H); 7.80–7.85 (m, 2H); 8.36 (t, J=5.60 Hz, 1H); IR 3400, 2930, 1730, 1600, 1550, 1470, 1210, 1075, and 700 cm$^{-1}$; mass spectrum [(−)ESI], m/z 510/512 [M−H]$^-$; Anal. Calcd. for C$_{19}$H$_{30}$BrClFNO$_4$: C, 97.99; H, 6.10; N, 2.73; Found: C, 66.89; H, 6.17; N, 2.61.

EXAMPLE 137

(3-Bromo-5-dodecylcarbamoyl-3'-methoxy-biphenyl-2-yloxy)acetic Acid

Step 1 3-Bromo-4-(2-hydroxyethoxy)-5-(3-methoxyphenyl)benzoic Acid Ethyl Ester

To a solution of K$_2$CO$_3$ (4.99 g, 36.1 mmol) in 18 mL H$_2$O was added 3-bromo-4-(2-hydroxyethoxy)-5-iodobenzoic acid ethyl ester (5.0 g, 12.04 mmol), 145 mL dioxane, and 3-methoxyphenylboronic acid (1.83 g, 12.04 mmol) at room temperature. This mixture was stirred for 5 min then it was degassed. Then [1,1 í-bis(diphenylphosphino)ferrocene]dichloropalladium(II), complex with CH$_2$Cl$_2$ (49 mg, 0.06 mmol) was added. The reaction was stirred for three hours then 98 mg, 0.12 mmol of the catalyst was added and the reaction was allowed to stir for 3d after which point 182 mg, 1.2 mmol of the boronic acid was added. The reaction was stirred for an additional 7d before being worked up as in Step 1 of Example 135. There yielded 475 mg, 10% of the monoarylated product; $^1$H NMR (CDCl$_3$) δ 1.38 (t, J=8.18 Hz, 3H); 1.83 (bs, 1H); 3.41 (t, J=5.43 Hz, 2H); 3.75 (t, J=5.43 Hz, 2H); 4.84 (s, 3H); 4.37 (q, J=8.18 Hz, 2H); 6.94 (dd, J=8.18 Hz, 2.72 Hz, 1H); 7.06–7.14 (m, 2H); 7.35 (t, J=8.18 Hz, 1H); 7.99 (d, J=2.73 Hz, 1H); 8.22 (d, J=2.73 Hz, 1H); 1.3 g, 25% of the bisarylated product and 2.1 g, 42% of recovered SM after the crude material was subjected to prep HPLC.

Step 2 N-Dodecyl-3-bromo-4-(2-hydroxyethoxy)-5-(3-methoxyphenyl)benzamide

N-Dodecyl-3-bromo-4-(2-hydroxyethoxy)-5-(3-methoxyphenyl)benzamide was made as a light yellow solid (500 mg, 92%) from 3-bromo-4-(2-hydroxyethoxy)-5-(3-methoxyphenyl)benzoic acid ethyl ester using a similar procedure to step 1 in Example 136. $^1$H NMR (CDCl$_3$) δ 0.80–0.88 (m, 3H); 1.14–1.40 (m, 19H); 1.48–1.63 (m, 2H); 3.40 (q, J=7.36 Hz, 2H); 3.60 (t, J=5.73 Hz, 2H); 3.48 (t, J=4.91 Hz, 2H); 4.84 (s, 3H); 6.02 (m, 1H); 6.93 (dd, J=8.18 Hz, 2.73 Hz, 1H); 7.08 (m, 2H); 7.36 (t, J=8.18 Hz, 1H); 7.67 (d, J=2.45 Hz, 1H); 7.95 (d, J=2.45 Hz, 1H) 7.95 (d, J=2.45 Hz, 1H)

Step 3 (3-Bromo-5-dodecylcarbamoyl-3'-methoxy-biphenyl-2-yloxyacetic Acid

To a solution of N-dodecyl-3-bromo-4-(2-hydroxyethoxy)-5-(3-methoxyphenyl)benzamide (200 mg, 0.374 mmol) in a mixture of 8 mL CH$_3$CN/300 μL THF was added 132 mg, 0.976 mmol NMMO. The reaction was stirred 30 min then 132 mg, 0.976 mmol NMMO was added. The reaction was then stirred overnight. The reaction was diluted with water and sodium metabisulfite/sodium bisulfite and sodium dithionite were added. This mixture was stirred for 1.5 hours then 2N HCl was added then the mixture was extracted with EtOAc (3×). The combined organic extracts were dried over Na$_2$SO$_4$ and the solvent removed under vacuum to give a black oil. This oil was subjected to flash chromatography (40% EtOAc:60% Hexanes with 1% HCOOH added) on HCOOH pretreated silica gel. There yielded 60 mg of the acid and 60 mg of the aldehyde intermediate which was then resubjected to reaction conditions again to give an additional 40 mg of acid. Total yield of the acid is 100 mg, 49% of an oily yellow foam. $^1$H NMR (DMSO-d$_6$) δ 0.84 (t, J=6.37 Hz, 3H); 1.15–1.27 (m, 18H); 1.47–1.51 (m, 2H); 3.23 (q, J=6.59 Hz, 2H); 3.79 (s, 3H); 4.105 (s, 2H); 6.97–7.00 (m, 1H); 7.11–7.14 (m, 2H); 7.38 (t, J=7.91 Hz, 1H); 7.83 (d, J=2.20 Hz, 1H); 8.07 (d, J=2.20 Hz, 1H); 8.56 (t, J=5.00 Hz, 1H); 12.75 (bs, 1H); IR 2930, 2850, 1740, 1650, 1550, 1450, 1320, and 1225 cm$^{-1}$; mass spectrum [(+)ESI], m/z 548/550 [M+H]$^+$; Anal Calcd for C$_{28}$H$_{38}$BrNO$_5$: C, 61.51; H, 6.98; N, 2.55; Found: C, 62.44; H, 6.86; N, 2.67.

EXAMPLE 138

5-Bromo-6-(2-tetrazol-1-yl-ethoxy)-3'-methoxy-biphenyl-3-carboxylic Acid dodecylamide Step 1 N-Dodecyl-3-bromo4-(2-bromoethoxy)-5-(3-methoxyphenyl)benzamide To a flamed dried flask was added triphenylphosphine (98 mg, 0.373 mmol) and 1.5 mL anhydrous THF. This was stirred until all the triphenylphosphine had dissolved. Then $CBr_4$ (123 mg, 0.373 mmol) was added. The reaction mixture was stirred for one-half hour at room temperature then it was cooled to ° C. before N-dodecyl-3-bromo-4-(2-hydroxyethoxy)-5-(3-methoxyphenyl)benzamide (200 mg, 0.373 mmol) was added. The cooling bath was removed after the addition was complete. After the reaction mixture had warmed up to room temperature, 0.2 eq each of triphenylphosphine (19.6 mg, 0.075 mmol) and $CBr_4$ (24.8 mg, 0.075 mmol) were added. The reaction was stirred for one-half hour then the solvent was removed under vacuum to give a yellow semisolid. This material was subjected to flash chromatography (25% EtOAc:75% Hexanes) to yield 150 mg, 67% of a yellow oil. $^1H$ NMR ($CDCl_3$) δ 1.25 (t, J=8.13 Hz, 3H); 1.22–1.40 (m, 18H); 1.52–1.63 (m, 2H); 3.35 (t, J=8.18 Hz, 2H); 3.40 (q, J=6.54 Hz, 2H); 3.84–3.90 (m, 5H); 6.00 (m, 1H); 6.93 (dd, J=8.18 Hz, 2.45 Hz, 1H); 7.07–7.11 (m, 2H); 7.35 (t, J=8.18 Hz, 1H); 7.65 (d, J=2.45 Hz, 1H); 7.39 (d, J=2.45 Hz, 1H).

Step 2 5-Bromo-6-(2-tetrazol-1-yl-ethoxy)-3'-methoxy-biphenyl-3-carboxylic Acid dodecylamide To a solution of 1H-tetrazole (28 mg, 0.4 mmol) in 1 mL anhydrous THF at 0° C. was added NaH (10 mg, 0.421 mmol). The reaction mixture was stirred for 10 min at 0° C. after which point a solution of N-dodecyl-3-bromo-4-(2-bromoethoxy)-5-(3-methoxyphenyl)benzamide (160 mg, 0.276 mmol) in 2.5 mL anhydrous THF was added. The reaction mixture was stirred at 0° C. for 10 min then allowed to warm up to room temperature for one-half hour. Then 700 μL of DMSO was added and the reaction was then heated at 65° C. overnight. Thr reaction was quenched and diluted with water and extracted with EtOAc (3×). The combined organic layers were dried over $Na_2SO_4$ and the solvent removed in vacuo to give a brown-yellow oil. The crude material was subjected to flash column chromatography (25% EtOAc:75% Hexanes to 40% EtOAc:60% Hexanes to 50% EtOAc:50% Hexanes) to yield 40 mg, 25% of a white solid. mp 100–1° C. ; $^1H$ NMR (DMSO-$d_6$) δ 0.88 (t, J=6.80 Hz, 3H); 1.25–1.37 (m, 18H); 1.60 (quintet, J=7.14 Hz, 2H); 3.43 (q, J=7.14 Hz, 2H); 3.84 (s, 3H); 3.96 (t, J=4.86 Hz, 2H); 4.57 (t, J=4.86 Hz, 2H); 6.01 (t, J=5.00 Hz, 1H); 6.93–6.95 (m, 3H); 7.27–7.32 (m, 1H); 7.64 (d, J=2.20 Hz, 1H); 7.94 (d, J=1.98 Hz, 1H); 8.68 (s, 1H); IR 3330, 2900, 2840, 1625, 1600, 1520, 1460, 1310, 1300, 1235, 1175, and 1030 cm$^{-1}$; mass spectrum [(+)ESI] m/z 586/588 [M+H]$^+$; Anal Calcd. For $C_{29}H_{40}BrN_5O_3$: C, 59.38; H, 6.87; N, 11.94; Found: C, 59.46; H, 6.68; N, 11.77.

Examples 139 and 140

5-Bromo-3'-chloro-6-(2-tetrazol-2-yl-ethoxy)-biphenyl-3-carboxylic Acid Dodecylamide and 5-Bromo-3'-chloro-6-(2-tetrazol-1-yl-ethoxy)-biphenyl-3-carboxylic Acid Dodecylamide Step 1 5-Bromo-3'-chloro-6-(2-hydroxy-ethoxy)-biphenyl-3-carboxylic Acid Dodecylamide To a cooled (0° C.) solution of dodecyl amine (3.22 g, 17.64 mmol) in 50 mL anhydrous THF was added n-BuLi (7.05 mL, 17.64 mmol) dropwise. When the addition was complete, the mixture was stirred for 10 min at 0° C. then at room temperature for 30 min. This lithiated amine was added dropwise to a cooled (0° C.) solution. of 5-bromo-3'-chloro-6-(2-hydroxy-ethoxy)-biphenyl-3-carboxylic acid ethyl ester (2.5 g, 5.78 mmol) in 40 mL anhydrous THF via cannula. The reaction was stirred for 10 min at 0° C. when the addition was complete then at room temperature overnight. Then the reaction mixture was heated to 35° C. for 1 hour then more n-BuLi was added (0.7 mL, 1.75 mmol). The reaction. was then worked up as in Step 2 of Example 135. There yielded 2.5 g, 80% of a yellow oil as desired product after flash chromatography (25% EtOAc:75% Hexanes) on silica gel.

Step 2 5-Bromo-3'-chloro-6-(2-bromoethoxy)-biphenyl-3-carboxylic Acid Dodecylamide 5-Bromo-3'-chloro-6-(2-bromoethoxy)-biphenyl-3-carboxylic acid dodecylamide was prepared from 5-bromo-3'-chloro-6-(2-hydroxy-ethoxy)-biphenyl-3-carboxylic acid dodecylamide as a yellow oil (900 mg, 67%) in a similar manner to Step 1 of Example 138. $^1H$ NMR ($CDCl_3$) δ 0.86 (t, J=8.18 Hz, 3H); 1.23–1.4 (m, 18H); 1.55–1.64 (m, 2H); 3.35–3.64 (m, 4H); 3.88 (t, J=5.73 Hz, 2H); 6.043 (m, 1H); 7.37–7.40 (m, 2H); 7.43 (quartet, J=4.09 Hz, 1H); 7.56 (s, 1H); 7.65 (d, J=2.45 Hz, 1H); 7.95 (d, J=2.45 Hz, 1H).

Step 3 5-Bromo-3'-chloro-6-(2-tetrazol-2-yl-ethoxy)-biphenyl-3-carboxylic Acid Dodecylamide and 5-Bromo-3'-chloro-6-(2-tetrazol-1-yl-ethoxy)-biphenyl-3-carboxylic Acid Dodecylamide These compounds were prepared from 5-bromo-3'-chloro-6-(2-bromoethoxy)-biphenyl-3-carboxylic acid dodecylamide. For 5-Bromo-3'-chloro-6-(2-tetrazol-2-yl-ethoxy)-biphenyl-3-carboxylic acid dodecylamide, (270 mg, 30.6%) a yellow oil that crystallized into a yellow solid, spectral data follows. mp 93–5° C.; $^1H$ NMR ($CDCl_3$) δ 0.88 (t, J=6.8 Hz, 3H); 1.25–1.38 (m, 18H); 1.60 (quartet, J=7.03 Hz, 2H); 3.42 (quartet, J=7.25 Hz, 2H); 4.12 (t, J=5.27 Hz, 2H); 4.82 (t, J=5.27 Hz, 2H); 6.01–6.04 (m, 1H); 7.30–7.32 (m, 2H); 7.35–7.38 (in, 1H); 7.43–7.44 (m, 1H); 7.63 (d, J=2.20 Hz, 1H); 7.92 (d, J=2.20 Hz, 1H); 8.48 (s, 1H); IR 3425, 3325, 2915, 2835, 1630, 1550, 1460, 1450, 700 cm$^{-1}$; mass spectrum [(+)APCI], m/z 590/592/594 [M+H]$^+$; Anal Calcd for $C_{28}H_{37}BrClN_5O_2$: C, 56.90; H, 6.31; N, 11.79; Found: C, 56.20; H, 6.04; N, 11.79. For 5-Bromo-3'-chloro-6-(2-tetrazol-1-yl-ethoxy)-biphenyl-3-carboxylic acid dodecylamide, (260 mg, 29.4%) an off white solid, spectral data follows. mp 95–6° C.; δ 0.87 (t, J=6.8 Hz, 3H); 1.25–1.39 (m, 18H); 1.57–1.64 (m, 2H); 3.40 (m, 2H); 3.94 (t, J=4.83 Hz, 2H); 6.11 (t, J=5.38 Hz, 1H); 7.22–7.32 (m, 2H); 7.37–7.40 (m, 1H); 7.43 (t, J=1.86 Hz, 1H); 7.65 (d, J=2.2 Hz, 1H); 7.94 (d, J=2.20 Hz, 1H); 8.74 (s, 1H); IR 3375, 3335, 2925, 2835, 1630, 1545, 1465, 1320, 1230, 1100, 1030, and 700 cm$^{-1}$; mass spectrum [(+)APCI], m/z 590/592/594 [M+H]$^+$; Anal Calcd for $C_{28}H_{37}BrClN_5O_2$: C, 56.90; H, 6.31; N, 11.79; Found: C, 56.29; H, 6.26; N, 12.01.

EXAMPLE 141

[3,5,3',5"-Tetramethyl-5'-(8-phenyl-octylcarbamoyl)-[1,1';3',1"]terphenyl-2'-yloxy]acetic Acid Step 1 3,5-Bis-(3,5-dimethylphenyl)-4-(2-hydroxyethoxy) benzoic Acid Ethyl Ester 3,5-Bis-(3,5-dimethylphenyl)-4-(2-hydroxyethoxy)benzoic acid ethyl ester was prepared from 3-bromo-4-(2-hydroxyethoxy)-5-iodobenzoic acid ethyl ester as a white solid (1.04 g, 20%) in a similar manner to Step 1 of Example 135. $^1H$ NMR ($CDCl_3$) δ 1.2–1.4 (bs, 1H); 1.37 (t, J=8.18 Hz, 3H); 2.37 (s, 12H); 3.25 (t, J=5.45 Hz, 2H); 3.40 (t, J=5.45 Hz, 2H); 4.37 (quartet, J=8.18 Hz, 2H); 7.02 (s, 2H); 8.00 (s, 2H).

Step 2 N-8-Phenyloctyl-3,5-bis-(3,5-dimethylphenyl)-4-(2-hydroxyethoxy)benzamide To a cooled solution (0° C.) of 8-phenyloctyl amine (1.56 g, 7.58 mmol, 1.51 ml) in 10 mL anhydrous THF was added n-BuLi (5.1 mL, 7.96 mmol) as a solution in hexanes dropwise. After the addition, the reaction was warmed up to room temperature and was stirred for one-half hour at room temperature. Then the lithiated amine was cooled back down to 0° C. and was added to a cooled (0 ° C. ) solution of 3,5-bis-(3,5-dimethylphenyl)-4-(2-hydroxyethoxy)benzoic acid ethyl ester (1.04 g, 2.49 mmol) in 10 mL anhydrous THF. The resulting reaction mixture was stirred for 5 min at 0° C. then allowed to warm up to room temperature. At that point, additional n-BuLi was added (2.04 mL, 3.18 mmol). When the reaction appeared to be practically complete (by TLC), it was worked up as in Step 2 of Example 135. After flash chromatography (25% EtOAc:75% Hexanes), there yielded 850 mg, 59.4% of the amide as a yellow oil. $^1$H NMR (CDCl$_3$) δ 1.25–1.40 (m, 8H); 1.40–1.64 (m, 5H); 2.37 (s, 12H); 2.57 (t, J=8.18 Hz, 2H); 3.25 (t, J=4.09 Hz, 2H); 3.36–3.47 (m, 4H); 6.06 (t, J=6.54 Hz, 1H); 7.02 (s, 2H); 7.11–7.19 (m, 4H); 7.20–7.48 (m, 5H); 7.69 (s, 2H).

Step 3 [3,5,3″,5″-Tetramethyl-5′-(8-phenyl-octylcarbamoyl)-[1,1′;3′1″]terphenyl-2′-yloxy]acetic Acid To a solution of N-8-phenyloctyl-3,5-bis-(3,5-dimethylphenyl)-4-(2-hydroxyethoxy)benzamide (850 mg, 1.47 mmol) in 15 mL of acetonitrile was added NMMO (415 mg, 3.05 mmol) and TPAP (52 mg, 0.149 mmol). The reaction was stirred for 2 hours then an additional 40 mg, 0.3 mmol NMMO and 52 mg, 0.149 mmol TPAP were added. The reaction was stirred overnight and an additional 40 mg, 0.3 mmol, NMMO was added. The reaction was stirred an additional two hours then water was added followed by the addition of sodium bisulfite/sodium dithionite. The aqueous mixture was stirred for 1 hour then it was extracted with EtOAc (3×). The combined extracts were dried with Na$_2$SO$_4$ and concentrated to give a black oil. This oil was subjected to flash chromatography (20%EtOAc:80% Hexanes acidified with 1% CH$_3$COOH) on HCOOH pretreated silica gel. There yielded 200 mg of the desired acid plus a fraction consisting of the desired acid and other impurities. This fraction was chromatographed again using the same solvent system to give 30 mg more of the acid for a total yield of 230 mg, 26.4% of the desired acid. $^1$H NMR (DMSO-d$_6$) δ 1.27 (bs, 8H); 1.45–1.60 (m, 4H); 2.31 (s, 12H); 2.53 (t, J=7.58 Hz, 2H); 3.23 (quartet, J=6.37 Hz, 2H); 3.81 (s, 2H); 7.00–7.01 (m, 2H); 7.13–7.15 (m, 3H); 7.19–7.25 (m 6H) 7.76 (s, 2H); 8.48 (t, J=6.00 Hz, 1H); 12.35 (bs, 1H); IR 3325, 2935, 2875, 1750, 1645, 1605, 1580, 1545, 1480, 1460, 1430, 1400, 1385, 1380, 1295, 1250, 1200, 1150, 850, and 700 cm-1; mass spectrum [(+)APCI], m/z 592 [M+H]+; Anal Calcd for C$_{39}$H$_{45}$NO$_4$.C$_2$H$_4$O$_2$.C$_4$H$_8$O$_2$: C, 73.03; 7.63; H, 7.63; N, 1.89; Found: C, 73.32, H, 7.88; N, 2.04.

EXAMPLE 142

[4,4″-Difluoro-3,3″-dimethyl-5′-(8-phenyloctylcarbamoyl)-[1,1′;3′,1″]terphenyl-2-yloxy]acetic Acid Step 1 N-8-Phenyloctyl-3,5-bis-(4-fluoro-3-methylphenyl)-4-(2-hydroxyethoxy)benzoic Acid Ethyl Ester N-8-Phenyloctyl-3,5-bis-(4-fluoro-3-methylphenyl)-4-(2-hydroxyethoxy)benzoic acid ethyl ester was made as a brown solid (470 mg 3-bromo-4-(2-hydroxyethoxy)-5-iodobenzoic acid ethyl ester in a similar manner t 1 of Example 135. $^1$H NMR (CDCl$_3$) δ 1.40 (t, J=7.14 Hz, 3H); 1.56 (bs, 1H); 2.21 (m, 6H); 3.30–3.31 (m, 2H); 3.38–3.40 (m, 2H); 4.40 (quartet, J=7.03 Hz, 2H); 7.09 (t, J=8.90 Hz, 2H); 7.39–7.44 (m, 4H); 7.99 (s, 1H).

Step 2 N-8-Phenyloctyl-3,5-bis-(4-fluoro-3-methylphenyl)-4-(2-hydroxyethoxy)benzamide N-8-Phenyloctyl-3,5-bis-(4-fluoro-3-methylphenyl)-4-(2-hydroxyethoxy)benzamide was prepared as a yellow oil (300 mg, 57.4%) from N-8-phenyloctyl-3,5-bis-(4-fluoro-3-methylphenyl)-4-(2-hydroxyethoxy)benzoic acid ethyl ester in a similar manner to Step 2 of Example 141. $^1$H NMR (CDCl$_3$) δ 1.40–1.60 (m, 8H); 1.50–1.63 (m, 4H); 1.6–2.2 (bs, 1H); 2.33 (s, 6H); 3.55 (t, J=8.18 Hz, 2H); 3.25 (t, J=4.91 Hz, 2H); 3.36 (t, J=4.09 Hz, 2H); 3.43 (quartet, J=8.18 Hz, 2H); 6.12 (t, J4.09 Hz, 1H); 7.04–7.19 (m, 5H); 7.35–7.55 (m, 4H); 7.68 (s, 1H).

Step 3 [4,4″-Difluoro-3,3″-dimethyl-5′-(8-phenyl-octylcarbamoyl)-[1,1′;3′,1″]terphenyl-2′-yloxylacetic Acid To a solution of N-8-phenyloctyl-3,5-bis-(4-fluoro-3-methylphenyl)-4-(2-hydroxyethoxy)benzamide (320 mg, 0.546 mmol) in 5 mL acetonitrile at room temperature was added NMMO (162 mg, 1.2 mmol) and TPAP (38.3 mg, 0.109 mmol). The reaction was stirred for 2 hours then additional TPAP (38.3 mg, 0.109 mmol) was added. The reaction was stirred overnight and an additional amount of NMMO (14.7 mg, 0.109 mmol) and TPAP (19 mg, 0.546 mmol) were added. The reaction was then stirred for three more hours and aqueous sodium metabisulfite/sodium dithionite was added. The reaction was then allowed to stir for 1 hour. Then IN HCl was added. The aqueous solution was extracted with EtOAc (3×). The combined organic extracts were dried over Na$_2$SO$_4$ and the solvent was removed under vacuum to give a black oil which was subjected to flash column chromatography (20% EtOAc:80% Hexanes acidified with AcOH) on silica gel that was pretreated with AcOH. There yielded 120 mg, 36.6% of the acid as a yellow oil. $^1$H NMR (DMSO-d$_6$) δ 1.22–1.27 (m, 4H); 1.53 (quintet, J=6.59 Hz, 4H); 2.27–2.28 (m, 6H); 2.52 (t, J=7.69 Hz, 2H); 3.23 (quartet, Hz, 2H); 3.82 (s, 2H); 7.11–7.25 (m, 7H); 7.41–7.45 (m, 2H); 7.52 (dd, J=7.58 Hz, 1.87 Hz, 2H); 7.80 (s, 2H); 8.49 (t, J=5.60 Hz, 1H); 12.57 (bs, 1H); IR 3375, 2915, 2835, 1630, 1540, 1500, 1450, 1230, 1120, and 970cm$^{-1}$; mass spectrum [(−)ESI], m/z 598 [M-H]; Anal Calcd for C$_{37}$H$_{39}$F$_2$NO$_4$0.17C$_6$H$_{12}$.0.2C$_4$H$_8$O$_2$.0.88C$_2$H$_3$O: C; 71.16; H, 6.84; N, 2.04; Found: C, 69.55; H, 6.65; N, 2.09.

EXAMPLE 143

2′-Hydroxy-3,5,3″,5″-tetramethyl-[1,1′;3′,1″] terphenyl-5′-carboxylic acid (7-phenyl-heptyl)-amide Step 1 3,5-Bis-(3,5-dimethylphenyl)-4-methoxymethoxybenzoic Acid Ethyl Ester To a solution of K$_2$CO$_3$ (11.39 g, 82.41 mmol) in 41 mL H$_2$O was added 280 mL dioxane, a 2:1 mixture of 3-bromo-4-methoxymethoxy-5-iodobenzoic acid ethyl ester and 3,5-dibromo.4-methoxymethoxybenzoic acid ethyl ester (4.85 g, 13.74 mmol) and 3-methylphenyl boronic acid (4.1 g, 27.47 mmol) at room temperature. The reaction was degassed and [1,1′-bis(diphenylphosphino)ferrocene]dichloropalladium (II), complex with CH$_2$Cl$_2$ (224 mg, 0.248 mmol) was added. The reaction was stirred for 2d then more of the catalyst was added (56 mg, 0.0687 mmol). The reaction was stirred for one more day and the reaction was worked up as in Step 1 of Example 135 to give crude material that was subjected to flash column chromatography (5% EtOAc:95% Hexanes). The major product from the column was further purified by prep HPLC to give 1.44 g, 23% of a white solid. $^1$H NMR (CDCl$_3$) a 1.33 (t, J=8.18 Hz, 3H); 2.37 (s, 12H); 2.69 (s, 3H), 4.33–4.40 (m, 4H); 6.97 (s, 2H); 7.20 (m, 4H); 7.97 (s, 2H).

Step 2 3,5-Bis-(3,5-dimethylphenyl)-4-methoxymethoxybenzoic Acid

To a suspension. of 3,5 bis-(3,5-dimethylphenyl)-4-methoxymethoxybenzoic acid (1.4 g, 3.12 mmol) in 4:1 MeOH/H$_2$O (total 50 mL) was added solid KOH (150 mg, 2.67 mmol) and the reaction mixture was refluxed until all the ester was consume The reaction mixture was then acidified with NaH$_2$PO$_4$ to pH 3 and the precipitated product was filtered off and washed with water. It was then dried in a vacuum over at 60° C. to 80 ° C. for 2 hours then the material was flash chromatographed (2% EtOAc:80% Hexanes to 25% EtOAc:75% Hexanes) on silica gel to yield 780 mg, 59.5% of the acid as a white solid. $^1$H NMR (CDCl$_3$) δ 2.40 (s, 12 H); 2.72 (s, 3H); 4.45 (s, 2H); 7.00 (s, 2H); 7.24 (m, 4H); 8.08 (s, 2H). There also yielded 280 mg of the methyl ester as a side product.

Step 3 N-7-Phenylheptyl-3,5-bis-(3,5-dimethylphenyl)-4-methoxymethoxybenzamide

A flamed dried round bottom flask was charged with 7-phenylheptyl amine (354 mg, 2.78 mmol) and 20 mL anhydrous CH$_2$Cl$_2$. To this solution was added 3,5-bis-(3,5-dimethylphenyl)-4-methoxymethoxybenzoic acid (780 mg, 1.85 mmol), triethyl amine (563 mg, 5.56 mmol, 726 μL), anhydrous 1-hydroxybenzotriazole (275 mg, 2.04 mmol), and DCC (459 mg, 2.22 mmol), all at room temperature. The reaction mixture was stirred at room temperature for one-half hour. Then the reaction was worked up by adding water then extracting with EtOAc (3×). The combined organic extracts were dried over Na$_2$SO$_4$ and the solvent removed in vacuo to give a semisolid to which CH$_2$Cl$_2$ was added. This suspension was subjected to column chromatography (15% EtOAc:85% Hexanes) to give 600 mg, 54.5% of the amide as a colorless oil. $^1$H NMR (CDCl$_3$) δ 1.34 (bs, 6H); 1.57 (m, 4H); 2.36 (s, 12H); 2.572 (t, J=8.18 Hz, 2H); 2.681 (s, 3H); 3.414 (quartet, J=8.18 Hz, 2H); 4.39 (s, 2H); 6.04 (t, J=5.73 Hz, 1H); 6.97 (s, 2H); 7.12–7.27 (m, 9H); 7.67 (s, 2H).

Step 4 2'-Hydroxy-3,5,3",5"-tetramethyl-[1,1';3,1"]terphenyl-5'-carboxylic Acid (7-phenyl-heptyl)-amide To a solution of N-7-phenylheptyl-3,5-bis-(3,5-dimethylphenyl)-4-methoxymethoxybenzamide (600 mg, 1.01 mmol) in 5 mL THF was added 1N HCl (1.1 mL, 1.1 mmol) at room temperature. The reaction was refluxed for 1.5 d and a catalytic amount of camphorsulfonic acid was added. Then the reaction was stirred at room temperature for 2 d then refluxed again until the reaction went to completion. The reaction was diluted with water and EtOAc. The organic layer was separated and the aqueous layer was extracted with EtOAc (2×). The combined organic layers were dried over Na$_2$SO$_4$ and the solvent was removed in vacuo. Thr resulting oil was passed through silica gel using 25% EtOAc.:75% Hexanes to get rid of camphorsulfonic acid. There yielded 500 mg, 90% of an oily white foam of the amide. 1.24–1.39 (m, 6H); 1.55–1.63 (m, 4H); 2.38 (s, 12H); 2.60 (t, J=7.69 Hz, 2H); 3.44 (quartet, J=7.14 Hz, 2H); 5.78 (s, 1H); 6.05 (t, J=7.64 Hz, 1H); 7.04–7.05 (m, 2H); 7.14–7.18 (m, 7H); 7.24–7.28 (m, 2H); 7.66 (s, 2H); IR 3520, 3315, 3030, 2930, 2850, 1630, 1600, 1550, 1470, 1200, 850, and 700 cm$^{-1}$; mass spectrum [EI], m/z 519 [M$^+$]; Anal Calcd for C$_{36}$H$_{41}$NO$_2$: C, 83.20; H, 7.95; N, 2.69; Found: C, 82.66; H, 7.87; N, 2.66.

EXAMPLE 144

2-Hydroxy-3,3"-dimethyl-[1,1';3',1"]terphenyl-5'-carboxylic Acid (7-Phenyl-heptyl)-amide Step 1 3,5-Bis-(3-methylphenyl)-4-methoxymethoxybenzoic Acid Ethyl Ester 3,5-Bis-(3-methylphenyl)-4-methoxymethoxybenzoic acid ethyl ester was prepared as a white solid (4.2 g, 30%) in a similar manner to Step 1 of Example 14 from a 2:1 mixture of 3-bromo-4-methoxymethoxy-5-iodobenzoic acid ethyl ester and 3,5-dibromo4-methoxymethoxybenzoic acid ethyl ester. $^1$H NMR (CDCl$_3$) δ 1.17 (t, J=8.18 Hz, 3H); 2.4 (s, 6H); 2.66 (s, 3H); 4.36 (quartet, J=8.18 Hz, 2H); 4.40 (s, 2H); 7.11–7.20 (m, 2H); 7.20–7.40 (m, 6H); 8.00 (s, 2H).

Step 2 3,5-Bis-(3-methylphenyl)-4-methoxymethoxybenzoic Acid 3,5-Bis-(3-methylphenyl)-4-methoxymethoxybenzoic acid was prepared as white solid (900 mg, 50%) in a similar manner to Step 2 of Example 143 from 3,5-bis-(3-methylphenyl)-4-methoxymethoxybenzoic acid ethyl ester. $^1$H NMR (CDCl$_3$) δ 2.40 (s, 6H); 3.67 (s, 3H); 4.40 (s, 2H); 7.14–7.20 (m, 2H); 7.31 (t, J=6.54 Hz, 2H); 7.37–7.43 (m, 4H); 8.07 (s, 2H).

Step 3 N-7-Phenylheptyl-3,5-bis-(3-methylphenyl)-4-methoxymethoxybenzamide

N-7-Phenylheptyl-3,5-bis-(3-methylphenyl)-4-methoxymethoxybenzamide was prepared as a colorless oil (1.04 g, 78.2%) in a similar manner to Step 3 of Example 143 from 3,5-bis-(3-methylphenyl)-4-methoxymethoxybenzoic acid. $^1$H NMR (CDCl$_3$) 1.26–1.40 (m, 6H); 1.48–1.66 (m, 4H); 2.40 (s, 6H); 2.57 (t, J=8.18 Hz, 2H 3H); 3.38 (quartet, J=6.54 Hz, 2H); 4.36 (s, 2H); 6.06 (t, J=4.91 Hz, 1H); 7.11–7.19 (m, 3H); 7.26 (s, 2H); 7.31 (t, J=8.18 Hz, 2H); 7.35–7.40 (m, 4H); 7.69 (s, 2H).

Step 4 2'-Hydroxy-3,3"-dimethyl-[1,1';3',1"]terphenyl-5'-carboxylic Acid (7-Phenyl-heptyl)-amide To a solution of N-7-phenylheptyl-3,5-bis-(3-methylphenyl methoxymethoxybenzamide (1.04 g, 1.94 mmol) in 3.5 mL THF was added 2N HCl (1.1 mL, 2.2 mmol) at room temperature and the reaction mixture was refluxed for 2 hours before a catalytic amount of camphorsulfonic acid was added. The reaction was refluxed overnight and the resulting goo was dissolved in EtOAc and washed with water. The organic layer was dried over Na$_2$SO$_4$ and the solvent was removed in vacuo. This yielded an oil that was passed through a pad of silica gel using 20% EtOAc:80% Hexanes. There yielded 730 mg, 81% of a light yellow viscous oil. $^1$H NMR (CDCl$_3$) δ 1.33–1.39 (m, 6H); 1.59–1.63 (m, 6H); 2.42 (s, 6H); 2.58 (t, J=7.69 Hz, 2H) (quartet, J=7.03 Hz, 2H); 6.06 (t, J=7.50 Hz, 1H); 7.14–7.18 (m, 3H); 7.22–7.28 (m, 4H); 7.34–7.40 (m, 6H); 7.68 (s, 2H); IR 3525, 3025, 2925, 2850, 1630, 1600, 1530, 1460, 1325, 1230, and 700 cm$^{-1}$; mass spectrum [(+)ESI], m/z 492 [M+H]$^+$; Anal Calcd. For C$_{34}$H$_{37}$NO$_2$: C, 83.06; H, 7.59; N, 2.85; Found: C, 83.80; H, 7.62; N, 2.93.

EXAMPLE 145

[3,3"-Dimethyl-5'-(7-phenyl-heptylcarbamoyl)-[1,1';3',1"]terphenyl-2'-yloxy]acetic Acid Step 1 [3,3"-Dimethyl-5'-(7-phenyl-heptylcarbamoyl)-[1,1';3',1"]terphenyl-2'-yloxy]acetic Acid tert-butyl Ester To a solution of 2'-hydroxy-3,3"-dimethyl-[1,1';3',1"]terphenyl-5'-carboxylic acid (7-phenyl-heptyl)-amide (240 mg, 0.516 mmol) in 2.5 mL anhydrous DMF was added solid K$_2$CO$_3$ (84 mg, 0.613 mmol). The reaction mixture was stirred at room temperature for 2 min before t-butyl bromoacetate (158 mg, 0.812 mmol, 812 μL) was added. The reaction was stirred overnight at room temperature after which point it was diluted with water and extracted with EtOAc (3×). The combined organic layers were washed with water to remove DMF. Then they were dried with Na$_2$SO$_4$ and the solvent was removed in vacuo to give an oil that was subjected to flash column chromatography (15% EtOAc:85% Hexanes) to yield 180 mg, 60% of a colorless oil. $^1$H NMR (CDCl$_3$) 1.25 (s, 9H); 1.25–1.40 (m, 6H);

1.28–1.47 (m, 4H); 2.40 (s, 6H); 2.57 (t, J=8.18 Hz, 2H); 3.43 (quartet, J=8.18 Hz, 2H); 3.73 (s, 2H); 6.06 (t, J=5.73 Hz, 1H); 7.08–7.20 (m, 5H); 7.20–7.32 (m, 4H); 7.37–7.46 (m, 4H); 7.68 (s, 2H).

Step 2 [3,3"-Dimethyl-5'-(7-phenyl-heptylcarbamoyl)-[1,1';3',1"]terphenyl-2'-yloxylacetic Acid A solution of [3,3"-Dimethyl-5'-(7-phenyl-heptylcarbamoyl) [1,1';3',1"]terphenyl-2'-yloxy]acetic acid tert-butyl ester (180 mg, 0.311 mmol) in 3.5 mL HCOOH was stirred at room temperature until all of the ester was consumed by TLC (1:1 EtOAc:Hexanes). The excess HCOOH was removed in vacuo (first on a rotoevaporator then pumping under high vacuum) then crystallized from $CH_2Cl_2$/Hexanes to yield 170 mg, 100% of the acid as a yellow foam. mp 58–62 °C.; $^1$H NMR (DMSO-$d_6$) δ 1.21–1.28 (m, 6H); 1.44–1.57 (m, 4H); 2.35 (s, 6H); 2.53 (t, J=7.69 Hz, 2H); 3.23 (quartet, J=6.37 Hz, 2H); 3.82 (s, 2H); 7.10–7.24 (m, 7H); 7.30–7.41 (m, 6H); 7.80 (s, 2H); 8.51 (t, J=5.49 Hz, 1H); 12.60 (bs, 1H); IR 3375, 3025, 2925, 2865, 1730, 1630, 1600, 1550, 1450, 1350, 1210, 1195, 1080, and 700cm$^{-1}$; mass spectrum [(–)ESI], m/z 548 [M–H]$^-$; Anal Calcd. for $C_{36}H_{39}NO_4$: C, 78.66; H, 7.15; N, 2.55; Found: C, 77.39; H, 7.42; N, 2.37.

EXAMPLE 146

4-[3,3"-Dimethyl-5'-(7-phenyl-heptylcarbamoyl)-[1,1';3',1"]terphenyl-2'-yloxy]butyric Acid Step 1 4-[3,3"-Dimethyl-5'-(7-phenyl-heptylcarbamoyl)-1,1';3',1"]terphenyl-2'-yloxy]-butyric Acid Ethyl Ester 4-[3,3"-Dimethyl-5'-(7-phenyl-heptylcarbamoyl)-[1,1';3',1"]terphenyl-2'-yloxy]-butyric acid ethyl ester was prepared as a light yellow oil (260 mg, 73.2%) similar manner to Step 1 of Example 145 from 2'-Hydroxy-3,3"-dimethylphenyl [1,1';3',1"]terphenyl-5'-carboxylic acid (7-phenyl-heptyl)-amide. $^1$H NMR (CDCl$_3$) 1.14 (t, J=8.18 Hz, 3H); 1.24–1.14 (m, 6H); 1.44 (quintet, J=6.54 Hz, 2H); 1.48(m, 4H); 1.91 (t, J=7.36 Hz, 2H); 2.55 (t, J=8.18 Hz, 2H); 3.20 (t, J=7.36 Hz, 2H); 3.38 (quartet, J=8.18 Hz, 2H); 3.60 (quartet, J=8.18 Hz, 2H); 6.08 (t, J=5.73 Hz, 1H); 7.07–7.17 (m, 6H); 7.18–7.37 (m, 7H), 7.66 (s, 2H).

Step 2 4-[3,3"-Dimethyl-5'-(7-phenyl-heptylcarbamoyl)-[1,1';3',1"]terphenyl-2-yloxy]-butyric Acid To a solution of [3,3"-dimethyl-5'-(7-phenyl-heptylcarbamoyl)-[1,1';3',1"]terphenyl-2'-yloxy]acetic acid ethyl ester (260 mg, 0.449 mmol) in MeOH was added 1 mL H$_2$O and solid KOH (25 mg, 0.449 mmol). The reaction mixture was refluxed for 2 d then it was cooled, acidified with 2N HCl, and extracted with EtOAc (3×). The combined organic extracts were dried over Na$_2$SO$_4$ and the solvent was removed in vacuo to give an oil which was subjected to flash column chromatography (20% EtOAc:80% Hexanes to 100% EtOAc) on silica gel to yield 80 mg of the desired acid and 150 mg of the methyl ester of the desired acid. This ester was subjected to the same reaction conditions to yield more desired acid. Total yield of desired acid is 150 mg, 60.7% as an oily light yellow foam. $^1$H NMR (DMSO-$d_6$) δ 1.23–1.35 (m, 8H); 1.46–1.55 (m, 4H); 1.83 (t, J=7.47 Hz, 2H); 2.37 (s, 6H); 2.53 (T, J=7.58 Hz, 2H); 3.18–3.27 (m, 4H); 7.10–7.15 (m, 3H); 7.19–7.24 (m, 4H); 7.32–7.40 (m, 6H); 7.80 (s, 2H); 8.50 (t, J=5.49 Hz, 1H); 11.87 (s, 1H); IR 3320, 2920, 2850, 1710, 1730, 1560, 1540, 1450, 1380, 1330, 1220, 1050, and 700 cm$^{-1}$; mass spectrum [(–)ESI], m/z 576 [M–H]$^-$; Anal Calcd. for $C_{38}H_{43}NO_4$: C, 79.00; H, 7.50; N, 2.42; Found: C, 77.76; H, 7.23; N, 2.69.

EXAMPLE 147

[3,5,3",5"-Tetramethyl-5'-(7-phenyl-heptylcarbamoyl)-[1,1';3',1"]terphenyl-2'-yloxymethyl]-phosphonic Acid Diethyl Ester Step 1 (Trifluoromethylsulfonyloxy)methyl Phosphonate Diethyl Ester A flamed dried round bottom flask was charged with hydroxymethyl phosphonate diethyl ester (200 mg, 1.19 mmol, 175 μL) and triethyl amine (157 mg, 1.55 mmol, 216 μL) and 5 mL CH$_2$Cl$_2$ and was cooled to –70 °C. Trifluoromethanesulfonic anhydride (369 mg, 1.31 mmol, 220 μL) was added dropwise. The reaction was stirred for 10 min while the reaction was warmed to 40 °C. At this point, the reaction mixture was diluted with EtOAc and extracted with water. The organic layer was dried over Na$_2$SO$_4$ and the solvent was removed in vacuo to yield 350 mg, 98% of an orange oil.

Step 2 [3,5,3", 5"-Tetramethyl-5'-(7-phenyl-heptylcarbamoyl)-[1,1';3',1"]terphenyl-2'-yloxymethyl]-phosphonic Acid Diethyl Ester To a flamed dried round bottom flask was added 2'-hydroxy-3,5,3",5"-tetramethyl-[1,1';3',1"]terphenyl-5'-carboxylic acid (7-phenyl-heptyl)-amide (180 mg, 0.327 mmol) and 5 mL anhydrous THF. This solution was cooled to 0° C. and NaH (9 mg, 0.36 mmol) was added. The reaction was stirred for 5 min at 0° C. then (trifluoromethylsulfonyloxy)methyl phosphonate diethyl ester (98 mg, 0.327 mmol) was added slowly to the reaction mixture. The reaction was stirred for one-half hour while the reaction was allowed to warm up to room temperature. After the reaction had been stirring at room temperature for 3 hours, 1–2 mg of NaH and 9.8 mg, 0.0327 mmol of the ester were added. The reaction was stirred at room temperature for 2 more hours and worked up as follows. Water was added to the reaction and the aqueous solution was extracted with EtOAc (3×). The combined organic layers were dried over Na$_2$SO$_4$ and the solvent was removed in vacuo to give a yellow oil that was subjected to flash column chromatography (25% EtOAc:75% Hexanes to 50% EtOAc:50% Hexanes) on silica gel to yield 90 mg, 41% of a colorless oil. $^1$H NMR (CDCl$_3$) δ 1.11 (t, J=7.03 Hz, 6H) 1.32–1.38 (m, 6H); 1.61–1.65 (m, 4H); 2.38 (s, 12H); 2.59 (t, J=7.69 Hz, 2H); 3.43 (quartet, J=7.03 Hz, 2H); 3.55–3.64 (m, 4H); 3.73–3.82 (m, 2H); 6.05 (t, J=6.00 Hz, 1H); 7.01–7.02 (m, 2H); 7.14–7.18 (m, 3H); 7.19–7.20 (m, 4H); 7.24–7.28 (m, 2H); 7.65 (s, 2H);. IR 3425, 2925, 1540, and 1030 cm$^{-1}$; mass spectrum [(+)APCI], m/z 670 [M+H]$^+$; Anal Calcd. for $C_{41}H_{52}NO_5P$: C, 73.52; H, 7.82; N, 2.09; Found: C, 73.15; H, 7.90; N, 2.18.

EXAMPLE 148

4-[3,5,3",5"-Tetramethyl-5'-(7-phenyl-heptylcarbamoyl)-[1,1';3',1"]terphenyl-2'-yloxy]-butyric Acid Step 1 4-[3,5,3",5"-Tetramethyl-5'-(7-phenyl-heptylcarbamoyl)-[1,1';3',1"]terphenyl-2'-yloxy]-butyric acid ethyl ester To a solution of 2'-Hydroxy-3,5,3",5"-tetramethyl-[1,1';3',1"]terphenyl-5-carboxylic acid (7-phenyl-heptyl)-amide (180 mg, 0.327 mmol) in 2 mL DMF was added K$_2$CO$_3$ (24 mg, 0.174 mmol) and the reaction mixture was stirred for10 min room temperature. Then 4-bromobutyric acid ethyl ester,(70 mg, 0.36 mmol) was ad slowly to the reaction mixture. The reaction was stirred at room temperature for 2 d it was heated for 45 min at a temperature between 40 and 50° C. Then it was worked as in Step 1 of Example 146. $^1$H NMR (CDCl$_3$) δ 1.18 (t, J=7.36 Hz, 3H); 127–(m, 6H); 1.44–1.64 (m, 6H); 1.95 (t, J=8.18 Hz, 2H); 2.54 (s, 12H); 2.57 (t, J=Hz, 2H); 3.25 (t, J=6,54 Hz, 2H); 3.41 (quartet, J=7.36 Hz, 2H); 400 (quartet, J=8.18 Hz, 2H); 6.04 (m, 1H); 6.00–6.08 (m, 1H); 6.99 (s, 2H); 7.10–7.26 (m, 9); 7.66 (s, 2H).

Step 2 4-[3,5,3",5"-Tetramethyl-5'-(7-phenyl-heptylcarbamoyl)-[1,1';3',1"]terphenyl-2'-yloxy]-butyric Acid To a suspension of 4-[3,5,3",5"-Tetramethyl-5'-(7-phenyl-heptylcarbamoyl)-[1,1';3',1"]terphenyl-2'-yloxy]-butyric acid ethyl ester (170 mg, 0.256 mmol) in 4 mL MeOH/1 mL H$_2$O was added solid KOH (12 mg, 0.213 mmol). The reaction mixture was refluxed for 2 d and then the reaction mixture was diluted with 2N HCl and water. The aqueous solution was extracted with EtOAc (3×) and the combined organic extracts were dried over Na$_2$SO$_4$. The solvent was removed in vacuo to give an oil that was flash chromatographed (10% EtOAc:90% Hexanes) on silica gel to yield 70 mg, 43% of the acid as an oily white foam. mp 64–66° C.; $^1$H NMR (DMSO-d$_6$) δ 1.29–1.30 (m, 6H); 1.32–1.39 (m, 2H); 1.46–1.48 (m, 4H); 1.86 (t, J=7.47 Hz, 2H); 2.33 (s, 12H); 2.53 (t, J=7.58 Hz, 2H); 3.19–3.31 (m, 2H); 7.01 (s, 2H); 7.12–7.16 (m, 3H); 7.17–7.19 (m, 4H); 7.21–7.24 (m, 2H) 7.71 (s, 2H); 8.48 (t, J=7.00 Hz, 1H); 11.86 (s, 1H); IR 3325, 2925, 2875, 1710, 1630, 1600, 1535, 1450, 1290, 1225, 1210, 850, and 700 cm$^{-1}$; mass spectrum [(+)APCI], m/z 606 [M+H]$^+$; Anal Calcd. for C$_{40}$H$_{47}$NO$_4$: C, 79.30; H, 7.82; N, 2.31; Found: C, 78.65; H, 7.86; N, 1.87.

EXAMPLES 149 and 150

3,3"-Diformyl-2'-methoxymethoxy-1,1';3',1"]terphenyl-5'-carboxylic Acid (7-Phenyl-heptyl)-amide and 3,3"-Diformyl-2'-hydroxy-[1,1';3',1"]terphenyl-5'-carboxylic Acid (7-Phenyl-heptyl)-amide Step 1  3,5-Bis-(3-formylphenyl)-4-methoxymethoxybenzoic Acid Ethyl Ester 3,5-Bis-(3-formylphenyl)-4-methoxymethoxybenzoic acid ethyl ester was prepared as a white solid (980 mg, 13.7%) in a similar manner to Step 1 of Example 143 from a 2:1 mixture of 3-bromo4-methoxymethoxy-5-iodobenzoic acid ethyl ester and 3,5-dibromo-4-methoxymethoxybenzoic acid ethyl ester. There also yielded 1.6 g of a mixture of benzaldehyde and the starting halogenated compound, and 1.4 g, 20.7% of the monoarylated material as a white solid. Bis-arylated compound: $^1$H NMR (CDCl$_3$) δ 1.38 (t, J=7.36 Hz, 3H); 2.59 (s, 3H); 4.33–4.42 (m, 4H); 7.62 (t, J=7.36 Hz, 2H); 7.79 (dd, J=8.18 Hz, 2.05 Hz, 4H); 7.97 (s, 2H); 8.02 (s, 2H); 10.11 (s, 2H). Monoarylated compound: $^1$H NMR (CDCl$_3$) δ 1.38 (t, J=8.18 Hz, 3H); 3.06 (s, 3H); 4.37 (quartet, J=8.18 Hz, 2H); 4.80 (s, 2H); 7.60 (t, J=7.36 Hz, 1H); 7.77–7.82 (m, 1H); 7.87–7.91 (m, 1H); 7.96–8.00 (m, 1H); 8.01–8.06 (m, 1H); 8.26–8.30 (m, 1H).

Step 2  3,5-Bis-(3-formylphenyl)-4-methoxymethoxybenzoic acid

To a solution of 3,5-bis-(3-formylphenyl)-4-methoxymethoxybenzoic acid ethyl ester (960 mg, 2.12 mmol) in 3 mL MeOH was added 3 mL H$_2$O and solid KOH (179 mg, 3.18 mmol). The reaction was refluxed for 5 to 6 hours then the cooled reaction mixture was diluted with 2N HCl and water. The aqueous solution was extracted with EtOAc (3×) and the combined organic layers were dried over Na$_2$SO$_4$. The solvent was removed in vacuo to give an oil that was flash chromatographed (10% MeOH:90% EtOAc) on silica gel. There yielded 650 mg of the desired acid along with some of the methyl ester of the desired acid. The methyl ester was resubjected to reaction conditions to give more of the desired acid for a total yield of 690 mg, 76.6%. $^1$H NMR (CDCl$_3$) δ 2.63 (s, 3H); 4.19 (s, 2H); 7.65 (t, J=7.36 Hz, 2H); 7.87–7.95 (m, 4H); 8.06–8.26 (m, 4H); 10.10 (s, 2H).

Step 3  3,3"-Diformyl-2'-methoxymethoxy-[1,1';3',1"]terphenyl-5'-carboxylic Acid (7-Phenyl-heptyl)-amide 3,3"-Diformyl-2'-methoxymethoxy-[1,1';3',1"]terphenyl-5'-carboxylic acid (7-phenyl-heptyl)-amide was prepared as an oily yellow foam (650 mg, 80%) in a similar manner to Step 3 of Example 143. $^1$H NMR (CDCl$_3$) δ 1.33–1.40 (m, 6H); 1.59–1.64 (m,4H); 2.57–2.61 (m, 5H); 3.45 (quartet, J=6.81 Hz, 2H); 4.35 (s, 2H); 6.17 (t, J=7.36 Hz, 1H); 7.14–7.17 (m, 3H); 7.24–7.28 (m, 2H); 7.64 (t, J=7.58 Hz, 2H); 7(s, 2H); 7.90–7.93 (m, 4H); 8.15 (t, J=1.43 Hz, 2H); 10.10 (s, 2H); IR 3375, 30 3025, 2950, 2825, 2725, 1790, 1700, 1630, 1600, 1580, 1530, 1450, 1150, and 950 cm$^{-1}$); mass spectrum [(+)ESI], m/z 564 [M+H]$^+$; Anal Calcd. for C$_{36}$H$_{37}$NO$_5$: C, 76.71; H, 6.62; N, 2.48; Found: C, 74.67; H, 6.35; N, 2.99.

Step 4  3,3"-Diformyl-2'-hydroxy-[1,1';3',1"]terphenyl-5'-carboxylic Acid (7-Phenyl-heptyl)-amide To a solution of ,3"-diformyl-2'-methoxymethoxy-[1,1';3',1"]terphenyl-5'-carboxylic acid (7-phenyl-heptyl)-amide (480 mg, 0.80 mmol) in 3 mL THF was added 2N HCl (400 μL, 0.80 mmol) and a catalytic amount of camphorsulphonic acid. The reaction was heated overnight at ca 50° C. then it was cooled and diluted with water. The aqueous solution was extracted with EtOAc (3×), the combined organic layers were dried over Na$_2$SO$_4$ and the solvent was removed in vacuo. The oil that was obtained was flash chromatographed (20% EtOAc:80% Hexanes to 40% EtOAc:60% Hexanes) on silica gel to yield 360 mg, 75% of the desired amide. mp 63–65° C.; $^1$H NMR (CDCl$_3$) δ 1.32–1.39 (m, 6H); 1.58–1.65 (m, 4H); 2.59 (t, J=7.69 Hz, 2H); 3.42 (quartet, J=7.03 Hz, 2H); 5.668 (s, 1H); 6.14 (t, J=5.60 Hz, 1H); 7.14–7.17 (m, 3H); 7.23–7.28 (m, 2H); 7.67 (t, J=7.69 Hz, 2H); 7.74 (s, 2H); 7.83 (ddd, J=8.30 Hz, 1.76 Hz, 1.32 Hz, 2H); 7.93 (td, J=7.87 Hz, 1.43 Hz, 2H); 8.08 (t, J=1.43 Hz, 2H); 10.07 (s, 2H); IR 3325, 3065, 3025, 2935, 2850, 2725, 1700, 1630, 1600, 1580, 1530, 1470, 1230, 1190, and 700 cm$^{-1}$; mass spectrum [(+)APCI], m/z 520 [M+H]$^+$; Anal Calcd. for C$_{34}$H$_{33}$NO$_4$

EXAMPLE 151

[3,3",4,4"-Bis-methylenedioxy-5"-(7-phenyl-heptylcarbamoyl)-[1,1';3',1"]terphenyl-2'-yloxy] acetic Acid Step 1  3,5-Bis-(3,4-methylenedioxyphenyl)-4-methoxymethoxybenzoic Acid Ethyl Ester 3,5-Bis-(3,4-methylenedioxyphenyl)-4-methoxymethoxybenzoic acid ethyl ester was prepared as a white solid (3.1 g, 42.4%) in a similar manner to Step 1 of Example 143 from a 2:1 mixture of 3-bromo-4-methoxymethoxy-5-iodobenzoic acid ethyl ester and 3,5-dibromo-4-methoxymethoxybenzoic acid ethyl ester. There also yielded 780 mg of the monoarylated product. $^1$H NMR (CDCl$_3$) δ 1.37 (t, J=8.18 Hz, 3H); 2.80 (s, 3H); 4.36 (quartet, J=8.18 Hz, 2H); 4.46 (s, 2H); 6.00 (s, 4H); 6.87 (d, J=8.18 Hz, 2H); 7.05 (dd, J=8.18 Hz, 1.63 Hz, 2H); 7.11 (d, J=1.23 Hz, 2H); 7.95 (s, 2H).

Step 2  3,5-Bis-(3,4-methylenedioxyphenyl)-4-methoxymethoxybenzoic Acid

The synthesis of 3,5-bis-(3,4-methylenedioxyphenyl)-4-methoxymethoxybenzoic acid was similar to Step 2 of Examples 149 and 150 from 3,5-bis-(3,4-methylenedioxyphenyl)-4-methoxymethoxybenzoic acid ethyl ester. Purification was done in this manner. The crude acid was dissolved in 2.5N NaOH and extracting with EtOAc three times. These combined EtOAc layers were set aside. The aqueous layer was acidified with 2N HCl then extracted with EtOAc (3×). These combined layers were dried over Na$_2$SO$_4$ and the solvent removed in vacuo to give about 1 g of the acid plus a minor amount of AcOH as a dark yellow solid. The solvent was removed from the EtOAc layers that had been set aside and the residue was resubjected to reaction conditions with a large excess of base. This part was diluted with water, acidified with 2N HCl, and extracted with EtOAc. The EtOAc was dried and the solvent removed in vacuo to give more of the desired acid. Total yield is 1.35 g, 95.7%. $^1$H NMR (CDCl$_3$) δ 2.76 (s, 3H); 4.46 (s, 2H); 6.123 (s, 4H); 7.07 (s, 4H); 7.84 (s, 2H); 13.00 (bs, 1H).

Step 3 3,3",4,4"-Bis-methylenedioxy-2'-methoxymethoxy-[1,1';3',1"]terphenyl-5'-carboxylic Acid (7-Phenyl-heptyl)-amide 3,3",4,4"-Bis-methylenedioxy-2'-methoxymethoxy-[1,1';3',1"]terphenyl-5'-carboxylic acid (7-phenyl-heptyl)-amide was prepared as a beige solid (1.2 g, 68.1%) in a similar manner to Step 3 of Example 143 from 3,5-bis-(3,4-methylenedioxyphenyl)-4-methoxymethoxybenzoic acid. $^1$H NMR (CDCl$_3$) δ 1.524–1.386 (m, 6H); 1.51–1.60 (m, 4H); 2.57 (t, J=8.18 Hz, 2H); 2.80 (s, 3H); 3.41 (quartet, J=6.54 Hz, 2H); 4.44 (s, 2H); 6.00 (s, 4H); 6.07 (m, 1H); 6.86 (d, J=8.18 Hz, 2H); 7.03 (dd, J=8.18 Hz, 1.20 Hz, 2H); 7.08 (s, 2H); 7.10–7.16 (m, 3H); 7.23–7.27 (m, 2H); 7.64 (s, 2H).

Step 4 2'-Hydroxy-3,4,3",4"-bis-methylenedioxyphenyl-[1,1';3'1"]terphenyl-5'-carboxylic Acid (7-Phenyl-heptyl)-amide To a solution of 3,3",4,4"-Bis-methylenedioxy-2'-methoxymethoxy-[1,1';3',1"]terphenyl-5'-carboxylic acid (7-phenyl-heptyl)-amide (1.2 g, 1.9 mmol) in 8 mL THF was added 2N HCl (800 μL, 1.9 mmol) and a catalytic amount of camphorsulfonic acid. The reaction mixture was refluxed until all of the starting material was consumed. Workup is as in Step 4 of Examples 149 and 150. Flash chromatography (20% EtOAc:80% Hexanes to 40% EtOAc:60% Hexanes) on silica gel yielded 870 mg, 74.3% of a light yellow foam as the desired product. $^1$H NMR (CDCl$_3$) δ 1.20–1.40 (m, 6H); 1.50–1.67 (m, 4H); 2.57 (t, J=7.64 Hz, 2H); 3.40 (quartet, J=7.09 Hz, 2H); 5.70 (s, 1H); 6.00 (s, 5H); 6.86–7.00 (m, 6H); 7.06–7.31 (m, 5H); 7.60 (s, 2H).

Step 5 [3,3",4,4"-Bis-methylenedioxy-5'-(7-phenyl-heptylcarbamoyl)-[1,1';3',1"]terphenyl-2'-yloxy]acetic Acid tert-Butyl Ester To a solution of 3,3",4,4"-bis-methylenedioxy-2'-methoxymethoxy-[1,1';3',1"]terphenyl-5'-carboxylic acid (7-phenyl-heptyl)-amide (400 mg, 0.648 mmol) in 5.5 m anhydrous DMF was stirred at room temperature while solid K$_2$CO$_3$ (45 mg, 0.324 mmol) was added. The reaction was stirred for one-half hour before t-butyl bromoacetate (139 mg, 0.712 mmol, 105 μL). The reaction was stirred overnight and worked up as in Step 1 of Example 146. Flash chromatography (10% EtOAc:90% Hexanes to 30% EtOAc:70% Hexanes) on silica gel yielded 420 mg, 88% of a white solid. 1.28–1.37 (m, 6H); 1.57 (s, 13H); 2.57 (t, J=8.18 Hz, 2H); 3.41 (quartet, J=8.18 Hz, 2H); 3.79 (s, 2H); 5.99 (s, 4H); 6.04 (m, 1H); 6.86 (d, J=9.00 Hz, 2H); 7.05 (dd, J=8.18 Hz, 1.23 Hz, 2H); 7.10–7.17 (m, 6H); 7.20–7.27 (m, 1H); 7.627 (s, 1H).

Step 6 [3,3",4,4"-Bis-methylenedioxy-5'-(7-phenyl-heptylcarbamoyl)-[1,1';3',1"]terphenyl-2'-yloxylacetic Acid

[3,3",4,4"-Bis-methylenedioxy-5'-(7-phenyl-heptylcarbamoyl)-[1,1';3',1"]terphenyl-2'-yloxy]acetic acid (420 mg, 0.57 mmol) was stirred in 5 mL HCOOH for 2 d then the excess HCOOH was removed in vacuo to give a viscous tan oil. The oil was placed under high vacuum to remove the remaining HCOOH then the oil was crystallized to a beige solid at −78° C. There yielded 345 mg, 89% of the solid. mp 157–8° C.; $^1$H NMR (DMSO-d$_6$) δ 1.23–1.29 (m, 6H); 1.47–1.57 (m, 4H); 2.53 (t, J=7.69 Hz, 2H); 3.23 (quartet, J=6.59 Hz, 2H); 3.86 (s, 2H); 6.06 (s, 4H); 6.99 (d, J=8.13 Hz, 2H); 7.06 (td, J=7.25 Hz, 0.77 Hz, 2H); 7.11–7.17 (m, 4H); 7.21–7.25 (m, 2H); 7.75 (d, J=0.88 Hz, 2H); 8.12 (s, 1H); 8.49 (t, J=5.49 Hz, 1H); 12.65 (bs, 1H); IR 3350, 2925, 2850, 1730, 1610, 1550, 1500, 1490, 1455, 1430, 1230, 1200, and 1035 cm$^{-1}$; mass spectrum [(+) APCI], m/z 610 [M+H]$^+$; Anal Calcd. For C$_{36}$H$_{35}$NO$_8$: C, 70.92; H, 5.79; N, 2.30; Found: C, 69.78; H, 5.70; N, 2.30.

EXAMPLE 152

3'-Bromo-2'-hydroxy-5'-(8-phenyl-octylcarbamoyl)-biphenyl-3-carboxylic Acid 4-chloro-butyl Ester Step 1 3-Bromo-3-formylphenyl-4-methoxymethoxybenzoic Acid To a suspension of 3-bromo-3-formylphenyl-4-methoxymethoxybenzoic acid ethyl ester (1.4 g, 3.56 mmol) in 10 mL MeOH/20 mL H$_2$O was added solid KOH (220 mg, 3.91 mmol). The reaction mixture was refluxed for 3 hours then additional solid KOH (23 mg, 0.42 mmol) was added and the temperature of the reaction was lowered to 10 ca 50° C. after which point the reaction was stirred overnight. The workup of the reaction consisted of diluting with water and acidifying with 2N HCl to pH 1 then extracting with EtOAc (3×). The combined organic layers were dried over Na$_2$SO$_4$ then the solvent was removed in vacuo to give a beige solid. This solid was subjected to flash chromatography (50% EtOAc:50% Hexanes to 100% EtOAc) to give the desired acid as a beige solid plus a fraction that contained starting ester and desired acid. This fraction was rechromatographed to give more acid for a total yield of 920 mg, 70.7%. $^1$H NMR (CDCl$_3$+DMSO-d$_6$) δ 2.91 (s, 3H); 4.67 (s, 2H); 5.2–6.6 (bs, 1H); 7.26 (t, J=8.18 Hz, 1H); 7.67 (d, J=8.18 Hz, 1H); 7.73 (d, J=8.18 Hz, 1H); 7.83–7.90 (m, 2H); 8.11 (d, J=1.64 Hz, 1H); 9.90 (s, 1H).

Step 2 1-Bromo-7-phenylheptane

To a solution of 7-phenyl-1-heptanol (29.1 g, 151.3 mmol) in 800 mL CH$_2$Cl$_2$ at room temperature was added CBr$_4$ (60.2 g, 181.6 mmol) then triphenylphosphine (47.6 g, 181.6 mmol). After 30 s, the reaction had turned a light green color. TLC indicated that the reaction was complete at this point. The solvent was removed in vacuo to give a greenish-white semisolid. To this material was added 10% EtOAc:90% Hexanes and the resulting suspension was filtered through a pad of silica gel washing well with the same solvent system. There yielded 57 g of a colorless oil as the desired bromide and triphenylphosphine oxide. This oil was then flash chromatographed (Hexanes) to yield 38.6 g, 100% of the bromide as a colorless oil. $^1$H NMR (CDCl$_3$) δ 1.30–1.49 (m, 6H); 1.60 (quintet, J=8.18 Hz, 2H); 2.60 (t, J=8.18 Hz, 2H); 3.39 (t, J=8.18 Hz, 2H); 7.13–7.20 (m, 3H); 7.21–7.31 (m, 2H).

Step 3 7-Phenyl-1-cyanoheptane

To solid dry KCN (260 mg, 4 mmol) in a flamed dried round bottom flask was added 1.1 mL anhydrous THF, 1-bromo-7-phenyl heptane (510 mg, 2 mmol) and BuNHSO$_4$ (136 mg, 0.4 mmol). The reaction was refluxed for 50 min before 100 μL anhydrous DMSO was added. The reaction was heated further and an additional 330 μL anhydrous, DMSO was added. The reaction was heated overnight then cooled. Water was added and the aqueous solution was extracted with EtOAc (3×). The combined organic layers were dried over Na$_2$SO$_4$ and the solvent was removed in vacuo to give an oil which was flash chromatographed (10% EtOAc:90% Hexanes) to yield 250 mg, 62.5% of the cyanide as a colorless oil. $^1$H NMR (CDCl$_3$) δ 1.254–1.482 (m, 6H); 1.51–1.67 (m, 4H); 2.30 (t, J=8.18 Hz, 2H); 2.55 (t, J=8.18 Hz, 2H); 7.10–7.20 (m, 7.20–7.30 (m, 2H).

Step 4 8-Phenyl-heptyl Amine

A flamed dried round bottom flask was charged with 7-phenyl-1-cyanoheptane (7.67 g, 38.1 mmol) and 180 mL anhydrous THF. Solid LiAlH$_4$ (2.42 g, 63.8 mmol) was added portionwise over 30 min at room temperature. The reaction was stirred overnight. Then workup was done in the following manner. 2.4 mL H$_2$O was added to the stirred reaction mixture. The reaction was cooled to 0° C. then 2.4 ML 15% NaOH was added. Then 7.2 mL H$_2$O was added. The resulting suspension was diluted with 100 mL THF and filtered. The filtrate was dried over Na$_2$SO$_4$ and the solvent was removed to give 6.67 g, 85.3% of a yellow oil as the amine. $^1$H NMR DMSO-d$_6$) δ 1.12–1.40 (m, 10H); 1.28–1.60 (m, 2H); 2.26–2.60 (m, 4H); 7.10–7.20 (m, 3H); 7.20–728 (m, 2H).

Step 5 N-(8-Phenyl-heptyl)-3-bromo-3-formylphenyl-4-methoxymethoxybenzamide

N-7-Phenyl-heptyl-3-bromo-3-formylphenyl-4-methoxymethoxybenzamide was prepared as a light yellow oil (610 mg, 43.9%) in a similar manner to Step 3 of Example 143 from 3-bromo-3-formylphenyl-4-methoxymethoxybenzoic acid. $^1$H NMR (CDCl$_3$) δ 1.26–1.40 (m, 8H); 1.51–1.60 (m, 4H); 2.57 (t, J=8.18 Hz, 2H); 3.05 (s, 3H); 3.40 (quartet, J=7.36 Hz, 2H); 5.79 (s, 2H); 6.06–6.13 (m, 1H); 7.10–7.20 (m, 3H); 7.20–7.28 (m, 2H); 7.60 (t, J=7.36 Hz, 1H); 7.80 (d, J=8.18 Hz, 1H); 7.97–8.03 (m, 2H); 10.06 (s, 1H).

Step 6 N-(8-Phenyl-heptyl)-3-bromo-3-carboxyphenyl-4-methoxymethoxybenzamide

To a solution of N-7-phenyl-heptyl-3-bromo-3-formylphenyl-4-methoxymethoxybenzamide (300 mg, 0.542 mmol) was added KMnO$_4$ (128 mg, 0.813 mmol) at room temperature and the reaction was stirred until all starting aldehyde was consumed by TLC. The reaction mixture was diluted with water and sodium bisulfite was added. Then 1 mL 1N HCl was added. This mixture was stirred until it was colorless then it was extracted with EtOAc (3×). The combined organic layers were washed with 2N HCl, dried over Na$_2$SO$_4$ and the solvent was removed to give 270 mg, 87.6% of the crude acid as a light yellow oil which was taken directly to the next step. $^1$H NMR (CDCl$_3$) δ 1.26–1.40 (m, 8H); 1.51–1.64 (m, 4H); 2.57 (t, J=8.18 Hz, 2H); 3.43 (quartet, J=8.18 Hz, 2H); 3.08 (s, 3H); 4.80 (s, 2H); 6.09 (m, 1H); 7.11–7.20 (m, 2H); 7.20–7.28 (m, 3H); 7.54 (t, J=8.18 Hz, 1H); 7.68 (d, J=1.23 Hz, 1H); 7.77 (d, J=4.09 Hz, 1H); 7.99 (d, J=1.23 Hz, 1H); 8.10 (d, J=8.18 Hz, 1H); 8.27 (s, 1H).

Step 7 3'-Bromo-2'-hydroxy-5'-(8-phenyl-octylcarbamoyl)-biphenyl-3-carboxylic Acid 4-chloro-butyl Ester To a solution of N-(7-Phenylheptyl)-3-bromo-3-carboxyphenyl-4-methoxymethoxybenzamide (270 mg, 0.474 mmol) in 5 mL THF was added 150 μL 2N HCl and a catalytic amount of camphorsulfonic acid. The reaction was refluxed for 3 hours then stirred at room temperature for 2 d. Then 2 drops of conc. HCl were added and the reaction mixture was refluxed further until all starting material was consumed. The reaction mixture was cooled, diluted with water, and extracted with EtOAc (3×). The combined organic layers were dried over Na$_2$SO$_4$ and the solvent was removed to give a solid that was flash chromatographed (25% EtOAc:75% Hexanes) to yield 130 mg, 44.5% of a yellow oil as the ester. $^1$H NMR (DMSO-d$_6$) δ 1.22–1.29 (m, 8H); 1.46–1.56 (m, 4H); 1.84 (t, 3.08 Hz, 4H); 2.53 (t, J=7.58 Hz, 2H); 3.21 (quartet, J=6.81 Hz, 2H); 3.70 (t, J=6.15 Hz, 2H); 4.33 (t, J=6.04 Hz, 2H); 7.12–7.16 (m, 3H); 7.21–7.25 (m, 2H); 7.62 (t, J=7.69 Hz, 1H); 7.74–7.79 (m, 2H); 7.97 (dt, J=7.69 Hz, 1,43 Hz, 1H); 8.05 (d, J=2.20 Hz, 1H); 8.09 (t, J=1.65 Hz, 1H); 8.42 (t, J=5.93 Hz, 1H); 9.78 (s, 1H); IR 3325, 2925, 2850, 1720, 1630, 1600, 1550, 1470, 1290, 1240, 1010, and 700 cm$^{-1}$; mass spectrum [(−)ESI], m/z 612/614 [M−H]$^{-1}$; Anal Calcd. for C$_{32}$H$_{37}$BrClNO$_4$: C, 62.49; H, 6.06; N, 2.28; Found: C, 61.27; H, 6.36; N, 2.09.

EXAMPLE 153

(3"-Chloro-5'-dodecylcarbamoyl-3-trifluoromethyl-[1,1';3',1"]terphenyl-2'-yloxy)acetic Acid Step 1 3-(3-chlorophenyl)-5-(3-trifluoromethyl)-4-(2-hydroxyethoxy)benzoic Acid Ethyl Ester To a stirred solution of K$_2$CO$_3$ (2.488 g, 18 mmol) in water (9 ml) was added dioxane (71 ml), 3-Bromo-5-(m-chlorophenyl)-4-(2-hydroxyethoxy)benzoic acid ethyl ester (2.398 g, 6 mmol), 3-(trifluoromethyl)phenylboronic acid (1.367 g, 7.2 mmol), and [1,1'bis(diphenylphosphino)ferrocene]dichloropalladium(II), complex with CH$_2$Cl$_2$ (.098 g, 0.12 mmol). The reaction was stirred at room temperature for 21 h then warmed to 59° C. During the course of the day additional boronic acid and catalyst were added as needed. The heating was stopped after 7 h. The reaction mixture was diluted with 0.2N HCl (160 ml) and extracted with EtOAc (1×100 ml, 3×50 ml). The combined organics were washed with 0.1N HCL (2×30ml), water (3×30 ml), brine (2×30 ml) and dried over Na$_2$SO$_4$. After concentrating, the residue was purified by flash chromatography (0 to 50% EtOAc/Hex gradient) and then HPLC (50% CH$_2$CH$_2$/Hex with 6% methyl t-butyl ether) to give the product as a colorless oil (2.436 g, 87%); $^1$H NMR (400 MHz, DMSO-d$_6$) δ 1.31 (t, J=7 Hz, 3H), 3.10 (t, J=5.7 Hz, 2H), 3.26 (t, J=5.7 Hz, 2H), 4.33 (q, J=7.0, 2H), 4.42 (s, broad, 1H), 7.47–7.54 (m, 2H), 7.56–7.60 (m, 1H), 7.69–7.80 (m, 3H) 7.89–7.98 (m, 3H): IR (film) 3500, 2950, 1720 cm$^{-1}$; mass spectrum (EI), m/z 464

Step 2 N-dodecyl-3-(3-chlorophenyl)-5-(3-trifluoromethyl)-4-(2-hydroxyethoxy)benzamide The product was prepared as a colorless oil (0.241 g, 84%) from 3-(3-chlorophenyl)-5-(3-trifluoromethyl)4-(2-hydroxyethoxy)benzoic acid ethyl ester using a procedure similar to step 2 of Example 1; $^1$H NMR (300 MHz, DMSO-d$_6$) δ 0.85 (t, J=7.5 Hz, 3H), 1.20–1.40 (m, 18H), 1.46–1.60 (m, 2H), 3.14 (q, J=7.5, 2H), 3.20–3.30 (m, 4H), 4.45 (t, J=7 Hz, 1H), 7.50–7.55 (m, 2H), 7.60–7.66 (m, 1H), 7.70 7.80 (m, 3H), 7.90–8.00 (m, 4H), 8.55 (t, J=7Hz, 1H); mass spectrum [(+)ESI], m/z 604/606 (M+H)$^+$.

Step 3 (3"-Chloro-5'-dodecylcarbamoyl-3-trifluoromethyl-[1,1';3',1"]terphenyl-2'-yloxy)acetic acid The title compound was prepared as an off white solid (0.104 g, 42%) from N-dodecyl-3-(3-chlorophenyl)-5-(3-trifluoromethyl)-4-(2-hydroxyethoxy)-benzamide using a procedure similar to step 3 of example 1; dec.>95° C.; $^1$H NMR (400 MHz, DMSO-d$_6$) δ 0.82 (t, J=7 Hz, 3H), 1.18–1.35 (m, 18H), 1.45–1.55 (m, 2H), 3.24 (dd, J=6.8, 12.7 Hz, 2H), 3.64 (s, 2H), 7.42–7.80 (m, 2H), 7.58–7.74 (m, 4H); 7.84–7.85 (m, 2H), 7.92–7.98 (m, 2H), 8.53 (t, J=5.5 Hz, 1H); IR (KBr) 3325, 2925, 2850, 1630 cm$^{-1}$; mass spectrum [(−)ESI], m/z 616 (M−H)$^-$; Anal. Calcd. for C$_{34}$H$_{39}$ClF3NO$_4$H$_2$O: C, 64.19; H, 6.50; N, 2.20, Found. C, 64.12; H, 6.34; N, 2.20.

EXAMPLE 154

(5'-Dodecylcarbamoyl-4"-methoxy-3-trifluoromethyl-[1,1';3',1"]terphenyl-2'-yloxy)acetic Acid Step 1 3-(4-methoxyphenyl)-5-(3-trifluoromethylphenyl)-4-(2-hydroxyethoxy)benzoic Acid Ethyl Ester The product was prepared as a colorless, viscous oil (2.609 g, 71%) from 3-bromo-5-(4-methoxyphenyl)-4-(2-hydroxyethoxy)benzoic acid ethyl ester using a procedure similar to step 1 of Example 153; $^1$H NMR (400 MHz, DMSO-d$_6$) δ 1.30 (t, J=7 Hz, 3H), 3.10 (dd, J=5.5, 11.2 Hz, 2H), 3.26 (t, J=6.2 Hz, 2H), 3.80 (s, 3H), 4. (dd, J=7.0, 14.3 Hz, 2H), 4.39 (t, J=5.5, 1H), 7.02–7.04 (m, 2H), 7.54–7.58 (m, 2H),7.68–7.8 (m, 2H), 7.88–7.90 (m, 3H), 7.95 (s, 1H); IR (film) 3500, 2950, 1725, 1625, 1525 cm$^{-1}$; mass spectrum [(+)APCI], m/z 461 (M+H)$^+$.

Step 2 N-dodecyl-3-(4-methoxyphenyl)-5-(3-trifluoromethylphenyl)4-(2-hydroxyethoxy)benzamide The product was prepared as a colorless oil (0.229 g, 89%) from 3-(4-methoxyphenyl)-5-(3-trifluoromethylphenyl)-4-(2-hydroxyethoxy)benzoic acid ethyl ester using a procedure similar to step 2 of example 1; $^1$H NMR (300 MHz, DMSO-d$_6$) δ 0.82 (t, J=7.5 Hz, 3H), 1.20–1.35 (m, 18H), 1.50–1.58 (m, 2H) 3.10 (q, J=7 Hz, 2H), 3.20–3.30 (m, 4H), 3.82 (s, 3H), 4.40 (s, 1H), 7.02–7.08 (m, 2H), 7.55 . 7.61 (m, 2H), 7.70–7.80 (m, 2H), 7.85–7.90 (m, 2H), 7.92–7.99 (m, 2H), 8.55 (t, J=7.5 Hz, 1H); mass spectrum [(−)ESI], m/z 598 (M−H)$^-$.

Step 3 (5'-Dodecylcarbamoyl-4"-methoxy-3-trifluoromethyl-[1,1';3',1"]terphenyl-2'-yloxy)acetic Acid The title compound was prepared as an off white solid (0.101 g, 44%) from N-dodecyl-3-(4-methoxyphenyl)-5-(3-trifluoromethylphenyl)-4-(2-hydroxyethoxy)benzamide using a procedure similar to step 3 of example 1; dec. 90–115° C.; $^1$H NMR (400 MHz, DMSO-d$_6$) δ 0.83 (t, J=7 Hz. 3H), 1.17–1.30 (m, 18H), 1.47–1.52 (m, 2H), 3.22–3.27 (m, 2H), 3.57 (s, 2H), 3.79 (s, 3H), 6.97–7.01 (m, 2H), 7.55–7.58 (m, 2H), 7.61–7.72 (m, 2H), 7.76–7.81 (m, 2H), 7.94–7.99 (m, 2H), 8.50 (t, J=5.5, 1H); IR (KBr) 3300, 2925, 2850, 1630 1520 cm$^{-1}$; mass spectrum [(+) ESI], m/z 614 (M+H)$^+$; Anal. Calcd. for C$_{35}$H$_{42}$F$_3$NO$_5$.1.33H$_2$O: C, 65.92; H, 7.06; N, 2.20, Found: C, 65.88; H, 7.09; N, 2.51.

EXAMPLE 155

(5'-Dodecylcarbamoyl-2"-fluoro-4-methoxy-[1,1';3',1"]terphenyl-2'-'yloxy)acetic Acid Step 1 N-dodecyl-3-(2-fluorophenyl) 5-(4-methoxyphenyl)-4-(2-hydroxyethoxy)benzamide The product was prepared as a colorless viscous oil (0.28 g, 82%) from 3-(2-fluorophenyl)-5-(4-methoxyphenyl)-4-(2-hydroxyethoxy)benzoic acid ethyl ester using a procedure similar to step 2 of example 1; $^1$H NMR (300 MHz, DMSO-d$_6$) δ 0.83 (t, J=7 Hz, 3H), 1.20–1.30 (m, 18H), 1.45–1.55 (m, 2H), 3.01–3.10 (m, 2H), 3.20–3.27 (m, 4H), 3.80 (s, 3H), 4.35 (t, J=6 Hz, 1H), 7.02–7.08 (m, 2H), 7.25–7.34 (m, 2H), 7.45–7.50 (m, 2H), 7.55–7.60 (m, 2H), 7.74 (d, J=3 Hz, 1H), 7.87 (d, J=3 Hz, 1H), 8.50 (t, J=5 Hz, 1H); mass spectrum [(+)ESI], m/z 550 (M+H)$^+$.

Step 2 (5'-Dodecylcarbamoyl-2"-fluoro-4-methoxy-[1,1';3',1"]terphenyl-2'-'yloxy)acetic acid The title compound was prepared, as a white solid (0.229 g, 47%) from N-dodecyl-3-(2-fluorophenyl) 5-(4-methoxyphenyl)-4-(2-hydroxyethoxy)benzamide using a procedure similar to step 3 of example 1. The product was purifed by preparatory plate chromatography (4% Methanol/EtOAc) followed by flash chromatography (15% EtOAc/Hex and 20% EtOAC/Hex, both with 1% formic acid); $^1$H NMR (400 MHz, DMSO-d$_6$) δ 0.84 (t, J=6.8 Hz, 3H), 1.17–1.27 (m, 18H), 1.44–1.51 (m, 2H), 3(dd, J=6.8, 13.0 Hz, 2H), 3.78 (s, 3H), 3.81 (s, 2H), 6.99–7.02 (m, 2H), 7.23– (m, 2H), 7.42–7.47 (m, 2H), 7.50–7.57 (m, 2H), 7.71 (d, J=2.2 Hz, 1H), 7.84 (d, J=2.4 Hz, 1H), 8.47 (t, J=5.5, 1H), 12.48 (broad s, 1H); IR (KBr) 3375, 2925, 2850, 1730, 1615, 1200 cm$^{-1}$; mass spectrum [(+)ESI], m/z 564 (M+H)$^+$; Anal. Calcd. for C$_{34}$H$_{42}$FNO$_5$: C, 72.44; H, 7.51; N, 2.48, Found, C, 72.48; H, 7.67; N, 2.46.

EXAMPLE 156

(3-Bromo-5-dodecylcarbamoyl-2'-fluoro-biphenyl-2-yloxy)acetic Acid

Step 1 N-dodecyl-3-bromo-5-(3-fluorophenyl)-4-(2-hydroxyethoxy)benzamide

The product was prepared as a yellow oil (0.256 g, 78%) from 3-bromo-5-(3-fluorophenyl)-4-(2-hydroxyethoxy)benzoic acid ethyl ester using a procedure similar to step 2 of example 1; $^1$H NMR (300 MHz, DMSO-d$_6$) δ 0.82 (t, J=7.5 Hz, 3H), 1.20–1.35 (m, 18H), 1.45–1.55 (m, 2H), 3.23 (q, J=7.5 Hz, 2H), 3.30–3.40 (m, 2H), (t, J=6 Hz, 2H), 4.62 (t, J=7 Hz, 1H), 7.30–7.38 (m, 2H), 7.45–7.55 (m, J=7.81 (d, J=2 Hz, 1H) 8.15 (d, J=2 Hz, 1H), 8.55 (t, J=5 Hz, 1H); mass spectrum [(+)ESI], m/z 522/524 (M+H)$^+$.

Step 2 (3-Bromo-5-dodecylcarbamoyl-2'-fluoro-biphenyl-2-yloxy)acetic Acid

The title compound was prepared as a brown solid from N-dodecyl-3-bromo-5-(3-fluorophenyl)-4-(2-hydroxyethoxy)benzamide using a procedure similar to step 3 of example 1; mp 128–138° C.; $^1$H NMR (400 MHz, DMSO-d$_6$) δ 0.85 (t, J=7 Hz, 3H), 1.20–1.30 (m, 18H) 1.45–1.55 (m, 2H), 3.20–3.25 (m, 2H), 3.80 (s, 2H), 7.27–7.32 (m, 2H), 7.44–7.50 (m, 2H), 7.74 (d, J=2 Hz, 1H), 8.11 (d, J=2 Hz, 1H), 8.51 (t, J=5.5 Hz, 1H); IR (KBr) 3300, 2925, 2850, 1625 cm$^{-1}$; mass spectrum [(+)ESI], m/z 536/538 (M+H)$^+$; Anal. Calcd. for C$_{27}$H$_{35}$BrFNO$_4$,2.5H$_2$O: C, 55.77; H, 6.93; N, 2.41, Found: C, 55.58; H, 6.13; N, 2.40.

EXAMPLE 157

[4"-Methoxy-5'-(6-phenyl-hexylcarbamoyl)-3-trifluoromethyl-[1,1';3',1"]terphenyl-2'-yloxy]acetic Acid Step 1 N-(6-phenythexyl)-3-(4-methoxyphenyl)-5-(3-trifluoromethylphenyl)-4-(2-hydroxyethoxy)benzamide The product was prepared as a yellow gum (0.191 g, 74%) from 3-(4-methoxyphenyl)-5-(3-trifluoromethylphenyl)-4-(2-hydroxyethoxy)benzoic acid ethyl ester and 6-phenylhexylamine using a procedure similar to step 2 of example 1; $^1$H NMR (300 MHz, DMSO-d$_6$) δ 1.27–1.38 (m, 4H), 1.47–1.60 (m, 4H), 2.55 (t, J=7.5 Hz, 2H), 3.10 (q, J=7 Hz, 2H), 3.20–3.30 (m, 4H), 3.80 (s, 3H), 4.38 (t, J=6 Hz, 1H), 7.02–7.08 (m, 2H), 7.10–7.18 (m, 3H), 7.23–7.26 (m, 2H), 7.55–7.60 (m, 2H), 7.68–7.78 (m, 2H), 7.83–7.88 (m, 2H), 7.91–7.96 (m, 2H), 8.55 (t, J=4 Hz, 1H); mass spectrum [(+)ESI], m/z 592 (M+H)$^+$.

Step 2 [4"-Methoxy-5'-(6-phenyl-hexylcarbamoyl)-3-trifluoromethl-[1,1';3',1"]terphenyl-2'-yloxy]acetic Acid The title compound was prepared as a white solid (0.067 g, 35%) from N-(6-phenylhexyl)-3-(4-methoxyphenyl)-5-(3-trifluoromethylphenyl)-4-(2-hydroxyethoxy)benzamide using a procedure similar to step 3 of example 1. The product was purified using preparatory plate chromatography (40% EtOAc/Hex with 1% formic acid); mp 153–159° C.; $^1$H NMR (400 MHz, DMSO-d$_6$) δ 1.30–1.38 (m, 4H), 1.49–1.61 (m, 4H), 2.56 (t, J=7.5 Hz, 2H), 3.24–3.30 (m, 2H), 3.82 (s, 3H), 3.84 (s, 2H), 7.02–7.07 (m, 2H), 7.12–7.19 (m, 3H), 7.22–7.27 (m, 2H), 7.55–7.59 (m, 2H), 7.68–7.78 (m, 2H), 7.85 (dd, J=2.2, 5.7 Hz, 2H), 7.91 (d, J=7.7, 1H), 7.97 (s, 1H), 8.56 (t, J=5.7, 1H), 12.60 (broad s, 1H); IR (KBr) 3350, 2925, 1725, 1615 cm$^{-1}$; mass spectrum [(+)APCI], m/z 606 (M+H)$^+$; Anal. Calcd. for C$_{35}$H$_{34}$F$_3$NO$_5$: C, 69.41; H, 5.66; N, 2.31, Found: C, 69.25; H, 5.68; N, 2.24.

EXAMPLE 158

[4"-Methoxy-5'-(8-phenyl-octylcarbamoyl)-3-trifluoromethyl-[1,1';3',1"]terphenyl-2'-yloxy]acetic Acid Step 1 N-(8-Phenyloctyl)-3-(4-methoxyphenyl)-5-(3-trifluoromethylphenyl)-4-(2-hydroxyethoxy)benzamide The product was prepared as a viscous yellow oil (0.165 g, 61%) from 3-(4-methoxyphenyl)-5-(3-trifluoromethylphenyl)4-(2-hydroxyethoxy)benzoic acid ethyl ester and 8-phenyloctylamine using a procedure similar to step 2 of example 1; $^1$H NMR (300 MHz, DMSO-$d_6$) δ 1.21–1.34 (m, 8H), 1.45–1.58 (m, 4H), 2.50 (t, J=7.5 Hz, 2H), 3.10 (q, J=6 Hz, 2H), 3.20–3.30 (m, 4H), 3.80 (s, 3H), 4.38 (t, J=6 Hz, 1H), 7.01–7.05 (m, 2H), 7.10–7.25 (m, 5H),7.60 (d, J=9 Hz, 2H), 7.68–7.78 (m, 2H), 7.84–7.88 (m, 2H), 7.90–7.95 (m, 2H), 8.54 (t, J=5 Hz, 1H); mass spectrum [(+)ESI], m/z 620 (M+H)$^+$.

Step 2 [4"-Methoxy-5'-(8-phenyl-octylcarbamoyl)-3-trifluoromethyl-[1,1';3',1"]terphenyl-2'-yloxy]acetic Acid The title compound was prepared as a white solid (0.61 g, 42%), from N-(8-phenyloctyl)-3-(4-methoxyphenyl)-5-(3-trifluoromethylphenyl)-4-(2-hydroxyethoxy)benzamide using a procedure similar to step 3 of example 1. The product was purified by flash chromatography (20% EtOAc/Hex with 1% formic acid) and then preparatory plate chromatography (40% EtOAc/Hex with 1% formic acid); mp 139–144° C.; $^1$H NMR (400 MHz, DMSO-$d_6$) δ 1.21–1.30 (m, 8H), 1.45–1.58 (m, 4H), 2.52 (t, J=7.2, 2H), 3.24–3.28 (m, 2H), 3.80 (s, 3H), 3.82 (s, 2H), 7.01–7.05 (m, 2H), 7.11–7.17 (m, 3H), 7.20–7.25 (m, 2H), 7.53–7.58 (m, 2H), 7.66–7.76 (m, 2H), 7.83 (dd, J=2.4, 5.9 Hz, 2H), 7.90 (d, J=7.7 Hz, 1H), 7.96 (s, 1H), 8.54 (t, J=6 Hz, 1H), 12.60 (broad s, 1H); IR (KBr) 3350, 2940, 1725, 1200, 1125, 1615 cm$^{-1}$; mass spectrum [(+)APCI], m/z 634 (M+H)$^+$; Anal. Calcd. for $C_{37}H_{38}F_3NO_5$: C, 70.13; H, 6.04; N, 2.21, Found: C, 69.80; H, 6.14; N, 2.20.

EXAMPLE 159

(3,5,3",5"-Tetrachloro-5'-dodecylcarbamoyl-[1,1';3',1"]terphenyl-2'-yloxy)acetic Acid Step 1 N-dodecyl-3,5-bis(3,5-dichlorophenyl)-4-(2-hydroxyethoxy)benzamide The product was prepared as a yellow oil (0.468 g, 91%) from 3,5-bis(3,5-dichlorophenyl)-4-(2-hydroxyethoxy) benzoic acid ethyl ester using a procedure similar to step 2 of example 1; $^1$H NMR (300 MHz, DMSO-$d_6$) δ 0.84 (t, J=7 Hz, 3H), 1.20–1.35 (m, 18H), 1.45–1.55 (m, 2H), 3.15–3.25 (m, 2H), 3.25–3.30 (m, 4H), 4.51 (broad s, 1H), 7.65 (m, 2H), 7.74 (d, J=2 Hz, 4H), 7.92 (s, 2H), 8.77 (t, J=6 Hz, 1H); mass spectrum [(−)ESI], 636 (M−H)$^-$.

Step 2 (3,5,3",5"-Tetrachloro-5'-dodecylcarbamoyl-[1,1';3',1"]terphenyl-2'-yloxy)acetic Acid The title compound was prepared as an off white solid (0.151 g, 32%) from N-dodecyl-3,5-bis(3,5-dichlorophenyl)-4-(2-hydroxyethoxy)benzamide using a procedure similar to step 3 of example 1. The product was purified by preparatory plate chromatography (20% EtOAc/Hex with 1% formic acid); mp 139–144° C.; $^1$H NMR (400 MHz, DMSO-$d_6$) δ 0.85 (t, J=7 Hz, 3H), 1.18–1.34 (m, 18H), 1.48–1.56 (m, 2H), 3.28 (q, J=6.6 Hz, 2H), 3.88 (s, 2H), 7.67 (t, J=2 Hz, 2H), 7.72 (d, J=2 Hz, 4H), 7.91 (s, 2H), 8.58 (t, J=5 Hz, 1H), 12.74 (broad s, 1H); IR (KBr) 3370, 2940, 2670, 1725, 1600, 1560, 1200 cm$^{-1}$; mass spectrum [(−)ESI], m/z 650 (M−H)$^-$; Anal. Calcd. for $C_{33}H_{37}Cl_4NO_4$: C, 60.66; H, 5.71, N, 2.14, Found: C, 60.78; H, 5.55; N, 2.08.

EXAMPLE 160

[3,5,3",5"-Tetrachloro-5'-(8-phenyl-octylcarbamoyl)-[1,1';3',1"]terphenyl-2'-yloxy]acetic Acid Step 1 N-(8-octylphenyl)-3,5-bis(3,5-dichlorophenyl)-4-(2-hydroxyethoxy)benzamide The product was prepared as a viscous, colorless oil (0.444 g, 84%) from 3,5-bis(3,5-dichlorophenyl)-4-(2-hydroxyethoxy)benzoic acid ethyl ester using a procedure similar to step 2 of example 1; $^1$H NMR (300 MHz, DMSO-$d_6$) δ 1.28 (broad s, 8H), 1.45–1.60 (m, 4H), 2.54 (t, J=7 Hz, 2H), 3.18 (broad s, 2H), 3.22–3.40 (m, 4H), 4.52 (broad s, 1H), 7.10–7.25 (m, 5H), 7.65 (m, 2H), 7.70 (d, J=2 Hz, 4H), 7.92 (s, 2H), 8.55 (t, J=4 Hz, 1H); mass spectrum [(−)ESI], m/z 656 (M−H)$^-$.

Step 2 [3,5,3",5"-Tetrachloro-5'-(8-phenyl-octylcarbamoyl)-[1,1';3'1"]terphenyl-2'-yloxy]acetic Acid The title compound was prepared as a white solid (0.161 g, 36%) from N-(8-octylphenyl)-3,5-bis(3,5-dichlorophenyl)-4-(2-hydroxyethoxy)benzamide and 8-phenyloctylamine using a procedure similar to step 3 of example 1. The crude product was purified as follows: flash chromatography (10% EtOAc/Hex with 1% formic acid), preparatory plate chromatography (30% EtOAc/Hex with 1% formic acid), preparatory plate chromatography (EtOAc), flash chromatography (20% EtOAc/Hex with 1% formic acid); mp 139–149° C., solidifies and melts again 175–178° C.; $^1$H NMR (400 MHz, DMSO-$d_6$) δ 1.22–1.32 (m, 8H), 1.46–1.57(m, 4H), 2.53 (t, J=7.5, 2H), 3.26 (q, J=6.6, 2H), 3.88 (s, 2H), 7.11–7.16 (m, 3H), 7.21–7.26 (m, 2H), 7.66 (t, J=2 Hz, 2H), 7.69 (d, J=2 Hz, 4H), 7.89 (s, 2H), (t, J=5.5 Hz, 1H), 12.75 (broad s, 1H); IR (KBr) 3375, 2910, 2850, 1715, 1605, 1560, 1200 cm$^{-1}$; mass spectrum [(−)ESI], m/z 670 (M−H)$^-$; Anal. Calcd. for $C_{35}H_{33}Cl_4NO_4$: C, 62.42; H, 4.94; N, 2.08, Found: C, 62.24; H, 4.95; N, 2.01.

EXAMPLE 161

[3,5,3",5"-Tetrachloro-5'-(6-phenyl-hexylcarbamoyl)-[1,1';3',1"]terphenyl-2'-yloxy]acetic Acid Step 1 N-(6-hexylphenyl)-35-bis(3,5-dichlorophenyl)-4-(2-hydroxyethoxy)benzamide The product was prepared as a colorless oil (0.41 g, 81%) from 3,5-bis(3,5-dichlorophenyl)-4-(2-hydroxyethoxy) benzoic acid ethyl ester and 6-phenylhexylamine using a procedure similar to step 2 of example 1; $^1$H NMR (300 MHz, DMSO-$d_6$) δ 1.25–1.40 (m, 4H), 1.46–1.61 (m, 4H), 2.55 (t, J=7.5 Hz, 2H), 3.16 (q, 6 Hz, 2H), 3.22–3.30 (m, 4H), (t, J=5 Hz, 1H), 7.12–7.25 (m, 5H), 7.65 (m, 2H), 7.77 (d, J=2 Hz, 4H), 7.90 (s, 2H), (t, J=5 Hz, 1H); mass spectrum [(+)APCI], m/z 630 (M+H)$^+$.

Step 2 [3,5,3",5"-Tetrachloro-5'-(6-phenyl-hexylcarbamoyl)-[1,1';3',1"]terphenyl-2'-yloxy]acetic Acid The tide compound was prepared as a white solid (0.228 g, 56%) from N-(6-hexylphenyl)-3,5-bis(3,5-dichlorophenyl)4-(2-hydroxyethoxy)benzamide using a procedure similar to step 3 of example 1. The crude product was purified first by preparatory plate chromatography (80% EtOAc/Hex) and then flash chromatography (20% EtOAc/Hex with 1% formic acid); mp 151–159° C.; $^1$H NMR (400 MHz, DMSO-$d_6$) δ 1.27–1.36 (m, 4H), 1.46–1.60 (m, 4H), 2.55 (t, J=7.5 Hz, 2H), 3.23–3.28 (m, 2H), 3.88 (s, 2H), 7.11–7.17 (m, 3H), 7.21–7.60 (m, 2H), 7.66 (t, J=2 Hz, 2H), 7.70 (d, J=2 Hz, 4H), 7.89 (s, 2H), 8.57 (t, J=5.3 Hz, 1H), 12.75 (broad s, 1H); IR (KBr) 3375, 2940, 1750, 1610, 1560, 1200, 800 cm$^{-1}$; mass spectrum [(−)ESI], m/z 642 (M−H)$^-$; Anal. Calcd. for $C_{33}H_{29}Cl_4NO_4$: C, 61.41; H, 4.53; N, 2.17, Found: C, 60.95; H, 4.44; N, 2.17.

EXAMPLE 162

[3,3''-Dichloro-5'-(4-heptyloxy-benzylcarbamoyl)-[1,1';3',1'']terphenyl-2'-yloxy]acetic Acid Step 1 4-(Heptyloxy)benzamide 4-(Heptyloxy)benzoic acid (7.089 g, 30 mmol) in $SOCl_2$ (50 ml) was refluxed for 19 h. After refluxing, the mixture was concentrated in vac. The residue was dissolved in $Et_2O$ and added dropwise into a saturated solution of $NH_3(g)$ in $Et_2O$ at −50° C. After stirring at room temperature overnight, the reaction mixture was concentrated in vac and the residue triturated with water and dried. The white solid was recrystallized from ethyl acetate to give the desired product (6.15 g, 87%); mp 149–152° C.; $^1$H NMR (400 MHz, DMSO-$d_6$) δ 0.87 (t, J=6.8. 3H), 1.23–1.45 (m, 8H), 1.67–1.75 (m, 2H), 4.01 (t, J=6.6, 2H), 6.94–6.97 (m, 2H), 7.16 (s, 1H), 7.79–7.85 (m, 3H); IR (KBr) 3375, 3170, 2900, 1650, 1605, 1400, 1260, 1175, 625 cm$^{-1}$; mass spectrum [(+)ESI], m/z 236 (M+H)$^+$.

Step 2 4-(Heptyloxy)benzylamine

To a stirred suspension of lithium aluminum hydride (1.928 g, 52.23 mmol) in THF (150 ml) at room temperature under nitrogen was added a suspension of 4-(heptyloxy)benzamide (6.146 g, 26.117 mmol). After refluxing for 22 h, reaction was cooled in an ice bath and quenched in the following order: water (2.09 ml), 15% NaOH (2.09 ml) and water (6.26 ml). The mixture was stirred for 3 h followed by the addition of $Na_2SO_4$. The mixture was filtered and concentrated in vac. The residue was taken up in $Et_2O$, filtered, concentrated, and the resulting residue taken up in hexane, filtered, concentrated, and dried to give the desired product as a hazy yellow oil (4.872 g, 84%); $^1$H NMR (400 MHz, DMSO-$d_6$) δ 0.86 (t, J=7 Hz, 3H), 1.22–1.42 (m, 8H), 1.64–1.72 (m, 2H), 1.82 (broad s, 2H), 3.13 (s, 2H), 3.89 (t, J=6.6 Hz, 2H), 6.80–6.84 (m, 2H), 7.17–7.21 (m, 2H); IR (film) 2940, 2850, 1510, 1250 cm$^{-1}$; mass spectrum [(+)ESI], m/z 222 (M+H)$^+$.

Step 3 [3,3''-Dichloro-5'-(4-heptyloxy-benzylcarbamoyl)-[1,1';3',1'']terphenyl-2'-yloxy]acetic Acid The title compound was prepared as an off white solid (0.199 g, 29%) from 3,5-bis(3-chlorophenyl)-4-(2-hydroxyethoxy)benzoic acid ethyl ester using a procedure similar to steps 2 and 3 of example 1. The crude product was purified first by preparatory plate chromatography (EtOAc) and then flash chromatography (20%, 40%, 70% EtOAc/Hex with 1% formic acid); dec. 170–175° C.; $^1$H NMR (400 MHz, DMSO-$d_6$) δ 0.85 (t, J=6.8, 3H), 1.23–1.41 (m, 8H), 1.63–1.71 (m, 2H), 3.84 (s, 2H), 3.91 (t, J=6.4 Hz, 2H), 4.41 (d, J=5.93 Hz, 2H), 6.84–6.87 (m, 2H), 7.20–7.24 (m, 2H), 7.44–7.50 (m, 4H), 7.56–7.59 (m, 2H), 7.69 (m, 2H), 7.91 (s, 2H), 9.08 (t, J=5.9 Hz, 1H) 12.65 ( broad s, 1H); IR (KBr) 3440, 3310, 1910, 1725, 1610, 1520, 1250, 1200 cm$^{-1}$; mass spectrum [(+)APCI], m/z 620 (M+H)$^+$; Anal. Calcd. for $C_{35}H_{35}Cl_2NO_5$: C, 67.74; H, 5.68; N, 2.26, Found: C, 67.62; H, 5.69; N, 2.22.

EXAMPLE 163

8-[(2'-Carboxymethoxy-3,3''-dichloro-[1,1';3',1''] terphenyl-5'-carbonyl)-amino]-octanoic Acid Methyl Ester Step 1 8-Amino octanoic Acid, Methyl Ester To 15 ml methanol under nitrogen, stirred, at −5° C. was added thionyl chloride (0.80 ml) dropwise. After 5 minutes, 8-aminooctanoic acid (1.592 g, 10 mmol) was added. The reaction was stirred at −5° C. for 1 h, room temperature for 45 minutes, and 40° C. for 2.25 h. After heating, the reaction mixture was concentrated. The residue was taken up in chloroform/water (40 ml/25 ml) and basified to pH 9–10 using 1N NaOH. Layers were shaken, separated and the aqueous layer washed with water (2×30 ml). The combined organics were dried over $Na_2SO_4$ and filtered. The filtrate was concentrated in vac and dried to give the product as an oily solid (1.568 g, 90%); $^1$H NMR (400 MHz, DMSO-$d_6$) δ 1.17–1.33 (m, 8H), 1.43–1.52 (m, 2H), 2.26 (t, J=7.5 Hz, 2H), 2.44–2.49 (m, 2H), 3.55 (s, 3H); IR (film) 3475, 2930, 2850, 1730 cm$^{-1}$; mass spectrum [EI], m/z 173 M$^+$.

Step 2 3,5-bis(3-Chlorophenyl)-4-(2-hydroxyethoxy) benzoic Acid

To a stirred solution of 3,5-bis(3-chlorophenyl)-4-(2-hydroxyethoxy)benzoic acid ethyl ester (2.009 g, 4.658 mmol) in THF (30 ml) and ethanol (15 ml) was added 1N KOH (9.32 ml). After $^{18}$ 20 h, the reaction was concentrated in vac. The residue was diluted with water (40 ml) and acidified with 2N HCl (9.32 ml). After 2 h, the solids were collected, rinsed with water, dissolved in EtOAc, dried over $Na_2SO_4$, filtered, concentrated in vac, and the residue dried to give the desired product as a white solid (1.708 g, 91%); mp 184–192 (partial melt), solidifies, and melts 200–202° C.; $^1$H NMR (300 MHz, DMSO-$d_6$) δ 3.12 (q, J=4 Hz, 2H), 3.28 (t, J=4 Hz, 2H), 4.45 (t, J=4 Hz, 1H), 7.45–7.60 (m, 6H), 7.70 (s, 2H), 7.91 (s, 2H), 13.10 (s, 1H).

Step 3 N-(8-Octanoic acid, Methyl Ester)-3,5-bis(3-chlorophenyl)-4-(2-hydroxyethoxy)benzamide A mixture of 3,5-bis(3-chlorophenyl)-4-(2-hydroxyethoxy)benzoic acid (0.565 g, 1.4 mmol), 8-amino octanoic acid, methyl ester (0.364 g, 2.1 mmol), $Et_3N$ (0.59 ml, 4.2 mmol), 1-hydroxybenzotriazole (0.208 g, 1.54 mmol), and 1,3-dicyclohexylcarbodiimide (0.347 g, 1.68 mmol) in methylene chloride (16 ml) was stirred under nitrogen at room temperature. After ~20 h, the reaction mixture was concentrated in vac. The residue was taken up in EtOAc, stirred and filtered. The filtrate was washed with 1 N HCl (3×15 ml), $NaHCO_3$ (3×15 ml), brine (2×15 ml), dried over $Na_2SO_4$, filtered and concentrated in vac. The residue was purified by flash chromatography (25%, 60% EtOac/Hex) to give the desired product as a viscous oil (0.475 g, 61%); $^1$H NMR (400 MHz, DMSO-d6) δ 1.22–1.33 (m, 6H), 1.47–1.55 (m, 4H), 2.28 (t, J=7.5 Hz, 2H), 3.13 (t, J=5.9 Hz, 2 h), 3.23–3.30 (m, 4H), 3.56 (s, 3H), 4.43 (broad s, 1H), 7.46–7.53 (m, 4H), 7.59–7.62 (m, 2H), 7.71 (m, 2H), 7.88 (s, 2H), 8.56 (t, J=5.5 Hz, 1H); mass spectrum [(+)ESI], m/z 558 M$^+$.

Step 4 8-[(2'-Carboxymethoxy-3,3''-dichloro-[1,1';3',1''] terphenyl-5'-carbonyl)-amino]-octanoic Acid Methyl Ester The title compound was prepared as a white solid (0.221 g, 46%) from N-(8-octanoic acid, methyl ester)-3,5-bis(3-chlorophenyl)-4-(2-hydroxyethoxy)benzamide and 8-amino octanoic acid, methyl ester using a procedure similar to step 3 of example 1. The crude product was purified by preparatory plate chromatography (10% MeOH/EtOAc) and then flash chromatography (25% EtOAc/Hex with 1% formic acid); dec. 131–133° C.; $^1$H NMR (400 MHz, DMSO-$d_6$) δ 1.20–1.32 (m, 6H), 1.46–1.55 (m, 4H), 2.27 (t, J=7.5 Hz, 2H), 3.25 (dd, J=6.8, 13.0, 2H), 3.55(s, 3H), 3.85 (s, 2H), 7.45–7.52 (m, 4H), 7.56–7.59 (m, 2H), 7.68 (s, 2H), 7.86 (s, 2H), 8.56 (t, J=5.7 Hz, 1H), 12.66 (broad s, 1H), IR (KBr) 3400, 2930, 1740,1630, 1550, 1450, 1200 cm$^-$; mass spectrum [(−)ESI], m/z 570 (M−H)$^-$; Anal. Calcd. for $C_{30}H_{31}Cl_2NO_6$: C, 62.94; H, 5.46; N, 2.45, Found: C, 62.86; H, 5.39; N, 2.38.

EXAMPLE 164

5-[3,3''-Dichloro-5'-(8-indol-1-yl-octylcarbamoyl)-[1,1';3',1'']terphenyl-2'-yloxy]-pentanoic Acid Step 1 N-(8-Indol-1-yl-octyl)-3,5-diiodo-4-hydroxybenzamide A mixture of 3,5-diiodo-4-hydroxybenzoic acid (5.037 g, 5.193 mmol) and thionyl chloride (45 ml) was refluxed for 2 h. The reaction mixture was then concentrated in vac. The residue was dissolved in THF and added into a solution of 8-indoloctylamine (2.631 g, 10.766) and triethylamine (5.25 ml, 37.681 mmol) at 0° C. After the addition, the reaction was stirred at room temperature. After 18 h, the reaction was concentrated in vac and the residue taken up in EtOAc (200 ml) and 2N HCl (25 ml). The layers were shaken, separated and the organic layer washed with 2 N HCl (2×25 ml), water (3×25 ml), and brine (2×25 ml) and dried over $Na_2SO_4$. After filtering, the filtrate was concentrated in vac and dried to give the crude product which was purified by flash chromatography (25% EtOAc/Hex) to give the desired product as a gummy foam (4.022 g, 61%); $^1$H NMR (300 MHz, DMSO-$d_6$) δ 1.22 (broad s, 8H), 1.40–1.50 (m, 2H), 1.68–1.79 (m, 2H), 3.15 (q, J=7 Hz, 2H), 4.13 (t, J=7 Hz, 2H), 6.40 (d, J=3 Hz, 1H), 6.95–7.00 (m, 1H), 7.07–7.12 (m, 1H), 7.32 (d, J=3 Hz, 1H), 7.44 (d, J=7.5 Hz, 1H), 7.52 (d, J=7.5 Hz, 1H), 8.21 (s, 2H), 8.37 (t, J=4 Hz, 1H), 10.04 (s, 1H); mass spectrum [(+)ESI], m/z 617 (M+H)$^+$.

Step 2 N-(8-Indol-1-yl-octyl)-3,5-bis(3-chlorophenyl)-4-hydroxybenzamide

A mixture of N-(8-indol-1-yl-octyl)-3,5-diiodo-4-hydroxybenzamide (4.016 g, 6.517 mmol), 2 M $K_2CO_3$ (9.8 ml in water), dioxane (100 ml), 3-chlorophenylboronic acid (2.242 g, 14.336 mmol), and [1,1'bis(diphenylphosphino)ferrocene]dichloropalladium(II), complex with $CH_2Cl_2$ (0.106 g, 0.130 mmol) was warmed to 66° C. After 2 h, the reaction mixture was cooled and concentrated in vac. The residue was taken up in EtOAc (200 ml) and 1N HCl (50 ml). The layers were shaken, separated and the organic layer was washed with 1N HCl (2×50 ml), brine (2×50 ml), dried over $Na_2SO_4$, filtered and the filtrate concentrated in vac and dried. The crude product was purified by flash chromatography (alumina, hexane to 60% EtOAc/Hex gradient) to give a light yellow foam (3.027 g, 79%); $^1$H NMR (300 MHz, DMSO-$d_6$) δ 1.24 (broad s, 8H), 1.43–1.52 (m, 2H), 1.65–1.75 (m, 2H), 3.16–3.26 (q, J=7.5 Hz, 2H), 4.12 (t, J=7.5 Hz, 2H) 6.38 (d, J=3 Hz, 1H), 6.94–7.00 (m, 1H), 7.05–7.13 (m, 1H), 7.33 (d, J=3 Hz, 1H), 7.40–7.53 (m, 8H), 7.62 (s, 2H), 7.76 (s, 2H), 8.40 (t, J=5 Hz, 1H), 9.19 (s, 1H); mass spectrum [(+)ESI], m/z 585 (M+H)$^+$.

Step 3 5-[3,3"-Dichloro-5'-(8-indol-1-yl-octylcarbamoyl)-[1,1';3',1"]terphenyl-2'-yloxy]-pentanoic Acid, Ethyl Ester A mixture of N-(8-indol-1-yl-octyl)-3,5-bis(3-chlorophenyl)-4-hydroxybenzamide (0.399 g, 0.68 mmol), $K_2CO_3$ (0.116 g, 0.84 mmol), and ethyl-5-bromovalerate (0.176 g, 0.84 mmol) in DMF was stirred at room temperature under nitrogen. After ~48 h, the reaction mixture was poured into water (40 ml) and extracted with EtOAc (1×20 ml, 4×10 ml). The combined extracts were washed with water (3×10 ml), brine (2×10 ml), dried over $Na_2SO_4$, filtered and the filtrate concentrated in vac and dried. The crude product was purified by flash chromatography (alumina, hexane, 10% and 60% EtOAc/Hex) to give the desired product as a light yellow oil (0.432 g, 86%); (400 MHz, DMSO-$d_6$) δ 1.12–1.30 (m, 15H), 1.44–1.55 (m, 2H), 1.67–1.76 (m, 2H), 1.92 (t, J=7 Hz, 2H), 3.16–3.27 (m, 4H), 3.98 (q, J=7 Hz, 2H), 4.12 (t, J=7.2 Hz, 2H), 6.38 (d, J=3.1 Hz, 1H), 6.95–6.99 (m, 1H), 7.06–7.10 (m, 1H), 7.32 (d, J=3.3 Hz, 1H), 7.40–7.52 (m, 6H), 7.56–7.59 (m, 2H), 7.68 (t, J=1.8 Hz, 2H), 7.87 (s, 2H), 8.53 (t, J=5.7 Hz, 1H); IR (film) 3320, 2940, 2950, 1730, 1630, 1540, cm$^{-1}$; mass spectrum [(+)APCI], m/z 713 (M+H)$^+$.

Step 4 5-[3,3"-Dichloro-5'-(8-indol-1-yl-octylcarbamoyl)-[1,1';3',1"]terphenyl-2'-yloxy]-pentanoic Acid A mixture of 5-[3,3"-Dichloro-5'-(8-indol-1-yl-octylcarbamoyl)-[1,1';3',1"]terphenyl-2'-yloxy]-pentanoic acid, ethyl ester (0.409 g, 0.573 mmol) and 1N KOH (1.15 ml) in THF (6 ml) and methanol (3 ml) was stirred under nitrogen. After ~18 h, the reaction mixture was concentrated. in vac. The residue was suspended in water (25 ml) and acidified with 2 N HCl (1.15 ml) then extracted with EtOAc (3×25 ml). The combined organics were washed with water (3×10 ml), brine (2×10 ml), dried over $Na_2SO_4$, filtered and the filtrate concentrated in vac and dried. The residue was purified by preparatory plate chromatography (50% EtOAc/Hex) to give the title compound as a light yellow foam (0.249 g, 63%); dec.>50° C.; $^1$H NMR (400 MHz, DMSO-$d_6$) δ 1.12–1.32 (m, 12H), 1.44–1.53 (m, 2H), 1.67–1.76 (m, 2H), 1.87 (t, J=7.0 Hz, 2H), 3.16–3.27 (m, 4H), 4.12 (t, J=7.0 Hz, 2H), 6.37–6.38 (m, 1H), 6.94–6.99 (m, 1H), 7.06–7.10 (m, 1H), 7.31 (d, J=3.1 Hz, 1H), 7.40–7.52 (m, 6H), 7.56–7.59 (m, 2H), 7.66–7.69 (m, 2H), 7.87 (s, 2H), 8.52 (t, J=5.7 Hz, 1H), 11.85 (s, 1H); IR (KBr) 3400, 2940, 1710, 1630, 1550, 1220 cm$^-$; mass spectrum [(+)APCI], m/z 685 (M+H)$^+$; Anal. Calcd. for $C_{40}H_{42}Cl_2N_2O_4$: C, 70.07; H, 6.17; N, 4.09, Found: C, 69.66; H, 6.17; N, 3.85.

EXAMPLE 165

4-{2-[3,3"-Dichloro-5'-(8-indol-1-yl-octylcarbamoyl)-[1,1';3',1"]terphenyl-2'-yloxy]ethoxy}benzoic Acid Step 1 N-(8-Indol-1-yl-octyl)-3,5-bis(3-chlorophenyl)-4-(2-hydroxyethoxy)-benzamide To a solution of N-(8-indol-1-yl-octyl)-3,5-bis(3-chlorophenyl)-4-hydroxybenzamide (0.205 g, 0.35 mmol) in DMF (2 ml) was added ethylene carbamate (0.039 g, 0.438 mmol) and tetraethylammonium bromide (0.007 g, 0.035 mmol). The reaction mixture was warmed to 140° C. After 2.5 h, the reaction mixture was poured into water (50 ml) and extracted with EtOAc (3×20 ml). The combined organics were washed with water (3×10 ml), brine (2×10 ml), dried over $Na_2SO_4$, filtered and the filtrate concentrated in vac and dried. The residue was purified by preparatory plate chromatography (50% EtOAc/Hex) to give the product as a viscous yellow oil (0.185 g, 84%); $^1$H NMR (300 MHz, DMSO-$d_6$)δ 1.25 (broad s, 8H), 1.44–1.55 (m, 2H), 1.65–1.77 (m, 2H), 3.07–3.17 (m, 2H), 3.20–3.30 (m, 4H), 4.14 (t, J=7.5 Hz, 2H), 4.44 (broad s, 1H), 6.38 (d, J=3 Hz, 1H), 6.98 (t, J=7.5 Hz, 1H), 7.09 (t, J=7.5 Hz, 1H), 7.34 (d, J=3 Hz, 1H), 7.40–7.52 (m, 6H), 7.56 7.65 (m, 2H), 7.70 (s, 2H), 7.88 (s, 2H), 8.54 (t, J=4 Hz, 1H); mass spectrum [(+)ESI], m/z 629 (M+H)$^+$.

Step 2 4-{2-[3,3"-Dichloro-5'-(8-indol-1-yl-octylcarbamoyl)-[1,1';3',1"]terphenyl-2'-yloxy]-ethoxy}benzoic Acid, Methyl Ester A mixture of N-(8-indol-1-yl-octyl)-3,5-bis(3-chlorophenyl)-4-(2-hydroxyethoxy)benzamide (0.175 g, 0.278 mmol), methyl-4-hydroxybenzoate (0.063 g, 0.417 mmol), triphenylphosine (0.109 g, 0.417 mmol), and DEAD (0.073 g, 0.417 mmol) in THF (4 ml) was stirred under nitrogen. After 18 h, the reaction mixture was concentrated in vac and purified by preparatory plate chromatography (2×)(30% EtOAc/Hex) to give the product as a yellow glass-like solid (0.132 g, 62%); $^1$H NMR (400 MHz, DMSO-$d_6$) δ 1.15–1.30 (m, 8H), 1.45–1.53 (m, 2H), 1.67–1.76 (m, 2H), 3.21–3.27 (m, 2H), 3.55–3.60 (m, 2H), 3.72–3.76 (m, 2H), 3.79 (s, 3H), 4.13 (t, J=7.0 Hz, 2H), 6.38 (dd, J=0.66, 2.48 Hz, 1H), 6.68–6.72 (m, 2H), 6.94–6.99 (m, 1H), 7.06–7.10 (m, 1H), 7.32 (d, J=3.1 Hz, 1H), 7.38–7.46 (m, 5H), 7.48–7.52 (m, 1H), 7.57–7.60 (m, 2H), 7.66–7.68 (m, 2H), 7.78–7.82 (m, 2H), 7.88 (s, 2H), 8.55 (t, J=Hz, 1H); IR (KBr) 3400 (broad), 2920, 1720, 1630, 1600, 1260 cm$^{-1}$; mass spectrum [(+)APCI], n/z 763 (M+H)$^+$.

Step 3 4-{2-[3,3"-Dichloro-5'-(8-indol-1-yl-octylcarbamoyl)-[1,1';3',1"]terphenyl-yloxy]-ethoxy}benzoic Acid The title compound was prepared as a light green solid (0.073 g, 62%) from 4-{2-[3,3"-Dichloro-5'-(8-indol-1-yl-octylcarbamoyl)-[1,1';3',1"]terphenyl-2'-yloxy]-ethoxy}benzoic acid, methyl ester using a procedure similar to step 4 of example 165; dec.>65° C.; $^1$H NMR (400 MHz, DMSO-d$_6$) δ 1.16–1.30 (m, 8H), 1.44–1.53 (m, 2H), 1.67–1.76 (m, 2H), 3.20–3.26 (m, 2H), 3.56–3.60 (m, 2H), 3.72–3.76 (m, 2H), 4.12 (t, J=7.0 Hz, 2H), 6.37 (dd, J=0.66, 3.1 Hz, 1H), 6.66–6.70 (m, 2H), 6.94–6.99 (m, 1H), 7.06–7.10 (m, 1H), 7.32 (d, J=3.1 Hz, 1H), 7.38–7.52 (m, 6H), 7.57–7.60 (m, 2H), 7.67 (t, J=1.8 Hz, 2H), 7.76–7.80 (m, 2H), 7.88 (s, 2H), 8.55 (t, J=5.7 Hz, 1H), 12.54 (broad s, 1H); IR (KBr) 3420, 2920, 1680, 1600, 1260, 1160 cm$^{-1}$; mass spectrum [(−)APCI], m/z 747 (M−H)$^-$; Anal. Calcd. for C$_{44}$H$_{42}$Cl$_2$N$_2$O$_5$: C, 70.49; H, 5.65; N, 3.74, Found: C, 70.12; H, 6.01; N, 3.44.

EXAMPLE 166

4-Methoxybenzoic Acid 6-[(2'-Carboxymethoxy-3,3"-dichloro-[1,1';3',1"]terphenyl-5'-carbonyl)-amino]-hexyl Ester Step 1 4-Methoxybenzoic Acid, 6-Bromohexylester To a stirred solution of 6-bromo-1-hexanol (1.086 g, 6 mmol) in THF (8 ml) was added p-anisoylchloride (1.228 g, 7.2 mmol) followed by triethylamine (0.911 g, 9 mmol). After 18 h, the mixture was concentrated in vac. The residue was taken up in EtOAc and washed with water (3×10 ml), brine (2×10 ml), dried over Na$_2$SO$_4$, filtered and the filtrate concentrated in vac and dried. The residue was purified by flash chromatography (2%, 50% EtOAc/Hex) to give the desired product as a colorless oil (1.405 g, 74%); $^1$H NMR (400 MHz, DMSO-d$_6$) δ 1.36–1.47 (m, 4H), 1.65–1.73 (m, 2H), 1.77–1.84 (m, 2H), 3.52 (t, J=6.6 Hz, 2H), 3.82 (s, 3H), 4.21 (t, J=6.6 Hz, 2H), 7.01–7.05 (m, 2H), 7.88–7.92 (m, 2H); IR (film) 2930, 1710, 1605, 1510, 1260 cm$^{-1}$; mass spectrum[EI], m/z 314 (M$^+$).

Step 2 4-Methoxybenzoic Acid, 6-Azidohexyl Ester

A mixture of 4-methoxybenzoic acid, 6-bromohexylester (1.384 g, 4.391 mmol) and sodium azide (1.427 g, 21.954 mmol) in DMF (15 ml) was stirred at room temperature under nitrogen. After 4 h, the reaction mixture was poured into water (100 ml) and extracted with EtOAc (4×30 ml). The combined organics were washed with water (3×15 ml), brine (2×15 ml), dried over Na$_2$SO$_4$, filtered and the filtrate concentrated in vac and dried. The residue was purified by flash chromatography (3% EtOAc/Hex) to give the desired product as a colorless oil (1.136 g, 93%); $^1$H NMR (400 MHz, DMSO-d$_6$) δ 1.36–1.44 (m, 4H), 1.51–1.58 (m, 2H), 1.66–1.72 (m, 2H) 3.31 (t, J=6.8 Hz, 2H), 3.82 (s, 3H), 4.21 (t, J=6.6 Hz, 2H), 7.01–7.05 (m, 2H), 7.88–7.92 (m, 2H); IR (film) 2940, 2100, 1720, 1605, 1520, 1260 cm$^{-1}$; mass spectrum[(+)ESI], m/z 278 (M+H)$^+$.

Step 3 4-Methoxybenzoic Acid, 6-Aminohexyl Ester

A mixture of 4-methoxybenzoic acid, 6-azidohexyl ester (1.119 g, 4.035 mmol), triphenylphosphine (1.164 g, 4.439 mmol), and water (0.08 ml) in THF was stirred under nitrogen at room temperature. After 144 h, the reaction mixture was diluted with EtOAc (50 ml), dried over Na$_2$SO$_4$, filtered and the filtrate concentrated in vac and dried. The residue was purified by flash chromatography (2×)(alumina, chloroform to 10% MeOH/CHCl$_3$ gradient) to give the desired product as a light yellow oil (0.0796 g, 78%); $^1$H NMR (400 MHz, DMSO-d$_6$)δ 1.18–1.40 (m, 6H), 1.63–1.71 (m, 2H), 2.50 (t, J=6.4 Hz, 2H), 3.82 (s, 3H), 4.21 (t, J=6.6 Hz, 2H), 7.01–7.06 (m, 2H), 7.87–7.92 (m, 2H); IR (KBr) 3410 (broad), 2940, 1710, 1605, 1510, 1260 cm$^-$; mass spectrum[(+)ESI], m/z 252 (M+H)$^+$.

Step 4 4-Methoxybenzoic Acid 6-[(2'-Hydroxyethoxy-3,3"-dichloro-[1,1';3',1"]terphenyl-5'-carbonyl)-amino]-hexyl Ester The product was prepared as a colorless, viscous oil (0.675 g, 71%) from 3,5-bis(3-chlorophenyl)-4-(2-hydroxyethoxy)benzoic acid (0.605 g, 1.5 mmol) and 4-methoxybenzoic acid, 6-aminohexyl ester (0.565 g, 2.25 mmol) using a procedure similar to step 3 of example 164; $^1$H NMR (400 MHz, DMSO-d$_6$) 1.33–1.46 (m, 4H), 1.50–1.58 (m, 2H), 1.65–1.73 (m, 2H), 3.10–3.15 (m, 2H), 3.22–3.30 (m, 4H), 3.80 (s, 3H), 4.21 (t, J=6.6 Hz, 2H), 4.44 (t, J=6.6 Hz, 1H), 6.99–7.03 (m, 2H), 7.45–7.52 (m, 4H), 7.57–7.61 (m, 2H), 7.69 (s, 2H), 7.85–7.91 (m, 4H), 8.56 (t, J=5.5 Hz, 1H); IR (film) 3350, 2940, 1710, 1640, 1605, 1540, 1510, 1275 cm$^{-1}$; mass spectrum[(+)ESI], m/z 636 (M+H)$^+$.

Step 5 4-Methoxybenzoic Acid 6-[(2'-carboxymethoxy-3,3"-dichloro-[1,1';3'1"]terphenyl-5'-carbonyl)-amino]-hexyl Ester The title compound was prepared as a white solid (0.279 g, 42%) from 4-Methoxybenzoic acid 6-[(2'-hydroxyethoxy-3,3"-dichloro-[1,140 ;3',1"]terphenyl-5'-carbonyl)-amino]-hexyl ester using a procedure similar to step 3 of example 1. The crude product was purified by preparatory plate chromatography (10% MeOH/CHCl$_3$) and then flash chromatography (35% EtOAc/Hex with 1% formic acid); dec. 129–133° C.; $^1$H NMR (400 MHz, DMSO-d$_6$) δ 1.34–1.46 (m, 4H), 1.50–1.58 (m, 2H), 1.65–1.73 (m, 2H), 3.24–3.35 (m, 2H), 3.81 (s, 3H), 3.84 (s, 2H), 4.21 (t, J=6.6 Hz, 2H), 6.99–7.03 (m, 2H), 7.44–7.51 (m, 4H), 7.55–7.58 (m, 2H), 7.67–7.69 (m, 2H), 7.85–7.90 (m, 4H), 8.56 (t, J=5.5 Hz, 1H), 12.65 (broad s, 1H); IR (KBr) 3340, 2940, 1710, 1605, 1550, 1260, 1170 cm$^{-1}$; mass spectrum [(+)APCI], m/z 650 (M+H)$^+$; Anal. Calcd. for C$_{35}$H$_{33}$Cl$_2$NO$_7$.0.25H$_2$O: C, 64.17; H, 5.15; N, 2.14, Found: C, 63.92; H, 5.09; N, 2.04.

EXAMPLE 167

[3,3"-Dichloro-5'-(6-hydroxy-hexylcarbamoyl)-[1,1';3',1"]terphenyl-2'-yloxy]acetic Acid The title compound was prepared as a white foam (0.61 g, 46%) from 4-Methoxybenzoic acid 6-[(2'-carboxymethoxy-3,3"-dichloro-[1,140 ;3',1"]terphenyl-5'-carbonyl)-amino]-hexyl ester using a procedure similar to step 4 of example 165. The crude product was purified by preparatory chromatography(3×): first with 10% MeOH/CHCl$_3$, secondly with 30% EtOAc/Hex and 1% formic acid, and thirdly with EtOAc; dec.>65° C.; $^1$H NMR (400 MHz, DMSO-d$_6$) δ 1.26–1.33 (m, 4H), 1.35–1.44 (m, 2H), 1.46–1.55 (m, 2H), 3.21–3.38 (m, 4H), 3.84 (s, 2H), 4.32 (t, J=5 Hz, 1H), 7.44–7.51 (m, 4H), 7.56–7.59 (m, 2H), 7.68–7.70 (m, 2H), 7.86 (s, 2H), 8.56 (t, J=5 Hz, 1H), 12.65 (broad s, 1H); IR (KBr) 3340, 2940, 1740, 1640, 1540, 1450, 1210 cm$^{-1}$; mass spectrum [(−)ESI], m/z 514 (M−H)$^-$; Anal. Calcd. for C$_{27}$H$_{27}$Cl$_2$NO$_5$.0.5H$_2$O.0.15EtOAc: C, 61.21; H, 5.46; N, 2.60, Found: C, 61.36; H, 5.46; N, 2.51.

EXAMPLE 168

{2-[3,3"-Dichloro-5'-(8-indol-1-yl-octylcarbamoyl)-[1,1';3',1"]terphenyl-2'-yloxy]-ethoxy}acetic Acid Step 1 {2-[3,3"-Dichloro-5'-(8-indol-1-yl-octylcarbamoyl)-[1,1';3',1"]terphenyl-2'-yloxy]-ethoxy}acetic Acid, Methyl Ester To a stirred solution of N-(8-indol-1-yl-octyl)-3,5-bis(3-chlorophenyl)-4-(2-hydroxyethoxy)benzamide (0.629 g, 1 mmol) in THF (10 ml) under nitrogen at room temperature was sodium hydride (0.055 g, 2.3 mmol). The mixture was refluxed for 45 minutes, cooled and methylbromoacetate (0.189 g, 1.2 mmol), 15-crown-5 ether (0.022 g, 0.1 mmol), and tetrabutylammoniumiodide (0.037 g, 0.1 mmol) were added. The mixture was refluxed. After 6 h, the reaction mixture was quenched with water and then diluted with water (100 ml) and extracted with EtOAc. This gave a thick emulsion which was separated by acidfying the mixture with 1N HCl. The combined extracts were washed with water (2×15 ml), brine (2×15 ml), dried over $Na_2SO_4$, filtered and the filtrate concentrated in vac and dried. The residue was purified by flash chromatography (15%, 20% EtOAc/Hex) and then preparatory plate chromatography (50% EtOAc/Hex) to give the desired product as a viscous, hazy oil (0.400 g, 57%); $^1$H NMR (400 MHz, DMSO-$d_6$) δ 1.16–1.31 (m, 8H), 1.45–1.53 (m, 2H), 1.68–1.76 (m, 2H), 3.20–3.26 (m, 4H), 3.45–3.48 (m, 2H), 3.58 (s, 3H), 3.71 (s, 2H), 4.12 (t, J=6.8 Hz, 2H), 6.37 (dd, J=0.8, 3.1 Hz, 1H), 6.95–6.99 (m, 1H), 7.06–7.10 (m, 1H), 7.32 (d, J=3.1 Hz, 1H), 7.40–7.52 (m, 6H), 7.57–7.60 (m, 2H), 7.67–7.70 (m, 2H), 7.87 (s, 2H), 8.52 (t, J=4.83 Hz, 1H); IR (film) 3300, 2800, 1750, 1630, 1540, 1470, 1220 $cm^{-1}$; mass spectrum [(+)APCI], m/z 701 $(M+H)^+$.

Step 2 {2-[3,3"-Dichloro-5'-(8-indol-1-yl-octylcarbamoyl)-[1,1';3',1"]terphenyl-2'-yloxy]-ethoxy}acetic Acid The title compound was prepared as a white foam (0.172 g, 47%) from {2-[3,3"-Dichloro-5'-(8-indol-1-yl-octylcarbamoyl)-[1,1';3',1"]terphenyl-2'-yloxy]-ethoxy}acetic acid, methyl ester using a procedure similar to Step 4 of example 165; dec.>50° C.; $^1$H NMR (400 MHz, DMSO-$d_6$) δ 1.16–1.32 (m, 8H), 1.44–1.53 (m, 2H), 1.67–1.76 (m, 2H), 3.17–3.42 (m, 6H), 3.61 (s, 2H), 4.12 (t, J=7 Hz, 2H), 6.37 (d, J=3.1 Hz, 1H), 6.95–6.99 (m, 2H), 7.06–7.10 (m, 2H), 7.32 (m, 1H), 7.41–7.55 (m, 6H), 7.57–7.60 (m, 2H), 7.68–7.77 (m, 2H), 7.87 (s, 2H), 8.54 (t, J=5.5 Hz, 1H), 12.50 (broad s, 1H); IR (KBr) 3410, 2940, 1625, 1560, 1540, 1460, 1220, 1130 $cm^{-1}$; mass spectrum [(+)APCI], m/z 687 $(M+H)^+$; Anal. Calcd. for $C_{39}H_{40}Cl_2N_2O_5 \cdot 0.5H_2O$: C, 67.24; H, 5.93; N, 4.02, Found: C, 67.26; H, 6.02; N, 3.96.

EXAMPLE 169

(5'-Hexyl-[1,1';3',1"]terphenyl-2'-yloxy)acetic Acid

Step 1 3,5-Diiodo-4-(2-methoxyethoxymethyloxy)-benzaldehyde

To a stirred solution of 3,5-diiodo-4-hydroxybenzaldehyde (18.696 g, 50 mmol) in THF (360 ml) under nitrogen at ~0° C. was added sodium hydride (2.6 g, 1.3 mmol), portionwise. After the addition, the mixture was stirred for 20 minutes followed by the dropwise addition of MEMCl (9.966 g, 80 mmol). The mixture was stirred at ~4° C. for 20 minutes and then at room temperature for 24 h. The reaction mixture was then concentrated to dryness and the residue diluted with EtOAc (300 ml) and washed with 1N NaOH (3×50 ml), water (2×50 ml), brine (2×50 ml), dried over $Na_2SO_4$, filtered and the filtrate concentrated in vac and dried. The residue was purified by flash chromatography (Hex, 10% and 20% EtOAc/Hex) to give the product as a white solid (19.209 g, 83%); mp 68–72° C.; $^1$H NMR (400 MHz, DMSO-$d_6$) δ 3.27 (s, 3H), 3.54–3.56 (m, 2H), 4.00–4.04 (m, 2H), 5.24 (s, 2H), 8.34 (s, 2H), 9.85 (s, 1H); IR (KBr) 3410, 2880, 1700, 1540, 1360 $cm^{-1}$; mass spectrum [EI], m/z 462 $M^+$.

Step 2 3,5-Diphenyl-4-[(2-methoxyethoxy)methoxy]-benzaldehyde

A mixture of 3,5-diiodo-4-(2-methoxyethoxymethyloxy)-benzaldehyde (19.094 g, 41.327 mmol), $Pd(OAc)_2$ (0.185 g, 0.02 mmol), phenylboronic acid (11.429 g, 90.920 mmol) and $Ba(OH)_2 \cdot 8H_2O$ (39.114 g, 123.981 mmol) in DME (700 ml) and water (110 ml) was refluxed. After 90 minutes, the reaction mixture was cooled, concentrated to about 400 ml and the residue extracted with EtOAc (1×300 ml, 3×100 ml). The combined organics were washed with saturated $NaHCO_3$ (3×75 ml), water (2×75 ml), brine (2×75 ml), dried over $Na_2SO_4$, filtered and the filtrate concentrated in vac and dried. The residue was purified by flash chromatography (hexane, 5% and 12% EtOAc/Hex) to give the product as a light yellow viscous oil (11.645 g, 78%); $^1$H NMR (400 MHz, DMSO-$d_6$) δ 2.79–2.82 (m, 2H), 2.89–2.92 (m, 2H), 3.02 (s, 3H), 4.42 (s, 2H), 7.42–7.46 (m, 2H), 7.48–7.54 (m, 4H), 7.62–7.66 (m, 4H), 7.91 (s, 2H), 10.07 (s, 1H); IR (film) 3050, 2880, 1690,1580 $cm^{-1}$; mass spectrum [EI], m/z 362 $M^+$.

Step 3 1-[3,5-Diphenyl-4-[(2-methoxyethoxy)methoxy]-1-yl]hexan-1-ol

To a stirred solution of n-pentylmagnesium bromide in diethylether (3.75 ml of a 2M solution) under nitrogen at 0° C. was added a solution of 3,5-diphenyl-4-[(2-methoxyethoxy)methoxy]-benzaldehyde (1.812 g, 5 mmol) in diethylether (13 ml), dropwise. After the addition, the reaction mixture was stirred at room temperature for 3 h, then poured into an $NH_4Cl$ solution (5 g in 30 ml water). The aqueous layer was extracted with $Et_2O$ and the combined extracts were washed with water (2×50 ml), brine (2×50 ml), dried over $Na_2SO_4$, filtered and the filtrate concentrated in vac and dried. The residue was purified by flash chromatography (11% and 20% EtOAc/Hex and EtOAc) to give the product as a viscous oil (1.394 g, 64%); $^1$H NMR (400 MHz, DMSO-$d_6$) δ 0.82–0.88 (m, 3H), 1.23–1.35 (m, 5H), 1.37–1.46 (m, 1H), 1.58–1.68 (m, 2H), 2.75–2.78 (m, 2H), 2.86–2.90 (m, 2H), 3.01 (s, 3H), 4.30 (s, 2H), 4.57 (t, J=6.4 Hz, 1H), 5.16 (broad s, 1H), 7.29 (s, 2H), 7.34–7.39 (m, 2H), 7.44–7.49 (m, 4H), 7.54–7.59 (m, 4H); IR (film) 3430, 2940, 1450 $cm^{-1}$; mass spectrum [EI], m/z 434 $M^+$.

Step 4 2,6-Diphenyl-3-hexyl-phenol

To a stirred solution of 1-[3,5-diphenyl-4-[(2-methoxyethoxy)methoxy]-1-yl]hexan-1-ol (1.361 g, 3.132 mmol) and triethylsilane (3.642 g, 31.32 mmol) in methylene chloride (20 ml) under nitrogen was added trifluoracetic acid (7.142 g, 62.64 mmol). After 24 h, the reaction mixture was poured into a saturated $NaHCO_3$ solution (50 ml) with stirring. The aqueous layer was extracted with methylene chloride (3×20 ml). The combined extracts were washed with saturated $NaHCO_3$ solution (2×20 ml), brine (1×50 ml), dried over $Na_2SO_4$, filtered and the filtrate concentrated in vac and dried. The residue was purified by flash chromatography (hexane and 1% EtOAc/Hex) to give the product as a colorless oil (0.892 g, 86%); $^1$H NMR (400 MHz, DMSO-$d_6$) δ 0.84–0.88 (m, 3H), 1.44–1.36 (m, 6H), 1.55–1.63 (m, 2H), 2.56 (t, J=7.7 Hz, 2H), 7.02 (s, 2H), 7.31–7.35 (m, 2H), 7.40–7.45 (m, 4H), 7.52–7.56 (m, 4H), 8.04 (s, 1H); IR (film) 3560, 2940, 1470 $cm^{-1}$; mass spectrum [EI], m/z 330 $M^+$.

Step 5 (5'-Hexyl-[1,1';3',1"]terphenyl-2'-yloxy)acetic Acid, Methyl Ester

The product was prepared as a colorless oil (0.883 g, 82%) from 2,6-diphenyl-3-hexyl-phenol (0.879 g, 2.66 mmol) and methyl bromoacetate (0.488 g, 3.192 mmol) using a procedure similar to step 3 of example 165; $^1$H NMR (400 MHz, DMSO-$d_6$) δ 1.33–1.38 (m, 3H), 1.25–1.38 (m, 6H), 1.57–1.66 (m, 2H), 2.63 (t, J=7.5 Hz, 2H), 3.38 (s, 3H), 3.84 (s, 2H), 7.17 (s, 2H), 7.34–7.39 (m, 2H), 7.41–7.46 (m, 4H), 7.54–7.57 (m, 4H); IR (film) 2930, 1760, 1200 $cm^{-1}$; mass spectrum [EI], m/z 402 $M^+$.

Step 6 (5'-Hexyl-[1,1';3',1"]terphenyl-2'-yloxy)acetic Acid

The title compound was prepared as a white solid (0.559 g, 67%) from (5'-Hexyl-[1,1';3',1"]terphenyl-2'-yloxy)acetic acid, methyl ester (0.870 g, 2.161 mmol) using a procedure similar to step 4 of example 165; mp 87–89° C.; $^1$H NMR (400 MHz, DMSO-d$_6$) δ 0.82–0.86 (m, 3H), 1.22–1.37 (m, 6H), 1.56–1.64 (m, 2H), 2.61 (t, J=7.5 Hz, 2H), 3.71 (s, 2H), 7.16 (s, 2H), 7.32–7.37 (m, 2H), 7.39–7.44 (m, 4H), 7.59 (m, 4H), 12.47 (broad s, 1H); IR (KBr) 3450, 2920, 1725, 1420, 1210 cm$^{-1}$; mass spectrum [EI], m/z 388 M$^+$; Anal. Calcd. for C$_{26}$H$_{28}$O$_3$: C, 80.38; H, 7.26; N, 0.00, Found: C, 79.99; H, 7.24; N, 0.13.

EXAMPLE 170

(5'-Nonyl-[1,1';3',1"]terphenyl-2'-yloxy)acetic Acid

The title compound was prepared as a white solid (0.346 g, 20%) from 3,5-diphenyl-4-[(2-methoxyethoxy)methoxy]-benzaldehyde (1.450 g, 4 mmol) and n-octylmagnesium bromide (6 ml of a 1M solution in Et$_2$O) using a procedure similar to steps 3 through 6 of example 169; mp 63–65° C.; $^1$H NMR (400 MHz, DMSO-d$_6$) δ 0.83 (t, J=6.8 Hz, 3H), 1.18–1.36 (m, 12H), 1.56–1.64 (m, 2H), 2.61 (t, J=7.5 Hz, 2H), 3.71 (s, 2H), 7.15 (s, 2H), 7.32–7.37 (m, 2H), 7.39–7.44 (m, 4H), 7.54–7.58 (m, 4H), 12.47 (broad s, 1H); IR (KBr) 3450, 2920, 1725, 1430, 1220 cm$^-$; mass spectrum [(-)ESI], m/z 429 (M–H)$^-$; Anal. Calcd. for C$_{29}$H$_{34}$O$_3$: C, 80.89; H, 7.96; N, 0.00, Found: C, 80.71; H, 8.28; N, 0.05.

EXAMPLE 171

(5'-Tridecyl-[1,1';3',1"]terphenyl-2'-yloxy)acetic Acid

The title compound was prepared as a white solid (0.479 g, 20%) from 3,5-diphenyl-4-[(2-methoxyethoxy)methoxy]-benzaldehyde (1.812 g, 5 mmol) and n-dodecylmagnesiumbromide (7.5 ml of a 1M solution in Et$_2$O) using a procedure similar to steps 3 through 6 of example 169; mp partially melts 58–62° C., resolidifies and melts 69–71° C.; $^1$H NMR (400 MHz, DMSO-d$_6$) δ 0.81–0.86 (m, 3H), 1.17–1.34 (m, 20H), 1.56–1.64 (m, 2H), 2.61 (t, J=7.5 Hz, 2H), 3.71 (s, 2H), 7.15 (s, 2H), 7.32–7.37 (m, 2H), 7.39–7.44 (m, 4H), 7.54–7.58 (m, 4H), 12.47 (broad s, 1H); IR (KBr) 3450, 2920, 1725, 1470, 1220 cm$^{-1}$; mass spectrum [(-)ESI], m/z 485 (M–H)$^-$; Anal. Calcd. for C$_{33}$H$_{42}$O$_3$: C, 81.44; H, 8.70; N, 0.00, Found: C, 81.27; H, 8.68; N, 0.01.

EXAMPLE 172

(5'-Decyloxy-1,1';3',1"]terphenyl-2'-yloxy)acetic Acid

Step 1 3,5-Diphenyl-4-[(2-methoxyethoxy)methoxy]-phenol

A solution of 3,5-diphenyl-4-[(2-methoxyethoxy) methoxy]-benzaldehyde (7.279 g, 20.084 mmol) and m-CPBA (4.159 g, 24.101 mmol) was refluxed. After 19 h, the reaction mixture was cooled, concentrated in vac and the residue taken up in EtOAC (80 ml) and washed with saturated NaHCO$_3$ solution (4×30 ml), brine (2×30 ml), dried over Na$_2$SO$_4$, filtered and the filtrate concentrated in vac and dried. The residue was dissolved in THF (72 ml) and methanol (48 ml) and 1N KOH (30 ml) was added. The reaction mixture was stirred for 24 h and then concentrated in vac to about 40 ml. The residue was diluted with water (50 ml), acidified with 2N HCl to pH 3, and extracted with EtOAc (1×50 ml, 3×30 ml). The combined organics were washed with water (2×20 ml), brine (2×20 ml), dried over Na$_2$SO$_4$, filtered and the filtrate concentrated in vac and dried. The residue was purified by flash chromatography (10%, 15%, and 20% EtOAc/Hex) to give an orange solid which was then recrystallized from methylene chloride and hexane to give the product as a peach solid (4.042 g, 58%); mp 103.5–108° C.; $^1$H NMR (400 MHz, DMSO-d$_6$) δ 2.69–2.72 (m, 2H), 2.84–2.87 (m, 2H), 3.00 (s, 3H), 4.18 (s, 2H), 6.71 (s, 2H), 7.31–7.36 (m, 2H), 7.40–7.45 (m, 4H), 7.49–7.54 (m, 4H), 9.48 (s, 1H); IR (KBr) 3340, 2900, 1600, 1425, 1190, 1080 cm$^{-1}$; mass spectrum [(+)ESI], m/z 368 (M+NH$_4$)$^+$.

Step 2 3,5-Diphenyl-4-[(2-methoxyethoxy)methoxy]-phenyl Decyl Ether

To a stirred solution of 3,5-diphenyl-4-[(2-methoxyethoxy)methoxy]-phenol (0.946 g, 2.7 mmol) in DMF (15ml) was added K$_2$CO$_3$ (0.746 g, 5.4 mmol) and iododecane (1.632 g, 5.4 mmol). The reaction mixture was warmed to ~63° C. After ~20 h, additional K$_2$CO$_3$ (0.373 g, 2.7 mmol) and iododecane (0.816 g, 2.7 mmol) were added. Heating was continued for an additional 20 h followed by stirring at room temperature for 20 h. The reaction mixture was concentrated in vac and the residue taken up in EtOAc (50 ml) and water (20 ml). The layers were shaken and separated and the organic layer was washed with water (3×10 ml), brine (2×10 ml), dried over Na$_2$SO$_4$, filtered and the filtrate concentrated in vac and dried. The residue was purified by flash chromatography (hexane and 5% EtOAc/Hex) to give the product as a brown oil (0.897 g, 68%); $^1$H NMR (400 MHz, DMSO-d$_6$) δ 0.83–0.88 (m, 3H), 1.20–1.37 (m, 12H), 1.37–1.46 (m, 2H), 1.68–1.76 (m, 2H), 2.71–2.75 (m, 2H), 2.86–2.88 (m, 2H), 3.01 (s, 3H), 4.03 (t, J=6.4 Hz, 2H), 4.22 (s, 2H), 6.87 (s, 2H), 7.34–7.39 (m, 2H), 7.42–7.48 (m, 4H), 7.56–7.60 (m, 4H); IR (film) 2940, 1590, 1460, 1190 cm$^{-1}$; mass spectrum [(+)ESI], m/z 508 (M+NH$_4$)$^+$.

Step 3 2,6-Diphenyl-4-decyloxy-phenol

A mixture of 3,5-diphenyl-4-[(2-methoxyethoxy) methoxy]-phenyl decyl ether (0.880 g, 1.793 mmol) and ZnBr$_2$ (2.019 g, 8.967 mmol) in methylene chloride (10 ml) under nitrogen was stirred at room temperature. After ~48 h, the reaction mixture was concentrated in vac and the residue was taken up in EtOAc (60 ml) and saturated NaHCO$_3$ solution (20 ml). The layers were shaken and separated and the organic layer was washed with saturated NaHCO$_3$ solution (2×10 ml), water (3×10 ml), brine (1×10 ml), dried over Na$_2$SO$_4$, filtered and the filtrate concentrated in vac and dried. The residue was purified by flash chromatography (hexane and 1% EtOAc/Hex) to give the product as a light brown oil (0.571 g, 79%); $^1$H NMR (400 MHz, DMSO-d$_6$) δ 0.83–0.88 (m, 3H), 1.20–1.36 (m, 12H), 1.36–1.45 (m, 2H), 1.65–1.73 (m, 2H), 3.96 (t, J=6.6 Hz, 2H), 6.77 (s, 2H), 7.31–7.36 (m, 2H), 7.40–7.45 (m, 4H), 7.54–7.58 (m, 4H), 7.80 (s, 1H); IR (film) 3550, 2940, 1600, 1460, 1180 cm$^{-1}$; mass spectrum [EI], m/z 402 M$^+$.

Step 4 (5'-Decyloxy-[1,1';3',1"]terphenyl-2'-yloxy)acetic Acid

The title compound was prepared as a white solid (0.383 g, 65%) from 2,6-diphenyl-4-decyloxy-phenol (0.517 g, 1.284 mmol) using a procedure similar to steps 5 and 6 of example Q; mp partially melts 88–90° C., resolidifies, and melts 98–99° C.; $^1$H NMR (400 MHz, DMSO-d$_6$) δ 0.81–0.87 (m, 3H), 1.17–1.35 (m, 12H), 1.35–1.44 (m, 2H), 1.66–1.74 (m, 2H), 3.64 (s, 2H), 4.01 (t, J=6.4 Hz, 2H), 6.86 (s, 2H), 7.33–7.38 (m, 2H), 7.39–7.44 (m, 4H), 7.56–7.60 (m, 4H), 12.43 (s, 1H); IR (KBr) 3450, 2910, 1725, 1460, 1190 cm$^{-1}$; mass spectrum [(-)ESI], m/z 459 (M–H)$^-$; Anal.

Calcd. for $C_{39}H_{36}O_4$: C, 78.23; H, 7.88; N, 0.00, Found: C, 78.03; H, 7.83; N, 0.10.

EXAMPLE 173

(5'-Tetradecyloxy-[1,1';3',1"]terphenyl-2'-yloxy) acetic Acid

The title compound was prepared as a white solid (0.556 g, 43%) from 3,5-diphenyl-4-[(2-methoxyethoxy)methoxy]-phenol (0.876 g, 2;5 mmol) and 1-bromotetradecane (1.387 g, 5 mmol) using a procedure similar to steps 2 through 4 of example 172; mp 89–90° C.; $^1$H NMR (400 MHz, DMSO-$d_6$) δ 0.83 (t, 6.6 Hz, 3H), 1.17–1.35 (m, 20H), 1.35–1.44 (m, 2H), 1.65–1.74 (m, 2H), 3.64 (s, 2H), 4.01 (t, J=6.4 Hz, 2H), 6.86 (s, 2H), 7.33–7.38 (m, 2H), 7.39–7.44 (m, 4H), 7.56–7.60 (m, 4H), 12.44 (s, 1H); IR (KBr) 3425, 2925, 1725, 1460, 1200 cm⁻; mass spectrum [EI], m/z 516 M⁺; Anal. Calcd. for $C_{34}H_{44}O_4$: C, 79.03; H,8.58; N, 0.00, Found: C, 78.66; H, 8.47; N, −0.07.

EXAMPLE 174

(5'-Trityl-[1,1';3',1"]terphenyl-2'-yloxy)acetic Acid

Step 1 2,6-Dibromo-4-trityl-phenol

To a stirred suspension of p-triphenylmethylphenol (5.046 g, 15 mmol) in chloroform (25 ml) was added bromine (4.795 g, 30 mmol). The reaction mixture was stirred for 18 h then concentrated in vac and dried. The residue was recrystallized from hexane to give the product as a white solid (5.837 g, 79%); mp 164–167° C.; $^1$H NMR (400 MHz, DMSO-$d_6$) δ 7.09–7.13 (m, 6H), 7.16 (s, 2H), 7.20–7.25 (m, 3H), 7.29–7.35 (m, 6H); IR (KBr) 3480, 3020, 1475, 1160 cm⁻¹.

Step 2 2,6-Diphenyl-4-trityl-phenol

A mixture of $Pd(OAc)_2$(0.094 g, 0.06 mmol), phenylboronic acid (2.817 g, 23.1 mmol) $Ba(OH)_2.8H_2O$ (6.625 g, 21 mmol) and 2,6-dibromo-4-trityl-phenol (3.46 g, 7 mmol) in DME (112 ml) and water (28 ml) was refluxed. After ~66 h, the reaction was cooled and concentrated in vac to about 20 ml. The residue was acidified with 2N HCl (35 ml) and extracted with EtOAc (5×30 ml). The combined organics were washed with water (3×30 ml), brine (2×20 ml), dried over $Na_2SO_4$, filtered and the filtrate concentrated in vac and dried. The residue was purified by flash chromatography: first on silica (1%, 60% EtOAc/Hex) and then on alumina (33% chloroform/hexane). This gave a solid which was recrystallized from methyl-t-butyl ether to give the product as a white solid (0.910 g, 27%); mp 212–215° C.; $^1$H NMR (400 MHz, DMSO-$d_6$) δ 6.97 (s, 2H), 7.16–7.42 (m, 25H), 8.34 (s, 1H); IR (KBr) 3505, 3025, 1600, 1420 cm⁻¹; mass spectrum [(+)FAB], m/z 488 M⁺; Anal. Calcd. for $C_{37}H_{28}O$: C, 90.95 H, 5.78; N, 0.00, Found: C, 90.76; H,5.81; N, 0.00.

Step 3 (5'-Tetradecyloxy-[1,1';3',1"]terphenyl-2'-yloxy) acetic Acid

The title compound was prepared as a white solid (0.355 g, 43%) from 2,6-diphenyl-4-trityl-phenol (0.733 g, 1.5 mmol) and methyl bromoacetate (0.281 g, 1.8 mmol) using a procedure similar to steps 3 and 4 of example 165; mp 211–214° C.; $^1$H NMR (400 MHz, DMSO-$d_6$) δ 3.77 (s, 2H), 7.10 (s, 2H), 7.17–7.26 (m, 9H ), 7.29–7.40 (m, 12H), 7.43–7.47 (m, 4H), 12.49 (s, 1H); IR (KBr) 3430, 3075, 1730, 1420, 1210 cm⁻¹; mass spectrum [(−1)ESI], m/z 545 (M−H)⁻; Anal. Calcd. for $C_{39}H_{30}O_3$: C, 85.69 H, 5.53; N, 0.00, Found: C, 85.54; H,5.74; N, −0.04.

EXAMPLE 175

(5'-Dodecylcarbamoyl-3,3"-bis-trifluoromethyl-{1,1';3',1"]terphenyl-2'-yloxy)-acetic Acid Step 1

To stirred solution of $K_2CO_3$ (2 M in $H_2O$) (1.9 mL, 3.6 mmol) at rt was added dioxane (14.3 mL), 3-bromo-4-(2-hydroxyethoxy)-5-iodo-benzoic acid ethyl ester (0.503 g, 1.21 mmol) and 3-trifluoromethyl-phenyl boronic acid (0.299 g, 1.57 mmol). The reaction mixture was purged with $N_2$ for a few minutes and then [1,1'bis(diphenylphosphino) ferrocene]dichloropalladium(II), complex with $CH_2Cl_2$ (0.030 g, 0.036 mmol) was added. The reaction was stirred at rt for 1.5 h and then heated at reflux for 2 h. After cooling to rt, it was poured into a 0.1 N HCl solution and extracted with EtOAc. The combined organic layers were washed with brine and dried over $MgSO_4$. After concentration in vacuo, the residue was first purified by flash chromatography (25% EtOAc:hexane) and then HPLC [60% $CH_2Cl_2$ (6% MTBE) :40% hexane to afford 3,5-bis-(m-trifluoromethylphenyl)-4-(2-hydroxyethoxy)-benzoic acid ethyl ester (0.215 g, 36%) as a white solid $^1$H NMR (CDCl$_3$) δ 8.09 (s, 2H); 7.94 (m, 2H); 7.86–7.80 (m, 2H); 7.71–7.58 (m, 4H); 4.42 (q, 2H) 3.63 (m, 4H); 1.42 (t, 3H) and 3-Bromo-5-(m-trifluoromethylphenyl)-4-(2-hydroxyethoxy)-benzoic acid ethyl ester (0.173 g, 33%) as a white solid $^1$H NMR (CDCl$_3$) δ 8.29 (d, 1H); 8.00 (d, 1H); 7.86 (m, 1H); 7.80–7.55 (m, 3H); 4.40 (q, 2H); 3.74–3.60 (m, 4H); 1.92 (t, 1H); 1.40 (t, 3H).

Step 2

To a flame-dried flask containing dodecyl amine (0.278 g, 1.5 mmol) in THF (5 mL) cooled to −78° C. was added n-BuLi (titrated to 2.37 M in hexanes) (0.670 mL, 1.59 mmol) dropwise. The solution was stirred at −78° C. for 20 min. and then warmed to rt over 20 min. The reaction was then recooled to −40° C. and 3,5-bis-(m-trifluoromethylphenyl)-4-(2-hydroxyethoxy)-benzoic acid ethyl ester (0.215 g, 0.43 mmol) in THF (5 mL) was added. This mixture was allowed to warm to rt over 20 min. The reaction mixture was then poured into 0.1 N HCl solution and extracted with EtOAc. The combined organic layers were washed with 2 N HCl solution (3×), dried over $MgSO_4$ and concentrated in vacuo. The residue was purified by flash chromatography (30% EtOAc:hexane) to afford N-dodecyl-3,5-bis(m-trifluoromethylphenyl)-4-(2-hydroxyethoxy) benzamide (0.254 g, 93%) as a white solid. $^1$H NMR (CDCl$_3$) δ 7.90 (m, 2H); 7.82–7.76 (m, 4H); 7.65–7.56 (m, 4H); 6.22 (bt, 1H); 3.45 (dd, 2H); 3.30 (m, 4H); 1.60 (m, 2H); 1.25 (m, 18H); 0.84 (m, 3H).

Step 3

To a solution of N-dodecyl-3,5-bis(m-trifluoromethylphenyl)-4-(2-hydroxyethoxy)benzamide (0.254 g, 0.40 mmol) in $CH_3CN$ was added NMO (0.145 g, 0.89 mmol) and TPAP (0.014 g, 0.04 mmol). The reaction was stirred at rt overnight. Additional NMO (0.045 g, 0.38 mmol) and TPAP (0.013 g, 0.04 mmol) were required as indicated by TLC. After stirring 48 h, 10% $NaHSO_3$ solution was added and the resulting biphasic mixture was stirred vigorously for 30 min. Conc. HCl (2 mL) was added and stirring was continued for 10 min. The layers were separated and the aqueous layer was extracted with EtOAc. The combined organics were washed with brine, dried over $Na_2SO_4$, and concentrated in vacuo. The residue was purified by flash chromatography (30% EtOAc:Hexane+1% Formic acid) followed by preparatory plate chromatography (30% EtOAc:Hexane+1% Formic acid) to afford the title compound (0.089 g, 34%) as a white solid. mp 154.3–158.2 ° C.; $^1$H NMR (DMSO-$d_6$) δ 8.55 (t, 1H); 7.98–7.88 (m, 6H); 7.78–7.67 (m, 4H); 3.57 (s, 2H); 3.25 (m, 2H); 1.50 (m, 2H), 1.23 (m, 18H); 0.82 (t, 3H); IR (KBr) 3275, 2900, 1725, 1600, 1575, 1460, 1325, 1190, 1125, 1075, 775, 725, 700, 625 cm$^{-1}$; mass spectrum [(−)ESI], m/z 650 (M−H)$^-$; Anal. Calcd. for $C_{35}H_{39}F_6NO_4$: C, 64.51; H. 6.03; N, 2.15, Found: C, 62.50; H, 5.99; N, 2.01.

EXAMPLE 176

(3-Bromo-5-dodecylcarbamoyl-3'-trifluoromethyl-biphenyl-2-yloxy)-acetic Acid

Step 1

N-Dodecyl-3-bromo-5-(m-trifluoromethylphenyl)-4-(2-hydroxyethoxy)-benzamide was prepared as a white solid (0.116 g, 51%) from 3-bromo-5-(m-trifluoromethylphenyl)-4-(2-hydroxyethoxy)-benzoic acid ethyl ester using a procedure similar to step 2 of Example 175. $^1$H NMR (CDCl$_3$) δ 7.98 (d, 1H); 7.85–7.54 (m, 5H); 6.25 (m, 1H); 3.70–3.58 (m, 4H); 3.48–3.36 (dd, 2H); 1.60 (m, 2H); 1.24 (m, 18H), 0.86 (m, 3H).

Step 2

The title compound was prepared as a white foam (0.058 g, 50%) from N-dodecyl-3-bromo-5-(m-trifluoromethylphenyl)-4-(2-hydroxyethoxy)-benzamide using a procedure similar to step 3 of Example 175. $^1$H NMR (DMSO-d$_6$) δ 13.75 (bs, 1H); 8.57 (t, 1H); 8.12 (d, 1H), 7.92–7.68 (m, 5H); 4.15 (s, 2H); 3.24 (dd, 2H); 1.49 (m, 2H); 1.26 (m, 18H); 0.83 (m, 3H); IR (KBr) 3350, 2910, 2830, 1740, 1650, 1550, 1460, 1440, 1340, 1175, 1140, 1050, 900, 800, 760, 700, 675 cm$^{-1}$; mass spectrum [(−)ESI], m/z 584/586 (M−H)$^-$; Anal. Calcd. for $C_{28}H_{35}BrF_3NO4$: C, 57.34; H, 6.02; N, 2.39, Found: C, 59.34; H, 6.64; N, 2.16.

EXAMPLE 177

(5'-(8-Phenyl-octylcarbamoyl-3,3''-bis-trifluoromethyl-{1,1';3',1''}terphenyl-2'-yloxy)-acetic Acid Step 1

N-(8-phenyl-octyl)-3,5-bis(m-trifluoromethylphenyl)-4-(2-hydroxyethoxy)-benz-amide was prepared as a white solid (0.331 g, 74%) from 3,5-bis-(m-trifluoromethylphenyl)-4-(2-hydroxyethoxy)-benzoic acid ethyl ester and phenyloctyl amine using a procedure similar to step 2 of Example 175. $^1$H NMR (CDCl$_3$) δ 7.96–7.50 (m, 10H); 7.35–7.10 (m, 5H); 6.28 (m, 1H); 3.45 (m, 2H); 3.31 (m, 4H), 2.60 (m, 2H); 1.60 (m, 4H); 1.33 (m, 8H).

Step 2

The title compound was prepared as a white solid (0.058 g, 50%) from N-(8-phenyl-octyl)-3,5-bis(m-trifluoromethylphenyl)-4-(2-hydroxyethoxy)-benzamide using a procedure similar to step 3 of Example 175. mp 143–145.4 ° C. $^1$H NMR (DMSO-d$_6$) δ 12.70 (bs, 1H); 8.56 (t, 1H); 7.97–7.91 (m, 2H); 7.78–7.69 (m, 4H); 7.25–7.21 (m, 2H); 7.15–7.10 (m, 3H); 3.78 (s, 2H); 3.26 (m, 2H); 2.49 (m, 2H); 1.50 (m, 4H); 1.27 (m, 8H) IR (KBr) 3370, 2920, 2880, 1725, 1625, 1560, 1475, 1340, 1225, 1175, 1125, 1075, 900, 810, 700, 660, 620 cm$^{-1}$; mass spectrum [(−)ESI], m/z 670 (M−H)$^-$; Anal. Calcd. for $C_{37}H_{35}F_6NO_4$: C, 66.16; H, 5.25; N, 2.08, Found: C, 65.58; H, 5.37; N, 2.05.

EXAMPLE 178

(3-Bromo-5-(8-phenyl-octylcarbamoyl)-3'-trifluoromethyl-biphenyl-2-yloxy)-acetic Acid Step 1

N-(8-phenyl-octyl)-3-bromo-5-(m-trifluoromethylphenyl)-4-(2-hydroxyethoxy)-benzamide was prepared as a white solid (0.221 g, 64%) from 3-bromo-5-(m-trifluoromethylphenyl)-4-(2-hydroxyethoxy)-benzoic acid ethyl ester using a procedure similar to step 2 of Example 175. $^1$H NMR (CDCl$_3$) δ 7.99 (d, 1H); 7.85 (s, 1H); 7.78–7.55 (m, 4H); 7.31–7.13 (m, 5H); 6.14 (bt, 1H); 3.77 (m, 4H); 3.44 (dd, 2H); 2.60 (t, 2H); 1.60 (m, 4H); 1.33 (m, 8H).

Step 2

The title compound was prepared as a white solid (0.099 g, 44%) from N-(8-phenyl-octyl)-3-bromo-5-(m-trifluoromethylphenyl)-4-(2-hydroxyethoxy)-benzamide using a procedure similar to step 3 of Example 175. $^1$H NMR (DMSO-d$_6$) δ 13.80 (bs, 1H); 8.58 (t, 1H); 8.12 (d, 1H); 7.94 (m, 5H); 7.26–7.10 (m, 5H); 4.15 (s, 2H); 3.22 (dd, 2H); 2.52 (t, 2H); 1.51 (m, 4H); 1.27 (m, 8H) IR (KBr) 3400, 2920, 2850, 1740, 1630, 1550, 1450, 1330, 1160, 1125, 1075, 900, 810, 700 cm$^{-1}$; mass spectrum [(+)APCI], m/z 606/608 (M+H)$^+$; Anal. Calcd. for $C_{30}H_{31}BrF_3NO_4$: C, 59.41; H, 5.15; N, 2.31, Found: C, 58.96; H, 5.19; N, 2.22.

EXAMPLE 179

4-(3-Bromo-5-dodecylcarbamoyl-3'-trifluoromethyl-biphenyl-2-yloxysulfonyl)-2-hydroxy-benzoic Acid Step 1

3-Bromo-4-hydroxy-5(m-trifluoromethylphenyl)-benzoic acid ethyl ester and 3,5-bis-(m-trifluoromethylphenyl)-4-hydroxy-benzoic acid ethyl ester were prepared as white solids (2.445 g, 34% and 2.811 g, 33%, respectively) from 3-bromo-4-hydroxy-5-iodobenzoic and 3-trifluoromethyl-phenyl boronic acid using a procedure similar to step 1 of Example 175. 3-Bromo-4-hydroxy-5(m-trifluoromethylphenyl)-benzoic acid ethyl ester $^1$H NMR (CDCl$_3$) δ 8.22 (d, 1H); 7.98 (d, 1H); 7.74 (s, 1H); 7.70 (d, 1H); 7.68–7.53 (m, 2H); 6.10 (s, 1H); 4.38 (q, 2H); 1.40 (t, 3H); 3,5-bis-(m-trifluoromethylphenyl)-4-hydroxy-benzoic acid ethyl ester ester $^1$H NMR (CDCl$_3$) δ 8.02 (s, 2H); 7.84 (bs, 2H); 7.77–7.60 (m, 6H); 5.67 (s, 1H); 4.38 (q, 2H); 1.40 (t, 3H).

Step 2

N-Dodecyl-3-bromo-4-hydroxy-5-(m-trifluoromethylphenyl)benzamide was prepared as a white solid (0.799 g, 78%) from 3-bromo-4-hydroxy-5(m-trifluoromethylphenyl)-benzoic acid ethyl ester using a procedure similar to step 2 of Example 175. $^1$H NMR (CDCl$_3$) δ 7.95 (d, 1H); 7.82–7.50 (m, 5H); 6.26 (bt, 1H); 3.42 (dd, 2H); 1.60 (m, 2H); 1.45–1.18 (m, 18H); 0.86 (t, 3H).

Step 3

To a suspension of N-dodecyl-3-bromo-4-hydroxy-5-(m-trifluoromethylphenyl)-benzamide (1.799 g, 1.51 mmol, 1 eq) in 0.05 N tris(hydroxymethyl)aminomethane pH 9 buffer/THF (10:3) (7.5 mL) was added 2.5 N NaOH (0.665 mL, 1.66 mmol, 1.1 eq) and THF (10 mL). The reaction was stirred at rt for 30 minutes and then cooled to 5° C. 4-Chlorosulfonyl-2-hydroxy-benzoic acid (0.715 g, 3.02 mmol, 2 eq) was added portionwise while keeping the pH at 9 by the addition of 2.5 N NaOH. This mixture was allowed to warm to rt and to stir for 2 days. The reaction was quenched by the addition of 2 M HCl solution and extracted with EtOAc. The combined organic layers were washed with brine, dried over MgSO$_4$ and concentrated in vacuo. The residue was purified by flash chromatography (30% EtOAc:hexane+1% Formic Acid ) to afford the title compound (0.895 g, 79%) as a yellow foam. $^1$H NMR (DMSO-d$_6$) δ 11.40 (bs, 1H); 10.35 (bs, 1H); 8.70 (t, 1H); 8.22 (d, 1H); 7.85 (d, 1H); 7.72–7.45 (m, 5H); 6.98 (dd, 1H); 6.86 (d, 1H); 3.25 (dd, 2H); 1.50 (dd, 2H); 1.25 (m, 18H); 0.85 (t, 3H); IR (KBr) 3410, 2800, 2700, 1690, 1640, 1605, 1390, 1330, 1180, 1120, 620, 600 cm$^{-1}$; mass spectrum [(+)APCI], m/z 728/730 (M+H)$^+$; Anal. Calcd. for $C_{33}H_{37}BrF_3NO_7S$+ 0.25 $C_4H_8O_2$: C, 54.40; H, 5.24; N, 1.87, Found: C, 53.23; H, 4.77; N, 1.79.

EXAMPLE 180

5-Bromo-6-(2-[1,2,3,]triazol-2-yl-ethoxy)-3'-trifluoromethyl-biphenyl-3-carboxylic Acid Dodecylamide To a solution of N-dodecyl-3-bromo-5-(m-trifluoromethylphenyl)-4-(2-hydroxyethoxy)-benzarnide (1.508 g, 0.89 mmol, 1 eq) in THF (7 mL) was added triphenylphosphine (0.296 g, 1.13 mmol, 1.27 eq) and 1-H-1,2,3-triazole (0.210 mL, 1.08 mmol, 1.21eq). The reaction was cooled to 0° C. and diethyl azodicarboxylate (0.170 mL, 1.08 mmol, 1.21 eq) was added. The cold bath was removed and the reaction was stirred overnight at rt. The reaction mixture was poured into 0.1 N HCl solution and extracted with EtOAc. The combined organic layers were washed with 2 N HCl solution, dried over $MgSO_4$ and concentrated in vacuo. The residue was purified by flash chromatography (30 to 50% EtOAc:hexane) to afford 5-Bromo-6-(2-[1,2,3]triazol-1-yl-ethoxy)-3'-trifluromethyl-biphenyl-3-carboxlyic acid dodecylamide (see next example) and the title compound (0.247 g, 45%) as a thick oil. $^1$H NMR (DMSO-d$_6$) δ 8.56 (bt, 1H); 8.09 (d, 1H); 7.84 (d, 1H); 7.78–7.70 (m, 3H); 7.67 (s, 2H); 7.62 (t, 1H); 4.51 (dd, 2H); 4.01 (dd, 2H); 3.22 (dd, 2H); 1.48 (dd, 2H); 1.23 (m, 18H); 0.82 (t, 3H); IR (KBr) 3300, 2920, 2850, 1640, 1550, 1460, 1450, 1330, 1170, 1120, 1080, 960, 805 cm$^{-1}$; mass spectrum [(+)APCI], m/z 623 (M+H)$^+$; Anal. Calcd. for $C_{30}H_{38}BrF_3N_4O_2$: C, 57.79; H, 6.14; N, 8.99, Found: C, 57.84; H, 5.99; N, 8.89.

EXAMPLE 181

5-Bromo-6-(2-[1,2,3]triazol-1-yl-ethoxy)-3'-trifluoromethyl-biphenyl-3-carboxylic Acid Dodecylamide 5-Bromo-6-(2-[1,2,3]triazol-1-yl-ethoxy)-3'-trifluoromethyl-biphenyl-3-carboxylic acid dodecylamide was prepared as a white solid (0.172 g, 31%) using the procedure of Example 180. mp 70.5–72.5° C. $^1$H NMR (DMSO-d$_6$) δ 8.63 (bt, 1H); 8.10 (d, 1H); 7.98 (d, 1H); 7.85 (d, 1H); 7.82–7.72 (m, 3H); 7.66 (d, 1H); 7.60 (m, 1H); 4.51 (dd, 2H); 3.92 (dd, 2H); 3.21 (dd, 2H); 1.48 (dd, 2H); 1.23 (m, 18H); 0.83 (t, 3H); IR (KBr) 3350, 3125, 2900, 2850, 1640, 1620, 1570, 1560, 1430, 1180, 1100 cm$^{-1}$; mass spectrum [(−)ESI], m/z 623/625 (M+H)$^+$; Anal. Calcd. for $C_{30}H_{38}BrF_3N_4O_2$: C, 57.79; H, 6.14; N, 8.99, Found: C, 57.56; H, 6.32; N, 8.87.

EXAMPLE 182

5-Bromo-6-(2-tetrazol-2-yl-ethoxy)-3'-trifluoromethyl-biphenyl-3-carboxylic Acid Dodecylamide The title compound was prepared as a white solid (0.296 g, 53%) from of N-dodecyl-3-bromo-5-(m-trifluoromethylphenyl)-4-(2-hydroxyethoxy)-benzamide and 1-H-tertazole using a procedure similar to Example 180. mp 75.6–76.2° C. $^1$H NMR (DMSO-d$_6$) δ 8.88 (s, 1H); 8.53 (bt, 1H); 8.11 (d, 1H); 7.86 (d, 1H); 7.78 (m, 2H); 7.70 (d, 1H); 7.63 (dd, 1H); 4.84 (dd, 2H); 4.08 (dd, 2H); 3.22 (dd, 2H); 1.50 (dd, 2H); 1.23 (m, 18H); 0.84 (t, 3H); IR (KBr) 3400, 3250, 3100, 2900, 2850, 1630, 1550, 1470, 1420, 1330, 1170; 1120, 900 cm$^{-1}$; mass spectrum [(+)APCI], m/z 624/626 (M+H)$^+$; Anal. Calcd. for $C_{29}H_{37}BrF_3N_5O_2$: C, 55.77; H, 5.97; N, 11.21, Found: C, 55.43; H. 6.03; N, 10.91.

EXAMPLE 183

5-Bromo-6-(2-tetrazol-1-yl-ethoxy)-3'-trifluoromethyl-biphenyl-3-carboxylic Acid Dodecylamide The title compound was prepared as a white solid (0.189 g, 34%) from of N-dodecyl-3-bromo-5-(m-trifluoromethylphenyl)-4-(2-hydroxyethoxy)-benzamide and 1-H-tertazole using a procedure of Example 182. mp 91.5–92.6° C. $^1$H NMR (DMSO-d$_6$) δ 9.34 (s, 1H); 8.58 (bt, 1H); 8.11 (d, 1H); 7.88 (d, 1H); 784–7.72 (m, 3H); 7.60 (dd, 1H); 4.63 (dd, 2H); 3.92 (dd, 2H); 3.23 (dd, 2H); 1.50 (dd, 2H); 1.25 (m, 18H); 0.84 (t, 3H); IR (KBr) 3410, 2900, 2850, 1640, 1550, 1470, 1460, 1330, 1170, 1120, 705 cm$^-$; mass spectrum [(+)APCI], m/z 624/626 (M+H)$^+$; Anal. Calcd. for $C_{29}H_{37}BrF_3N_5O_2$: C, 55.77; H, 5.97; N, 11.21, Found: C, 54.08; H, 5.85; N, 10.65.

EXAMPLE 184

Carbamic Acid 2-[3-bromo-5-(8-phenyl-octylcarbamoyl)-3'-trifluoromethyl-biphenyl-2-yloxy]-ethyl Ester To a solution of N-(8-phenyl-octyl)-3-bromo-5-(m-trifluoromethylphenyl)-4-(2-hydroxyethoxy)-benzamide (0.463 g, 0.78 mmol, 1 eq) in $CH_2Cl_2$ (10 mL) was added trichloroacetyl isocyanate (0.100 mL, 0.84 mmol, 1.1 eq) The reaction was stirred at rt 15 minutes and oven-dried alumina was added. The reaction was stirred overnight at rt and concentrated in vacuo. The residue was purified by flash chromatography (30 to 60% EtOAc:hexane) to afford the title compound (0.308 g, 62%) as a oil. $^1$H NMR (DMSO-d$_6$) δ 8.56 (bt, 1H); 8.13 (d, 1H); 7.89 (m, 3H); 7.72 (dd, 1H); 7.24 (m, 2H); 7.14 (m, 3H); 6.40 (bs, 2H); 3.90 (dd, 2H); 3.70 (dd, 2H); 3.23 (dd, 2H); 2.52 (t, 2H); 1.25 (m, 4H); 1.27 (m, 8H); IR (KBr) 3330, 2920, 2850, 1720, 1640, 1600, 1550, 1460, 1410, 1330, 1180, 1120 cm$^{-1}$; mass spectrum [(+)ESI], m/z 635/637 (M+H)$^+$; Anal. Calcd. for $C_{31}H_{34}BrF_3N_2O_4$: C, 58.59; H, 5.39; N, 4.41, Found: C, 57.26; H, 5.46; N, 4.38.

EXAMPLE 185

5-Bromo-6-(2-morpholin4-yl-ethoxy)-3'-trifluoromethyl-biphenyl-3-carboxylic Acid Dodecylamide Step 1

To a solution of N-dodecyl-3-bromo-5-(m-trifluoromethylphenyl)-4-(2-hydroxyethoxy)-benzamide (0.996 g, 1.74 mmol, 1 eq) in $CH_2Cl_2$ (9 mL) was added carbon tetrabromide (0.760 g, 2.29 mmol 1.3 eq) and triphenylphosphine (0.603 g, 2.29 mmol, 1.3 eq). The reaction was stirred at overnight at rt and concentrated in vacuo. The residue was purified by flash chromatography (15% EtOAc:hexane) to afford N-dodecyl-3-bromo4-(2-bromo-ethoxy)-5-(m-trifluoromethylphenyl)-benzamide (0.951 g, 89%) as a colorless oil. $^1$H NMR (CDCl$_3$) δ 7.98 (d, 1H); 7.78–7.40 (m, 5H); 6.20 (bt, 1H); 4.52 (dd, 2H); 3.95 (dd, 2H); 3.42 (dd, 2H); 1.50 (m, 2H); 1.30 (m, 18H); 0.92 (t, 3H).

Step 4

To a solution of N-dodecyl-3-bromo-4-(2-bromoethoxy)-5-(m-trifluoromethylphenyl)-benzamide (0.294 g, 0.46 mmol, 1 eq) in CH$_3$CN (4 mL) was added morpholine (0.50 mL, 0.57 mmol 1.24 eq) and K$_2$CO$_3$ (0.509 g, 3.68 mmol, 8 eq). The reaction was heated at reflux overnight. The solids were filtered off and the filtrate was concentrated in vacuo. The residue was purified by flash chromatography (50% EtOAc:hexane) to afford the title compound (0.296 g, 100%) as a colorless oil. $^1$H NMR (DMSO-d$_6$) δ 8.53 (bt, 1H); 8.11 (d, 1H); 7.88–7.83 (m, 3H); 7.78 (d, 1H); 7.72 (dd, 1H); 3.63 (dd, 2H); 3.40 (dd, 4H); 3.21 (dd, 2H); 2.38 (dd, 2H); 2.15 (dd, 4H); 1.48 (dd, 2H); 1.22 (m, 18H); 0.82 (t, 3H); IR (KBr) 3400, 2900, 2800, 1630, 1540, 1450, 1330, 1310, 1170, 1120, 700 cm$^{-1}$; mass spectrum [(+)APCI], m/z 641/643 (M+H)$^+$; Anal. Calcd. for C$_{31}$H$_{34}$BrF$_3$N$_2$O$_4$: C, 59.90; H, 6.91; N, 4.37, Found: C, 58.58; H, 7.01; N, 4.18.

EXAMPLE 186

6-(Amino-ethoxy)-5-bromo-3'-trifluoromethyl-biphenyl-3-carboxylic Acid Dodecylamide To a solution of N-dodecyl-3-bromo-4-(2-bromo-ethoxy)-5-(m-trifluoromethylphenyl)-benzamide (1.431 g, 2.25 mmol, 1 eq) in benzene (2 mL) was added tetrabutyl ammonium bromide (0.053 g, 0.16 mmol, 0.07 eq) and sodium azide (0.216 g, 3.32 mmol, 1.48 eq). The reaction was heated at reflux overnight. Additional tetrabutyl ammonium bromide (0.064 g, 0.20 mmol, 0.09 eq) and sodium azide (0.224 g, 3.45 mmol, 1.53 eq) were required as indicated by TLC. The reaction was cooled to rt and the solids were filtered off. The filtrate was washed with H$_2$O and dried over MgSO$_4$. Triethyl phosphite (0.390 mL, 2.27 mmol, 1.0 eq) was then added to the filtrate and the reaction was stirred overnight at rt. Additional triethyl phosphite (0.780 mL, 4.54 mmol, 2.0 eq) was required. After 48 h, HCl gas was bubbled through the reaction mixture and stirred was continued for 72 h. The reaction was then concentrated in vacuo, dissolved in THF and washed with 2 M HCl. The washes were then adjusted pH 10 with 2.5 M NaOH and were extracted with CH$_2$Cl$_2$. All organics were combined, dried over MgSO$_4$ and concentrated in vacuo. The residue was purified by flash chromatography (7 to 12% MeOH:CH$_2$Cl$_2$) to afford the title compound (0.0738 g, 57%) as a colorless oil. $^1$H NMR (DMSO-d$_6$) δ 8.57 (bt, 1H); 8.12 (d, 1H); 7.90 (m, 3H); 7.80 (d, 1H); 7.73 (dd, 1H); 3.51 (dd, 2H); 3.30 (bs, 2H); 3.23 (dd, 2H); 2.58 (dd, 2H); 1.450 (dd, 2H); 1.25 (m, 18H); 0.83 (t, 3H); IR (film) 3300, 3080, 2920, 2850, 1640, 1600, 1550, 1450, 1330, 1160, 1120, 1080 cm$^{-1}$; mass spectrum [(+)ESI], m/z 571/573 (M+H)$^+$; Anal. Calcd. for C$_{28}$H$_{38}$BrF$_3$N$_2$O$_2$: C, 58.84; H, 6.70; N, 4.90, Found: C, 56.61; H, 6.61; N, 4.71.

EXAMPLE 187

5-Bromo-3'-trifluoromethyl-6-(2-ureido-ethoxy)-biphenyl-3-carboxylic Acid Dodecylamide Step 1

To a solution of 6-(amino-ethoxy)-5-bromo-3'-trifluoromethyl-biphenyl-3-carboxylic acid dodecylamide (0.257 g, 0.45 mmol, 1 eq) in CH$_2$Cl$_2$ (6 mL) was added chloroacetyl isocyanate (0.060 mL, 0.050 mmol, 1.11 eq). The reaction was stirred at rt 15 min. and then concentrated in vacuo. The residue was purified by flash chromatography (30% EtOAc:hexane) to afford 5-bromo-N-(8-phenyloctyl)-6-[2-({[(2,2,2-trichloroacetyl)amino]carbonyl}amino)ethoxy]-3'-(trifluoromethyl)[1,1'-biphenyl]-3-carboxamide (0.273 g, 80%) as a colorless oil. $^1$H NMR (DMSO-d$_6$) δ 11.28 (s, 1H); 8.60 (bt, 1H); 8.15 (d, 1H); 8.05–7.85 (m, 4H); 7.80–7.64 (m, 2H); 3.64 (t, 2H); 3.24 (m, 4H); 1.52 (m, 2H); 1.26 (m, 18H); 0.87 (t, 3H).

Step 2

To a solution of 5-bromo-N-(8-phenyloctyl)-6-[2-({[(2,2,2-trichloroacetyl)amino]carbonyl}amino)ethoxy]-3'-(trifluoromethyl)[1,1'-biphenyl]-3-carboxamide in CH$_2$Cl$_2$/MeOH (10/4) (14 mL) was added 1M NaOH (2 mL). The reaction was stirred at rt overnight and concentrated in vacuo. The residue was extracted with CH$_2$Cl$_2$, dried over MgSO$_4$ and concentrated in vacuo. The residue was purified by flash chromatography (3 to 5% MeOH:CH$_2$Cl$_2$) to afford the title compound (0.203 g, 92%) as a white solid. mp 122.5–125.1° C. $^1$H NMR (DMSO-d$_6$) δ 8.58 (bt, 1H); 8.12 (d, 1H); 7.90 (m, 3H); 7.78 (d, 1H); 7.73 (dd, 1H); 6.95 (t, 1H); 5.44 (s, 2H); 3.48 (dd, 2H); 3.24 (dd, 2H); 3.05 (ddd, 2H); 1.48 (dd, 2H); 1.25 (m, 18H); 0.84 (t, 3H); (KBr) 3300, 2950, 2820, 1650, 1600, 1550, 1460, 1330, 1180, 1120, 1080, 1030, 900, 805 cm$^{-1}$; mass spectrum [(+)ESI], m/z 614/616 (M+H)$^+$; Anal. Calcd. for C$_{29}$H$_{39}$BrF$_3$N$_3$O$_3$: C, 56.68; H, 6.40; N, 6.84, Found: C, 56.37; H, 6.25; N, 6.49.

EXAMPLE 188

[2-(3-Bromo-5-dodecylcarbamoyl-3'-trifluoromethyl-biphenyl-2-yloxy)-ethyl]-carbamic Acid Methyl Ester To a solution of 6-(amino-ethoxy)-5-bromo-3'-trifluoromethyl-biphenyl-3-carboxylic acid dodecylamide (0.273 g, 0.48 mmol, 1 eq) in THF (6 mL) at 0° C. was added triethylamine (0.150 mL, 1.08 mmol, 2.25 eq) followed by methyl chloroformate (0.040 mL, 0.052 mmol, 1.11 eq). The reaction was stirred for 15 min, then poured into pH 7 buffer and extracted with Et$_2$O. The combined organics were dried over MgSO$_4$ and concentrated in vacuo. The residue was purified by flash chromatography (30% EtOAc:hexane ) to afford the title compound (0.282 g, 93%) as a white solid. mp 79.6–80.5° C. $^1$H NMR (DMSO-d$_6$) δ 8.56 (bt, 1H); 8.12 (d, 1H); 7.88 (m, 3H); 7.79 (d, 1H); 7.70 (t, 1H); 7.02 (t, 1H); 3.54 (dd, 2H); 3.44 (s, 3H); 3.24 (dd, 2H); 3.08 (ddd, 2H); 1.48 (dd, 2H); 1.23 (m, 18H); 0.83 (t, 3H); IR (KBr) 3330, 2950, 2840, 1695, 1640, 1540, 1340, 1180, 1110, 920, 805 cm$^{-1}$; mass spectrum [(+)MAT900], m/z 629/631 (M+H)$^+$; Anal. Calcd. for C$_{30}$H$_{40}$BrF$_3$N$_2$O$_4$: C, 57.23; H, 6.40; N, 4.45, Found: C, 56.12; H, 6.29; N, 4.29.

EXAMPLE 189

[5'-(6-Phenyl-hexylcarbamoyl)-3,3"-bis-trifluoromethyl-[1,1';3',1"]terphenyl-2'-yloxy]-acetic Acid Step 1

To a solution of 3,5-bis-(m-trifluoromethylphenyl)-4-(2-hydroxyethoxy)-benzoic acid ethyl ester (0.560 g, 1.12 mmol, 1 eq) in THF/EtOH (3/2) (25mL) was added 1M NaOH (4 mL) and the reaction was stirred at rt overnight. It was then concentrated in vacuo, diluted with H$_2$O, and acidified with 2M HCl to pH 1. It was extracted with CH$_2$Cl$_2$, dried over MgSO$_4$ and concentrated in vacuo.

To a solution of the residue in CH$_2$Cl$_2$ (20 mL) was added phenylhexylamine (0.310 mL, 1.69 mmol, 1.5 eq), 1-hydroxybenzotriazole (0.174 g, 1.29 mmol, 1.15 eq), triethylamine (0.500 mL, 3.58 mmol, 3.2 eq) and dicyclohexylcarbodiimide (0.290 g, 1.41 mmol, 1.26 eq). The reaction was stirred at rt overnight, diluted with EtOAc, then washed with 1 M HCl solution, brine, saturated sodium bicarbonate solution and brine. The organics were dried over MgSO$_4$ and concentrated in vacuo. The residue was purified by flash chromatography (30% EtOAc:hexane ) to afford the N-(8-phenyl-hexyl)-3,5-bis(m-trifluoromethylphenyl)-4-(2- hydroxyethoxy)-benzamide (0.701 g, 99%) as a white solid. $^{1}$H NMR (CDCl$_{3}$) δ 7.92 (s, 2H); 7.84 (m, 4H); 7.70–7.54 (m, 4H); 7.30–7.14 (m, 5H) 6.55 (t, 1H); 3.43 (dd, 2H); 3.32 (m, 4H); 2.59 (t, 2H); 1.64 (m, 4H), 1.38 (m, 4H).
Step 2

The title compound was prepared as a white solid (0.058 g, 50%) from N-(6-phenyl-hexyl)-3,5-bis(m-trifluoromethylphenyl)-4-(2-hydroxyethoxy)-benzamide using a procedure similar to step 3 of Example 175. mp 166.5–168.8° C. $^{1}$H NMR (DMSO-d$_{6}$) δ 12.60 (bs, 1H); 8.56 (t, 1H); 7.98 (s, 2H); 7.94–7.90 (m, 4H); 7.80–7.68 (m, 4H); 7.26–7.10 (m, 5H); 3.80 (s, 2H); 3.22 (dd, 2H); 2.54 (t, 2H); 1.54 (m, 4H); 1.06 (m, 4H) IR (KBr) 3350, 2930, 2860, 1720, 1610, 1570, 1470, 1320, 1200, 1120 cm$^{-1}$; mass spectrum [(–)ESI], m/z 642 (M–H)$^{-}$; Anal. Calcd. for C$_{35}$H$_{31}$F$_{6}$NO$_{4}$: C, 65.32; H, 4.85; N, 2.18, Found: C, 64.85; H, 4.92; N, 2.13.

EXAMPLE 190

[3-Bromo-5-(6-phenyl-hexylcarbamoyl)-3'-trifluoromethyl-biphenyl-2-yloxy]-acetic Acid Step 1

N-(6-hexyl-octyl)-3-bromo-5-(m-trifluoromethylphenyl)-4-(2-hydroxyethoxy)-benzamide was prepared as a white solid (0.221 g, 64%) from 3-bromo-5-(m-trifluoromethylphenyl)-4-(2-hydroxyethoxy)-benzoic acid ethyl ester using a procedure similar to step 1 of Example 189. $^{1}$H NMR (CDCl$_{3}$) δ 7.98 (d, 1H); 7.84–7.50 (m, 5H); 7.30–7.14 (m, 5H); 6.66 (bt, 1H); 3.62 (m, 4H); 3.41 (dd, 2H); 2.58 (t, 2H); 2.24 (bs, 1H) 1.64 (m, 4H); 1.46 (m, 4H).
Step 2

The title compound was prepared as a white foam (0.099 g, 44%) from N-(6-hexyl-octyl)-3-bromo-5-(m-trifluoromethylphenyl)-4-(2-hydroxyethoxy)-benzamide using a procedure similar to step 3 of Example 175. $^{1}$H NMR (DMSO-d$_{6}$) δ 12.85 (bs, 1H); 8.56 (t, 1H); 8.12 (d, 1H); 7.92–7.84 (m, 3H); 7.77 (d, 1H); 7.69 (t, 1H); 7.22–7.10 (m, 5H); 4.14 (s, 2H); 3.22 (dd, 2H); 2.53 (t, 2H); 1.50 (m, 4H); 1.30 (m, 4H); IR (KBr) 3330, 2950, 2850, 1740, 1630, 1550, 1450, 1420 1330, 1180, 1100, 900 cm$^{-1}$; mass spectrum [(–)ESI], m/z 606/608 (M–H)$^{+}$; Anal. Calcd. for C$_{28}$H$_{27}$BrF$_{3}$NO$_{4}$: C, 58.14; H, 4.71; N, 2.42, Found: C, 57.62; H, 4.80; N, 2.35.

EXAMPLE 191

2'-Hydroxy-3,3"-bis-trifluoromethyl-[1,1';3',1"]terphenyl-5'-carboxylic Acid (8-phenyl-octyl)-amide To 3,5-bis-(m-trifluoromethylphenyl)-4-hydroxy-benzoic acid ethyl ester (0.315 g, 0.74 mmol, 1 eq) was added thionyl chloride (2 mL) and the reaction was stirred overnight at rt and concentrated in vacuo. It was then added to a solution of phenyl octyl amine (0.222 mL, 1.12 mmol, 1.51 eq) and triethylamine (0.470 mL, 3.37 mmol, 4.6 eq). The reaction was stirred at rt 1h, poured into 0.1 N HCl solution and extracted with Et$_{2}$O. The combined organics were washed with 1N HCl (×3), dried over MgSO$_{4}$ and concentrated in vacuo. The residue was purified by flash chromatography (20% EtOAc:hexane) to afford title compound (0.393 g, 86%) as a colorless oil. $^{1}$H NMR (DMSO-d$_{6}$) δ 9.30 (s, 1H); 8.42 (t, 1H); 7.91–7.85 (m, 4H); 7.82 (s, 2H); 7.75–7.65 (m, 4H); 7.26–7.10 (m, 5H); 3.23 (dd, 2H); 2.52 (t, 2H); 1.52 (m, 4H); 1.27 (m, 8H); IR (film) 3330, 2980, 2840, 1640, 1600, 1550, 1470, 1320, 1180, 1120, 1080, 900, 805 cm$^{-1}$; mass spectrum [(+)APCI], m/z 614 (M+H)$^{+}$; Anal. Calcd. for C$_{35}$H$_{33}$F$_{6}$NO$_{2}$: C, 68.51; H, 5.42; N, 2.28, Found: C, 66.76; H, 5.46; N, 2.18.

EXAMPLE 192

5-[5'-(8-Phenyl-octylcarbamoyl)-3,3"-bis-trifluoromethyl-1,1';3',1"]terphenyl-2'yloxy]-pentanoic Acid Step 1

To a solution of 2'-hydroxy-3,3"-bis-trifluoromethyl-[1,1';3',1"]terphenyl-5'-carboxylic acid (8-phenyl-octyl)-amide (0.313 g, 0.64 mmol, 1 eq) in acetone (6 mL) was added K$_{2}$CO$_{3}$ (0.460 g, 3.33 mmol, 5.2 eq) and 5-bromo methyl valerate (0.090 mL, 0.63 mmol, 1 eq). The reaction was heated at reflux for 2 days, cooled to rt and concentrated in vacuo. The residue was partitioned between EtOAc and brine, dried over MgSO$_{4}$ and concentrated in vacuo. The residue was purified by flash chromatography (25% EtOAc:hexane) to afford N-(8-phenyl-hexyl)-3,5-bis(m-trifluoromethylphenyl)-4-hydroxy benzamide (0.396 g, 85%) as a colorless oil. $^{1}$H NMR (CDCl$_{3}$) δ 7.91 (s, 2H); 7.80 (m, 4H); 7.66–7.54 (m, 4H); 7.28–7.12 (m, 5H); 6.23 (bt, 1H); 3.59 (s, 3H); 3.44 (dd, 2H); 3.17 (t, 2H); 2.58 (t, 2H); 1.95 (t, 2H); 1.60 (m, 4H); 1.52 (m, 12H).
Step 2

To a solution of N-(8-phenyl-hexyl)-3,5-bis(m-trifluoromethylphenyl)-4-hydroxy benzamide (0.396 g, 0.54 mmol, 1 eq) in THF/EtOH (3/2) (10 mL) was added 1M NaOH (4 mL) and the reaction was stirred at rt overnight. It was then concentrated in vacuo, diluted with H$_{2}$O, and acidified with 2M HCl to pH 1. It was extracted with CH$_{2}$Cl$_{2}$, dried over MgSO$_{4}$ and concentrated in vacuo. The residue was purified by flash chromatography (25% EtOAc:Hexane+1% Formic acid) to afford the title compound (0.367 g, 95%) as a colorless oil. $^{1}$H NMR (DMSO-d$_{6}$) δ 11.91 (bs, 1H); 8.56 (t, 1H); 7.98–7.90 (m, 6H); 7.80–7.70 (m, 4H); 7.26–7.12 (m, 5H); 3.25 (dd, 2H); 3.13 (t, 2H); 2.52 (t, 2H); 1.80 (t, 2H); 1.50 (m, 4H); 1.27 (m, 8H); 1.12 (m, 4H) IR (film) 3300, 2950, 2800, 1710, 1620, 1550, 1490, 1460, 1320, 1160, 1120 cm$^{-}$; mass [(+)ESI], m/z 714 (M+H)$^{+}$; Anal. Calcd. for C$_{40}$H$_{41}$F$_{6}$NO$_{4}$: C, 67.31; H, 5.70; N, 1.96; Found: C, 64.95; H, 5.99; N, 1.57.

EXAMPLE 193

5-Bromo-6-(2-piperazin-1-yl-ethoxy)-3'trifluoromethyl-biphenyl-3-carboxylic Acid (8-phenyl-octyl)-amide The tide compound was prepared as a yellow oil (0.302 g, 45%) from N-(8-phenyl-octyl)-3-bromo-5-(m-trifluoromethylphenyl)-4-(2-hydroxyethoxy)-benzamide and piperazine using a procedure similar to Example 185. $^{1}$H NMR (DMSO-d$_{6}$) 8.58 (t, 1H); 8.12 (d, 1H); 7.90–7.84 (m, 3H); 7.69 (d, 1H); 7.52 (dd, 1H); 7.26–7.10 (m, 5H); 3.61 (t, 2H); 3.23 (dd, 2H); 2.62 (t, 4H); 2.52 (t, 2H); 2.36 (t, 2H); 2.18 (m, 5H); 1.50 (m, 4H); 1.24 (m, 8H); IR (film) 3290, 2920, 2850, 1720, 1630, 1600, 1545, 1460, 1330, 1170, 1120, 1080 cm$^{-1}$; mass spectrum [(+)ESI], m/z 660/662 (M+H)$^{+}$; Anal. Calcd. for C$_{34}$H$_{41}$Br F$_{3}$N$_{3}$O$_{2}$: C, 61.82; H, 6.26; N, 6.36, Found: C, 58.20; H, 6.00; N, 5.47.

EXAMPLE 194

5-Bromo-6-hydroxy-3'-trifluoromethyl-biphenyl-3-carboxylic Acid (8-phenyl-octyl)-amide The title compound was prepared as a white gum (0.976 g, 58%) from N-(8-phenyl-octyl)-3,5-bis(m-trifluoromethylphenyl)-4-hydroxy-benzamide using a procedure similar to Example 191. $^{1}$H NMR (DMSO-d$_{6}$) δ 9.84 (s, 1H); 8.42 (t, 1H); 8.04 (d, 1H); 7.85–7.67 (m, 5H);

7.26–7.10 (m, 5H); 3.21 (dd, 2H); 2.52 (t, 2H); 1.50 (m, 4H); 1.26 (m, 8H); IR (KBr) 3330, 2950, 2850, 1620, 1550, 1495, 1470, 1330, 1220, 1170, 1120, 1100, 1080 cm$^{-1}$; mass spectrum [(+)APCI], m/z 549 (M+H)$^+$; Anal. Calcd. for $C_{28}H_{29}F_3NO_2$: C, 61.32; H, 5.33; N, 2.55, Found: C, 61.02; H, 5.29; N, 2.51.

EXAMPLE 195

4-[3-Bromo-5-(8-phenyl-octylcarbamoyl)-3'-trifluoromethyl-biphenyl-2-yloxysulfonyl]-2-hydroxy-benzoic Acid The title compound was prepared as an orange foam (0.455 g, 76%) from 5-bromo-6-hydroxy-3'-trifluoromethyl-biphenyl-3-carboxylic acid (8-phenyl-octyl)-amide and 4-chlorosulfonyl-2-hydroxy-benzoic acid using a procedure similar to step 3 of Example 179. $^1$H NMR (DMSO-d$_6$) 12.60 (bs, 7H); 11.60 (bs, 1H); 8.68 (t, 4H); 8.21 (d, 1H); 7.84 (d, 1H); 7.71–7.62 (m, 2H); 7.56–7.44 (m, 3H); 7.26–7.10 (m, 5H); 6.96 (dd, 5H); 6.82 (d, 1H); 3.21 (dd, 2H); 2.62 (t, 4H); 2.53 (t, 2H); 1.52 (m, 4H); 1.25 (m, 8H); IR (KBr) 3370, 2950, 2825, 1690, 1640, 1605, 1560, 1540, 1390, 1325, 1195, 1170, 1125 cm$^{-1}$; mass spectrum [(–)ESI], m/z 660/662 (M–H)$^-$; Anal. Calcd. for $C_{35}H_{33}BrF_3NO_7S$: C, 56.16; H, 4.44; N, 1.87, Found: C, 55.65; H, 4.27; N, 1.90.

EXAMPLE 196

7-[5'-(8-Phenyl-octylcarbamoyl)-3,3"-bis trifluoromethyl-[1,1';3',1"]terphenyl-2'-yloxy]-heptanoic Acid The title compound was prepared as a colorless oil (0.189 g, 64%) from 2'-hydroxy-3,3"-bis-trifluoromethyl-[1, 1';3',1"]terphenyl-5'-carboxylic acid (8-phenyl-octyl)-amide and ethyl 7-bromo heptanoate using a procedure similar to Example 192. $^1$H NMR (DMSO-d$_6$) δ 11.90 (bs, 2H); 8.56 (t, 1H); 7.95–7.90 (m, 6H); 7.80–7.70 (m, 4H); 7.25–7.10 (m, 5H); 3.27 (dd, 2H); 3.14 (t, 2H); 2.523(t, 2H); 2.02 (t, 2H); 1.52 (m, 4H); 1.26 (m, 10H); 1.08 (m, 2H) 0.84 (m, 4H); IR (film) 3375, 2980, 2870, 1705, 1630, 1550, 1460, 1320, 1120, 1080 cm$^{-1}$; mass spectrum [(–)ESI], m/z 740 (M–H)$^-$; Anal. Calcd. for $C_{42}H_{45}F_6NO_4$: C, 68.00; H, 6.11; N, 1.89, Found: C, 66.26; H, 5.14; N, 1.65.

EXAMPLE 197

2'-(2-Hydroxy-3,4-dioxo-cyclobut-1-enylamino)-ethoxy-3,3"-bis-trifluoromethyl-[1,1';3',1"]terphenyl-5'-carboxylic Acid (8-phenyl-octyl Amine)

Step 1

N-(8-Phenyloctyl)-4-(2-amino-ethoxy)-3,5-bis(m-trifluoromethylphenyl)-benzamide was prepared as an colorless oil (0.189 g, 64%) from N-(2-phenyl-octyl)-3,5-bis(m-trisfluoromethylphenyl)-4-(2-hydroxyethoxy)-benzamide using a procedure similar to Example 186. $^1$H NMR (CDCl$_3$) δ 7.91–7.76 (m, 6H); 7.7 0–7.54 (m, 4H); 7.26–7.10 (m, 5H); 6.34 (bt, 2H); 3.45 (dd, 2H); 32.2 (t, 2H); 2.56 (t, 2H); 2.45 (t, 2H); 1.93 (bs, 2H); 1.60 (m, 4H); 1.32 (m, 8H).

Step 2

To a solution of diethoxycyclobutane (0.060 mL, 0.41 mmol, 1.6 eq) in EtOH (2 mL) was added a solution of N-(8-phenyl octyl)-4-(2-amino-ethoxy)-3,5-bis(m-trifluoromethylphenyl) benzamide (0.170 g, 0.26 mmol, 1 eq) in EtOH (2 mL). The reaction was stirred at rt overnight and then concentrated in vacuo. The residue was purified by flash chromatography (30 to 50% EtOAc:Hexane+1% Formic acid) to afford a colorless oil.

The oil was dissolved in HCl saturated 10% aqueous THF and stirred overnight at rt. It was then concentrated and partitioned between brine and CH$_2$Cl$_2$ and extracted with CH$_2$Cl$_2$. The combined organics were dried over MgSO$_4$ and concentrated in vacuo. The residue was purified by flash chromatography (5% MeOH: CH$_2$Cl$_2$) to afford the title compound (0.143 g, 83%) as a purple foam. $^1$H NMR (DMSO-d$_6$) δ 8.56 (t, 1H); 7.78–7.70 (m, 6H); 7.74–7.62 (m, 5H); 7.26–7.12 (m, 5H); 3.60 (s, 1H); 3.31 (t, 2H); 3.25 (dd, 2H); 3.14 (t, 2H); 2.52 (t, 2H); 1.52 (m, 4H); 1.27 (m, 8H); IR (KBr) 3375, 2950, 2840, 1810, 1700, 1600, 1550, 1460, 1410, 1350, 1320, 1210, 1160, 1120, 1080 cm$^{-1}$; mass spectrum [(+)APCI], m/z 753 (M+H)$^+$; Anal. Calcd. for $C_4H_{38}F_6N2O_5$: C, 65.42; H, 5.09; N, 3.72, Found: C, 63.77; H, 4.96; N, 3.63.

EXAMPLE 198

2'-[4-(1H-Tetrazol-5-yl)-butoxy-3,3"-bis-trifluoromethyl-[1,1';3',1"]terphenyl-5'-carboxylic Acid (8-phenyl-octyl)-amide Step 1

To a solution of 2'-hydroxy-3,3"-bis-trifluoromethyl-[1, 1';3',1"]terphenyl-5'-carboxylic acid (8-phenyl-octyl)-amide (0.557 g, 0.91 mmol, 1 eq) in acetone (8 mL) was added K$_2$CO$_3$ (0.648 g, 4.68 mmol, 5.14 eq) and 5-bromo valeronitrile (0.110 mL, 0.94 mmol, 1.03 eq). The reaction was heated at reflux for overnight, cooled to rt and concentrated in vacuo. The residue was partitioned between EtOAc and brine, dried over MgSO$_4$ and concentrated in vacuo. The residue was purified by flash chromatography (25% EtOAc:hexane) to afford N-(8-phenyl-hexyl)-3,5-bis(m-trifluoromethylphenyl)-4-(4-cyano-butoxy) benzamide (0.527 g, 83%) as a colorless oil. $^1$H NMR (CDCl$_3$) δ 7.98–7.45 (m, 10H); 7.25–7.10 (m, 5H); 6.25 (bt, 1H); 3.45 (dd, 2H); 3.18 (t, 2H); 2.58 (t, 2H); 1.97 (t, 2H); 1.62 (m, 4H); 1.54 (m, 12H).

Step 2

To a solution of N-(8-phenyl-hexyl)-3,5-bis(m-trifluoromethylphenyl)-4-(4-cyano-butoxy) benzamide (0.527 g, 0.76 mmol, 1 eq) in xylenes (8 mL) was added sodium azide (0.065 g, 1.0 mmol, 1.3 eq) and tributyltin chloride (0.300 mL, 1.11 mmol, 1.46 eq). The reaction was heated at reflux for 4 days and cooled to rt. 6 M HCl (4 mL) solution was added and the reaction was stirred 3 days. It was poured into brine and extracted with EtOAc. The combined organics were dried over MgSO$_4$ and concentrated in vacuo. The residue was first purified by flash chromatography (5% MeOH:CH$_2$Cl$_2$) and then HPLC [85% CH$_3$CN in 0.1% TFA) to give the title compound (0.265 g, 47%) as a white solid. mp 145.4–150.8° C. $^1$H NMR (DMSO-d$_6$) δ 8.55 (t, 1H); 7.97–7.70 (m, 6H); 7.76–7.68 (m, 4H); 7.26–7.20 (m, 2H); 7.16–7.10 (m, 3H); 3.26 (dd, 2H); 3.17 (t, 2H); 2.52 (t, 2H); 1.52 (m, 4H); 1.27 (m, 12H); 1.12 (m, 2H); IR (KBr) 3400, 3300, 2950, 2875, 1680, 1630, 1550, 1450, 1330, 1120, 1080 cm$^1$; mass spectrum [(+)APCI], m/z 738 (M+H)$^+$; Anal. Calcd. for $C_{40}H_{41}F_6N_5O_2$: C, 65.12; H, 5.60; N, 9.49, Found: C, 58.55; H, 5.10; N, 7.98.

EXAMPLE 199

2-Methoxy-4-[5'-(8-phenyl-octylcarbamoyl)-3,3"-bis-trifluoromethyl-[1,1';3',1"]terphenyl-2'yloxymethyl]-benzoic Acid Step 1

To a solution of 2'-hydroxy-3,3"-bis-trifluoromethyl-[1,1';3',1"]terphenyl-5'-carboxylic acid (8-phenyl-octyl)-amide (0.755 g, 1.23 mmol, 1 eq) in acetone (12 mL) was added $K_2CO_3$ (0.857 g, 6.2 mmol, 5.0 eq) and 4-bromomethyl-2-methoxy benzoic acid methyl ester (Julia, M.; Chastrette, F.; BSCFAS; Bull. Soc. Chim. Fr.; FR; 1962; 2255–2261).

(0.325 g, 1.25 mmol, 1.0 eq). The reaction was heated at reflux overnight. Additional 4-bromomethyl-2-methoxy benzoic acid methyl ester (0.072 g, 0.28 mmol, 0.2 eq) was added and reflux was continued for 1 h. The reaction was cooled to rt and concentrated in vacuo. The residue was partitioned between EtOAc and brine, washed with brine, dried over $MgSO_4$ and concentrated in vacuo. The residue was purified by flash chromatography (20% EtOAc/hexane) to afford 2-methoxy4-[5'-(8-phenyl-octylcarbamoyl)-3,3"-bis-trifluoromethyl-[1,1';3',1"]terphenyl-2'yloxymethyl]-benzoic acid methyl ester. (0.847, 87%) as a colorless oil. $^1$H NMR (CDCl$_3$) δ 7.88–7.42 (m, 10H); 7.25–7.10 (m, 5H); 6.24–6.10 (m, 3H); 4.18 (s, 2H); 3.85 (s, 3H); 3.65 (s, 3H); 3.46 (dd, 2H); 2.58 (t, 2H); 1.60 (m, 4H); 1.34 (m, 8H).

Step 2

To a solution of 2-methoxy-4-[5'-(8-phenyl-octylcarbamoyl)-3,3"-bis-trifluoromethyl-[1,1';3',1"]terphenyl-2'yloxymethyl]-benzoic acid methyl ester (0.352 g, 0.44 mmol, 1 eq) in THF/EtOH (3/2) (10 mL) was added 1M NaOH (4 mL) and the reaction was stirred at rt overnight. It was then concentrated in vacuo, diluted with $H_2O$, and acidified with 2M HCl to pH 1. It was extracted with EtOAc, dried over $MgSO_4$ and concentrated in vacuo. The residue was purified by flash chromatography (20% EtOAc/hexane+1% Formic acid) to afford the title compound (0.342 g, 865) as a white foam. $^1$H NMR (DMSO-d$_6$) δ 12.50 (bs, 1H); 8.59 (t, 1H); 7.99–7.92 (m, 6H); 7.80–7.68 (m, 4H); 7.37 (d, 1H); 7.26–7.10 (m, 5H); 6.38 (s, 1H); 6.30 (d, 1H); 4.21 (s, 2H); 3.58 (s, 3H); 3.26 (dd, 2H); 2.52 (t, 2H); 1.53 (m, 4H); 1.28 (m, 8H); IR (KBr) 3350, 2950, 2850, 1720, 1640, 1620, 1550, 1495, 1475, 1415, 1320, 1160, 1150, 1120, 1095, 1080, 1030 cm$^{-1}$; mass spectrum [(+)APCI], m/z 778 (M+H)$^+$; Anal. Calcd. for $C_{44}H_{41}F_6NO_5$: C, 67.95; H, 5.31; N, 1.80, Found: C, 67.22; H, 5.22; N, 1.74.

EXAMPLE 200

2-Hydroxy-4-[5'-(8-phenyl-octylcarbamoyl)-3,3"-bis-trifluoromethyl-[1,1';3',1"]terphenyl-2'-yloxymethyl]-benzoic Acid To a solution of 2-methoxy-4-[5'-(8-phenyl-octylcarbamoyl)-3,3"-bis-trifluoromethyl-[1,1';3',1"]terphenyl-2'yloxymethyl]-benzoic acid methyl ester (0.418 g, 0.53 mmol, 1 eq) in $CH_2Cl_2$ (9 mL) cooled to 0° C. was added BBr$_3$ (1M in $CH_2Cl_2$) (0.800 mL, 0.53 mmol, 1 eq). The reaction was stirred at 0° C. for 40 min, poured over ice and extracted with EtOAc. The combined organics were washed with brine, dried over $MgSO_4$ and concentrated in vacuo. The residue was purified by flash chromatography (20 to 30% EtOAc:hexane+1% Formic Acid) to afford 2-hydroxy-4-[5'-(8-phenyl-octylcarbamoyl)-3,3"-bis-trifluoromethyl-[1,1';3',1"]terphenyl-2'yloxymethyl]-benzoic acid methyl ester (see next example) and the title compound (0.201 g, 50%) as a white foam. $^1$H NMR (DMSO-d$_6$) δ 13.60 (bs, 1H); 11.10 (bs, 1H); 8.59 (bt, 1H); 7.96–7.92 (m, 6H); 7.78–7.66 (m, 4H); 7.48 (d, 1H); 7.26–7.10 (m, 5H); 6.26. (d, 1H); 6.21 (dd, 1H); 4.18 (dd, 2H); 3.24 (dd, 2H); 2.52 (t, 2H); 1.52 (m, 4H); 1.27 (m, 8H); IR (film) 3300, 2950, 2800, 1680, 1630, 1590, 1540, 1440, 1320, 1260, 1205, 1160, 1120, 1095, 1080, 990 cm$^{-1}$; mass spectrum [(–)ESI], m/z 776 (M–H)$^-$; Anal. Calcd. for $C_{43}H_{39}F_6NO_5$: C, 67.62; H, 5.15; N, 1.83, Found: C, 67.21; H, 5.11; N, 1.71.

EXAMPLE 201

2-Hydroxy-4-5'-(8-phenyl-octylcarbamoyl)-3,3"-bis-trifluoromethyl-[1,1';3'1"]terphenyl-2'yloxymethyl[-benzoic Acid Methyl Ester The title compound was prepared as a yellow oil (0.198 g, 48%) using the procedure of Example 200. $^1$H NMR (DMSO-d$_6$) δ 10.36 (s, 1H); 8.59 (bt, 1H); 7.94 (m, 6H); 7.76–7.66 (m, 4H); 7.47 (d, 1H); 7.25–7.10 (m, 5H); 6.82 (d, 1H); 6.74 (dd, 1H); 4.18 (dd, 2H); 3.84 (s, 3H); 3.26 (dd, 2H); 2.52 (t, 2H); 1.52 (m, 4H); 1.27 (m, 8H); IR (film) 3330, 2950, 2850, 1680, 1600, 1580, 1550, 1460, 1420, 1320, 1210, 1150, 1115, 1080, cm$^{-1}$; mass spectrum [(–)ESI], m/z 762 (M–H)$^-$; Anal. Calcd. for $C_{44}H_{41}F_6NO_5$: C, 67.95; H, 5.31; N, 1.80, Found: C, 67.11; H, 5.29; N, 1.73.

EXAMPLE 202

4-{2-[3-Bromo-5-(8-phenyl-octylcarbamoyl)-3'-trifluoromethyl-biphenyl-2-yloxy]-ethoxy}-2-hydroxy-benzoic Acid Step 1

To a solution of N-(8-phenyl-octyl)-3-bromo-5-(m-trifluoromethylphenyl)-4-(2-hydroxyethoxy)-benzamide (0.687 g, 1.16 mmol, 1 eq) in THF (10 mL) was added triphenylphosphine (0.680 g, 2.59 mmol, 2.23 eq) and methyl 2,4 dihydroxybenzoate (0.388 g, 2.30 mmol, 2.0 eq). The reaction was cooled to 0° C. and diethyl azodicarboxylate (0.220 mL, 1.40 mmol, 1.2 eq) was added. The cold bath was removed and the reaction was stirred overnight at rt. The reaction mixture was then poured into 0.1 N HCl solution and extracted with EtOAc. The combined organic layers were washed with brine, dried over $MgSO_4$ and concentrated in vacuo. The residue was purified by flash chromatography (20% EtOAc:hexane) to afford 4-{2-[3-Bromo-5-(8-phenyl-octylcarbamoyl)-3'-trifluoromethyl-biphenyl-2-yloxy]-ethoxy}-2-hydroxy-benzoic acid methyl ester $^1$H NMR (CDCl$_3$) δ 11.90 (s, 1H); 7.97 (d, 1H); 7.84–7.50 (m, 6H); 7.28–7.12 (m, 5H); 6.40 (m, 1H); 6.24 (m, 1H); 6.10 (bt, 1H); 4.12 (dd, 2H); 4.00 (m, 2H); 3.92 (s, 3H); 3.45 (dd, 2H); 2.59 (t, 2H); 1.60 (m, 4H); 1.33 (m, 8H).

Step 2

To a solution of 4-{2-[3-Bromo-5-(8-phenyl-octylcarbamoyl)-3'-trifluoromethyl-biphenyl-2-yloxy]-ethoxy}-2-hydroxy-benzoic acid methyl ester (1.16 mmol, 1 eq) in EtOH (20 mL) was added 1M NaOH (10 mL) and the reaction was heated at reflux 90 min. It was then cooled to rt, concentrated in vacuo, diluted with $H_2O$, and acidified with 2M HCl to pH 1. It was extracted with EtOAc, dried over $MgSO_4$ and concentrated in vacuo. The residue was purified by flash chromatography (30% EtOAc:Hexane+1% Formic Acid) to afford the title compound (0.607 g, 79%) as a white foam. $^1$H NMR (DMSO-d$_6$) δ 13.55 (bs, 1H); 11.49 (bs, 1H); 8.58 (t, 1H); 8.14 (d, 1H); 7.90–7.84 (m, 3H); 7.73–7.61 (m, 3H); 7.26–7.12 (m, 5H); 6.27–6.23 (m, 2H); 4.00 (m, 2H); 3.92 (m, 2H); 3.23 (dd, 2H); 2.52 (t, 2H); 1.52 (m, 4H); 1.28 (m, 8H); IR (KBr) 3400, 2950, 2850, 1660, 1620, 1550, 1450, 1420, 1330, 1220, 1160, 1120 cm$^{-1}$; mass spectrum [(−)ESI], m/z 726/728 (M−H)⁻; Anal. Calcd. for $C_{37}H_{37}F_3NO_6$: C, 60.99; H, 5.12; N, 1.92, Found: C, 60.32; H, 5.17; N, 1.83.

EXAMPLE 203

2-Hydroxy-4-[5'-(8-phenyl-octylcarbamoyl)-3,3"-bis-trifluoromethyl-[1,1';3'1"]terphenyl-2'-yloxysulfonyl]-benzoic Acid The title compound was prepared as an white foam (0.541 g, 78%) from 2'-Hydroxy-3,3"-bis-trifluoromethyl-[1,1';3'1"]terphenyl-5'-carboxylic acid (8-phenyl-octyl)-amide and 4-chlorosulfonyl-2-hydroxy-benzoic acid using a procedure similar to step 3 of Example 179. ¹H NMR (DMSO-d₆) δ 11.60 (bs, 2H); 8.70 (t, 1H); 7.94 (s, 2H); 7.88–7.80 (m, 4H); 7.69–7.57 (m, 5H); 7.26–7.10 (m, 5H); 6.68 (dd, 1H); 6.57 (d, 1H); 3.25 (dd, 2H); 2.52 (t, 2H); 1.53 (m, 4H); 1.28 (m, 8H); IR (KBr) 3400, 2950, 2840, 1690, 1640, 1600, 1550, 1460, 1380, 1320, 1280, 1200, 1170, 1120, 1080 cm⁻¹; mass spectrum [(−)ESI], m/z 812 (M−H)⁻; Anal. Calcd. for $C_{42}H_{37}F_6NO_7S$: C, 61.99; H, 4.58; N, 1.72, Found: C, 61.40; H, 4.80; N, 1.68.

EXAMPLE 204

4-[3-Bromo-5-(8-phenyl-octylcarbamoyl)-3'-trifluoromethyl-biphenyl-2-yloxymethyl]-2-methoxy-benzoic Acid The title compound was prepared as an white foam (0.400 g, 90%) from 5-Bromo-6-hydroxy-3'-trifluoromethyl-biphenyl-3-carboxylic acid (8-phenyl-octyl)-amide using a procedure similar to Example 199. ¹H NMR (DMSO-d₆) δ 12.50 (bs, 1H); 8.58 (t, 1H); 8.18 (d, 1H); 7.90 (d, 1H); 7.85 (m, 2H); 7.77 (d, 1H); 7.69 (t, 1H); 7.50 (d, 1H); 7.25–7.10 (m, 5H); 6.80 (d, 1H); 6.69 (dd, 1H); 4.63 (s, 2H); 3.70 (s, 3H) 3.24 (dd, 2H); 2.53 (t, 2H); 1.54 (m, 4H); 1.28 (m, 8H) IR (KBr) 3300, 2950, 2850, 1720, 1630, 1610, 1550, 1460, 1420, 1380, 1320, 1180, 1120 cm⁻¹; mass spectrum [(−)ESI], m/z 710 (M−H)⁻; Anal. Calcd. for $C_{37}H_{37}BrF_3NO_5$: C, 62.36; H, 5.23; N, 1.97, Found: C, 61.50; H, 5.75; N, 1.91.

EXAMPLE 205

5-Bromo-6-(1H-tetra-5-ylmethoxy)-3'-trifluoromethyl-biphenyl-3-carboxylic Acid (8-phenyl-octyl)-amide 5-bromo-6-(cyanomethoxy)-N-(8-phenyloctyl)-3'-(trifluoromethyl)[1,1'-biphenyl]-3-carboxamide prepared as an white foam (0.400 g, 90%) from 5-Bromo-6-hydroxy-3'-trifluoromethyl-biphenyl-3-carboxylic acid (8-phenyl-octyl)-amide and bromo acetonitrile using a procedure similar to step 1 of Example 198. ¹H NMR (CDCl₃) δ 8.00 (d, 1H); 7.83–7.58 (m, 5H); 7.28–7.10 (m, 5H); 6.09 (m, 1H); 4.40 (s, 2H); 3.43 (dd, 2H); 2.58 (t, 2H); 1.58 (m, 4H); 1.32 (m, 8H)

Step 2

To trimethyl aluminum (2 M in toluene) (0.380 mL, 0.76 mmol, 1.22 eq) was added azidotrimethylsilane (0.100 mL, 0.75 mmol, 1.2 eq) dropwise. The 5-bromo-6-(cyanomethoxy)-N-(8-phenyloctyl)-3'-(trifluoromethyl)[1,1'-biphenyl]-3-carboxamide (0.365 g, 0.62 mmol, 1 eq) was then added as a solution in toulene (1.5 mL). The reaction was heated at reflux for 7 days until TLC indicated consumption of most of the starting material. The reaction mixture turned partially solid. It was cooled to rt and partitioned between toluene and 6M HCl solution. The aqueous layer was extracted with EtOAc, the combined organics were dried over MgSO₄, and concentrated in vacuo. The residue was purified by flash chromatography (30% EtOAc:Hexane+1% Formic acid) to afford the title compound (0.150 g, 37%) as a light yellow foam. ¹H NMR (DMSO-d₆) δ 8.62 (t, 1H); 8.15 (d, 1H); 7.87 (d, 1H); 7.79–7.70 (m, 4H); 7.66–7.61 (t, 1H); 7.26–7.12 (m, 5H); 5.00 (s, 2H); 3.24 (dd, 2H); 2.52 (t, 2H); 1.52 (m, 4H); 1.28 (m, 8H); IR (KBr) 3330, 2950, 2850, 1620, 1550, 1460, 1320, 1170, 1120 cm⁻¹; mass spectrum [(+)APCI], m/z 630 (M+H)⁺; Anal. Calcd. for $C_{30}H_{31}BrF_3N_5O_2$: C, 57.15; H, 4.96; N, 11.11, Found: C, 55.24; H, 4.92; N, 10.50.

EXAMPLE 206

2'-(1H-Tetrazol-5-ylmethoxy)-3,3"-bis-trifluoromethyl-[1,1';3'1"]terphenyl-5'-carboxylic Acid (8-phenyl-octyl)-amide The title compound was prepared as an white foam (0.486 g, 84%) from 2'-hydroxy-3,3"-bis-trifluoromethyl-[1,1';3'1"]terphenyl-5'-carboxylic acid (8-phenyl-octyl)-amide using a procedure similar to Example 205. ¹H NMR (DMSO-d₆) δ 8.59 (t, 1H); 7.93–7.84 (m, 6H); 7.74–7.64 (m, 5H); 7.25–7.10 (m, 5H); 4.56 (s, 2H); 3.26 (dd, 2H); 2.53 (t, 2H); 1.52 (m, 4H); 1.26 (m, 8H); IR (KBr) 3400, 2950, 2850, 1620, 1550, 1460, 1330, 1260, 1220, 1080 cm⁻¹; mass spectrum [(+)APCI], m/z 696 (M+H)⁺; Anal. Calcd. for $C_{37}H_{38}F_6N_5O_2$: C, 63.88; H, 5.07; N, 10.07, Found: C, 61.94; H, 5.12; N, 9.75.

EXAMPLE 207

4-[3-Bromo-5-(8-phenyl-octylcarbamoyl)-3'-trifluoromethyl-biphenyl-2-yloxymethyl]-2-hydoxy-benzoic Acid Methyl Ester The title compound was prepared as a light yellow oil (0.361 g, 37%) from 4-[3-Bromo-5-(8-phenyl-octylcarbamoyl)-3'-trifluoromethyl-biphenyl-2-yloxymethyl]-2-methoxy-benzoic acid methyl ester using a procedure similar to Example 200. ¹H NMR (DMSO-d₆) δ 10.45 (s, 1H); 8.59 (bt, 1H); 8.18 (d, 1H); 7.90–7.58 (m, 6H); 7.25–7.10 (m, 5H); 6.70–6.60 (m, 2H); 4.60 (s, 2H); 3.88 (s, 3H); 3.24 (dd, 2H); 2.52 (t, 2H); 1.50 (m, 4H); 1.25 (m, 8H); IR (KBr) 3400, 2950, 2850, 1685, 1620, 1550, 1440, 1400, 1180, 1120 cm⁻¹; mass spectrum [(−)APCI], m/z 710 (M−H)⁻; Anal. Calcd. for $C_{37}H_{37}BrF_3NO_5$: C, 61.90; H, 5.05; N, 2.01, Found: C, 60.59; H, 5.09; N, 1.86.

EXAMPLE 208

4-[3-Bromo-5-(8-phenyl-octylcarbamoyl)-3'-trifluoromethyl-biphenyl-2-yloxymethyl]-2-hydroxy-benzoic Acid The title compound was prepared as a light yellow oil (0.202 g, 22%) from 4-[3-Bromo-5-(8-phenyl-octylcarbamoyl)-3'-trifluoromethyl-biphenyl-2-yloxymethyl]-2-methoxy-benzoic acid methyl ester using the procedure of Example 207. ¹H NMR (DMSO-d₆) δ 13.50 (bs, 1H); 11.20 (bs, 1H); 8.59 (bt, 1H); 8.16 (d, 1H); 7.90–7.62 (m, 6H); 7.25–7.10 (m, 5H); 6.64–6.58 (m, 2H); 4.60 (s, 2H); 3.23 (dd, 2H); 2.52 (t, 2H); 1.52 (m, 4H); 1.25 (m, 8H); IR (film) 3400, 2950, 2850, 1660, 1640, 1550, 1495, 1450, 1420, 1320, 1220, 1160, 1120, 1070 cm⁻¹; mass spectrum [(−)APCI], m/z 690 (M−H)⁻; Anal. Calcd. for $C_{36}H_{35}BrF_3NO_5$: C, 61.90; H, 5.05; N, 2.01, Found: C, 60.59; H, 5.09; N, 1.86.

EXAMPLE 209

2'-Amino-3,3"-bis-trifluoromethyl-[1,1';3'1"] terphenyl-5'-carboxylic Acid (8-phenyl-octyl)-amide Step 1

2'-Amino-3,3"-bis-trifluoromethyl-[1,1';3'1"]terphenyl-5'-carboxylic acid was prepared as an off white solid (0.992 g, 94%) from 4-amino-3,5-diiodobenzoic acid and 3-trifluoromethylphenyl boronic acid using a procedure similar to step 1 of Example 175. $^1$H NMR (CDCl$_3$) δ 7.90 (s, 2H); 7.78 (m, 2H); 7.74–7.60 (m, 6H); 4.24 (bs, 2H).

Step 2

To a solution of 2'-amino-3,3"-bis-trifluoromethyl-[1,1';3'1"]terphenyl-5'-carboxylic acid (0.113 g, 0.27 mmol 1 eq) in DMF (2.7 mL) was added 1,1'-carbonyldiimidazole (0.120 g, 0.74 mmol 2.7 eq) and phenyl octylamine (0.070 mL, 0.35 mmol, 1.3 eq) and the reaction was stirred overnight at rt. Additional 1,1'-carbonyldiimidazole (0.124 g, 0.76 mmol 2.8 eq) and phenyl octylamine (0.070 mL, 0.35 mmol, 1.3 eq) was added and stirring was continued overnight. The solids were then filtered off and washed with EtOAc. The filtrate was washed with saturated NaHCO$_3$ solution, 0.1 N HCl and brine. It was dried over MgSO$_4$ and concentrated in vacuo. The residue was purified by flash chromatography (20% EtOAc:Hexane+1% Formic acid) to afford the title compound (0.150 g, 37%) as a light yellow oil. $^1$H NMR (DMSO-d$_6$ δ 8.20 (t, 1H); 7.81–7.70 (m, 8H); 7.61 (s, 2H); 7.25–7.12 (m, 5H); 4.87 (s, 2H); 3.19 (dd, 2H); 2.52 (t, 2H); 1.50 (m, 4H); 1.28 (m, 8H); IR (KBr) 3540, 3350, 2950, 2850, 1620, 1545, 1480, 1420, 1325, 1180, 1120, 1110, 1080 cm$^{-1}$; mass spectrum [(+)APCI], m/z 613 (M+H)$^+$; Anal. Calcd. for C$_{35}$H$_{34}$F$_6$N$_2$O: C, 68.62; H, 5.59; N, 4.57, Found: C, 67.66; H, 5.96; N, 4.33.

EXAMPLE 210

4-[2-Bromo-4-(8-phenyl-octylcarbamoyl)-phenoxysulfonyl]-2-hydroxy-benzoic Acid

Step 1

3-Bromo-4-hydroxy-N-(8-phenyloctyl)benzamide was prepared as a yellow oil (1.15 g, 61%) from 3-bromo-4-hydroxybenzoic acid and phenyl octylamine using a procedure similar to Example 191. $^1$H NMR (CDCl$_3$) δ 7.92 (d, 1H); 7.70 (dd, 1H); 7.27–7.10 (m, 5H); 7.04 (d, 1H); 6.65 (t, 1H); 6.18 (bs; 1H); 3.41 (dd, 2H); 2.48 (t, 2H); 1.58 (m, 4H); 1.32 (m, 8H).

Step 2

The title compound was prepared as a white solid (0.388 g, 40%) from 3-bromo-4-hydroxy-N-(8-phenyloctyl) benzarnide and 4-chlorosulfonyl-2-hydroxy-benzoic acid using a procedure similar to step 3 of Example 179. $^1$H NMR (DMSO-d$_6$) δ 8.57 (bt, 1H); 8.50 (d, 1H); 7.99 (dd, 1H); 7.86 (dd, 1H); 7.38–7.32 (m, 3H); 7.26–7.10 (m, 5H); 3.50 (bs, 2H); 3.20 (dd, 2H); 2.53 (t, 2H); 1.50 (m, 4H); 1.28 (m, 8H); IR (KBr) 3480, 3350, 2950, 2850, 1900, 1690, 1630, 1600, 1580, 1540, 1480, 1450, 1360, 1285, 1250, 1205, 1180, 1110, 1080, 1040, 930, 860 cm$^{-1}$; mass spectrum [(+)APCI], m/z 604 (M+H)$^+$; Anal. Calcd. for C$_{28}$H$_{30}$BrNO$_7$S: C, 55.63; H, 5.00; N, 2.32, Found: C, 54.33; H, 5.11; N, 1.95.

EXAMPLE 211

2-Hydroxy-4-{2-[5'-(8-phenyl-octylcarbamoyl)-3,3"-bis-trifluoromethyl-[1,1';3',1"]terphenyl-2'-yloxy]-ethoxy}-benzoic Acid Step 1

N-(8-Phenyl-octyl)-4-(2-bromo-ethoxy)-3,5-bis(m-trifluoromethylphenyl) benzamide was prepared as an colorless oil (1.48 g, 95%) from N-(8-phenyl-octyl)-3,5-bis(m-trifluoromethylphenyl)-4-(2-hydroxyethoxy)-benzamide using a procedure similar to step 1 of Example 185. $^1$H NMR (CDCl$_3$) δ 7.95–7.78 (m, 6H); 7.72–7.54 (m, 4H); 7.32–7.10 (m, 5H); 6.18 (bt, 1H); 3.45 (m, 4H); 2.98 (t, 2H); 2.55 (t, 2H); 1.60 (m, 4H); 1.30 (m, 8H).

Step 2

To a solution of N-(8-phenyl octyl)-4-(2-bromo-ethoxy)-3,5-bis(m-trifluoromethylphenyl)benzamide (1.48 g, 2.05 mmol, 1 eq) in acetone (21 mL) was added K$_2$CO$_3$ (1.42 g, 10.25 mmol, 5 eq) and methyl 2,4-dihydroxybenzoate (0.340 g, 2.05 mmol, 1.0 eq). The reaction was heated at reflux for overnight, cooled to rt and concentrated in vacuo. The residue was partitioned between EtOAc and brine, dried over MgSO$_4$ and concentrated in vacuo. The residue was purified by flash chromatography (30% EtOAc:hexane) to afford 2-hydroxy-4-{2-[5'-(8-phenyl-octylcarbamoyl)-3,3"-bis-trifluoromethyl-[1,1';3',1"]terphenyl-2'-yloxy]-ethoxy}-benzoic acid methyl ester (0.98 g, 60%) as a colorless oil. $^1$H NMR (CDCl$_3$) δ 10.90 (s, 1H); 7.92–7.78 (m, 7H); 7.66–7.50 (m, 4H); 7.27–7.12 (m, 5H); 6.18–6.10 (m, 3H); 3.92 (s, 3H); 3.66–3.40 (m, 6H); 2.58 (t, 2H); 1.60 (m, 4H); 1.28 (m, 8H).

Step 3

To a solution of 2-hydroxy-4-{2-[5'-(8-phenyl-octylcarbamoyl)-3,3"-bis-trifluoromethyl[1,1';3',1"] terphenyl-2'-yloxy]-ethoxy}-benzoic acid methyl ester (0.980 g, 1.21 mmol, 1 eq) in EtOH (20 mL) was added 50% NaOH (10 mL) and the reaction was heated at reflux overnight. It was cooled to rt, diluted with H$_2$O, and acidified with 2M HCl to pH 1. It was extracted with EtOAc, dried over MgSO$_4$ and concentrated in vacuo. The residue was purified by flash chromatography (30% EtOAc:hexane) to afford the title compound (0.92 g, 96%) as a white foam. $^1$H NMR (DMSO-d$_6$) δ 13.60 (bs, 1H); 11.40 (bs, 1H); 8.59 (bt, 1H); 8.00–7.92 (m, 6H); 7.74–7.65 (m, 4H); 7.56 (d, 1H); 7.25–7.10 (m, 5H); 6.08–6.00 (m, 2H); 3.66 (bd, 2H); 3.52 (bd, 2H); 3.25 (dd, 2H); 2.52 (t, 2H); 1.53 (m, 4H); 1.27 (m, 8H); IR (KBr) 3350, 2950, 2850, 1670, 1620, 1550, 1500, 1460, 1320, 1230, 1220, 1160, 1120, 1095, cm$^{-1}$; mass spectrum [(-)APCI], m/z 792 (M-H)$^-$; Anal. Calcd. for C$_{44}$H$_{41}$F$_6$NO$_6$: C, 66.58; H, 5.21; N, 1.76, Found: C, 64.86; H, 5.22; N, 1.68.

EXAMPLE 212

{3-Bromo-5-[methyl-(8-phenyl-octyl)-carbamoyl]-3'-trifluoromethyl-biphenyl-2-yloxy}-acetic Acid Step 1

To a solution of 8-phenyl octanoic acid (28.6 g, 129.8 mmol, 1 eq) in CH$_2$Cl$_2$ (100 mL) cooled to 0° C. was added oxalyl chloride (17 mL, 195 mmol, 1.5 eq) dropwise via an addition funnel over 30 minutes. Upon the completion of the addition, the ice bath was removed and the reaction was stirred at rt for 2 h. It was then heated at reflux for 30 minutes. The reaction was cooled to rt and concentrated in vacuo to afford a yellow oil. It was added as a solution in Et$_2$O (100 mL) to a solution of condensed methyl amine (~20 mL) in Et$_2$O (200 mL) at −78° C. Immediately, a white precipitate formed. The cold bath was removed and the reaction was allowed to stir overnight warming to rt under a stream of N$_2$. The residue was washed with Et$_2$O and concentrated to afford N-methyl-8-phenyloctanamide (25.2 g, 83%) as a yellow-white solid. $^1$H NMR.(CDCl$_3$) δ 7.68–7.10 (m, 5H); 5.42 (bs, 1H); 3.80 (m, 3H); 2.60 (m, 2H); 2.18 (m, 2H); 1.60 (m, 4H); 1.30 (m, 8H).

Step 2

To a solution of N-methyl-8-phenyloctanamide (25.2 g, 108.0 mmol, 1 eq) in THF (500 mL) cooled to 0° C. was added lithium aluminum hydride (12.3 g, 466.8 mmol, 4.3 eq) portionwise over 20 minutes. The cold bath was removed and the reaction was stirred at rt 3 hours. The reaction was then heated at reflux for 2-hours. It was then cooled to rt and quenched by the slow addition of H$_2$O (30 mL). EtOAc (300 mL) was added, followed by 2 M NaOH (40 mL). The solids were then filtered off and washed with EtOAc. The filtrate was dried over MgSO$_4$ and concentrated in vacuo to afford N-methyl-N-(8-phenyloctyl)amine (19.7 g, 83%) as a light yellow oil. $^1$H NMR (CDCl$_3$) δ 7.30–7.14 (m, 5H); 2.63–2.52 (m, 4H); 2.43 (s, 3H); 2.05 (s, 1H); 1.62 (m, 4H); 1.30 (m, 8H).

Step 3

5-bromo-6-(2-hydroxyethoxy)-N-methyl-N-(8-phenyloctyl)[1,1'-biphenyl]-3-carboxamide was prepared as a colorless oil (0.200 g, 56%) from 3-bromo-5-(m-trifluoromethylphenyl)-4-(2-hydroxyethoxy)-benzoic acid ethyl ester and N-methyl-N-(8-phenyloctyl)amine using a procedure similar to step 2 of Example 175. $^1$H NMR (CDCl$_3$) δ 7.87–7.54 (m, 5H); 7.38–7.12 (m, 6H); 3.65 (m, 4H); 3.50 and 3.03 (2bt, 2H); 3.03 (2s, 3H); 2.58 (m, 2H); 1.98 (bs, 1H); 1.60 (m, 4H); 1.40–1.22 (m, 8H).

Step 4

The title compound was prepared as a foam (0.108 g, 44%) from 5-bromo-6-(2-hydroxyethoxy)-N-methyl-N-(8-phenyloctyl)[1,1'-biphenyl]-3-carboxamide using a procedure similar to step 3 of Example 175. $^1$H NMR (DMSO-d$_6$) δ 12.87 (bs, 1H); 7.92–7.62 (m, 5H); 7.43 (m, 1H); 7.26–7.08 (m, 5H); 4.12 (s, 2H); 3.40 and 3.18 (2m, 2H); 2.90 (s, 3H); 2.52 (m, 2H); 1.53 (m, 4H); 1.30–1.12 (m, 8H) IR (film) 2930, 2850, 1735, 1640, 1600, 1495, 1400, 1270, 1150, 1130 cm$^{-1}$; mass spectrum [(–)ESI], m/z 618/620 (M–H)$^-$; Anal. Calcd. for C$_{31}$H$_{33}$BrF$_3$NO$_4$: C, 60.01; H, 5.36; N, 2.26, Found: C, 59.96; H, 5.43; N, 2.22.

EXAMPLE 213

{3,3"-Dichloro-4,4"difluoro-5'-[methyl-(8-phenyl-octyl)-carbamoyl]-[1,1';3',1"terphenyl-2'yloxy}-acetic Acid Step 1

N-Methyl-N-(8-phenyloctyl)-3,5-bis[m-chloro-p-fluoro-phenyl)-4-(2-hydroxyethoxy)-benzamide was prepared as a white solid (0.313 g, 78%) from 3,5-bis[(m-chloro)-(p-fluoro)-phenyl)-4-(2-hydroxyethoxy)-benzoic acid ethyl ester and N-methyl-N-(8-phenyloctyl)amine using a procedure similar to step 2 of Example 175. $^1$H NMR (CDCl$_3$) δ 7.71–7.66 (dd, 2H); 7.52–7.45 (m, 2H); 7.36 (m, 2H); 7.30–7.12 (m, 7H); 3.52 and 3.28 (2bt, 2H); 3.27 (m, 4H); 3.04 (2s, 3H); 2.58 (m, 2H); .160 (m, 4H); 1.42–1.10 (m, 9H).

Step 2

The title compound was prepared as a white foam (0.177 g, 62%) from N-methyl-N-(8-phenyloctyl)-3,5-bis[(m-chloro)-(p-fluoro)-phenyl)-4-(2-hydroxyethoxy)-benzamide using a procedure similar to step 3 of Example 175. $^1$H NMR (DMSO-d$_6$) δ 12.60 (bs, 1H); 7.82 (d, 2H); 7.62–7.56 (m, 2H); 7.51–7.32 (m, 4H); 7.26–7.06 (m, 5); 3.82–3.64 (2s, 2H); 3.40 and 3.24 (2m, 2H); 2.94 (2s, 3H); 2.52 (m, 2H); 1.55 (m, 4H); 1.33–1.00 (m, 8H); IR (KBr) 3450, 2955, 2860, 1750, 1640, 1600, 1500, 1440, 1400, 1375, 1260, 1150, 1060 cm$^{-1}$; mass spectrum [(+)ESI], m/z 654 (M+H)$^+$; Anal. Calcd. for C$_{36}$H$_{35}$Cl$_2$F$_2$NO$_4$: C, 66.06; H, 5.39; N, 2.14, Found: C, 65.30; H, 5.44; N, 2.09.

EXAMPLE 214

[5-Methyl-(8-phenyl-octyl)-carbamoyl]-3,3"-bis-trifluoromethyl-[1,1';3',1"terphenyl-2'yloxy}-acetic Acid Step 1

N-methyl-N-(8-phenyloctyl)-3,5-bis(m-trifluoromethylphenyl)-4-(2-hydroxyethoxy)-benzarnide was prepared as a white solid (0.238 g, 67%) from 3,5-bis-(m-trifluoromethylphenyl)-4-(2-hydroxyethoxy)-benzoic acid ethyl ester and N-methyl-N-(8-phenyloctyl)amine using a procedure similar to step 2 of Example 175. $^1$H NMR (CDCl$_3$) δ 7.94 (s, 2H); 7.84 (d, 2H); 7.68–7.56 (m, 4H); 7.44 (s, 2H); 7.30–7.12 (m, 5H); 3.24 (t, 2H); 3.52 and 3.33 (2bt, 2H); 3.40 (t, 2H); 3.08 (2s, 3H); 2.58 (bt, 2H); 1.60 (m, 4H); 1.42–1.12 (m, 8H).

Step 2

The title compound was prepared as a foam (0.149 g, 57%) from N-methyl-N-(8-phenyloctyl)-3,5-bis(m-trifluoromethylphenyl)-4-(2-hydroxyethoxy)-benzamide using a procedure similar to step 3 of Example 175. $^1$H NMR (DMSO-d$_6$) δ 12.60 (bs, 1H); 7.96 (s, 2H); 7.90 (d, 2H); 7.78–7.65 (m, 4H); 7.46 (m, 2H); 7.26–7.08 (m, 5H); 3.78 (s, 2H); 3.41 and 3.28 (2m, 2H); 2.95 (s, 3H); 2.50 (m, 2H); 1.55 (m, 4H); 1.30–1.00 (m, 8H) IR (KBr) 3400, 2950, 2850, 1760, 1740, 1630, 1600, 1490, 1450, 1405, 1320, 1170, 1160, 1120, 1080. 1050 cm$^{-1}$; mass spectrum [(+)ESI], m/z 686 (M+H)$^+$; Anal. Calcd. for C$_{38}$H$_{37}$F$_6$NO$_4$: C, 66.56; H, 5.44; N, 2.4, Found: C, 65.83; H, 5.50; N, 1.99.

EXAMPLE 215

[5'-(3-Benzyloxy-benzylcarbamoyl)-3,3"-bis-trifluoromethyl-[1,1';3',1"]terphenyl-2'-yloxy]-acetic Acid Step 1

4-(Benzyloxy)benzylamine (3.00 g, 67%) was prepared from 4-(benzyloxy)benzoic acid using a procedure similar to steps 1 and 2 of Example 212. $^1$H NMR (CDCl$_3$) δ 8.10 (s, 4H); 7.38–7.22 (m, 5H); 6.90 (d, 2H); 4.98 (s, 2H); 4.00 (s, 2H).

Step 2

2'-Hydroxy-3,3"-bis-trifluoromethyl-[1,1';3'1"]terphenyl-5'-carboxylic acid (3-benzyloxy-benzylcarbamoyl)-amide (0.460 g, 72%) was prepared from 3,5-bis-(m-trifluoromethylphenyl)-4-(hydroxy)-benzoic acid ethyl ester and 4-(benzyloxy)benzylamine using a procedure similar to Example 190. $^1$H NMR (CDCl$_3$) δ 7.78–7.54 (m, 10H); 7.48–7.22 (m, 7H); 6.95 (d, 2H); 6.32 (m, 1H); 5.52 (s, 1H); 5.05 (s, 2H); 4.40 (d, 2H).

Step 3

[5'-(3-Benzyloxy-benzylcarbamoyl)-3,3"-bis-trifluoromethyl-[1,1';3',1"]terphenyl-2'-yloxy]-acetic acid methyl ester (0.513 g, 92%) was prepared from 2'-hydroxy-3,3"-bis-trifluoromethyl-[1,1';3'1"]terphenyl-5'-carboxylic acid (3-benzyloxy-benzylcarbamoyl)-amide and methyl bromoacetic acid using a procedure similar to step 1 of Example 192. $^1$H NMR (CDCl$_3$) δ 7.92 (m, 6H); 7.70–7.52 (m, 5H); 7.44–7.21 (m, 6H); 6.96 (d, 2H); 6.35 (m, 1H); 5.08 (s, 2H); 4.60 (d, 2H); 3.80 (s, 2H); 3.45 (s, 3H).

Step 4

The title compound was prepared as a white foam (0.286 g, 74%) from [5'-(3-benzyloxy-benzylcarbamoyl)-3,3"-bis-trifluoromethyl-[1,1';3',1"]terphenyl-2'-yloxy]-acetic acid methyl ester using a procedure similar to step 2 of Example 192. $^1$H NMR (DMSO-d$_6$) δ 12.60 (bs, 1H); 9.50 (bt, 1H); 8.00–7.92 (m, 6H); 7.80–7.68 (m, 4H); 7.44–7.22 (m, 7H), 6.98–6.94 (m, 2H); 5.08 (s, 2H); 4.42 (s, 2H); 3.81 (s, 2H)

IR (KBr) 3350, 2950, 1720, 1630, 1610, 1540, 1510, 1460, 1320, 1230, 1210, 1180, 1160, 1120, 1080 cm$^{-1}$; mass spectrum [(−)ESI], m/z 678 (M−H)$^-$; Anal. Calcd. for $C_{37}H_{27}F_6NO_5$: C, 65.39; H, 4.00; N, 2.06, Found: C, 63.35; H, 4.31; N, 2.59.

EXAMPLE 216

(2-(R)-3-Phenyl-2-[5-(8-phenyl-octylcarbamoyl)-4'-trifluromethyl-biphenyl-2-yloxy]-propionic Acid Step 1 3-Iodo-4-hydroxy-benzoic Acid To a stirring solution of 4-hydroxy-benzoic acid (6.91 g, 50.03 mmol) in dry acetonitrile (250 mL) at −20° C. under an atmosphere of N$_2$ was added HBF$_4$·Et$_2$O (10.50 g, 9.50 mL, 55.00 mmol) dropwise via syringe. The solution was stirred at 0° for 0.5 hours at which time solid N-iodosuccinimide (13.5 g, 60 mmol) was added at one time. The solution was left to stir for 16 hours and then filtered to remove precipitated succinimide. The solution was diluted with water (500 mL) and extracted with ethyl acetate (2×250 mL). The organic portions were combined and washed with 10% sodium bisulfite (250 mL), water (2×250 mL) and saturated aqueous NaCl (250 mL). The solvent was removed in vacuo to yield 8.76 g of crude solid. The crude solid was purified by column chromatography (6:4:0.1 hexane:ethyl acetate:formic acid) to yield 7.54 g (57%) of the desired product as white crystals. $^1$H NMR (DMSO-d$_6$) δ 12.74 (br s, 1H), 11.18 (s, 1H), 8.20 (s, 8.20, 1H), 7.79 (d, 1H), 6.94 (d, 1H).

Step 2 N-(8-Phenyloctyl)-3-iodo-4-hydroxybenzamide

To a stirring solution of 3-iodo-4-hydroxy-benzoic acid (2.64 g, 10.00 mmol) in fresh DMF (50 mL) at ambient temperature under an atmosphere of N$_2$ was added EDC (2.11 g, 11.00 mmol), HOBt (1.49 g, 11.00 mmol) and DIPEA (1.94 g, 2.61 mL, 15.00 mmol). The solution was allowed to stir at ambient temperature for 1 hour at which time 8-phenyl-octylamine (2.46 g, 2.39 mL, 12 mmol) was added at one time. The solution was allowed to stir for an additional 4 hours at which time the it was diluted with water (250 mL) and extracted with ethyl acetate (250 mL). The organic phase was washed with water (2×250 mL), saturated aqueous NaHCO$_3$ (250 mL) and saturated aqueous NaCl (250 mL). The solvent was removed in vacuo to yield 4.62 g of crude oil. The crude oil was purified by column chromatography (7:3 hexane:ethyl acetate) to yield 4.47 g (99%) of the desired product as a clear oil, which crystallized upon standing. $^1$H NMR (CDCl$_3$) δ 8.19 (dd, 2H), 7.60 (dd, 1H), 7.20 (m, 4H), 6.97 (dd, 1H), 6.32 (t, 1H), 3.39 (q, 2H), 2.57 (t, 2H), 1.58 (m, 4H), 1.30 (m, 8H).

Step 3 2-(R)-3-Phenyl-2-[2-iodo-4-(8-phenyl-octylcarbamoyl)-phenyl-2-yloxy]-methyl Propionate To a stirring solution of N-(8-phenyloctyl)-3-iodo-4-hydroxybenzamide (4.47 g, 9.90 mmol), L-phenyl lactic acid methyl ester (2.68 g, 15.00 mmol) and triphenylphosphine (3.91 g, 15.00 mmol) in freshly distilled THF (250 mL) at 0° C. under an atmosphere of N$_2$ was added DEAD (2.60 g, 2.35 mL, 15.00 mmol) dropwise via syringe. The solution was left to stir for 4 hours at which time it was diluted with water (500 mL) and extracted with ethyl acetate (2×250 mL). The organic portions were combined and washed with water (2×250 mL) and saturated aqueous NaCl (250 mL). The solvent was removed in vacuo to yield 5.27 g of crude oil. The crude oil was purified by column chromatography (7:3 hexane:ethyl acetate) to yield 4.34 g (71%) of the desired product as a clear oil, which crystallized upon standing. $^1$H NMR (DMSO-d$_6$) δ 8.36 (t, 1H), 7.55 (m, 13H), 5.30 (dd, 1H), 3.64 (s, 3H), 3.23 (m, 4H), 2.55 (t, 2H), 1.50 (m, 4H), 1.27 (m, 8H).

Step 4 2-(R)-3-Phenyl-2-[5-(8-phenyl-octylcarbamoyl)-4'-trifluoromethyl-biphenyl-2-yloxy]-propionic Acid A 25 mL round bottom flask was charged with 2-(R)-3-Phenyl-2-[2-iodo-4-(8-phenyl-octylcarbamoyl)-phenyl-2-yloxy]-methyl propionate (0.225 g, 0.37 mmol), 4-trifluoromethylbenzeneboronic acid (0.106 g, 0.56 mmol), 2N aqueous potassium carbonate (0.55 mL, 1.10 mmol), [1,1'-bis(diphenylphosphino)ferrocene]-dichloropalladium (II) complex with dichloromethane (1:1) (0.016 g, 0.019 mmol) and freshly distilled dioxane (10 mL) and heated to 70° C. with stirring for 16 hours. The reaction mixture was then cooled and diluted with ethyl acetate (150 mL), washed with water (2×150 mL), saturated aqueous sodium bicarbonate (150 mL), saturated aqueous odium chloride (150 mL) and the organic phase was filtered through celite. The solvent as removed in vacuo to yield 0.251 g of crude oil. The crude oil was purified by column chromatography (8:2 hexane:ethyl acetate) to yield 0.172 g of the desired intermediate which was then dissolved in 2:1 tetrahydrofuran/methanol (10 mL) and stirred with 1N aqueous KOH (1.1 mL, 1.10 mmol) for 1 hour. The solution was acidified to pH 2 with 1N HCl and filtered. The solvent was removed in vacuo to yield 0.142 g of crude solid which was subjected to column chromatography (4:6:0.1 hexane:ethyl acetate::formic acid). Solvent was removed in vacuo to yield 0.120 g (53%) of the desired product as a white solid: mp 78–80° C.; $^1$H NMR (DMSO-d$_6$) δ 8.33 (t, 1H), 7.41 (m, 17H), 5.20 (dd, 1H), 3.21 (m, 4H), 3.06 (m, 1H), 2.53 (m, 1H), 1.50 (m, 4H), 1.26 (m, 8H); IR (KBr) 3450, 2930, 2850, 1740, 1620, 1600, 1560, 1490, 1320, 1160, 1130, 1070, 700 cm$^{-1}$; mass spectrum [(−) APCI]m/z 616 [(M−H)$^-$]; Anal. Calcd. for $C_{37}H_{38}F_3NO_4$·0.25 H$_2$O: C, 71.42; H, 6.24; N, 2.25; Found: C, 71.47; H, 6.66; N, 2.18.

EXAMPLE 217

2-(R)-3-Phenyl-2-[4'-chloro-5-(8-phenyl-octylcarbamoyl)-biphenyl-2-yloxy]-propionic Acid In a manner similar to Example 216, Step 4, the title compound (0.2 10 g, 36%) was prepared from 2-(R)-3-Phenyl-2-[2-iodo-4-(8-phenyl-octylcarbamoyl)-phenyl-2-yloxy]-methyl propionate (0.614 g, 1.00 mmol) and 4-chlorobenzeneboronic acid (0.188 g, 1.20 mmol): mp 99–100° C.; $^1$H NMR (DMSO-d$_6$) δ 8.33 (t, 1H), 7.36 (m, 17H), 5.18 (dd, 1H), 3.27 (m, 4H), 3.05 (m, 1H), 2.53 (m, 1H), 1.51 (m, 4H), 1.25 (m, 8H); IR (ATR solid) 3350, 2940, 2870, 1720, 1600, 1560, 1500, 1480, 1200, 1070, 830, 700 cm$^-$; mass spectrum [(−) APCI] m/z 582 [(M−H)$^-$]; Anal. Calcd. for $C_{36}H_{38}ClNO_4$·0.5 H$_2$O: C, 72.90; H, 6.63; N, 2.36; Found: C, 72.92; H, 6.43; N, 2.35.

EXAMPLE 218

2-(R)-3-Phenyl-2-[4'-fluoro-5-(8-phenyl-octylcarbamoyl)-biphenyl-2-yloxy]-propionic Acid In a manner similar to Example 216, Step 4, the title compound (0.356 g, 61%) was prepared from 2-(R)-3-Phenyl-2-[2-iodo-4-(8-phenyl-octylcarbamoyl)-phenyl-2-yloxy]-methyl propionate (0.614 g, 1.00 mmol) and 4-fluorobenzeneboronic acid (0.168 g, 1.20 mmol): mp 105–106° C.; $^1$H NMR (DMSO-d$_6$) δ 8.33 (t, 1H), 7.41 (m, 17H), 5.20 (dd, 1H), 3.21 (m, 4H), 3.06 (m, 1H), 2.53 (m, 1H), 1.50 (m, 4H), 1.26 (m, 8H); IR (ATR solid) 3350, 2940, 2870, 1720, 1600, 1560, 1490, 1220, 1200, 1080, 840, 700 cm$^{-1}$; mass spectrum [(+) APCI] m/z 568 [(M+H)$^+$]; Anal. Calcd. for $C_{36}H_{38}FNO_4$·0.5 H$_2$O: C, 74.98; H, 6.82; N, 2.43; Found: C, 75.20; H, 6.72; N, 2.41.

EXAMPLE 219

2-(R)-3-Phenyl-2-[4'-methoxy-5-(8-phenyl-octylcarbamoyl)-biphenyl-2-yloxy]-propionic Acid In a manner similar to Example 216, Step 4, the title compound (0.225 g, 39%) was prepared from 2-(R)-3-Phenyl-2-[2-iodo-4-(8-phenyl-octylcarbamoyl)-phenyl-2-yloxy]-methyl propionate (0.614 g, 1.00 mmol) and 4-methoxybenzeneboronic acid (0.182 g, 1.20 mmol) and isolated as a clear oil: $^1$H NMR (DMSO-$d_6$) δ 8.31 (t, 1H), 7.32 (m, 17H), 5.13 (dd, 1H), 3.81 (s, 3H), 3.25 (m, 4H), 3.05 (m, 1H), 2.54 (m, 1H), 1.51 (m, 4H), 1.26 (m, 8H); IR (ATR solid) 2920, 2850, 1730, 1600, 1480, 1240, 1180, 840, 700 cm$^{-1}$; mass spectrum [(−) APCI] m/z 578 [(M−H)$^-$]; Anal. Calcd. for $C_{37}H_{41}NO_5 \cdot 0.5\ H_2O$: C, 75.48; H, 7.19; N, 2.37; Found: C, 75.36; H, 7.16; N, 2.38.

EXAMPLE 220

2-(R)-3-Phenyl-2-[5-(8-phenyl-octylcarbamoyl)-4'-trifluoromethoxy-biphenyl-2-yloxy]-propionic Acid In a manner similar to Example 216 Step 4, the title compound (0.163 g, 26%) was prepared from 2-(R)-3-Phenyl-2-[2-iodo-4-(8-phenyl-octylcarbamoyl)-phenyl-2-yloxy]-methyl propionate (0.614 g, 1.00 mmol) and 4-trifluoromethoxybenzeneboronic acid (0.247 g, 1.20 mmol) and isolated as a clear oil: $^1$H NMR (DMSO-$d_6$) δ 8.33 (t, 1H), 7.37 (m, 17H), 5.17 (dd, 1H), 3.25 (m, 4H), 3.05 (m, 1H), 2.53 (m, 1H), 1.51 (m, 4H), 1.25 (m, 8H); IR (ATR solid) 2930, 2850, 1730, 1600, 1490, 1250, 1230, 1160, 1080, 700; mass spectrum [(+) ESI] m/z 634 ([M+H]$^+$); Anal. Calcd. for $C_{37}H_{38}F_3NO_5 \cdot 0.25\ H_2O$: C, 69.63; H, 6.08; N, 2.19; Found: C, 69.55; H, 5.89; N, 2.18.

What is claimed is:

1. A compound of formula I having the structure

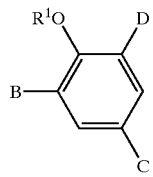

(I)

wherein:

B is aryl;

D is halogen or aryl;

$R^1$ is hydrogen, alkyl of 1–6 carbon atoms, —$SO_2Ph(OH)(CO_2H)$, —$CH(R^2)W$, —$CH_2CH_2Y$, or —$CH_2CH_2CH_2Y$;

$R^2$ is —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), or —$CH_2$(3-pyridyl);

W is —$CO_2R^3$, —$CONHOH$, —$CN$, —$CONHR^3$, aryl, heteroaryl, —$CHO$, —$CH=NOR^3$, or —$CH=NHNHR^3$;

Y is —W, —$OCH_2CO_2R^3$, aryl, heteroaryl, —$C(=NOH)NH_2$, —$OR^3$, —$O(C=O)NR^4R^5$, —$NR^3(C=O)OR^3$, —$NR^3(C=O)NR^4R^5$, or —$NR^4R^5$;

$R^3$ is hydrogen or alkyl of 1–6 carbon atoms;

$R^4$ and $R^5$ are each, independently, hydrogen, or alkyl of 1–6 carbon atoms or $R^4$ and $R^5$ are, together, —$(CH_2)_n$—, or —$CH_2CH_2XCH_2CH_2$—;

X is O, S, SO, $SO_2$, $NR^3$, or $CH_2$;

n is 2 to 5;

C is —$CONR^6R^7$;

$R^6$ and $R^7$ are each, independently, hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —$(CH_2CH_2O)_nCH_3$, —$(CH_2)_mA$ or $R^6$ and $R^7$ are, together, —$(CH_2)_p$—, —$(CH_2)_2N(CH_3)(CH_2)_4$—, —$(CH_2)_2N(R^8)(CH_2)_2$—, or —$(CH_2)_2CH(R^8)$-$(CH_2)_2$— with the proviso that at least one of $R^1$, $R^6$ or $R^7$ is heteroaryl;

$R^8$ is hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —$(CH_2CH_2O)_nCH_3$, —$(CH_2CH_2O)_nCH_3$, or —$(CH_2)_mA$;

A is aryl, heteroaryl, aryloxy, heteroaryloxy, arylthio, heteroarylthio, arylsulfoxy, heteroarylsulfoxy, arylsulfonyl, heteroarylsulfonyl, —$CHF_2$, —$CH_2F$, —$CF_3$, —$(CH_2CH_2O)_nCH_3$, —$(CH_2CH_2O)_nCH_3$, —$CO_2R^3$, —$O(C=O)NR^6R^7$, aralkyl or heteroaralkyloxy;

m is 2 to 16;

p is 2 to 12;

or a pharmaceutically acceptable salt thereof.

2. The compound according to claim 1, wherein is —$CO_2H$ or a pharmaceutically acceptable salt thereof.

3. The compound according to claim 2, wherein D is aryl or halogen or a pharmaceutically acceptable salt thereof.

4. The compound according to claim 1, which is [3,3"-Dichloro-5'-(2-pyridin-2-yl-ethylcarbamoyl)-[1,1';3'1"]terphenyl-2'-yloxy]acetic acid or a pharmaceutically acceptable salt thereof.

5. The compound according to claim 1, which is [3-Bromo-3'-chloro-5-(2-pyridin-2-yl-ethylcarbamoyl)-biphenyl-2-yloxy]acetic acid or a pharmaceutically acceptable salt thereof.

6. The compound according to claim 1, which is [3"-Chloro-5'-(2-pyridin-2-yl-ethylcarbamoyl)-3-trifluoromethyl-[1,1';3'1"]-terphenyl-2'-yloxy]acetic acid or a pharmaceutically acceptable salt thereof.

7. The compound according to claim 1, which is [4"-Methoxy-5'-(2-pyridin-2-yl-ethylcarbamoyl)-3-trifluoromethyl-[1,1';3'1"]-terphenyl-2'-yloxy]acetic acid or a pharmaceutically acceptable salt thereof.

8. The compound according to claim 1, which is [2-Fluoro-4"-methoxy-5'-(2-pyridin-2-yl-ethylcarbamoyl)-[1,1';3'1"]-terphenyl-2'-yloxy]acetic acid or a pharmaceutically acceptable salt thereof.

9. The compound according to claim 1, which is [3-Bromo-2'-fluoro-5-(2-pyridin-2-yl-ethylcarbamoyl)-biphenyl-2-yloxy]acetic acid or a pharmaceutically acceptable salt thereof.

10. The compound according to claim 1, which is [3,3"-Dichloro-5'-(8-morpholin-4-yl-octylcarbamoyl)-[1,1';3'1"]terphenyl-2'-yloxy]acetic acid or a pharmaceutically acceptable salt thereof.

11. The compound according to claim 1, which is {5'-[8-(Benzoxazol-2-ylsulfanyl)-octylcarbamoyl]-3,3"-dichloro-[1,1';3'1"]-terphenyl-2'-yloxy}acetic acid or a pharmaceutically acceptable salt thereof.

12. The compound according to claim 1, which is [3,3"-Dichloro-5'-(8-indol-1-yl-octylcarbamoyl)-[1,1';3'1"]terphenyl-2'-yloxy]acetic acid or a pharmaceutically acceptable salt thereof.

13. The compound according to claim 1, which is [3,3"-Dichloro-5'-(8-imidazol-1-yl-octylcarbamoyl)-[1,1';3'1"]

terphenyl-2'-yloxy]acetic acid or a pharmaceutically acceptable salt thereof.

14. The compound according to claim 1, which is {3,3''-Dichloro-5'-[8-(5-fluoro-indol-1-yl)-octylcarbamoyl]-[1,1';3'1"]terphenyl-2'-yloxy}acetic acid or a pharmaceutically acceptable salt thereof.

15. The compound according to claim 1, which is {3,3''-Dichloro-5'-[8-(5-methoxy-indol-1-yl)-octylcarbamoyl]-[1,1';3'1"]terphenyl-2'-yloxy}acetic acid or a pharmaceutically acceptable salt thereof.

16. The compound according to claim 1, which is {3,3''-Dichloro-5'-[8-(2,5-dimethyl-indol-1-yl)-octylcarbamoyl]-[1,1';3'1"]-terphenyl-2'-yloxy}acetic acid or a pharmaceutically acceptable salt thereof.

17. The compound according to claim 1, which is {3,3''-Dichloro-5'-[8-(5-methoxy-2-methyl-indol-1-yl)-octylcarbamoyl]-[1,1';3'1"]-terphenyl-2'-yloxy}-acetic acid or a pharmaceutically acceptable salt thereof.

18. The compound according to claim 1, which is 5-[3,3''-Dichloro-5'-(8-indol-1-yl-octylcarbamoyl)-[1,1';3',1"]terphenyl-2'-yloxy]-pentanoic acid or a pharmaceutically acceptable salt thereof.

19. The compound according to claim 1, which is 4-{2-[3,3''-Dichloro-5'-(8-indol-1-yl-octylcarbamoyl)-[1,1';3',1"]terphenyl-2'-yloxy]-ethoxy}benzoic acid or a pharmaceutically acceptable salt thereof.

20. The compound according to claim 1, which is {2-[3,3''-Dichloro-5'-(8-indol-1-yl-octylcarbamoyl)-[1,1';3',1"]terphenyl-2'-yloxy]-ethoxy}acetic acid or a pharmaceutically acceptable salt thereof.

21. A method of treating metabolic disorders mediated by insulin resistance or hyperglycemia in a mammal in need thereof which comprises administering to said mammal or therapeutically effective amount of a compound of formula I having the structure

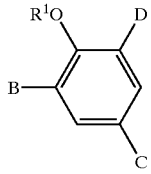

wherein:
B is aryl;
D is halogen or aryl;
$R^1$ is hydrogen, alkyl of 1–6 carbon atoms, —$SO_2Ph(OH)(CO_2H)$, —$CH(R^2)W$, —$CH_2CH_2Y$, or —$CH_2CH_2CH_2Y$;
$R^2$ is —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), or —$CH_2$(3-pyridyl);
W is —$CO_2R^3$, —CONHOH, —CN, —$CONHR^3$, aryl, heteroaryl, —CHO, —CH=$NOR^3$, or —CH=$NHNHR^3$;
Y is —W, —$OCH_2CO_2R^3$, aryl, heteroaryl, —C(=NOH)$NH_2$, —$OR^3$, —O(C=O)$NR^4R^5$, —$NR^3$(C=O)$OR^3$, —$NR^3$(C=O)$NR^4R^5$, or —$NR^4R^5$;
$R^3$ is hydrogen or alkyl of 1–6 carbon atoms;
$R^4$ and $R^5$ are each, independently, hydrogen, or alkyl of 1–6 carbon atoms or $R^4$ and $R^5$ are, together, —$(CH_2)_n$—, or —$CH_2CH_2XCH_2CH_2$—;
X is O, S, SO, $SO_2$, $NR^3$, or $CH_2$;
n is 2 to 5;
C is —$CONR^6R^7$;
$R^6$ and $R^7$ are each, independently, hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —$(CH_2CH_2O)_nCH_3$, —$(CH_2)_mA$ or $R^6$ and $R^7$ are, together, —$(CH_2)_p$—, —$(CH_2)_2N(CH_3)(CH_2)_4$—, —$(CH_2)_2N(R^8)(CH_2)_2$—, or —$(CH_2)_2CH(R^8)$—$(CH_2)_2$— with the proviso that at least one of $R^1$, $R^6$ or $R^7$ is heteroaryl;
$R^8$ is hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —$(CH_2CH_2O)_nCH_3$, —$(CH_2CH_2CH_2O)_nCH_3$, or —$(CH_2)_mA$;
A is aryl, heteroaryl, aryloxy, heteroaryloxy, arylthio, heteroarylthio, arylsulfoxy, heteroarylsulfoxy, arylsulfonyl, heteroarylsulfonyl, —$CHF_2$, —$CH_2F$, —$CF_3$, —$(CH_2CH_2O)_nCH_3$, —$(CH_2CH_2CH_2O)_nCH_3$, —$CO_2R^3$, —O(C=O)$NR^6R^7$, aralkyloxy, or heteroaralkyloxy;
m is 2 to 16;
p is 2 to 12;
or a pharmaceutically acceptable salt thereof.

22. A method of treating or inhibiting type II diabetes in a mammal in need thereof which comprises administering to said mammal a therapeutically effective amount of a compound of formula I having the structure

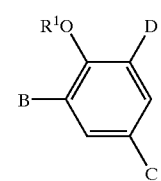

wherein:
B is aryl;
D is halogen or aryl;
$R^1$ is hydrogen, alkyl of 1–6 carbon atoms, —$SO_2Ph(OH)(CO_2H)$, —$CH(R^2)W$, —$CH_2CH_2Y$, or —$CH_2CH_2CH_2Y$;
$R^2$ is —$CH_2$(1H-imidazol-4-yl), —$CH_2$(3-1H-indolyl), —$CH_2CH_2$(1,3-dioxo-1,3-dihydro-isoindol-2-yl), —$CH_2CH_2$(1-oxo-1,3-dihydro-isoindol-2-yl), or —$CH_2$(3-pyridyl);
W is —$CO_2R^3$, —CONHOH, —CN, —$CONHR^3$, aryl, heteroaryl, —CHO, —CH=$NOR^3$, or —CH=$NHNHR^3$;
Y is —W, —$OCH_2CO_2R^3$, aryl, heteroaryl, —C(=NOH)$NH_2$, —$OR^3$, —O(C=O)$NR^4R^5$, —$NR^3$(C=O)$OR^3$, —$NR^3$(C=O)$NR^4R^5$, or —$NR^4R^5$;
$R^3$ is hydrogen or alkyl of 1–6 carbon atoms;
$R^4$ and $R^5$ are each, independently, hydrogen, or alkyl of 1–6 carbon atoms or $R^4$ and $R^5$ are, together, —$(CH_2)_n$—, or —$CH_2CH_2XCH_2CH_2$—;
X is O, S, SO, $SO_2$, $NR^3$, or $CH_2$;
n is 2 to 5;
C is —$CONR^6R^7$;
$R^6$ and $R^7$ are each, independently, hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —(CH$_2$CH$_2$O)$_n$CH$_3$, —(CH$_2$)$_m$A or R$^6$ and R$^7$ are, together, —(CH$_2$)$_p$—, —(CH$_2$)$_2$N(CH$_3$)(CH$_2$)$_4$—, —(CH$_2$)$_2$N(R$^8$)(CH$_2$)$_2$—, or —(CH$_2$)$_2$CH(R$^8$)—(CH$_2$)$_2$— with the proviso that at least one of R$^1$, R$^6$ or R$^7$ is heteroaryl;

R$^8$ is hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —(CH$_2$CH$_2$O)$_n$CH$_3$, —(CH$_2$CH$_2$CH$_2$O)$_n$CH$_3$, or —(CH$_2$)$_m$A;

A is aryl, heteroaryl, aryloxy, heteroaryloxy, arylthio, heteroarylthio, arylsulfoxy, heteroarylsulfoxy, arylsulfonyl, heteroarylsulfonyl, —CHF$_2$, —CH$_2$F, —CF$_3$, —(CH$_2$CH$_2$O)$_n$CH$_3$, —(CH$_2$CH$_2$CH$_2$O)$_n$CH$_3$, —CO$_2$R$^3$, —O(C=O)NR$^6$R$^7$, aralkyloxy, or heteroaralkyloxy;

m is 2 to 16;

p is 2 to 12;

or a pharmaceutically acceptable salt thereof.

23. A method of modulating glucose levels in a mammal in need thereof which comprises administering to said mammal a therapeutically effective amount of a compound of formula I having the structure

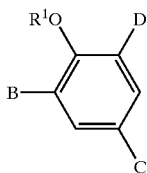

(I)

wherein:

B is aryl;

D is halogen or aryl;

R$^2$ is hydrogen, alkyl of 1–6 carbon atoms, —SO$_2$Ph(OH)(CO$_2$H), —CH(R$^2$)W, —CH$_2$CH$_2$Y, or —CH$_2$CH$_2$CH$_2$Y;

R$^2$ is —CH$_2$(1H-imidazol-4-yl), —CH$_2$(3-1H-indolyl), —CH$_2$CH$_2$(1,3-dioxo-1,3-dihydro-isoindol-2-yl), —CH$_2$CH$_2$(1-oxo-1,3-dihydro-isoindol-2-yl), or —CH$_2$(3-pyridyl);

W is —CO$_2$R$^3$, —CONHOH, —CN, —CONHR$^3$, aryl, heteroaryl, —CHO, —CH=NOR$^3$, or —CH=NHNHR$^3$;

Y is —W, —OCH$_2$CO$_2$R$^3$, aryl, heteroaryl, —C(=NOH)NH$_2$, —OR$^3$, —O(C=O)NR$^4$R$^5$, NR$^3$(C=O)OR$^3$, —NR$^3$(C=O)NR$^4$R$^5$, or —NR$^4$R$^5$;

R$^3$ is hydrogen or alkyl of 1–6 carbon atoms;

R$^4$ and R$^5$ are each, independently, hydrogen, or alkyl of 1–6 carbon atoms or R$^4$ and R$^5$ are, together, —(CH$_2$)$_n$—, or —CH$_2$CH$_2$XCH$_2$CH$_2$—;

X is O, S, SO, SO$_2$, NR$^3$, or CH$_2$;

n is 2 to 5;

C is —CONR$^6$R$^7$;

R$^6$ and R$^7$ are each, independently, hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —(CH$_2$CH$_2$O)$_n$CH$_3$, —(CH$_2$)$_m$A or R$^6$ and R$^7$ are, together, —(CH$_2$)$_p$—, —(CH$_2$)$_2$N(CH$_3$)(CH$_2$)$_4$—, —(CH$_2$)$_2$N(R$^8$)(CH$_2$)$_2$—, or —(CH$_2$)$_2$CH(R$^8$)—(CH$_2$)$_2$— with the proviso that at least one of R$^1$, R$^6$ or R$^7$ is heteroaryl;

R$^8$ is hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —(CH$_2$CH$_2$O)$_n$CH$_3$, —(CH$_2$CH$_2$CH$_2$O)$_n$CH$_3$, or —(CH$_2$)$_m$A;

A is aryl, heteroaryl, aryloxy, heteroaryloxy, arylthio, heteroarylthio, arylsulfoxy, heteroarylsulfoxy, arylsulfonyl, heteroarylsulfonyl, —CHF$_2$, —CH$_2$F, —CF$_3$, —(CH$_2$CH$_2$O)$_n$CH$_3$, —(CH$_2$CH$_2$CH$_2$O)$_n$CH$_3$, —CO$_2$R$^3$, —O(C=O)NR$^6$R$^7$, aralkyloxy, or heteroaralkyloxy;

m is 2 to 16;

p is 2 to 12;

or a pharmaceutically acceptable salt thereof.

24. A pharmaceutical composition which comprises a compound of formula I having the structure

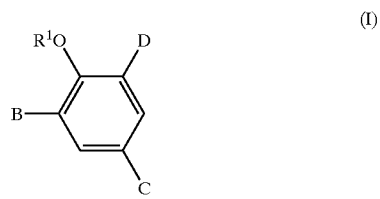

(I)

wherein:

B is aryl;

D is halogen or aryl;

R$^1$ is hydrogen, alkyl of 1–6 carbon atoms, —SO$_2$Ph(OH)(CO$_2$H), —CH(R$^2$)W, —CH$_2$CH$_2$Y, or —CH$_2$CH$_2$CH$_2$Y;

R$^2$ is —CH$_2$(1H-imidazol-4-yl), —CH$_2$(3-1H-indolyl), —CH$_2$CH$_2$(1,3-dioxo-1,3-dihydro-isoindol-2-yl), —CH$_2$CH$_2$(1-oxo-1,3-dihydro-isoindol-2-yl), or —CH$_2$(3-pyridyl);

W is —CO$_2$R$^3$, —CONHOH, —CN, —CONHR$^3$, aryl, heteroaryl, —CHO, —CH=NOR$^3$, or —CH=NHNHR$^3$;

Y is —W, —OCH$_2$CO$_2$R$^3$, aryl, heteroaryl, —C(=NOH)NH$_2$, —OR$^3$, —O(C=O)NR$^4$R$^5$, —NR$^3$(C=O)OR$^3$, —NR$^3$(C=O)NR$^4$R$^5$, or —NR$^4$R$^5$;

R$^3$ is hydrogen or alkyl of 1–6 carbon atoms;

R$^4$ and R$^5$ are each, independently, hydrogen, or alkyl of 1–6 carbon atoms or R$^4$ and R$^5$ are, together, —(CH$_2$)$_n$—, or —CH$_2$CH$_2$XCH$_2$CH$_2$—;

X is O, S, SO, SO$_2$, NR$^3$, or CH$_2$;

n is 2 to 5;

C is —CONR$^6$R$^7$;

R$^6$ and R$^7$ are each, independently, hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —(CH$_2$CH$_2$O)$_n$CH$_3$, —(CH$_2$)$_m$A or R$^6$ and R$^7$ are, together, —(CH$_2$)$_p$—, —(CH$_2$)$_2$N(CH$_3$)(CH$_2$)$_4$—, —(CH$_2$)$_2$N(R$^8$)(CH$_2$)$_2$—, or —(CH$_2$)$_2$CH(R$^8$)—(CH$_2$)$_2$— with the proviso that at least one of R$^1$, R$^6$ or R$^7$ is heteroaryl;

R$^8$ is hydrogen, alkyl of 1–18 carbon atoms, aryl, heteroaryl, aralkyl of 6–20 carbon atoms, heteroaralkyl of 6–20 carbon atoms, cycloalkyl of 3–10 carbon atoms, —(CH$_2$CH$_2$O)$_n$CH$_3$, —(CH$_2$CH$_2$CH$_2$O)$_n$CH$_3$, or —(CH$_2$)$_m$A;

A is aryl, heteroaryl, aryloxy, heteroaryloxy, arylthio, heteroarylthio, arylsulfoxy, heteroarylsulfoxy, arylsulfonyl, heteroarylsulfonyl, $-CHF_2$, $-CH_2F$, $-CF_3$, $-(CH_2CH_2O)_nCH_3$, $-(CH_2CH_2CH_2O)_nCH_3$, $-CO_2R^3$, $-O(C=O)NR^6R^7$, aralkloxy, or heteroaralkyloxy;

m is 2 to 16;

p is 2 to 12;

or a pharmaceutically acceptable salt thereof, and a pharmaceutical carrier.

* * * * *